US007741118B1

(12) United States Patent
Fischhoff et al.

(10) Patent No.: US 7,741,118 B1
(45) Date of Patent: Jun. 22, 2010

(54) SYNTHETIC PLANT GENES AND METHOD FOR PREPARATION

(75) Inventors: David A. Fischhoff, Webster Groves, MO (US); Frederick J. Perlak, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 08/434,105

(22) Filed: May 3, 1995

Related U.S. Application Data

(60) Division of application No. 07/959,506, filed on Oct. 9, 1992, now Pat. No. 5,500,365, which is a continuation of application No. 07/476,661, filed on Feb. 12, 1990, now abandoned, which is a continuation-in-part of application No. 07/315,355, filed on Feb. 24, 1989, now abandoned.

(51) Int. Cl.
*C12N 15/09* (2006.01)

(52) U.S. Cl. ..................................................... 435/440

(58) Field of Classification Search ....................... None
See application file for complete search history.

(56) References Cited

U.S. PATENT DOCUMENTS

| | | | | |
|---|---|---|---|---|
| 4,356,270 | A | 10/1982 | Itakura | |
| 4,448,885 | A | 5/1984 | Schnepf et al. | |
| 4,771,131 | A | 9/1988 | Herrnstadt et al. | |
| 4,859,596 | A | 8/1989 | Hollenberg et al. | |
| 4,888,282 | A * | 12/1989 | Beremand et al. | 435/193 |
| 4,943,674 | A | 7/1990 | Houck et al. | |
| 5,082,767 | A | 1/1992 | Hatfield et al. | |
| 5,250,515 | A | 10/1993 | Fuchs et al. | |
| 5,254,799 | A | 10/1993 | De Greve et al. | |
| 5,270,200 | A | 12/1993 | Sun et al. | |
| 5,380,831 | A | 1/1995 | Adang et al. | |
| 5,495,071 | A | 2/1996 | Fischhoff et al. | |
| 5,496,732 | A | 3/1996 | Smigocki et al. | |
| 5,500,365 | A | 3/1996 | Fischhoff et al. | |
| 5,567,600 | A | 10/1996 | Adang et al. | |
| 5,567,862 | A | 10/1996 | Adang et al. | |
| 5,625,136 | A | 4/1997 | Koziel et al. | |
| 5,689,052 | A | 11/1997 | Brown et al. | |
| 5,763,241 | A | 6/1998 | Fischhoff et al. | |
| 5,866,784 | A | 2/1999 | Van Mellaert et al. | |
| 5,880,275 | A | 3/1999 | Fischhoff et al. | |
| 6,075,185 | A | 6/2000 | Koziel et al. | |
| 6,180,774 | B1 | 1/2001 | Brown et al. | |
| 6,204,246 | B1 | 3/2001 | Bosch et al. | |
| 6,284,949 | B1 | 9/2001 | Fischhoff et al. | |
| 6,320,100 | B1 | 11/2001 | Koziel et al. | |
| 6,403,865 | B1 | 6/2002 | Koziel et al. | |
| 6,689,356 | B1 | 2/2004 | Zlotkin et al. | |
| 6,833,449 | B1 | 12/2004 | Barton et al. | |
| 2001/0003849 | A1 | 6/2001 | Barton et al. | |

FOREIGN PATENT DOCUMENTS

| | | |
|---|---|---|
| AU | B-36568/89 | 12/1989 |
| AU | B-46881/89 | 6/1990 |
| EP | 0063949 | 11/1982 |
| EP | 0108580 | 5/1984 |
| EP | 0142924 | 5/1985 |
| EP | 0159884 | 10/1985 |
| EP | 0192319 | 8/1986 |
| EP | 0193259 | 9/1986 |
| EP | 0221024 | 5/1987 |
| EP | 0267159 | 5/1988 |
| EP | 0269601 | 6/1988 |
| EP | 0275957 | 7/1988 |
| EP | 0305275 | 3/1989 |
| EP | 0318143 | 5/1989 |
| EP | 0332104 | 9/1989 |
| EP | 0340948 | 11/1989 |
| EP | 0348348 | 12/1989 |
| EP | 0359472 | 3/1990 |
| EP | 0385962 | 9/1990 |
| EP | 0431829 | 6/1991 |
| EP | 0228838 | 4/1992 |
| EP | 0140556 | 7/1992 |
| EP | 0126546 | 3/1994 |
| EP | 0408403 | 8/1994 |
| EP | 0612848 | 8/1994 |
| EP | 0223452 | 4/1996 |
| JP | 62319288 | 7/1989 |
| JP | 61283228 | 10/1998 |
| WO | WO-88/08880 | 11/1988 |
| WO | WO-90/10076 | 9/1990 |
| WO | WO-90/15139 | 12/1990 |
| WO | WO-91/10725 | 7/1991 |
| WO | WO-93/07278 | 4/1993 |

OTHER PUBLICATIONS

U.S. Appl. No. 07/285,924, filed Dec. 19, 1988.
U.S. Appl. No. 07/286,002, filed Dec. 19, 1988.
U.S. Appl. No. 07/286,087, filed Dec. 19, 1988.
U.S. Appl. No. 07/320,195, filed Mar. 7, 1989.
Adami et al., "Adenovirus mRNA Processing—In a Regulated Manner a Splice Site Choice Dominates Over Selection of a Poly A Site Located in an Intron," *RNA Processing Meeting*, pp. 26, May 11-15, 1988.
Adang et al., "Characterized Full-Length and Truncated Plasmid Clones of the Crystal Protein of *Bacillus Thuringiensis* subsp. *Kurstaki* HD-73 and their Toxicity to *Manduca Sexta*," *Genes*, 36:289-300 (1985).

(Continued)

*Primary Examiner*—Anne Marie Grunberg
(74) *Attorney, Agent, or Firm*—Marshall, Gerstein & Borun LLP

(57) ABSTRACT

A method for modifying structural gene sequences to enhance the expression of the protein product is disclosed. Also disclosed are novel structural genes which encode insecticidal proteins of B.t.k. HD-1, B.t.k. HD-73, *B.t. tenebrionis*, *B.t. entomocidus*, 2 protein of B.t.k. HD-1, and the coat protein of potato leaf roll virus.

103 Claims, 46 Drawing Sheets

OTHER PUBLICATIONS

Adang et al., "Engineering Crop Plants for Insect Resistence," *154th National American Assoc. Adv. Sci.*, pp. 59, Feb. 11-15, 1988.
Adang et al., "Expression of a *Bacillus Thuringiensis* Insecticidal Crystal Protein Gene in Tobacco Plants," *Mol. Strat. Crop Protec.*, 345-353 (1987).
Adang et al., "The Reconstruction and Expression of a *Bacillus Thuringiensis CryIIIA* Gene in Protoplasts and Potato Plants," *Plant Mol. Biol.*, 21:1131-1145 (1993).
Aota et al., Codon Usage Tabulated from the GenBank Genetic Sequence Data, *Nucl. Acids Res.*, 16(Supp): r315-r402 (1988).
Aronson et al., "*Bacillus Thuringiensis* and Related Insect Pathogens," *Microbiol. Rev.*, 50(1):1-24 (1986).
Audtho et al., "Production of Chymotrypsin-Resistant *Bacillus Thuringiensis* Cry2Aa1 δ-Endotoxin by Protein Engineering," *Appl. Environ. Microbiol.*, 65(10);4601-4605 (1999).
Barker et al., "Nucleotide Sequence of the T-DNA Region from the *Agrobacterium tumefaciens* Octopine Ti Plasmid pTi15955," *Plant Mol. Biol.*, 2:335-350 (1983).
Barton et al., "*Bacillus thuringiensis* δ-Endotoxin Expressed in Transgenic *Nicotiana tabacum* Provides Resistance to Lepidopteran Insects," *Plant Phys.*, 85:1103-1109 (1987).
Barton et al., "Production of *Bacillus thuringiensis* Insecticidal Proteins in Plants," *Transgenic Plants*, 1:297-315 (1993).
Barton et al., "Prospects in Plant Genetic Engineering," *Science*, 219:671-676 (1983).
Barton et al., "Regeneration of Intact Tobacco Plants Containing Full Length Copies of Genetically Engineered T-DNA, and Transmission of T-DNA to R1 Progeny," *Cell*, 32:1033-1043 (1983).
Bashe et al., "Codon Usage Table for Maize Based on Sequences of 25 Nuclear Genes," *63 Maize Genetics Cooperation Newsletter* (1989).
Bauer et al., "Chemie der Pflanzenschutz-und Sch,,dlings-bek,,mpfungsmittel," Ch. 6, pp. 289-395 (1981).
Beck et al., "Nucleotide Sequence and Exact Localization of the Neomycin Phosphotransferase Gene from Transposon Tn5," *Gene*, 19:327-336 (1982).
BioTech Reporter, "Registration of Plant-Pesticides," *Government News* (1996).
Borlaug, "Contributions of Conventional Plant Breeding to Food Production," *Science*, 219:689-693 (1983).
Boudraa, "Coding Strategy Variation in the Plant System," *Genet. Sel. Evol.*, 19:143-154 (1987).
Bozouklian et al., "Nucleotide Sequence of the *Azospirillum brasilense* Sp 7 Glutamine Synthetase Structural Gene," *Biochemie*, 68:1181-1187 (1986).
Brady et al., "Competition Between Splicing and Polyadenylation Determines which Adenovirus Region E3 mRNAs are Synthesized," *RNA Processing Meeting*, pp. 224, May 11-15, 1988.
Bravo et al., "Immunocytochemical Localization of *Bacillus thuringiensis* Insecticidal Crystal Proteins in Intoxicated Insects," *J. Inv. Pathol.*, 60:237-246 (1992).
Brizzard et al., "Nucleotide Sequence of an Additional Crystal Protein Gene Cloned from *Bacillus thuringiensis* subsp. *thuringiensis*," *Nucl. Acids Res.*, 16:2723-2724 (1988).
Brown, "A Catalogue of Splice Junction and Putative Branch Point Sequences from Plant Introns," *Nucl. Acids Res.*, 14:9549-9559 (1986).
Callis et al., "Introns Increase Gene Expression in Cultured Maize Cells," *Genes & Devel.*, 1:1183-1200 (1987).
Campbell et al., "Codon Usage in Higher Plants, Green Algae, and Cyanobacteria," *Plant Physiol.*, 92 (1990).
Caplan et al., "Introduction of Genetic Material into Plant Cells," *Science*, 222:815-821 (1983).
Chilton et al., "Tailoring the Agrobacterium Ti Plasmid as a Vector for Plant Genetic Engineering," *Stadler Symposium*, 13:39-51 (1981).
Chilton, "A Vector for Introducing New Genes into Plants," *Scientific American*, 248:51-59 (1983).
Church et al., "Genomic Sequencing," *PNAS USA*, 82:1991-1995 (1984).
Conway et al., "Identification of Bases and Phosphates of SV40 Late Pre-mRNAs that are Required for 3' End Formation In Vitro," *RNA Processing Meeting*, pp. 40, May 11-15, 1988.
Daar et al., "Premature Translation Termination Mediates Mammalian mRNA Degradation," *RNA Processing Meeting*, pp. 45, May 11-15, 1988.
Dalbadie et al., "Oligonucleotide-Directed Mutagenesis as a General and Powerful Method for Studies of Protein Function," *PNAS USA*, 79:6409-6413 (1982).
Dandekar et al., "Low Levels of Expression of Wild Type *Bacillus thuringiensis* var. *Kurstaki cryIA* (c) Sequences in Transgenic Walnut Somatic Embryos," *Plant Science*, 96:151-162 (1994).
De Cleene et al., "The Host Range of Crown Gall," *Botanical Review*, 42:409-413 (1976).
De Greve et al., "Regeneration of Normal and Fertile Plants that Express Octopine Synthase, from Tobacco Crown Gails after Deletion of Tumour-Controlling Functions," *Nature*, 300:752-755 (1982).
Dean et al., "mRNA Transcripts of Several Plant Genes are Polyadenylated at Multiple Sites In Vivo," *Nucl. Acids Res.*, 14:2229-2240 (1986).
Dedrick et al., "Purified RNA Polymerase II Recognizes Specific Termination Sites During Transcription in Vitro," *J. Biol. Chem.*, 262:9098-9108 (1987).
Devonshire et al., "A Carboxylesterase with Broad Substrate Specificity Causes Organophosphorus, Carbamate and Pyrethroid Resistance in Peach-Potato Aphids (*Myzus persicae*)," *Pest. Biochem. Physiol.*, 18:235-246 (1982).
Dhaese et al., "Identification of Sequences Involved in the Polyadenylation of Higher Plant Nuclear Transcripts Using Agrobacterium T-DNA Genes as Models," *EMBO J.*, 2(3):419-426 (1983).
Diehn et al., "Problems That Can Limit the Expression of Foreign Genes in Plants: Lessons to be Learned from B.t. Toxin Genes," *18 Genetic Engineering 83* (1996).
Donovan et al., "Amino Acid Sequences and Entomocidal Activity of the P2 Crystal Protein," *J. Biol. Chem.*, 263:561-567 (1988).
Drummond, "Launching Genes Across Phylogenetic Barriers," *Nature*, 303:198-199 (1983).
Ernst, "Codon Usage and Gene Expression," *TiBiotechnol.*, 6:196-199 (1988).
Ferre et al., "Resistance to the *Bacillus thuringiensis* Bioinsecticide in a Field Population of *Plutella xylostella* is Due to a Change in a Midgut Membrane Receptor," *PNAS USA*, 88:5119-5123 (1991).
Fischhoff et al., "Insect Tolerant Transgentic Tomato Plants," *BioTechnology*, 5:807-813 (1987).
Foard et al., "Engineering of Crop Plants with Resistance to Herbivores and Pathogens: An Approach Using Primary Gene Products," *Plant Mol. Biol.*, 223-233 (1983).
Fraley et al., "Use of a Chimeric Gene to Confer Antibiotic Resistance to Plant Cells," *Molecular Genetics of Plants and Animals, Miami Winter Symposium*, 22:211-221 (1983).
Fujimura et al., "Regeneration of Rice Plants from Protoplasts," *Plant Tissue Culture Lett.*, 2(2):74-75 (1985).
Gallego et al., "Mutually Exclusive Splicing of Myosin Light Chain (MLC) 1/3 Transcripts is Cis Regulated: Hierarchy Among Donor and Acceptor Splice Site Pairs," *RNA Processing Meeting*, pp. 61, May 11-15, 1988.
Ge et al., "Functional Domains of *Bacillus thuringiensis* Insecticidal Crystal Proteins," *J. Biol. Chem.*, 266:17954-17958 (1991).
Gelvin et al., "Use of a $T_R$ T-DNA Promoter to Express Genes in Plants and Bacteria," *Mol. Gen. Genet.*, 199:240-248 (1985).
Genovese et al., "Alterations in Immunoglobulin mRNA Stability During B Cell Development," *RNA Processing Meeting*, pp. 62, May 11-15, 1988.
George et al., "High-Level Expression in *Escherichia coli* of Biologically Active Bovine Growth CHormone," *DNA*, 4:273-281 (1985).
Gil et al., "A Sequence Downstream of AAUAAA is Required for Rabbit β-Globin mRNA 3'-End Formation,"C59 *Nature*, 312:473-474 (1984).
Goldsbrough et al., "Expression of Maize Zein Genes in Transformed Sunflower Cells," *Mol. Gen. Genet.*, 202:3C6174-381 (1986).

Gonzales-Cabrera et al., "Binding of *Bacillus thuringiensis* Toxins in Resistant and Susceptible Strains of Pink BollCworm (*Pectinophora gossypiella*)," *Insect Biochem. Mol. Biol.*, 33:929-935 (2003).
Goodall et al., "Specifically of Nuclear pre-RNA Splicing in Plants," *RNA Processing Meeting*, pp. 63, May 11-15, 1988.
Gould et al., "Transformation of *Zeta mays* L. Using Agrobacterium Tumefaciens and the Shoot Apex," *Plant Physiol*, 95:426-434 (1991).
Gould, "Genetic Engineering, Integrated Pest Management and the Evolution of Pests," *TiBiotechnol*, 6:312-315 (1988).
Gould, "Simulation Models for Predicting Durability of Insect-Resistant Germ Plasm: Hessian Fly (Diptera: Cecidomyiidae)-Resistant Winter Wheat," *Environ. Entomol.*, 15:11-23 (1986).
Gouy, "Codon Contexts in Enterobacterial and Coliphage Genes," *Mol. Biol. Evol.*, 4:426-444 (1987).
Green et al., "Wound-Induced Proteinase Inhibitor in Plant Levels: A Possible Defense Mechanism Against Insects," *Science*, 175:776-777 (1972).
Grimsley et al., "Agrobacterium-Mediated Delivery of Infectious Maize Streak Virus into Maize Plants," *Nature*, 325(8):177-179 (1987).
Gritz et al., "Plasmid-Encoded Hygromycin B Resistance: The Sequence of Hygromycin B Phosphotransferase Gene and its Expression in *Escherichia coli* and *Saccharomyces cerevisiae," Gene*, 25:179-188 (1983).
Hampson et al., "Alternative Processing of Bovine Growth Hormone Precursor mRNA is Strongly Influenced by Sequences within the Downstream Exon," *RNA Processing Meeting*, pp. 68, May 11-15, 1988.
Hanley et al., "Plant Intron Sequences: Evidence for Distinct Groups of Introns," *Nucl. Acids Res.*, 16:7159-7176 (1988).
Held et al., "Cloning and Localization of the Lepidopteran Protoxin Gene of *Bacillus thuringiensis* subsp. *Kurstaki," PNAS USA*, 79:6065-6069 (1982).
Helfman et al., "Studies of Alternative RNA Splicing of Tropomyosin pre-mRNAs in Vitro," *RNA Processing Meeting*, pp. 219, May 11-15, 1988.
Herrera-Estrella et al., "Expression of Chimaeric Genes Transferred into Plant Cells Using a Ti-Plasmid-Derived Vector," *Nature*, 303:210-213 (1983).
Hilder et al., "A Novel Mechanism of Insect Resistance Engineering into Tobacco," *Nature*, 330:160-163 (1987).
Hinchee et al., "Production of Transgenic Soybean Plants Using *Agrobacterium*—Mediated DNA Transfer," *BioTechnol*, 6:915-922 (1988).
Hoekema et al., "Codon Replacement in the *PGKI* Gene of *Saccharomyces cerevisiae*: Experimental Approach to Study the Role of Biased Codon Usage in Gene Expression," *Mol. Cell Biol.*, 7:2914-2924 (1987).
Hofmann et al., "Binding of the Delta Endotoxin from *Bacillus thuringiensis* to Brush-Border Membrane Vesicles of the Cabbage Butterfly (*Pieris brassicae*)," *Eur. J. Biochem.*, 173:85-91 (1988).
Hofmann et al., "Specificity of *Bacillus thuringiensis* δ-Endotoxins is Correlated with the Presence of High-Affinity Binding Sites in the Brush Border Membrane of Target Insect Midguts," *PNAS USA*, 85:7844-7848 (1988).
Hofmann, "The Binding of *Bacillus thuringiensis* Delta-Endotoxin to Cultured Insect Cells and to Brush Border Membrane Vesicles," *A Dissertation Submitted to the Swiss Federal Institiute of Technology Zurich*, ETH No. 8498 (1988).
Hofte et al., "Fusion Proteins with Both Insecticidal and Neomycin Phosphotransferase II Activity," *FEBS Lett.*, 226:364-370 (1988).
Hofte et al., "Insecticidal Crystal Proteins of *Bacillus thuringiensis," Microbiol. Rev.*, 53:242-255 (1989).
Hofte et al., "Nucleotide Sequence of a Gene Encoding an Insecticidal Protein of *Bacillus thuringiensis* var. *Tenebrionis* Toxic Against Coleoptera," *Nucl. Acids Res.*, 15(17):7183 (1987).
Hofte et al., "Structural and Functional Analysis of a Cloned Delta Endotoxin of *Bacillus thuringiensis Berliner* 1715," *Eur. J. Biochem.*, 161:273-280 (1986).
Honee et al., "Nucleotide Sequence of Crystal Protein Gene Isolated from *B. thuringiensis* subsp. *entomocidus* 60.5 Coding: For a Toxin Highly Active Against *Spodoptem* Species," *Nucl. Acids Res.*, 16, 6240 (1988).
Honee et al., *Chemical Abstracts* No. 193742, 112(21):262 (1990).
Honigman et al., "Cloning and Expression of the Lepidopteran Toxin Produced by *Bacillus thuringiensis* var. *Thuringiensis* is *Escherichia coli*," *Gene*, 42:69-77 (1986).
Hooykaas et al., "The *Agrobacterium tumefaciens* T-DNA Gene $6^b$ is an *Onc* Gene," *Plant Mol. Biol.*, 11:791-794 (1988).
Horsch et al., "A Simple and General Method for Transferring Genes into Plants," *Science*, 227:1229-1231 (1985).
Hunt et al., "Deletion Analysis of the Polyadenylation Signal of a Pea Ribulose-1,5-Bisphosphate Carboxylase Small Subunit Gene," *Plant Mol. Biol.*, 13:125-138 (1989).
Hunt et al., "Plant Cells Do Not Properly Recognize Animal Gene Polyadenylatioin Signals," *Plant Mol. Biol.*, 8:23-35 (1987).
Ikemura, "Codon Usage and tRNA Content in Unicellular and Multicellular Organisms," *Mol. Biol. Evol.*, 2(1):13-34 (1985).
Ikemura, "Correlation Between the Abundance of *Escherichia coli* Transfer RNAs and the Occurence of the Respective Codons in its Protein Genes," *J. Mol. Biol.*, 146:1-21 (1981).
Janssen et al., "Localized Transient Expression of GUS in Leaf Discs Following Cocultivation with *Agrobacterium," Plant Mol. Biol.*, 14:61-72 (1989).
Janzen et al., "Insecticidal Action of the Phytohemagglutinin in Black Beans on a Bruchid Beetle," *Science*, 192:795-796 (1976).
Jones et al., "High Level Expression of Introduced Chimaeric Genes in Regenerated Transformed Plants," *EMBO J.*, 4:2411-2418 (1985).
Joshi, "Putative Polyadenylation Signals in Nuclear Genes of Higher Plants: A Compilation and Analysis," *Nuc. A.R.*, 15:9627-9640 (1987).
Karim et al., "Toxicity and Receptor Binding Properties of *Bacillus thuringinesis* δ-Endotoxins to the Midgut Brush Border Membrane Vesicles of the Rice Leaf Folders, *Cnaphalocrocis medinalis* and *Marasmia patnalis," Curr. Microbiol.*, 41:276-283 (2000).
Keith et al., "Moncot and Dicot pre-mRNAs are Processed with Different Efficiencies in Transgenic Tobacco," *EMBO J.*, 5(10):2419-2425 (1986).
Kemp et al., "Agrobacterium-Mediated Transfer of Foreign Genes into Plants," *Genetic Engineering*, 7:215-228 (1983).
Kemp et al., "Transfer of a Functional Gene via the T1 Plasmid," *Chem. Abst.*, 101(3):176-177 (1984).
Kessler et al., "A Novel Transcription Elongation Block is Active within the Late Leader Sequences of SV40," *RNA Processing Meeting*, pp. 85, May 11-15, 1988.
Klier et al., "Cloning and Expression of the Crystal Protein Genes from *Bacillus thuringiensis* Strain *Berliner* 1715," *EMBO J.*, 7:791-799 (1982).
Knight, "Biological Controls Squash Insect Pests," *BioTechnol*, 6:1137 (1988).
Kniskem et al., "Unusually High-Level Expression of a Foreign Gene (Hepatitis B Virus Core Antigen) in *Saccharomyces cerevisiae," Gene*, 46:135-141 (1986).
Korber et al., "T-DNA Gene 5 of *Agrobacterium* Modulates Auxin Response by Autoregulated Synthesis of a Growth Hormone Antagonist in Plants," *EMBO J.*, 10:3983-3991 (1991).
Kozak, Influences of mRNA Secondary Structure on Initiation by Eukaryotic Ribosomes, *PNAS USA*, 83:2850-2854 (1986).
Koziel et al., "The Insecticidal Crystal Proteins of *Bacillus thuringiensis*: Past, Present and Future Uses," *BioTechnol. Genet. Eng. Rev.*, 11:171-228 (1993).
Kronstad et al., "Diversity of Locations for *Bacillus thuringiensis* Crystal Protein Genes," *J. Bacteriol.*, 154:419-428 (1983).
Kronstad et al., "Three Classes of Homologous *Bacillus thuringiensis* Crystal-Protein Genes," *Gene*, 43:29-40 (1986).
Ledeboer et al., "Advances in Gene Technology for Plants and Animals," *BioTechnology*, 169-171 (1983).
Lee et al., "Determination of Binding of *Bacillus thuringiensis* §-Endotoxin Receptors to Rice Stem Borer Midguts," *Appl. Environ. Microbiol.*, 63:1453-1459 (1997).
Leemans et al., "Genetic Identification of Functions of TL-DNA Transcripts in Octopine Crown Galls," *EMBO J.*, 1:147-152 (1982).
Lereclus et al., "Role, Structure and Molecular Organization of the Genes Coding for the Parasporal §-Endotoxins of *Bacillus thuringiensis," Regulation of Procaryotic Development*, Ch.13:255-275 (1989).

Levitt et al., "Definition of An Efficient Synthetic Poly(A) Site," *Genes and Dev.*, 3:1019-1025 (1989).
Lewin, "Genes IV," *Oxford Univ. Press*, Ch.30:596-597 (1990).
Lim et al., "Tissue Specificity of mRNA Degradation," *RNA Processing Meeting*, pp. 128, May 11-15, 1988.
Logan et al., "A Poly(A) Addition Site and a Downstream Termination Region are Required for Efficient Cessation of Transcription by RNA Polymerase II in the Mouse Maj-Globin Gene," *Proc. Natl. Acad. Sci.* (*USA*), 84:8306-8310 (1987).
Luthy et al., "The Entomocidal Toxins of *Bacillus thuringiensis*," *Pharmac. Ther.*, 13:257-283 (1981).
Lycett et al., "Are Plant Genes Different?" *FEBS Lett.*, 153:43-46 (1983).
MacIntosh et al., "Binding of *Bacillus thuringiensis* Proteins to a Laboratory-Selected Line of *Heliothis virescens*," *PNAS USA*, 88:8930-8933 (1991).
MacIntosh et al., "Specificity and Efficacy of Purified *Bacillus thuringiensis* Proteins Against Agronomically Important Insects," *J. Invert. Pathology*, 56:258-266 (1990).
MacKenzie et al., "Attachment of *Agrobacterium tumefaciens* to Mechanically Isolated *Asparagus* Cells," *Plant Sci. Lett.*, 29:227-236 (1983).
Makoff et al., "Expression of Tetapus Toxin Fragment C in *E coli*: High Level Expression by Removing Rare Codons," *Nuc. A.R.*, 17(24):10191-10202 (1989).
Mani et al., "Evolution of Resistance in the Presence of Two Insecticides," *Genetics*, 109:761-783 (1985).
Marx, "Ti Plasmids as Gene Carriers," *Science*, 214:1305 (1982).
Marzluff et al., "Intervening Sequences Interfere with Formation of 3' Ends of Histone mRNAs," *RNA Processing Meetings*, pp. 244, May 11-15, 1988.
Maugh, "Exploring Plant Resistance to Insects," *Science*, 216:722-733 (1982).
Mazodier et al., "Completion of the Nucleotide Sequences of the Central Region of Tn5 Confirms the presence of Three Resistance Genes," *Nucl. Acids Res.*, 13:195-205 (1985).
McDevitt et al., "Requirement of a Downstream Sequence for Generation of a Poly(A) Addition Site," *Cell*, 37:993-999 (1984).
McGaughey et al., "Indianmeal Moth (*Lepidoptera: pyralidae*) Resistance to Different Strains and mixtures of *Bacillus thuringiensis*," *J. Econ. Entomol.*, 85:1594-1600 (1992).
McGaughey et al., "Toxicity of Different Serotypes and Toxins of *Bacillus thuringiensis* to Resistant and Susceptible Indianmeal Moths (*Lepidoptera: pyralidae*)," *J. Econ. Entomol.*, 80:1122-1126 (1987).
McGaughey, "Problems of Insect Resistance to *Bacillus thuringiensis*," *Agricult. Ecosyt. & Environment*, 49:95-102 (1994).
McPherson et al., "Characterization of the Coleopteran-Specific Protein Gene of *Bacillus thuringiensis* var. *tenebrions*," *BioTechnology*, 6:61-66 (1988).
Messing et al., "Plant Gene Structure," *Genetic Engineering of Plants*, 211-227 (1983).
Metcalf, "Insect Resistance to Insecticides," *Pestic. Sci.*, 26:333-358 (1989).
Miller et al., "Bacterial, Viral, and Fungal Insecticides," *Science*, 219:715-721 (1983).
MPEP, "Simulated or Predicted Test Results or Prophetic Examples," 5th Ed., 608.01(q)D (1983).
Murai et al., "T-DNA of pTi-15955 et etc.," *Chem Abst.*, 96:156 (1982).
Murray et al., "Analysis of Unstable RNA Transcripts of Insecticidal Crystal Protein Genes of *Bacillus thuringiensis* in transgenic Plants and Electroporated Protoplasts," *Plant Mol. Biol.*, 16:1035-1050 (1991).
Murray, "Codon Usage in Plant Genes," *Nucl. Acids Res.*, 17(2):477-498 (1989).
Nassal et al., "Structure-Functions Studies on Bacteriorhodopsin," *J. Biol. Chem.*, 262:9264-9270 (1987).
Norris et al., "Biochemical and Morphological Bases of Resistance," *Breeding Plants*, 29:56-57 (1980).
Ohnie-Takagi et al., "The Effect of Sequences with High AU Content on mRNA Stability in Tobacco," *Proc. Natl. Acad. Sci.* (*USA*), 90:1181-11815 (1993).
Oneill et al., "Overproduction from a Cellulase Gene with a High Guanosine-Plus-Cytosine Content in *Escherichia coli*," *Appl. Environ. Microbiol.*, 52:737-743 (1986).
Osborn et al., "Insecticidal Activity and Lectin Homology of Arcelin Seed Protein," *Science*, 240:207-210 (1988).
Pandey et al., "Processing and Stability of Transcripts from Chimeric Histone-Globin Genes," *RNA Processing Meeting*, pp. 133, May 13-17, 1987.
Payne, "Current Uses and Future Prospects for Microbial Pest Control Agents," *Med. Fac. Landbouww. Rijksuniv. Gent.*, 52(2a):113-123 (1987).
Peerbolte et al., "Clones from a Shooty Tobacco Crown Gall Tumor I: Deletions, Rearrangements and Amplifications Resulting in Irregular T-DNA Structures and Organizations," *Plant Mol. Biol.*, 7:265-284 (1986).
Perlak et al., "Insect Resistant Cotton Plants," *BioTechnol*, 8:939-943 (1990).
Perlak et al., "Modification of the Coding Sequence Enhances Plant Expression of Insect Control Protein Genes," *PNAS USA*, 88:3324-3328 (1991).
Potrykus, "Gene Transfer to Cereals: An Assessment," *BioTechnology*, 535-542 (1990).
Proudfoot et al., "Termination of Transcription and 3' End Processing in Eukaryotic Genes Transcribed by RNA Polymerase II: The Signals Involved and Their Role in Gene Regulation," *RNA Processing Meeting*, pp. 17, May 13-17, 1987.
Ream et al., "Multiple Mutations in the T Region of the *Agrobacterium tumefaciens* Tumor-Inducing Plasmid," *PNAS USA*, 80:1660-1664 (1983).
Reines et al., "Identification of Intrinsic Termination Sites in Vitro for RNA Polymerase II Within Eukaryotic Gene Sequences," *J. Mol. Biol.*, 196:299-312 (1987).
Rogan et al., "Enzyme-Linked Immunosorbent Assay for Quantitation of Neomycin Phosphotransferase II in Genetically Modified Cotton Tissue Extracts," *J. Agricul Food Chem.*, 40:1453-1458 (1992).
Rousch, "Designing Resistance Management Programs: How Can You Choose?" *Pestic Sci.*, 26:423-441 (1989).
Sadofsky et al., "Sequences on the 3' Side of Hexanucleotide AAUAAA Affect Efficiency of Cleavage at the Polyadenylation Site," *Mol. Cell Biol.*, 4:1460-1468 (1984).
Saghai-Maroof et al., "Ribosomal DNA Spacer-Length Polymorphisms in Barley: Mendelian Inheritance, Chromosomal Location, and Population Dynamics," *PNAS USA*, 81:8014-8018 (1984).
Schafer et al., "T-DNA Integration and Expression in a Monocot Crop Plant After Induction of *Agrobacterium*," *Nature*, 327:529-532 (1987).
Schell et al., "Leben mit Fremden Genen," *Naturwiss Rundschau*, 36:254-260 (1983).
Schell et al., "The Ti Plasmids as Natural and as Practical Gene Vectors for Plants," *Biotechnol.*, 175-180 (1983).
Schell et al., "Ti Plasmids as Experimental Gene Vectors for Plants," *15th Miami Winter Symposium*, 20:191-209 (1983).
Schesser et al., "Bioassay for Homogeneous Parasporal Crystal of *Bacillus thuringiensis* Using the Tobacco Hornworm, *Manduca sexta*," *Appl. Environ. Microbiol.*, 33:878-880 (1977).
Schnepf et al., "*Bacillus thuringiensis* and Its Pesticidal Crystal Proteins," *MMBR*, 62:775-806 (1998).
Schnepf et al., "Cloning and Expression of the *Bacillus thuringiensis* Crystal Protein Gene in *Escherichia coli*," *PNAS USA*, 78:2893-2897 (1981).
Schnepf et al., "Expression of a Cloned *Bacillus thuringiensis* Crystal Protein Gene in *Escherichia coli*," *J. Bacteriol*, 169:4110-4118 (1987).
Schnepf, "The Amino Acid Sequence of a Crystal Protein from *Bacillus thuringiensis* Deduced from the DNA Base Sequence," *J. Biol. Chem.*, 260:6264-6272 (1985).
Sekar et al., "Molecular Cloning and Characterization of the Insecticidal Crystal Protein Gene of *Bacillus thuringiensis* var. *Tenebrionis*," *PNAS USA*, 84:7036-7040 (1987).

Sharp et al., "Codon Usage in Yeast: Cluster Analysis Clearly Differentiates Highly and Lowly Expressed Genes," *Nucl. Acids Res.*, 14:5125-5143 (1986).
Sharp et al., "The Codon Adaptation Index—A Measure of Directional Synonymous Codon Usage Bias, and its Potential Applications," *Nucl. Acids Res.*, 15:1281-1295 (1987).
Shaw et al., "A Conserved AU Sequence from the 3' Untranslated Region of GM-CSF mRNA Mediates Selective mRNA Degradation," *Cell*, 46:659-667 (1986).
Shaw et al., "Characterization of AU Sequences Functioning as mRNA Destabilizers," *RNA Processing Meeting*, pp. 220, May 13-17, 1987.
Shaw, "Genetic Engineering of Crop Plants: A Strategy for the Future, and the Present," *Chem. Indust.*, 817-824 (1984).
Shimizu et al., "Cloning and Expression in *Escherichia coli* of the 135-kDa Insecticidal Protein Gene from *Bacillus thuringiensis* subsp. *aizawai* IPL7," *Chem.*, 52:1565-1573 (1988).
Smigocki et al., "Cytokinin-Mediated Insect Resistance in *Nicotiana* Plants Transformed with the *ipt* Gene," *Plant Mol. Biol.*, 23:325-335 (1993).
Smith et al., "Diseases Caused by Viruses," *Biol. Abst. Phytopathology*, 87(1):AB9696 (1989).
Spanier et al., "A Functional Analysis of T-DNA Gene *6b*: The Fine Tuning of Cytokinin Effects on Shoot Development," *Mol. Gen. Genet.*, 219:209-216 (1989).
Spencer et al., "Segregation of Transgenes in Maize," *Plant Mol. Biol.*, 18:201-210 (1992).
Springer et al., "High-Level Expression of Sperm Whale Myoglobin in *Escherichia coil," PNAS USA*, 84:8961-8965 (1987).
Stone et al., "Insect Resistance to *Bacillus thuringiensis*," Biotech. for Biol. Control of Pests & Vectors, 53-66 (1991).
Stone et al., "Selection of Tobacco Budworm for Resistance to a Genetically Engineered *Pseudomonas fluorescens* Containing the §-Endotoxin of *Bacillus thuringiensis* subsp. *Kurstaki," J. Inv. Pathol.*, 53:228-234 (1989).
Taylor et al., "Optimizing the Expression of Chimeric Genes in Plant Cells," *Mol. Gen. Genet.*, 210:572-577 (1987).
Thurston, "Toxicity of Trichome Exudates of *Nicotiana* and *Petunia* Species to Tobacco Hornworm Larvae," *J. Economic. Entomol.*, 63:271-274 (1970).
Tinland et al., "*Agrobacterium tumefaciens* T-DNA Gene *6b* Stimulates *rol*-Induced Root Formation, Permits Growth at High Auxin Concentrations and Increases Root Size," *Mol. Gen. Genet.*, 223:1-10 (1990).
Tokunaga et al., "Expression of a Synthetic Human Growth Hormone Gene in Yeast," *Gene*, 39:117-120 (1985).
Toriyama et al., "Haploid and Diploid Plant Regeneration from Protoplasts of Another Callus in Rice," *Theor. Appl. Genet.*, 73:16-19 (1986).
Trolinder et al., "Somatic Embryogenesis and Plant Regeneration in Cotton (*Gossypium hirsutum* L.)" *Plant Cell Reports*, 6:231-234 (1987).
Tsurushita et al., "Regulation of Differential Processing of Mouse Immunoglobulin Mu Heavy-Chain mRNA," RNA Processing Meeting, pp. 215, May 13-17, 1987.
Uchimiya et al., "Expression of a Foreign Gene in Callus Derived from DNA-Treated Protoplasts of Rice (*Oryza sativa* L.)" *Mol. Gen. Genet.*, 204:204-207 (1986).
Urdea et al., "Chemical Synthesis of a Gene for Human Epidermal Growth Factor Urogastrone and its Expression in Yeast," *PNAS USA*, 80:7461-7465 (1983).
Vaeck et al., "Transgenic Plants Protected from Insect Attack," *Nature*, 328:33-37 (1987).
Van Mellaert et al., "Binding of Different Types of *Bacillus thuringiensis* Delta-Endotoxins to Midgut Brush Border Membrane Vesicles is Correlated with the Insecticidal Spectrum," *XXI Ann. Meeting Soc. Inv. Pathol. UCSD*, pp. 27, Aug. 14-18, 1988.
Van Rie et al., "Mechanism of Insect Resistance to *Bacillus thuringiensis* in *Plutella xylostella* (L.) (*Lepidoptera: plutellidae*)," T-Y Feng et al. (*eds*), 1:277-295 (1995).
Van Rie et al., "Mechanism of Insect Resistance to the Microbial Insecticide *Bacillus thuringiensis," Science*, 247:72-74 (1990).
Van Rie et al., "Specificity of *Bacillus thuringiensis* δ-Endotoxins," *Eur. J. Biochem.*, 186:239-247 (1989).
Vancanneyt et al., "Construction of an Intron-Containing Marker Gene: Splicing of the Intron in Transgenic Plants and its use in Monitoring Early Events in *Agrobacterium*-Mediated Plant Transformation," *Mol. Gen. Genet.*, 220:245-250 (1990).
Vasil et al., "Plant Regeneration From Protoplasts of Napier Grass (*Pennisetum purpureum* Schum.)," *Pflanzenphysiol. Bd.*, 111:232-239 (1983).
Wendel, "New World Tetraploid Cottons Contain Old World Cytoplasm," *PNAS USA*, 86:4132-4136 (1989).
Whiteley at al., "Cloning the Crystal Protein Gene of *B thuringiensis* in *E. coli," Mol. Clon. Gene Reg. Baci. Acad. Press Inc.*, pp. 131-144 (1992).
Wickens et al., "Cleavage and Polyadenylation of SV40 Late pre-mRNAs in Vitro," *RNA Processing Meeting*, pp. 9, May 11-17, 1987.
Wiebauer et al., "Nuclear pre-mRNA Processing in Plants: Distinct Modes of 3'-Splice-Site Selection in Plants and Animals," *Mol. Cell Biol.*, 8:2042-2051 (1988).
Wigley et al., "Conservation of *Bacillus thuringiensis* Efficacy in New Zealand through the Planned Deployment of *Bt* Genes in Transgenic Crops," *Biocontrol Sci. & Technol.*, 4:527-534 (1994).
Williams et al., "Design, Synthesis and Expression of a Human Interleukin-2 Gene Incorporating the Codon Usage Bias Found in Highly expressed *Escherichia coli* Genes," *Nuc. A.R.*, 16(22):10453-10467 (1988).
Winnacker et al., "From Genes to Clones," pp. 404-411 (1987).
Wong at al., "Cloning and Nucleotide Sequence of the Gene Coding for a 135-KDAL Protein of *Bacillus thuringiensis Aizawai," XXI Ann. Meeting Soc. Inv. Pathol., USCD*, pp. 27(13), Aug. 14-18, 1988.
Wong at al., "Differential Accumulation of Proteinase Inhibitor I in Normal and Crown Gall Tissues of Tobacco, Tomato, and Potato," *Plant Physiol.*, 57:214-217 (1976).
Wong et al., "Transcriptional and Translational Start Sites for the *Bacillus thuringiensis* Crystal Protein Gene," *J. Bio. Chem.*, 258:1960-1967 (1983).
Yamada at al., "Plant Regeneration from Protoplast-Derived Callus of Rice (*Oryza sativa* L.)," *Plant Cell Reports*, 5:85-88 (1986).
Zambryski et al., "Ti Plasmid Vector for the Introduction of DNA into Plant Cells Without Alteration of Their Normal Regeneration Capacity," *EMBO J.*, 2(2):2143-2150 (1983).
Zambryski et al., "Tumor Induction by *Agrobacterium tumefaciens*: Analysis of the Boundaries of T-DNA," *J. Mol. Appl. Genet.*, 1:361-370 (1982).
Zeigler, "Lehrbuch der Botanik," *Strasburger, 32nd Ed.*, pp. 286 (1983).
File history for U.S. Appl. No. 07/315,355, United States and Trademark Patent Office, filed Feb. 24, 1989 (part 1).
File history for U.S. Appl. No. 07/315,355, United States and Trademark Patent Office, filed Feb. 24, 1989 (part 2).
File history for U.S. Appl. No. 07/476,661, United States Patent and Trademark Office, filed Dec. 12, 1990.
File history for U.S. Appl. No. 07/959,506, United States Patent and Trademark Office, filed Oct. 19, 1992.
Office Action, U.S. Appl. No. 10/102,469, United States Patent and Trademark Office, mailed Jun. 19, 2007.
Response to Office Action (Jun. 19, 2007) and Amendment, U.S. Appl. No. 10/102,469, filed Nov. 19, 2007.

* cited by examiner

*POLYADENYLATION SIGNAL SEQUENCES

```
   1  ATGGCTATAGAAACTGGTTACACCCCAATCGATATTTCCT   40

  41  TGTCGCTAACGCAATTTCTTTTGAGTGAATTTGTTCCCGG   80

  81  TGCTGGATTTGTGTTAGGACTAGTTGATATAATATGGGGA   120
                                    T  C
 121  ATTTTTGGTCCCTCTCAATGGGACGCATTTCTTGTACAAA   160

 161  TTGAACAGTTAATTAACCAAAGAATAGAAGAATTCGCTAG   200
              C C  C     G     C     G
 201  GAACCAAGCCATTTCTAGATTAGAAGGACTAAGCAATCTT   240
         T
 241  TATCAAATTTACGCAGAATCTTTTAGAGAGTGGGAAGCAG   280

 281  ATCCTACTAATCCAGCATTAAGAGAAGAGATGCGTATTCA   320

 321  ATTCAATGACATGAACAGTGCCCTTACAACCGCTATTCCT   360

 361  CTTTTTGCAGTTCAAAATTATCAAGTTCCTCTTTTATCAG   400
                                      CC C  C
 401  TATATGTTCAAGCTGCAAATTTACATTTATCAGTTTTGAG   440
       G  C           C  CC C  CC C
 441  AGATGTTTCAGTGTTTGGACAAAGGTGGGGATTTGATGCC   480

 481  GCGACTATCAATAGTCGTTATAATGATTTAACTAGGCTTA   520

 521  TTGGCAACTATACAGATCATGCTGTACGCTGGTACAATAC   560

 561  GGGATTAGAGCGTGTATGGGGACCGGATTCTAGAGATTGG   600

 601  ATAAGATATAATCAATTTAGAAGAGAATTAACACTAACTG   640
        C  G  C  C  G  C        GC T
 641  TATTAGATATCGTTTCTCTATTTCCGAACTATGATAGTAG   680

 681  AACGTATCCAATTCGAACAGTTTCCCAATTAACAAGAGAA   720
```

FIG. 2A

```
 721  ATTTATACAAACCCAGTATTAGAAAATTTTGATGGTAGTT   760

 761  TTCGAGGCTCGGCTCAGGGCATAGAAGGAAGTATTAGGAG   800

 801  TCCACATTTGATGGATATACTTAATAGTATAACCATCTAT   840

 841  ACGGATGCTCATAGAGGAGAATATTATTGGTCAGGGCATC   880
                             C  C     C  T  C
 881  AAATAATGGCTTCTCCTGTAGGGTTTTCGGGGCCAGAATT   920
       G  C
 921  CACTTTTCCGCTATATGGAACTATGGGAAATGCAGCTCCA   960

 961  CAACAACGTATTGTTGCTCAACTAGGTCAGGGCGTGTATA  1000

1001  GAACATTATCGTCCACCTTATATAGAAGACCTTTTAATAT  1040
                                           C
1041  AGGGATAAATAATCAACAACTATCTGTTCTTGACGGGACA  1080
      C     C  C  C
1081  GAATTTGCTTATGGAACCTCCTCAAATTTGCCATCCGCTG  1120

1121  TATACAGAAAAAGCGGAACGGTAGATTCGCTGGATGAAAT  1160

1161  ACCGCCACAGAATAACAACGTGCCACCTAGGCAAGGATTT  1200

1201  AGTCATCGATTAAGCCATGTTTCAATGTTTCGTTCAGGCT  1240

1241  TTAGTAATAGTAGTGTAAGTATAATAAGAGCTCCTATGTT  1280

1281  CTCTTGGATACATCGTAGTGCTGAATTTAATAATATAATT  1320
                              G  C  C  C  C  C
1321  CCTTCATCACAAATTACACAAATACCTTTAACAAAATCTA  1360
                    C  C     C  AC C  C  G
1361  CTAATCTTGGCTCTGGAACTTCTGTCGTTAAAGGACCAGG  1400
```

FIG. 2B

```
1401  ATTTACAGGAGGAGATATTCTTCGAAGAACTTCACCTGGC  1440

1441  CAGATTTCAACCTTAAGAGTAAATATTACTGCACCATTAT  1480

1481  CACAAAGATATCGGGTAAGAATTCGCTACGCTTCTACCAC  1520

1521  AAATTTACAATTCCATACATCAATTGACGGAAGACCTATT  1560
         CC T  G     C
1561  AATCAGGGGAATTTTTCAGCAACTATGAGTAGTGGGAGTA  1600

1601  ATTTACAGTCCGGAAGCTTTAGGACTGTAGGTTTTACTAC  1640

1641  TCCGTTTAACTTTTCAAATGGATCAAGTGTATTTACGTTA  1680

1681  AGTGCTCATGTCTTCAATTCAGGCAATGAAGTTTATATAG  1720

1721  ATCGAATTGAATTTGTTCCGGCA  1743
```

FIG. 2C

```
  1   ATGGATAACAATCCGAACATCAATGAATGCATTCCTTATA   40
           C     C  A        C           A  C
 41   ATTGTTTAAGTAACCCTGAAGTAGAAGTATTAGGTGGAGA   80
       C  C  G        A     T      C T
 81   AAGAATAGAAACTGGTTACACCCCAATCGATATTTCCTTG  120
       C C  T     C        T  C     C  C
121   TCGCTAACGCAATTTCTTTTGAGTGAATTTGTTCCCGGTG  160
        CT G  A  G     GC C  C  G  C  G  A
161   CTGGATTTGTGTTAGGACTAGTTGATATAATATGGGGAAT  200
          G  C  TC C           C  C  C     T
201   TTTTGGTCCCTCTCAATGGGACGCATTTCTTGTACAAATT  240
      C        A           T     C  G  G
241   GAACAGTTAATTAACCAAAGAATAGAAGAATTCGCTAGGA  280
        G     G  C     G  G  C     G     C
281   ACCAAGCCATTTCTAGATTAGAAGGACTAAGCAATCTTTA  320
          G     C     G  G      T G        C
321   TCAAATTTACGCAGAATCTTTTAGAGAGTGGGAAGCAGAT  360
      C     C  T     GAGC  C              C
361   CCTACTAATCCAGCATTAAGAGAAGAGATGCGTATTCAAT  400
              C     TC CC C  G  A
401   TCAATGACATGAACAGTGCCCTTACAACCGCTATTCCTCT  440
          C           C   T G  C  A     C  AT
441   TTTTGCAGTTCAAAATTATCAAGTTCCTCTTTTATCAGTA  480
      G  C     C  G  C  C           C  G  C  G
481   TATGTTCAAGCTGCAAATTTACATTTATCAGTTTTGAGAG  520
        C        A  T   C T  CC CAGC  GC TC
521   ATGTTTCAGTGTTTGGACAAAGGTGGGGATTTGATGCCGC  560
       C   AGC        G              C     T
561   GACTATCAATAGTCGTTATAATGATTTAACTAGGCTTATT  600
      A  C        C     C  C  CC T        G
601   GGCAACTATACAGATcATGCTGTaCGCTGGTACAATACGG  640
        A     C  C  CC C     T  T        C  T
641   GATTAGAGCGTGTATGGGGACCGGATTCTAGAGATTGGAT  680
       C  G        C     T  T
```

FIG. 3A

```
               .         .         .         .
 681  AAGATATAATCAATTTAGAAGAGAATTAACACTAACTGTA   720
      T     C  C  G  C  G        G  C  C  A  T

               .         .         .         .
 721  TTAGATATCGTTTCTCTATTTCCGAACTATGATAGTAGAA   760
        G  C  T  G     C  C           CTCC

               .         .         .         .
 761  CGTATCCAATTCGAACAGTTTCCCAATTAACAAGAGAAAT   800
       C  C  T  C  T     G      C T  C

               .         .         .         .
 801  TTATACAAACCCAGTATTAGAAAATTTTGATGGTAGTTTT   840
      C     T        TC T  G  C  C  C     C  C

               .         .         .         .
 841  CGAGGCTCGGCTCAGGGCATAGAAGGAAGTATTAGGAGTC   880
        T  T  T  C  A  T  C     CTCC  C     C

               .         .         .         .
 881  CACATTTGATGGATATACTTAATAGTATAACCATCTATAC   920
          C        C   CTG  C  C     T     C

               .         .         .         .
 921  GGATGCTCATAGAGGAGAATATTATTGGTCAGGGCATCAA   960
      C        C        G     C     T  A  C  G

               .         .         .         .
 961  ATAATGGCTTCTCCTGTAGGGTTTTCGGGGCCAGAATTCA   1000
        C     C     A  T  A  CAGC     C  G  T

               .         .         .         .
1001  CTTTTCCGCTATATGGAACTATGGGAAATGCAGCTCCACA   1040
       C     T  C                 C  C

               .         .         .         .
1041  ACAACGTATTGTTGCTCAACTAGGTCAGGGCGTGTATAGA   1080
               C                    T  C  C

               .         .         .         .
1081  ACATTATCGTCCACCTTATATAGAAGACCTTTTAATATAG   1120
        C  G  T        G  C        C  C     C

               .         .         .         .
1121  GGATAAATAATCAACAACTATCTGTTCTTGACGGGACAGA   1160
       T  C  C  C  G     T  C           A

               .         .         .         .
1161  ATTTGCTTATGGAACCTCCTCAAATTTGCCATCCGCTGTA   1200
      G  C  C           T  T  C              T

               .         .         .         .
1201  TACAGAAAAAGCGGAACGGTAGATTCGCTGGATGAAATAC   1240
              G        C  T     CT    C     C

               .         .         .         .
1241  CGCCACAGAATAACAACGTGCCACCTAGGCAAGGATTTAG   1280
       A        C     T        C           CTC

               .         .         .         .
1281  TCATCGATTAAGCCATGTTTCAATGTTTCGTTCAGGCTTT   1320
      C  CA G  G     C  G  C     C     C  A  C

               .         .         .         .
1321  AGTAATAGTAGTGTAAGTATAATAAGAGCTCCTATGTTCT   1360
        C  C   TCC  G  C  C  C

               .         .         .         .
1361  CTTGGATACATCGTAGTGCTGAATTTAATAATATAATTCC   1400
       A     T              G  C  C     C
```

FIG. 3B

```
                .         .         .         .
1401   TTCATCACAAATTACACAAATACCTTTAACAAAATCTACT   1440
          C  T     C  C     C  A  G  C  G
                .         .         .         .
1441   AATCTTGGCTCTGGAACTTCTGTCGTTAAAGGACCAGGAT   1480
         C     A                 G           C
                .         .         .         .
1481   TTACAGGAGGAGATATTCTTCGAAGAACTTCACCTGGCCA   1520
        C        T         A          T
                .         .         .         .
1521   GATTTCAACCTTAAGAGTAAATATTACTGCACCATTATCA   1560
           AGC   C C     T  C  C         C T  T
                .         .         .         .
1561   CAAAGATATCGGGTAAGAATTCGCTACGCTTCTACCACAA   1600
                  T  C  G     T     A        A
                .         .         .         .
1601   ATTTACAATTCCATACATCAATTGACGGAAGACCTATTAA   1640
        C  G        C  C  C  C        G     C
                .         .         .         .
1641   TCAGGGGAATTTTTCAGCAACTATGAGTAGTGGGAGTAAT   1680
             T  C  C  C     C   TCA  C  C  C  C
                .         .         .         .
1681   TTACAGTCCGGAAGCTTTAGGACTGTAGGTTTTACTACTC   1720
        G   A     C     C  A  C  C     C
                .         .         .         .
1721   CGTTTAACTTTTCAAATGGATCAAGTGTATTTACGTTAAG   1760
        T  C     C  T  C        C  T  C  CC T
                .         .         .         .
1761   TGCTCATGTCTTCAATTCAGGCAATGAAGTTTATATAGAT   1800
       C        G        T           G  C  T  C
                .         .         .         .
1801   CGAATTGAATTTGTTCCGGCAGAAGTAACCTTTGAGGCAG   1840
         T     G     G  T  C     T     C     T

1841   AATAT   1845
        G  C
```

FIG. 3C

```
              .         .         .         .
  1  ATGGATAACAATCCGAACATCAATGAATGCATTCCTTATA  40
          C     C  A        C           A  C

              .         .         .         .
 41  ATTGTTTAAGTAACCCTGAAGTAGAAGTATTAGGTGGAGA  80
      C  C  G        A     T      C T

              .         .         .         .
 81  AAGAATAGAAACTGGTTACACCCCAATCGATATTTCCTTG  120
      C C  T     C        T  C     C  C

              .         .         .         .
121  TCGCTAACGCAATTTCTTTTGAGTGAATTTGTTCCCGGTG  160
       CT G  A  G     GC C  C  G  C  G  A

              .         .         .         .
161  CTGGATTTGTGTTAGGACTAGTTGATATAATATGGGGAAT  200
         G  C  TC C           C  C  C     T

              .         .         .         .
201  TTTTGGTCCCTCTCAATGGGACGCATTTCTTGTACAAATT  240
     C        A           T     C  G  G

              .         .         .         .
241  GAACAGTTAATTAACCAAAGAATAGAAGAATTCGCTAGGA  280
       G     G  C     G  G  C     G     C

              .         .         .         .
281  ACCAAGCCATTTCTAGATTAGAAGGACTAAGCAATCTTTA  320
         G     C     G  G      T G        C

              .         .         .         .
321  TCAAATTTACGCAGAATCTTTTAGAGAGTGGGAAGCAGAT  360
     C     C  T     GAGC  C              C

              .         .         .         .
361  CCTACTAATCCAGCATTAAGAGAAGAGATGCGTATTCAAT  400
             C     TC CC C  G  A

              .         .         .         .
401  TCAATGACATGAACAGTGCCCTTACAACCGCTATTCCTCT  440
         C           C   T G  C  A     C  AT

              .         .         .         .
441  TTTTGCAGTTCAAAATTATCAAGTTCCTCTTTTATCAGTA  480
     G  C     C  G  C  C           C  G  C  G

              .         .         .         .
481  TATGTTCAAGCTGCAAATTTACATTTATCAGTTTTGAGAG  520
       C        A  T   C T  CC CAGC  GC TC

              .         .         .         .
521  ATGTTTCAGTGTTTGGACAAAGGTGGGGATTTGATGCCGC  560
      C   AGC        G              C     T

              .         .         .         .
561  GACTATCAATAGTCGTTATAATGATTTAACTAGGCTTATT  600
     A  C        C     C  C CC  T        G

              .         .         .         .
601  GGCAACTATACAGATTATGCTGTACGCTGGTACAATACGG  640
       A     C  C  CC C     T  T        C  T

              .         .         .         .
641  GATTAGAACGTGTATGGGGACCGGATTCTAGAGATTGGGT  680
      C  G  G     C     T  T               A
```

FIG. 4A

```
681   AAGGTATAATCAATTTAGAAGAGAATTAACACTAACTGTA   720
      T  A  C  C  G  C  G        G  C  C  A  T

721   TTAGATATCGTTGCTCTGTTCCCGAATTATGATAGTAGAA   760
        G  C  T  GT    C        C     CTCC

761   GATATCCAATTCGAACAGTTTCCCAATTAACAAGAGAAAT   800
      CC  C  T  C  T     G      C T  C

801   TTATACAAACCCAGTATTAGAAAATTTGATGGTAGTTTT   840
      C     T        TC T  G  C  C  C     C  C

841   CGAGGCTCGGCTCAGGGCATAGAAAGAAGTATTAGGAGTC   880
        T  T  T  C  A  T  C   G CTCC  C     C

881   CACATTTGATGGATATACTTAACAGTATAACCATCTATAC   920
          C        C   CT G    C     T     C

921   GGATGCTCATAGGGGTTATTATTATTGGTCAGGGCATCAA   960
      C        C  A  AG G     C     T  A  C  G

961   ATAATGGCTTCTCCTGTAGGGTTTTCGGGGCCAGAATTCA   1000
        C     C     A  T  A  CAGC     C  G  T

1001  CTTTTCCGCTATATGGAACTATGGGAAATGCAGCTCCACA   1040
       C     T  C                 C  C

1041  ACAACGTATTGTTGCTCAACTAGGTCAGGGCGTGTATAGA   1080
               C                    T  C  C

1081  ACATTATCGTCCACTTTATATAGAAGACCTTTTAATATAG   1120
        C  G  T     C  G  C        C  C     C

1121  GGATAAATAATCAACAACTATCTGTTCTTGACGGGACAGA   1160
       T  C  C  C  G     T  C           A

1161  ATTTGCTTATGGAACCTCCTCAAATTTGCCATCCGCTGTA   1200
      G  C  C           T  T  C              T

1201  TACAGAAAAAGCGGAACGGTAGATTCGCTGGATGAAATAC   1240
              G        C  T     CT    C     C

1241  CGCCACAGAATAACAACGTGCCACCTAGGCAAGGATTTAG   1280
       A        C     T        C           CTC

1281  TCATCGATTAAGCCATGTTTCAATGTTTCGTTCAGGCTTT   1320
      C  CA G  G     C  G  C     C     C  A  C

1321  AGTAATAGTAGTGTAAGTATAATAAGAGCTCCTATGTTCT   1360
        C  C   TCC  G  C  C  C

1361  CTTGGATACATCGTAGTGCTGAATTTAATAATATAATTGC   1400
                C           G  C  C  C  C  C
```

FIG. 4B

```
1401  ATCGGATAGTATTACTCAAATCCCTGCAGTGAAGGGAAAC  1440
         C
1441  TTTCTTTTTAATGGTTCTGTAATTTCAGGACCAGGATTTA  1480
           C  C  C        C                  C
1481  CTGGTGGGGACTTAGTTAGATTAAATAGTAGTGGAAATAA  1520
             A   C C      C C  C  C
1521  CATTCAGAATAGAGGGTATATTGAAGTTCCAATTCACTTC  1560

1561  CCATCGACATCTACCAGATATCGAGTTCGTGTACGGTATG  1600
           C               A          GA
1601  CTTCTGTAACCCCGATTCACCTCAACGTTAATTGGGGTAA  1640
             G     T
1641  TTCATCCATTTTTTCCAATACAGTACCAGCTACAGCTACG  1680
               C  C           T              C
1681  TCATTAGATAATCTACAATCAAGTGATTTTGGTTATTTTG  1720
        C  G        C     C  C     C     C
1721  AAAGTGCCAATGCTTTTACATCTTCATTAGGTAATATAGT  1760
                                C C     C  C
1761  AGGTGTTAGAAATTTTAGTGGACTGCAGGAGTGATAATA  1800
      G           C                       T  C
1801  GACAGATTTGAATTTATTCCAGTTACTGCAACACTCGAGG  1840
              C  G  C
1841  CTGAATATAATCTGGAAAGAGCGCAGAAGGCGGTGAATGC  1880
                                        A TGCG
1881  GCTGTTTACGTCTACAAACCAACTAGGGCTAAAAACAAAT  1920
      CTGT  ACGTCTACA  C AGCT G ACTC  G CA  TG
1921  G  1921
```

FIG. 4C

```
  1 GAAAGAATAGAAACTGGTTACACCCCAATCGATATTTCCT  40
    ATGGCC  T     C        T  C     C  C

 41 TGTCGCTAACGCAATTTCTTTTGAGTGAATTTGTTCCCGG  80
        CT G  A  G     GC C  C  G  C  G  A

 81 TGCTGGATTTGTGTTAGGACTAGTTGATATAATATGGGGA 120
          G  C  TC C           C  C  C     T

121 ATTTTTGGTCCCTCTCAATGGGACGCATTTCTTGTACAAA 160
      C        A           T     C  G  G

161 TTGAACAGTTAATTAACCAAAGAATAGAAGAATTCGCTAG 200
        G     G  C     G  G  C     G     C

201 GAACCAAGCCATTTCTAGATTAGAAGGACTAAGCAATCTT 240
          G     C     G  G      T G        C

241 TATCAAATTTACGCAGAATCTTTTAGAGAGTGGGAAGCAG 280
      C     C  T     GAGC  C              C

281 ATCCTACTAATCCAGCATTAAGAGAAGAGATGCGTATTCA 320
              C     TC CC C  G  A

321 ATTCAATGACATGAACAGTGCCCTTACAACCGCTATTCCT 360
          C           C   T G  C  A     C  A

361 CTTTTTGCAGTTCAAAATTATCAAGTTCCTCTTTTATCAG 400
    T G  C     C  G  C  C           C  G  C

401 TATATGTTCAAGCTGCAAATTTACATTTATCAGTTTTGAG 440
     G  C        A  T   C T  CC CAGC  GC TC

441 AGATGTTTCAGTGTTTGGACAAAGGTGGGGATTTGATGCC 480
       C   AGC        G              C     T

481 GCGACTATCAATAGTCGTTATAATGATTTAACTAGGCTTA 520
      A  C        C     C  C  CC T        G

521 TTGGCAACTATACAGATTATGCTGTACGCTGGTACAATAC 560
        A     C  C  CC C     T  T        C

561 GGGATTAGAACGTGTATGGGGACCGGATTCTAGAGATTGG 600
    T  C  G  G     C     T  T

601 GTAAGGTATAATCAATTTAGAAGAGAATTAACACTAACTG 640
    A T  A  C  C  G  C  G        G  C  C  A

641 TATTAGATATCGTTGCTCTGTTCCCGAATTATGATAGTAG 680
     T  G  C  T  GT    C        C     CTCC
```

FIG.8A

```
 681  AAGATATCCAATTCGAACAGTTTCCCAATTAACAAGAGAA  720
        CC  C  T  C  T     G      C T  C
 721  ATTTATACAAACCCAGTATTAGAAAATTTTGATGGTAGTT  760
        C     T        TC T  G  C  C  C     C
 761  TTCGAGGCTCGGCTCAGGGCATAGAAAGAAGTATTAGGAG  800
       C  T  T  T  C  A  T  C   G CTCC  C
 801  TCCACATTTGATGGATATACTTAACAGTATAACCATCTAT  840
      C     C        C  CT G     C     T     C
 841  ACGGATGCTCATAGGGGTTATTATTATTGGTCAGGGCATC  880
        C        C  A  AG G     C     T  A  C
 881  AAATAATGGCTTCTCCTGTAGGGTTTTCGGGGCCAGAATT  920
       G  C     C     A  T  A  CAGC     C  G
 921  CACTTTTCCGCTATATGGAACTATGGGAAATGCAGCTCCA  960
      T  C     T  C                 C  C
 961  CAACAACGTATTGTTGCTCAACTAGGTCAGGGCGTGTATA  1000
                 C                    T  C  C
1001  GAACATTATCGTCCACTTTATATAGAAGACCTTTTAATAT  1040
          C  G  T     C  G  C        C  C
1041  AGGGATAAATAATCAACAACTATCTGTTCTTGACGGGACA  1080
      C  T  C  C  C  G     T  C           A
1081  GAATTTGCTTATGGAACCTCCTCAAATTTGCCATCCGCTG  1120
        G  C  C           T  T  C
1121  TATACAGAAAAAGCGGAACGGTAGATTCGCTGGATGAAAT  1160
       T        G        C  T     CT    C
1161  ACCGCCACAGAATAACAACGTGCCACCTAGGCAAGGATTT  1200
      C  A        C     T        C           C
1201  AGTCATCGATTAAGCCATGTTTCAATGTTTCGTTCAGGCT  1240
      TCC  CA G  G     C  G  C     C     C  A
1241  TTAGTAATAGTAGTGTAAGTATAATAAGAGCTCCTATGTT  1280
       C  C  C   TCC  G  C  C  C
1281  CTCTTGGATACATCGTAGTGCTGAATTTAATAATATAATT  1320
                  C           G  C  C  C  C  C
1321  GCATCGGATAGTATTACTCAAATCCCTGCAGTGAAGGGAA  1360
           C
1361  ACTTTCTTTTTAATGGTTCTGTAATTTCAGGACCAGGATT  1400
             C  C  C        C
```

FIG. 8B

```
               .         .         .         .
1401  TACTGGTGGGGACTTAGTTAGATTAAATAGTAGTGGAAAT  1440
      C        A   C C      C C  C  C
               .         .         .         .
1441  AACATTCAGAATAGAGGGTATATTGAAGTTCCAATTCACT  1480

               .         .         .         .
1481  TCCCATCGACATCTACCAGATATCGAGTTCGTGTACGGTA  1520
             C               A          GA
               .         .         .         .
1521  TGCTTCTGTAACCCCGATTCACCTCAACGTTAATTGGGGT  1560
               G     T
               .         .         .         .
1561  AATTCATCCATTTTTTCCAATACAGTACCAGCTACAGCTA  1600
                 C  C           T
               .         .         .         .
1601  CGTCATTAGATAATCTACAATCAAGTGATTTTGGTTATTT  1640
       C  C  G        C     C  C     C     C
               .         .         .         .
1641  TGAAAGTGCCAATGCTTTTACATCTTCATTAGGTAATATA  1680
                                  C C     C  C
               .         .         .         .
1681  GTAGGTGTTAGAAATTTTAGTGGACTGCAGGAGTGATAA   1720
        G           C                       T
               .         .         .         .
1721  TAGACAGATTTGAATTTATTCCAGTTACTGCAACACTCGA  1760
       C        C  G  C

1761  GGCTGAA  1767
            G
```

FIG. 8C

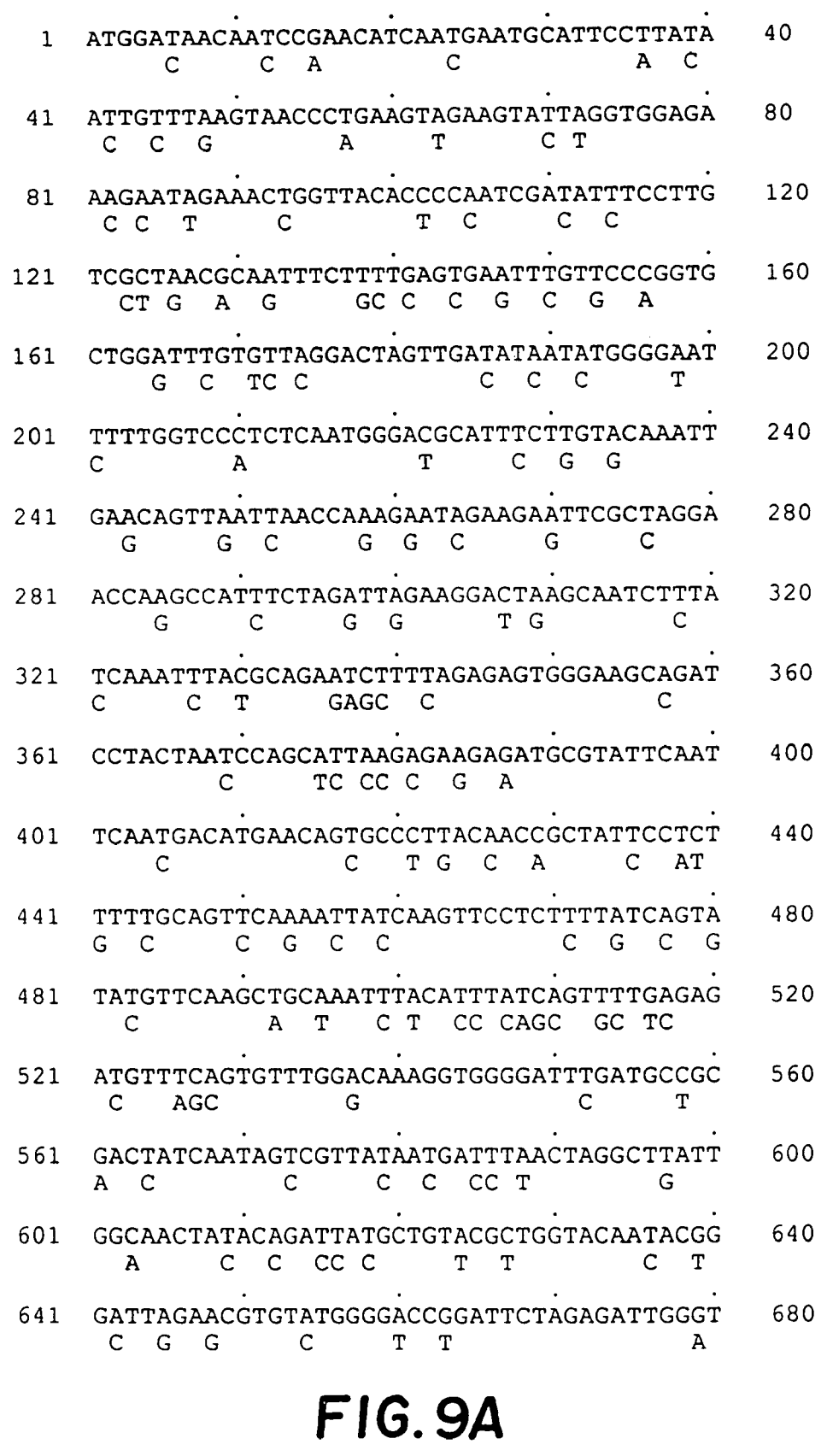

```
   1  ATGGATAACAATCCGAACATCAATGAATGCATTCCTTATA   40
           C     C  A        C           A  C
  41  ATTGTTTAAGTAACCCTGAAGTAGAAGTATTAGGTGGAGA   80
       C  C  G        A     T      C T
  81  AAGAATAGAAACTGGTTACACCCCAATCGATATTTCCTTG  120
       C C  T     C        T  C     C  C
 121  TCGCTAACGCAATTTCTTTTGAGTGAATTTGTTCCCGGTG  160
        CT G  A  G     GC C  C  G  C  G  A
 161  CTGGATTTGTGTTAGGACTAGTTGATATAATATGGGGAAT  200
          G  C  TC C           C  C  C     T
 201  TTTTGGTCCCTCTCAATGGGACGCATTTCTTGTACAAATT  240
      C        A           T     C  G  G
 241  GAACAGTTAATTAACCAAAGAATAGAAGAATTCGCTAGGA  280
        G     G  C     G  G  C     G     C
 281  ACCAAGCCATTTCTAGATTAGAAGGACTAAGCAATCTTTA  320
          G     C     G  G      T G        C
 321  TCAAATTTACGCAGAATCTTTTAGAGAGTGGGAAGCAGAT  360
      C     C  T     GAGC  C              C
 361  CCTACTAATCCAGCATTAAGAGAAGAGATGCGTATTCAAT  400
              C     TC CC C  G  A
 401  TCAATGACATGAACAGTGCCCTTACAACCGCTATTCCTCT  440
          C           C   T G  C  A     C  AT
 441  TTTTGCAGTTCAAAATTATCAAGTTCCTCTTTTATCAGTA  480
      G  C     C  G  C  C           C  G  C  G
 481  TATGTTCAAGCTGCAAATTTACATTTATCAGTTTTGAGAG  520
        C         A  T  C T  CC CAGC  GC TC
 521  ATGTTTCAGTGTTTGGACAAAGGTGGGGATTTGATGCCGC  560
       C   AGC        G              C     T
 561  GACTATCAATAGTCGTTATAATGATTTAACTAGGCTTATT  600
      A  C        C     C  C  CC T        G
 601  GGCAACTATACAGATTATGCTGTACGCTGGTACAATACGG  640
        A     C  C  CC C     T  T        C  T
 641  GATTAGAACGTGTATGGGGACCGGATTCTAGAGATTGGGT  680
       C  G  G     C     T  T               A
```

FIG. 9A

```
               .         .         .         .
681    AAGGTATAATCAATTTAGAAGAGAATTAACACTAACTGTA   720
       T  A  C  C  G  C  G        G  C  C  A  T
               .         .         .         .
721    TTAGATATCGTTGCTCTGTTCCCGAATTATGATAGTAGAA   760
         G  C  T  GT    C        C     CTCC
               .         .         .         .
761    GATATCCAATTCGAACAGTTTCCCAATTAACAAGAGAAAT   800
       CC  C  T  C  T     G      C T  C
               .         .         .         .
801    TTATACAAACCCAGTATTAGAAAATTTTGATGGTAGTTTT   840
       C     T        TC T  G  C  C  C     C  C
               .         .         .         .
841    CGAGGCTCGGCTCAGGGCATAGAAAGAAGTATTAGGAGTC   880
         T  T  T  C  A  T  C   G CTCC  C     C
               .         .         .         .
881    CACATTTGATGGATATACTTAACAGTATAACCATCTATAC   920
           C        C  CT G     C     T     C
               .         .         .         .
921    GGATGCTCATAGGGGTTATTATTATTGGTCAGGGCATCAA   960
       C        C  A  AG G     C     T  A  C  G
               .         .         .         .
961    ATAATGGCTTCTCCTGTAGGGTTTTCGGGGCCAGAATTCA   1000
         C     C     A  T  A  CAGC     C  G  T
               .         .         .         .
1001   CTTTTCCGCTATATGGAACTATGGGAAATGCAGCTCCACA   1040
        C     T  C                 C  C
               .         .         .         .
1041   ACAACGTATTGTTGCTCAACTAGGTCAGGGCGTGTATAGA   1080
                C                    T  C  C
               .         .         .         .
1081   ACATTATCGTCCACTTTATATAGAAGACCTTTTAATATAG   1120
         C  G  T     C  G  C        C  C     C
               .         .         .         .
1121   GGATAAATAATCAACAACTATCTGTTCTTGACGGGACAGA   1160
        T  C  C  C  G     T  C           A
               .         .         .         .
1161   ATTTGCTTATGGAACCTCCTCAAATTTGCCATCCGCTGTA   1200
       G  C  C           T  T  C              T
               .         .         .         .
1201   TACAGAAAAAGCGGAACGGTAGATTCGCTGGATGAAATAC   1240
               G        C  T     CT   C     C
               .         .         .         .
1241   CGCCACAGAATAACAACGTGCCACCTAGGCAAGGATTTAG   1280
        A        C     T        C           CTC
               .         .         .         .
1281   TCATCGATTAAGCCATGTTTCAATGTTTCGTTCAGGCTTT   1320
       C  CA G  G     C  G  C     C     C  A  C
               .         .         .         .
1321   AGTAATAGTAGTGTAAGTATAATAAGAGCTCCTATGTTCT   1360
         C  C   TCC  G  C  C  C
               .         .         .         .
1361   CTTGGATACATCGTAGTGCTGAATTTAATAATATAATTGC   1400
                 C           G  C  C  C  C  C
```

FIG. 9B

```
1401 ATCGGATAGTATTACTCAAATCCCTGCAGTGAAGGGAAAC 1440
        C
1441 TTTCTTTTAATGGTTCTGTAATTTCAGGACCAGGATTTA 1480
          C  C  C        C                 C
1481 CTGGTGGGGACTTAGTTAGATTAAATAGTAGTGGAAATAA 1520
            A   C C      C C  C  C
1521 CATTCAGAATAGAGGGTATATTGAAGTTCCAATTCACTTC 1560

1561 CCATCGACATCTACCAGATATCGAGTTCGTGTACGGTATG 1600
          C               A          GA
1601 CTTCTGTAACCCCGATTCACCTCAACGTTAATTGGGGTAA 1640
            G     T
1641 TTCATCCATTTTTTCCAATACAGTACCAGCTACAGCTACG 1680
              C  C           T              C
1681 TCATTAGATAATCTACAATCAAGTGATTTTGGTTATTTTG 1720
       C  G        C     C  C     C     C
1721 AAAGTGCCAATGCTTTTACATCTTCATTAGGTAATATAGT 1760
                               C C     C  C
1761 AGGTGTTAGAAATTTTAGTGGGACTGCAGGAGTGATAATA 1800
     G           C                       T  C
1801 GACAGATTTGAATTTATTCCAGTTACTGCAACACTCGAGG 1840
             C  G  C
1841 CTGAATATAATCTGGAAAGAGCGCAGAAGGCGGTGAATGC 1880

1881 GCTGTTTACGTCTACAAACCAACTAGGGCTAAAAACAAAT 1920

1921 GTAACGGATTATCATATTGATCAAGTGTCCAATTTAGTTA 1960

1961 CGTATTTATCGGATGAATTTTGTCTGGATGAAAAGCGAGA 2000

2001 ATTGTCCGAGAAAGTCAAACATGCGAAGCGACTCAGTGAT 2040

2041 GAACGCAATTTACTCCAAGATTCAAATTTCAAAGACATTA 2080

2081 ATAGGCAACCAGAACGTGGGTGGGGCGGAAGTACAGGGAT 2120
```

FIG. 9C

2121 TACCATCCAAGGAGGGGATGACGTATTTAAAGAAAATTAC 2160

2161 GTCACACTATCAGGTACCTTTGATGAGTGCTATCCAACAT 2200

2201 ATTTGTATCAAAAAATCGATGAATCAAAATTAAAAGCCTT 2240

2241 TACCCGTTATCAATTAAGAGGGTATATCGAAGATAGTCAA 2280

2281 GACTTAGAAATCTATTTAATTCGCTACAATGCAAAACATG 2320

2321 AAACAGTAAATGTGCCAGGTACGGGTTCCTTATGGCCGCT 2360

2361 TTCAGCCCAAAGTCCAATCGGAAAGTGTGGAGAGCCGAAT 2400

2401 CGATGCGCGCCACACCTTGAATGGAATCCTGACTTAGATT 2440

2441 GTTCGTGTAGGGATGGAGAAAAGTGTGCCCATCATTCGCA 2480

2481 TCATTTCTCCTTAGACATTGATGTAGGATGTACAGACTTA 2520

2521 AATGAGGACCTAGGTGTATGGGTGATCTTTAAGATTAAGA 2560

2561 CGCAAGATGGGCACGCAAGACTAGGGAATCTAGAGTTTCT 2600

2601 CGAAGAGAAACCATTAGTAGGAGAAGCGCTAGCTCGTGTG 2640

2641 AAAAGAGCGGAGAAAAAATGGAGAGACAAACGTGAAAAAT 2680

2681 TGGAATGGGAAACAAATATCGTTTATAAAGAGGCAAAAGA 2720

2721 ATCTGTAGATGCTTTATTTGTAAACTCTCAATATGATCAA 2760

2761 TTACAAGCGGATACGAATATTGCCATGATTCATGCGGCAG 2800

2801 ATAAACGTGTTCATAGCATTCGAGAAGCTTATCTGCCTGA 2840

FIG. 9D

2841 GCTGTCTGTGATTCCGGGTGTCAATGCGGCTATTTTTGAA 2880

2881 GAATTAGAAGGGCGTATTTTCACTGCATTCTCCCTATATG 2920

2921 ATGCGAGAAATGTCATTAAAAATGGTGATTTTAATAATGG 2960

2961 CTTATCCTGCTGGAACGTGAAAGGGCATGTAGATGTAGAA 3000

3001 GAACAAAACAACCAACGTTCGGTCCTTGTTGTTCCGGAAT 3040

3041 GGGAAGCAGAAGTGTCACAAGAAGTTCGTGTCTGTCCGGG 3080

3081 TCGTGGCTATATCCTTCGTGTCACAGCGTACAAGGAGGGA 3120

3121 TATGGAGAAGGTTGCGTAACCATTCATGAGATCGAGAACA 3160

3161 ATACAGACGAACTGAAGTTTAGCAACTGCGTAGAAGAGGA 3200

3201 AATCTATCCAAATAACACGGTAACGTGTAATGATTATACT 3240

3241 GTAAATCAAGAAGAATACGGAGGTGCGTACACTTCTCGTA 3280

3281 ATCGAGGATATAACGAAGCTCCTTCCGTACCAGCTGATTA 3320

3321 TGCGTCAGTCTATGAAGAAAAATCGTATACAGATGGACGA 3360

3361 AGAGAGAATCCTTGTGAATTTAACAGAGGGTATAGGGATT 3400

3401 ACACGCCACTACCAGTTGGTTATGTGACAAAAGAATTAGA 3440

3441 ATACTTCCCAGAAACCGATAAGGTATGGATTGAGATTGGA 3480

3481 GAAACGGAAGGAACATTTATCGTGGACAGCGTGGAATTAC 3520

3521 TCCTTATGGAGGAA 3534

FIG. 9E

```
   1  ATGGATAACAATCCGAACATCAATGAATGCATTCCTTATA   40
           C     C  A        C           A  C
  41  ATTGTTTAAGTAACCCTGAAGTAGAAGTATTAGGTGGAGA   80
       C  C  G        A     T      C T
  81  AAGAATAGAAACTGGTTACACCCCAATCGATATTTCCTTG  120
       C C  T     C        T  C     C  C
 121  TCGCTAACGCAATTTCTTTTGAGTGAATTTGTTCCCGGTG  160
        CT G  A  G     GC C  C  G  C  G  A
 161  CTGGATTTGTGTTAGGACTAGTTGATATAATATGGGGAAT  200
          G  C  TC C           C  C  C     T
 201  TTTTGGTCCCTCTCAATGGGACGCATTTCTTGTACAAATT  240
      C        A           T     C  G  G
 241  GAACAGTTAATTAACCAAAGAATAGAAGAATTCGCTAGGA  280
        G     G  C     G  G  C     G     C
 281  ACCAAGCCATTTCTAGATTAGAAGGACTAAGCAATCTTTA  320
          G     C     G  G      T G        C
 321  TCAAATTTACGCAGAATCTTTAGAGAGTGGGAAGCAGAT   360
      C     C  T     GAGC  C              C
 361  CCTACTAATCCAGCATTAAGAGAAGAGATGCGTATTCAAT  400
              C     TC CC C  G  A
 401  TCAATGACATGAACAGTGCCCTTACAACCGCTATTCCTCT  440
          C           C   T G  C  A     C  AT
 441  TTTTGCAGTTCAAAATTATCAAGTTCCTCTTTTATCAGTA  480
      G  C     C  G  C  C           C  G  C  G
 481  TATGTTCAAGCTGCAAATTTACATTTATCAGTTTTGAGAG  520
        C        A  T   C T  CC CAGC  GC TC
 521  ATGTTTCAGTGTTTGGACAAAGGTGGGGATTTGATGCCGC  560
       C   AGC        G              C     T
 561  GACTATCAATAGTCGTTATAATGATTTAACTAGGCTTATT  600
      A  C        C     C  C  CC T        G
 601  GGCAACTATACAGATTATGCTGTACGCTGGTACAATACGG  640
        A     C  C  CC C     T  T        C  T
```

FIG. 10A

```
641   GATTAGAACGTGTATGGGGACCGGATTCTAGAGATTGGGT   680
       C  G  G     C     T  T               A

681   AAGGTATAATCAATTTAGAAGAGAATTAACACTAACTGTA   720
      T  A  C  C  G  C  G        G  C  C  A  T

721   TTAGATATCGTTGCTCTGTTCCCGAATTATGATAGTAGAA   760
        G  C  T  GT    C        C     CTCC

761   GATATCCAATTCGAACAGTTTCCCAATTAACAAGAGAAAT   800
      CC  C  T  C  T     G        C T  C

801   TTATACAAACCCAGTATTAGAAAATTTTGATGGTAGTTTT   840
      C     T        TC T  G  C  C  C     C  C

841   CGAGGCTCGGCTCAGGGCATAGAAAGAAGTATTAGGAGTC   880
        T  T  T  C  A  T  C   G CTCC  C     C

881   CACATTTGATGGATATACTTAACAGTATAACCATCTATAC   920
         C        C  CT G     C     T     C

921   GGATGCTCATAGGGGTTATTATTATTGGTCAGGGCATCAA   960
      C        C  A  AG G     C     T  A  C  G

961   ATAATGGCTTCTCCTGTAGGGTTTTCGGGGCCAGAATTCA   1000
        C     C     A  T  A  CAGC     C  G  T

1001  CTTTTCCGCTATATGGAACTATGGGAAATGCAGCTCCACA   1040
        C     T  C                 C  C

1041  ACAACGTATTGTTGCTCAACTAGGTCAGGGCGTGTATAGA   1080
               C                   T  C  C

1081  ACATTATCGTCCACTTTATATAGAAGACCTTTTAATATAG   1120
        C  G  T     C  G  C        C  C     C

1121  GGATAAATAATCAACAACTATCTGTTCTTGACGGGACAGA   1160
        T  C  C  C  G     T  C           A

1161  ATTTGCTTATGGAACCTCCTCAAATTTGCCATCCGCTGTA   1200
      G  C  C           T  T  C              T

1201  TACAGAAAAAGCGGAACGGTAGATTCGCTGGATGAAATAC   1240
               G        C  T     CT    C     C

1241  CGCCACAGAATAACAACGTGCCACCTAGGCAAGGATTTAG   1280
        A        C     T        C           CTC

1281  TCATCGATTAAGCCATGTTTCAATGTTTCGTTCAGGCTTT   1320
      C  CA G  G     C  G  C     C     C  A  C

1321  AGTAATAGTAGTGTAAGTATAATAAGAGCTCCTATGTTCT   1360
        C  C   TCC  G  C  C  C
```

FIG. 10B

```
1361  CTTGGATACATCGTAGTGCTGAATTTAATAATATAATTGC  1400
                C           G  C  C  C  C  C

1401  ATCGGATAGTATTACTCAAATCCCTGCAGTGAAGGGAAAC  1440
         C

1441  TTTCTTTTTAATGGTTCTGTAATTTCAGGACCAGGATTTA  1480
           C  C  C        C                 C

1481  CTGGTGGGGACTTAGTTAGATTAAATAGTAGTGGAAATAA  1520
             A   C C      C C  C  C

1521  CATTCAGAATAGAGGGTATATTGAAGTTCCAATTCACTTC  1560

1561  CCATCGACATCTACCAGATATCGAGTTCGTGTACGGTATG  1600
           C               A          GA

1601  CTTCTGTAACCCCGATTCACCTCAACGTTAATTGGGGTAA  1640
             G     T

1641  TTCATCCATTTTTTCCAATACAGTACCAGCTACAGCTACG  1680
               C  C           T              C

1681  TCATTAGATAATCTACAATCAAGTGATTTTGGTTATTTTG  1720
        C  G        C     C  C     C     C

1721  AAAGTGCCAATGCTTTTACATCTTCATTAGGTAATATAGT  1760
                                C C     C  C

1761  AGGTGTTAGAAATTTTAGTGGGACTGCAGGAGTGATAATA  1800
      G           C                       T  C

1801  GACAGATTTGAATTTATTCCAGTTACTGCAACACTCGAGG  1840
              C  G  C

1841  CTGAATATAATCTGGAAAGAGCGCAGAAGGCGGTGAATGC  1880

1881  GCTGTTTACGTCTACAAACCAACTAGGGCTAAAAACAAAT  1920
                           G  C  C  C  G  C

1921  GTAACGGATTATCATATTGATCAAGTGTCCAATTTAGTTA  1960
        G                             C  G  C

1961  CGTATTTATCGGATGAATTTTGTCTGGATGAAAAGCGAGA  2000
       C  CC CAGC     G  C

2001  ATTGTCCGAGAAAGTCAAACATGCGAAGCGACTCAGTGAT  2040

2041  GAACGCAATTTACTCCAAGATTCAAATTTCAAAGACATTA  2080
```

FIG. 10C

2081 ATAGGCAACCAGAACGTGGGTGGGGCGGAAGTACAGGGAT 2120

2121 TACCATCCAAGGAGGGATGACGTATTTAAAGAAAATTAC 2160
              G     T  C     G  C  G  G  C

2161 GTCACACTATCAGGTACCTTTGATGAGTGCTATCCAACAT 2200

2201 ATTTGTATCAAAAAATCGATGAATCAAAATTAAAAGCCTT 2240
      CC C  C  G  G     C  G  C  G  G

2241 TACCCGTTATCAATTAAGAGGGTATATCGAAGATAGTCAA 2280

2281 GACTTAGAAATCTATTTAATTCGCTACAATGCAAAACATG 2320
        C C  G     CC C  C

2321 AAACAGTAAATGTGCCAGGTACGGGTTCCTTATGGCCGCT 2360

2361 TTCAGCCCAAAGTCCAATCGGAAAGTGTGGAGAGCCGAAT 2400

2401 CGATGCGCGCCACACCTTGAATGGAATCCTGACTTAGATT 2440

2441 GTTCGTGTAGGGATGGAGAAAAGTGTGCCCATCATTCGCA 2480

2481 TCATTTCTCCTTAGACATTGATGTAGGATGTACAGACTTA 2520

2521 AATGAGGACCTAGGTGTATGGGTGATCTTTAAGATTAAGA 2560

2561 CGCAAGATGGGCACGCAAGACTAGGGAATCTAGAGTTTCT 2600

2601 CGAAGAGAAACCATTAGTAGGAGAAGCGCTAGCTCGTGTG 2640

2641 AAAAGAGCGGAGAAAAAATGGAGAGACAAACGTGAAAAAT 2680
                                        G  G

2681 TGGAATGGGAAACAAATATCGTTTATAAAGAGGCAAAAGA 2720
               G  C  C     C  C

2721 ATCTGTAGATGCTTTATTTGTAAACTCTCAATATGATCAA 2760

2761 TTACAAGCGGATACGAATATTGCCATGATTCATGCGGCAG 2800

FIG. 10D

```
2801  ATAAACGTGTTCATAGCATTCGAGAAGCTTATCTGCCTGA  2840

2841  GCTGTCTGTGATTCCGGGTGTCAATGCGGCTATTTTTGAA  2880

2881  GAATTAGAAGGGCGTATTTTCACTGCATTCTCCCTATATG  2920
                                         C  C
2921  ATGCGAGAAATGTCATTAAAAATGGTGATTTTAATAATGG  2960
          C     C     C  G  C     C  C  C
2961  CTTATCCTGCTGGAACGTGAAAGGGCATGTAGATGTAGAA  3000

3001  GAACAAAACAACCAACGTTCGGTCCTTGTTGTTCCGGAAT  3040

3041  GGGAAGCAGAAGTGTCACAAGAAGTTCGTGTCTGTCCGGG  3080

3081  TCGTGGCTATATCCTTCGTGTCACAGCGTACAAGGAGGGA  3120

3121  TATGGAGAAGGTTGCGTAACCATTCATGAGATCGAGAACA  3160

3161  ATACAGACGAACTGAAGTTTAGCAACTGCGTAGAAGAGGA  3200

3201  AATCTATCCAAATAACACGGTAACGTGTAATGATTATACT  3240

3241  GTAAATCAAGAAGAATACGGAGGTGCGTACACTTCTCGTA  3280

3281  ATCGAGGATATAACGAAGCTCCTTCCGTACCAGCTGATTA  3320

3321  TGCGTCAGTCTATGAAGAAAAATCGTATACAGATGGACGA  3360

3361  AGAGAGAATCCTTGTGAATTTAACAGAGGGTATAGGGATT  3400

3401  ACACGCCACTACCAGTTGGTTATGTGACAAAAGAATTAGA  3440

3441  ATACTTCCCAGAAACCGATAAGGTATGGATTGAGATTGGA  3480

3481  GAAACGGAAGGAACATTTATCGTGGACAGCGTGGAATTAC  3520

3521  TCCTTATGGAGGAA  3534
```

FIG. 10E

```
  1  ATGGATAACAATCCGAACATCAATGAATGCATTCCTTATA   40
          C     C  A        C           A  C
 41  ATTGTTTAAGTAACCCTGAAGTAGAAGTATTAGGTGGAGA   80
      C  C  G        A     T      C T
 81  AAGAATAGAAACTGGTTACACCCCAATCGATATTTCCTTG  120
      C C  T     C        T  C     C  C
121  TCGCTAACGCAATTTCTTTTGAGTGAATTTGTTCCCGGTG  160
       CT G  A  G     GC C  C  G  C  G  A
161  CTGGATTTGTGTTAGGACTAGTTGATATAATATGGGGAAT  200
         G  C  TC C           C  C  C     T
201  TTTTGGTCCCTCTCAATGGGACGCATTTCTTGTACAAATT  240
     C        A           T     C  G  G
241  GAACAGTTAATTAACCAAAGAATAGAAGAATTCGCTAGGA  280
       G     G  C     G  G  C     G     C
281  ACCAAGCCATTTCTAGATTAGAAGGACTAAGCAATCTTTA  320
         G     C     G  G      T G        C
321  TCAAATTTACGCAGAATCTTTTAGAGAGTGGGAAGCAGAT  360
     C     C  T     GAGC  C              C
361  CCTACTAATCCAGCATTAAGAGAAGAGATGCGTATTCAAT  400
             C     TC CC C  G  A
401  TCAATGACATGAACAGTGCCCTTACAACCGCTATTCCTCT  440
         C           C   T G  C  A     C  AT
441  TTTTGCAGTTCAAAATTATCAAGTTCCTCTTTTATCAGTA  480
     G  C     C  G  C  C           C  G  C  G
481  TATGTTCAAGCTGCAAATTTACATTTATCAGTTTTGAGAG  520
       C        A  T   C T  CC CAGC  GC TC
521  ATGTTTCAGTGTTTGGACAAAGGTGGGGATTTGATGCCGC  560
      C   AGC        G              C     T
561  GACTATCAATAGTCGTTATAATGATTTAACTAGGCTTATT  600
     A  C        C     C  C  CC T        G
601  GGCAACTATACAGATTATGCTGTACGCTGGTACAATACGG  640
       A     C  C  CC C     T  T        C  T
641  GATTAGAACGTGTATGGGGACCGGATTCTAGAGATTGGGT  680
      C  G  G     C     T  T               A
```

FIG. 11A

```
               .         .         .         .
681   AAGGTATAATCAATTTAGAAGAGAATTAACACTAACTGTA   720
      T  A  C  C  G  C  G        G  C  C  A  T
               .         .         .         .
721   TTAGATATCGTTGCTCTGTTCCCGAATTATGATAGTAGAA   760
        G  C  T  GT    C        C     CTCC
               .         .         .         .
761   GATATCCAATTCGAACAGTTTCCCAATTAACAAGAGAAAT   800
      CC  C  T  C  T     G      C T  C
               .         .         .         .
801   TTATACAAACCCAGTATTAGAAAATTTTGATGGTAGTTTT   840
      C     T        TC T  G  C  C  C     C  C
               .         .         .         .
841   CGAGGCTCGGCTCAGGGCATAGAAAGAAGTATTAGGAGTC   880
        T  T  T  C  A  T  C   G CTCC  C     C
               .         .         .         .
881   CACATTTGATGGATATACTTAACAGTATAACCATCTATAC   920
          C        C  CT G     C     T     C
               .         .         .         .
921   GGATGCTCATAGGGGTTATTATTATTGGTCAGGGCATCAA   960
      C        C  A  AG G     C     T  A  C  G
               .         .         .         .
961   ATAATGGCTTCTCCTGTAGGGTTTTCGGGGCCAGAATTCA   1000
        C     C     A  T  A  CAGC     C  G  T
               .         .         .         .
1001  CTTTTCCGCTATATGGAACTATGGGAAATGCAGCTCCACA   1040
       C     T  C                 C  C
               .         .         .         .
1041  ACAACGTATTGTTGCTCAACTAGGTCAGGGCGTGTATAGA   1080
               C                    T  C  C
               .         .         .         .
1081  ACATTATCGTCCACTTTATATAGAAGACCTTTTAATATAG   1120
        C  G  T     C  G  C        C  C     C
               .         .         .         .
1121  GGATAAATAATCAACAACTATCTGTTCTTGACGGGACAGA   1160
       T  C  C  C  G     T  C           A
               .         .         .         .
1161  ATTTGCTTATGGAACCTCCTCAAATTTGCCATCCGCTGTA   1200
      G  C  C           T  T  C              T
               .         .         .         .
1201  TACAGAAAAAGCGGAACGGTAGATTCGCTGGATGAAATAC   1240
              G        C  T     CT    C     C
               .         .         .         .
1241  CGCCACAGAATAACAACGTGCCACCTAGGCAAGGATTTAG   1280
       A        C     T        C           CTC
               .         .         .         .
1281  TCATCGATTAAGCCATGTTTCAATGTTTCGTTCAGGCTTT   1320
      C  CA G  G     C  G  C     C     C  A  C
               .         .         .         .
1321  AGTAATAGTAGTGTAAGTATAATAAGAGCTCCTATGTTCT   1360
        C  C   TCC  G  C  C  C
               .         .         .         .
1361  CTTGGATACATCGTAGTGCTGAATTTAATAATATAATTGC   1400
                C           G  C  C  C  C  C
```

FIG. 11B

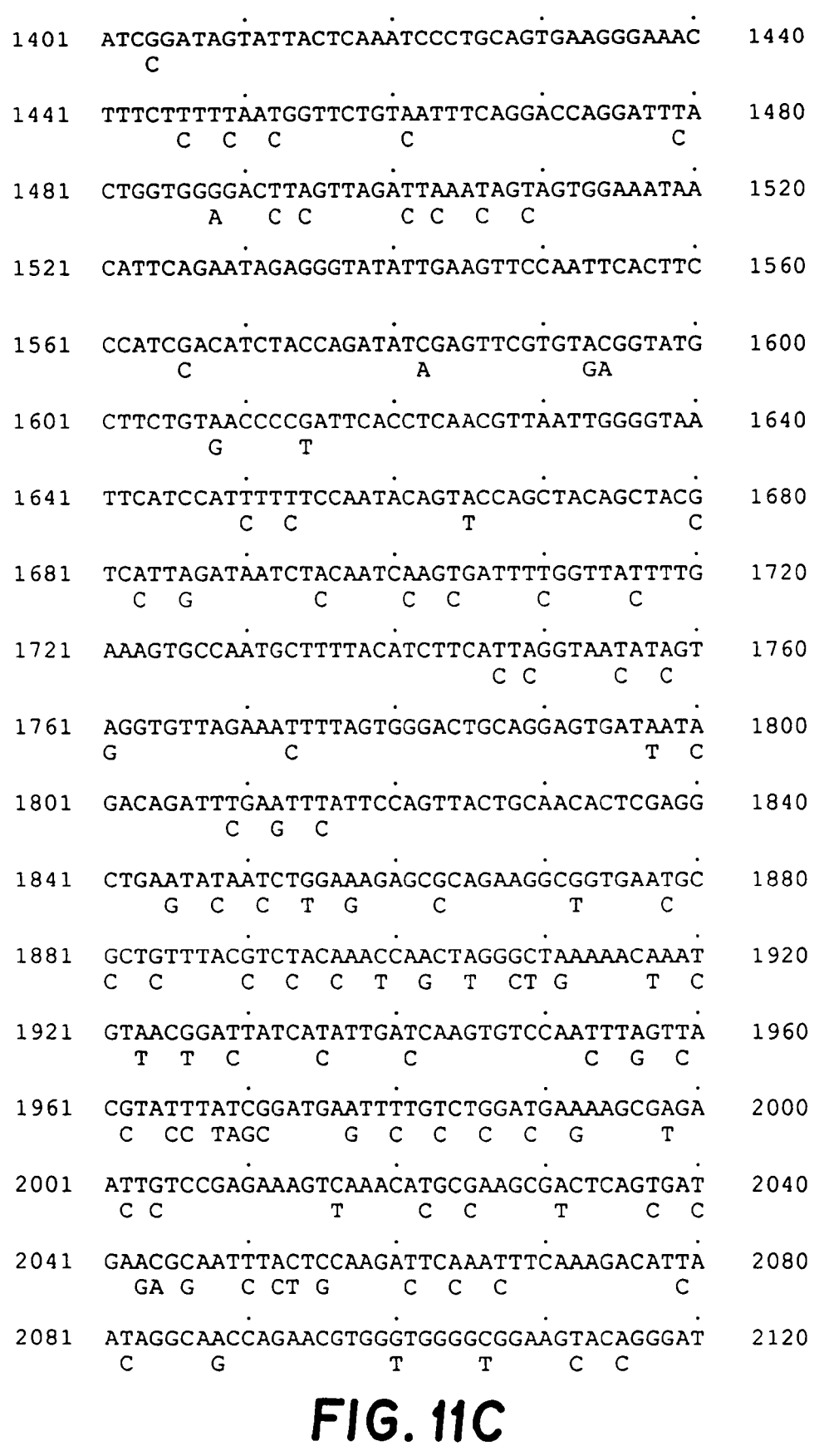

```
1401  ATCGGATAGTATTACTCAAATCCCTGCAGTGAAGGGAAAC  1440
         C

1441  TTTCTTTTTAATGGTTCTGTAATTTCAGGACCAGGATTTA  1480
           C  C  C        C                 C

1481  CTGGTGGGGACTTAGTTAGATTAAATAGTAGTGGAAATAA  1520
             A   C C      C C  C  C

1521  CATTCAGAATAGAGGGTATATTGAAGTTCCAATTCACTTC  1560

1561  CCATCGACATCTACCAGATATCGAGTTCGTGTACGGTATG  1600
           C               A          GA

1601  CTTCTGTAACCCCGATTCACCTCAACGTTAATTGGGGTAA  1640
             G     T

1641  TTCATCCATTTTTTCCAATACAGTACCAGCTACAGCTACG  1680
               C  C           T              C

1681  TCATTAGATAATCTACAATCAAGTGATTTTGGTTATTTTG  1720
        C  G        C     C  C     C     C

1721  AAAGTGCCAATGCTTTTACATCTTCATTAGGTAATATAGT  1760
                                C C     C  C

1761  AGGTGTTAGAAATTTTAGTGGGACTGCAGGAGTGATAATA  1800
      G           C                       T  C

1801  GACAGATTTGAATTTATTCCAGTTACTGCAACACTCGAGG  1840
              C  G  C

1841  CTGAATATAATCTGGAAAGAGCGCAGAAGGCGGTGAATGC  1880
          G  C  C  T  G     C        T     C

1881  GCTGTTTACGTCTACAAACCAACTAGGGCTAAAAACAAAT  1920
      C  C     C  C  C  T  G  T  CT G     T  C

1921  GTAACGGATTATCATATTGATCAAGTGTCCAATTTAGTTA  1960
        T  T  C     C     C           C  G  C

1961  CGTATTTATCGGATGAATTTTGTCTGGATGAAAAGCGAGA  2000
       C  CC TAGC     G  C  C  C  C  G     T

2001  ATTGTCCGAGAAAGTCAAACATGCGAAGCGACTCAGTGAT  2040
       C C           T     C  C     T     C  C

2041  GAACGCAATTTACTCCAAGATTCAAATTTCAAAGACATTA  2080
        GA G   C CT G     C  C  C           C

2081  ATAGGCAACCAGAACGTGGGTGGGGCGGAAGTACAGGGAT  2120
       C     G           T     T     C  C
```

FIG. 11C

```
2121  TACCATCCAAGGAGGGGATGACGTATTTAAAGAAAATTAC  2160
      C              C  C  T  G  C  G  G  C

2161  GTCACACTATCAGGTACCTTTGATGAGTGCTATCCAACAT  2200
           C  C  C  A  T  C  C        C  T  C

2201  ATTTGTATCAAAAAATCGATGAATCAAAATTAAAAGCCTT  2240
       C     C  G  G        G  C   C C

2241  TACCCGTTATCAATTAAGAGGGTATATCGAAGATAGTCAA  2280
      C   A G      C T     C  C        C  C

2281  GACTTAGAAATCTATTTAATTCGCTACAATGCAAAACATG  2320
         C T        C CG  CA G        C  G  C

2321  AAACAGTAAATGTGCCAGGTACGGGTTCCTTATGGCCGCT  2360
       G  C  G     C        T      C C     A

2361  TTCAGCCCAAAGTCCAATCGGAAAGTGTGGAGAGCCGAAT  2400
         T      TC   C  T  G              T  C

2401  CGATGCGCGCCACACCTTGAATGGAATCCTGACTTAGATT  2440
      A       T           G              G  C

2441  GTTCGTGTAGGGATGGAGAAAAGTGTGCCCATCATTCGCA  2480
       C  C  C        C  G           C     T

2481  TCATTTCTCCTTAGACATTGATGTAGGATGTACAGACTTA  2520
         C        G     C     G        T   C G

2521  AATGAGGACCTAGGTGTATGGGTGATCTTTAAGATTAAGA  2560
                 C  A  C     C     C     C

2561  CGCAAGATGGGCACGCAAGACTAGGGAATCTAGAGTTTCT  2600
       C     C  A           T  C  C  T

2601  CGAAGAGAAACCATTAGTAGGAGAAGCGCTAGCTCGTGTG  2640
                     G  C  T     T  C

2641  AAAAGAGCGGAGAAAAAATGGAGAGACAAACGTGAAAAAT  2680
        G     A     G  G     G           G   C

2681  TGGAATGGGAAACAAATATCGTTTATAAAGAGGCAAAAGA  2720
       C           T  C        C  G     C

2721  ATCTGTAGATGCTTTATTTGTAAACTCTCAATATGATCAA  2760
      G  C  G        G  C  G     C           G

2761  TTACAAGCGGATACGAATATTGCCATGATTCATGCGGCAG  2800
        G     C  C  C  C  C        C  C  C

2801  ATAAACGTGTTCATAGCATTCGAGAAGCTTATCTGCCTGA  2840
       C        G  C        T  G     CT
```

FIG. 11D

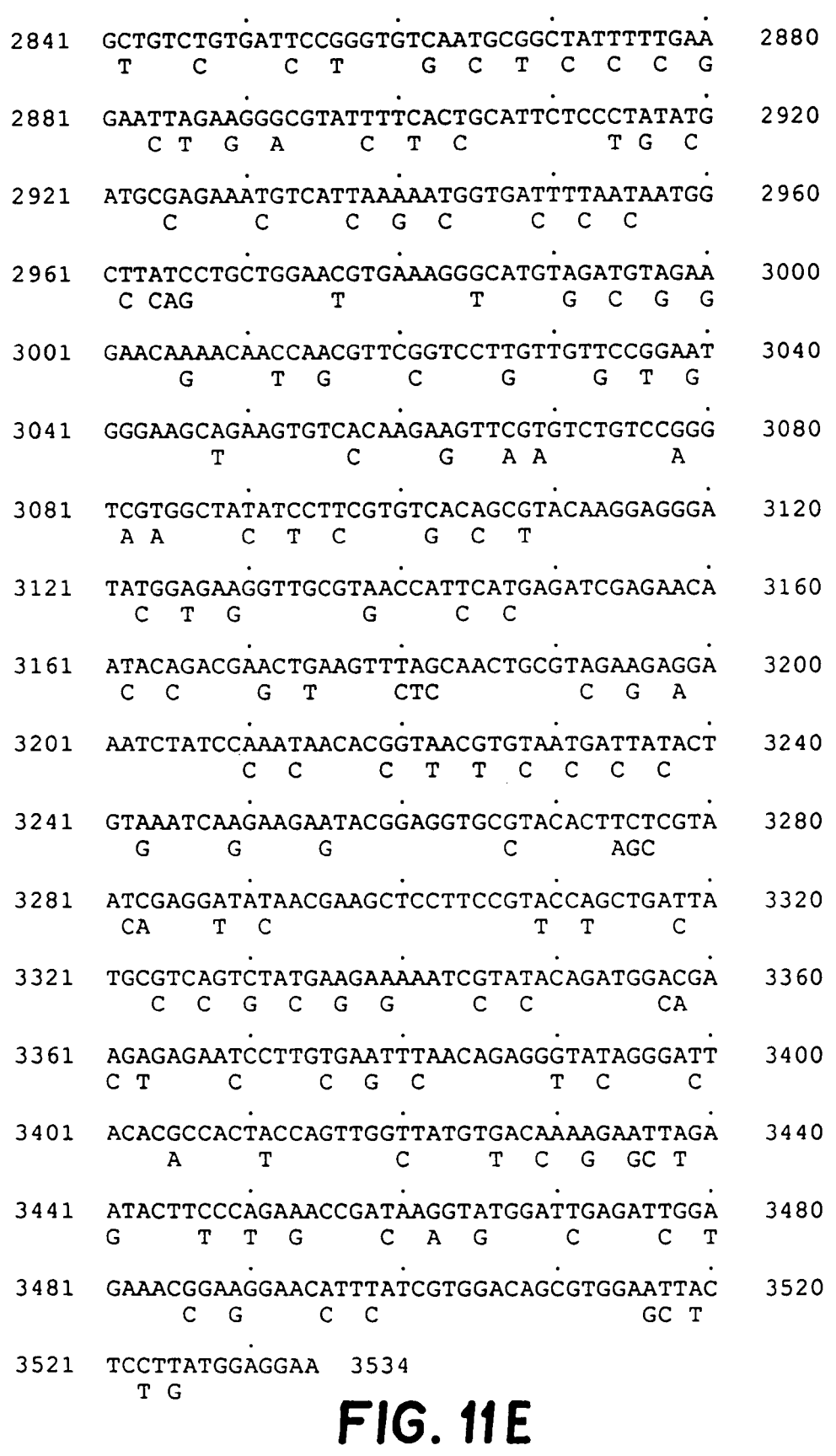

```
2841  GCTGTCTGTGATTCCGGGTGTCAATGCGGCTATTTTTGAA  2880
       T    C     C  T     G  C  T  C  C  C  G

2881  GAATTAGAAGGGCGTATTTTCACTGCATTCTCCCTATATG  2920
         C T  G  A     C  T  C         T G  C

2921  ATGCGAGAAATGTCATTAAAAATGGTGATTTTAATAATGG  2960
          C     C     C  G  C     C  C  C

2961  CTTATCCTGCTGGAACGTGAAAGGGCATGTAGATGTAGAA  3000
       C CAG         T        T     G  C  G  G

3001  GAACAAAACAACCAACGTTCGGTCCTTGTTGTTCCGGAAT  3040
           G     T  G     C     G     G  T  G

3041  GGGAAGCAGAAGTGTCACAAGAAGTTCGTGTCTGTCCGGG  3080
             T        C     G   A A        A

3081  TCGTGGCTATATCCTTCGTGTCACAGCGTACAAGGAGGGA  3120
       A A     C  T  C     G  C  T

3121  TATGGAGAAGGTTGCGTAACCATTCATGAGATCGAGAACA  3160
        C  T  G        G     C  C

3161  ATACAGACGAACTGAAGTTTAGCAACTGCGTAGAAGAGGA  3200
       C  C     G  T     CTC         C  G  A

3201  AATCTATCCAAATAACACGGTAACGTGTAATGATTATACT  3240
               C  C     C  T  T  C  C  C  C

3241  GTAAATCAAGAAGAATACGGAGGTGCGTACACTTCTCGTA  3280
        G     G     G           C      AGC

3281  ATCGAGGATATAACGAAGCTCCTTCCGTACCAGCTGATTA  3320
       CA    T  C                 T  T     C

3321  TGCGTCAGTCTATGAAGAAAAATCGTATACAGATGGACGA  3360
         C  C  G  C  G  G     C  C        CA

3361  AGAGAGAATCCTTGTGAATTTAACAGAGGGTATAGGGATT  3400
      C T     C     C  G  C        T  C     C

3401  ACACGCCACTACCAGTTGGTTATGTGACAAAAGAATTAGA  3440
          A     T        C     T  C  G  GC T

3441  ATACTTCCCAGAAACCGATAAGGTATGGATTGAGATTGGA  3480
      G     T  T  G     C  A  G     C     C  T

3481  GAAACGGAAGGAACATTTATCGTGGACAGCGTGGAATTAC  3520
           C  G     C  C                 GC T

3521  TCCTTATGGAGGAA  3534
        T G
```

FIG. 11E

```
  1 ATGACTGCAGATAATAATACGGAAGCACTAGATAGCTCTA   40
               C  C  C  C     C  C  C  T

 41 CAACAAAAGATGTCATTCAAAAAGGCATTTCCGTAGTAGG   80
     C  T  G     T  C  G  G  T  C     T  G

 81 TGATCTCCTAGGCGTAGTAGGTTTCCCGTTTGGTGGAGCG  120
    A  C   T G     G  T  A  T  C  C        C

121 CTTGTTTCGTTTTATACAAACTTTTTAAATACTATTTGGC  160
      C  GAGC  C            C C  C  C

161 CAAGTGAAGACCCGTGGAAGGCTTTTATGGAACAAGTAGA  200
        C  G     T     A  A  C     G     T

201 AGCATTGATGGATCAGAAAATAGCTGATTATGCAAAAAAT  240
       TC T           G  T  A        C  G  C

241 AAAGCTCTTGCAGAGTTACAGGGCCTTCAAAATAATGTCG  280
      G   T G     AC C           G  C     G

281 AAGATTATGTGAGTGCATTGAGTTCATGGCAAAAAAATCC  320
     G  C  C            TCCAGC     G  G  C

321 TGTGAGTTCACGAAATCCACATAGCCAGGGGCGGATAAGA  360
       T  C  CA       T  C     A  TA    C

361 GAGCTGTTTTCTCAAGCAGAAAGTCATTTTCGTAATTCAA  400
       T    C        C   TCC  C  CA A     C

401 TGCCTTCGTTTGCAATTTCTGGATACGAGGTTCTATTTCT  440
         AGC     T  C  C  T           T  C

441 AACAACATATGCACAAGCTGCCAACACACATTTATTTTTA  480
    C  T  C     T              C  C  G   C C

481 CTAAAAGACGCTCAAATTTATGGAGAAGAATGGGGATACG  520
      T  G           C           G

521 AAAAAGAAGATATTGCTGAATTTTATAAAAGACAACTAAA  560
     G     G  C        G  C  C  GC T     T

561 ACTTACGCAAGAATATACTGACCATTGTGTCAAATGGTAT  600
    G  C  C     G  C           C  G

601 AATGTTGGATTAGATAAATTAAGAGGTTCATCTTATGAAT  640
      C     TC C     GC C     C  T  C  C  G

641 CTTGGGTAAACTTTAACCGTTATCGCAGAGAGATGACATT  680
           G     C   A A  CA G           C
```

FIG. 12A

```
               .         .         .         .
681   AACAGTATTAGATTTAATTGCACTATTTCCATTGTATGAT    720
      G  T   GCC   C T  C     C     C     C
               .         .         .         .
721   GTTCGGCTATACCCAAAAGAAGTTAAAACCGAATTAACAA    760
        GA A  C        G     G     T  GC T  C
               .         .         .         .
761   GAGACGTTTTAACAGATCCAATTGTCGGAGTCAACAACCT    800
             GC C  T  C  T
               .         .         .         .
801   TAGGGGCTATGGAACAACCTTCTCTAATATAGAAAATTAT    840
            T        T      AGC     C     C  C
               .         .         .         .
841   ATTCGAAAACCACATCTATTTGACTATCTGCATAGAATTC    880
         A G           C  C        T  C
               .         .         .         .
881   AATTTCACACGCGGTTCCAACCAGGATATTATGGAAATGA    920
          C     AA    T           C     T  C
               .         .         .         .
921   CTCTTTCAATTATTGGTCCGGTAATTATGTTTCAACTAGA    960
         C     C              C        C  C
               .         .         .         .
961   CCAAGCATAGGATCAAATGATATAATCACATCTCCATTCT    1000
              T     T     C  C           C
               .         .         .         .
1001  ATGGAAATAAATCCAGTGAACCTGTACAAAATTTAGAATT    1040
          T  C  G              G  G  CC T  G
               .         .         .         .
1041  TAATGGAGAAAAAGTCTATAGAGCCGTAGCAAATACAAAT    1080
      C  C  C  G                 C     C  C
               .         .         .         .
1081  CTTGCGGTCTGGCCGTCCGCTGTATATTCAGGTGTTACAA    1120
        C  T  G     A     A  T  C     C  C
               .         .         .         .
1121  AAGTGGAATTTAGCCAATATAATGATCAAACAGATGAAGC    1160
       G     G     T  G     C     G  C     G
               .         .         .         .
1161  AAGTACACAAACGTACGACTCAAAAAGAAATGTTGGCGCG    1200
      C  C  C  G  T        C   C T  C        A
               .         .         .         .
1201  GTCAGCTGGGATTCTATCGATCAATTGCCTCCAGAAACAA    1240
         TCT              C                 C
               .         .         .         .
1241  CAGATGAACCTCTAGAAAAGGGATATAGCCATCAACTCAA    1280
          C     AT G  G     C  C     C     T
               .         .         .         .
1281  TTATGTAATGTGCTTTTTAATGCAGGGTAGTAGAGGAACA    1320
      C     G        C  G     A   TCC     G  C
               .         .         .         .
1321  ATCCCAGTGTTAACTTGGACACATAAAAGTGTAGACTTTT    1360
        T        G  C        C  GTCC  G     C
               .         .         .         .
1361  TTAACATGATTGATTCGAAAAAAATTACACAACTTCCGTT    1400
       C        C   AGC  G  G  C  T        C
```

FIG.12B

```
1401  AGTAAAGGCATATAAGTTACAATCTGGTGCTTCCGTTGTC  1440
      G  G  A  C  C   C G
1441  GCAGGTCCTAGGTTTACAGGAGGAGATATCATTCAATGCA  1480
              C  A  C  T     T  C     C  G
1481  CAGAAAATGGAAGTGCGGCAACTATTTACGTTACACCGGA  1520
          G  C  C  C  A  T     C     G     T
1521  TGTGTCGTACTCTCAAAAATATCGAGCTAGAATTCATTAT  1560
            T        G  G  CA G  AC T        C
1561  GCTTCTACATCTCAGATAACATTTACACTCAGTTTAGACG  1600
        A     CAGC     C  C  C        C  G  T
1601  GGGCACCATTTAATCAATACTATTTCGATAAAACGATAAA  1640
       A     C  C  C  G  T  C  T  C  G  C  C
1641  TAAAGGAGACACATTAACGTATAATTCATTTAATTTAGCA  1680
      C     T      TC C A  C  AGC   C  C  G
1681  AGTTTCAGCACACCATTCGAATTATCAGGGAATAACTTAC  1720
                       T   C C     C  C  TC T
1721  AAATAGGCGTCACAGGATTAAGTGCTGGAGATAAAGTTTA  1760
       G  C        C  TC C  C  C     C     C
1761  TATAGACAAAATTGAATTTATTCCAGTGAAT  1791
      C  C     G     G  C  C        C
```

FIG.12C

```
  1  ATG   AATAATGTATTGAATAGTGGAAGAACAACTATTT    40
        GAC  C  C  C     CTC    T        C  C

 41  GTGATGCGTATAATGTAGTAGCCCATGATCCATTTAGTTT   80
      C  C  A  C  C  C  G  T  C        C  C

 81  TGAACATAAATCATTAGATACCATCCAAAAAGAATGGATG   120
     C     C  GAGCC C  C  T  T  G  G  G

121  GAGTGGAAAAGAACAGATCATAGTTTATATGTAGCTCCTG   160
       A      C T  T  C  CTC C C  C  C  A

161  TAGTCGGAACTGTGTCTAGTTTTTTGCTAAAGAAAGTGGG   200
      G  T    A     C  C  CC T  C     G  C

201  GAGTCTTATTGGAAAAAGGATATTGAGTGAATTATGGGGG   240
     CTC    C  C      C T  C    TCC   C C    T

241  ATAATATTTCCTAGTGGTAGTACAAATCTAATGCAAGATA   280
       C  C     ATC   GTCC   T     C        C

281  TTTTAAGGGAGACAGAACAATTCCTAAATCAAAGACTTAA   320
      C  G          C     G  T  C  C  GC T  C

321  TACAGATACCCTTGCTCGTGTAAATGCAGAATTGATAGGG   360
     C  T      T G   A A  C  C  T  G     C  T

361  CTCCAAGCGAATATAAGGGAGTTTAATCAACAAGTAGATA   400
              A  C  TC T     C  C  G     G  C

401  ATTTTTTAAACCCTACTCAAAACCCTGTTCCTTTATCAAT   440
      C  C  G  T  A     G  T     G  C T  C

441  AACTTCTTCGGTTAATACAATGCAGCAATTATTTCTAAAT   480
     C        C  G  C  T           C C  C  C  C

481  AGATTACCCCAGTTCCAGATACAAGGATACCAGTTGTTAT   520
         G  T     T     T     C           C CC

521  TATTACCTTTATTTGCACAGGCAGCCAATATGCATCTTTC   560
      TC T  AC C     T     T     C     CT G

561  TTTTATTAGAGATGTTATTCTTAATGCAGATGAATGGGGT   600
     C  C  AC T  C  G  C  C  C  T  C          A

601  ATTTCAGCAGCAACATTACGTACGTATCGAGATTACCTGA   640
       C  T     C  TC TA G  A  CA    C  T

641  GAAATTATACAAGAGATTATTCTAATTATTGTATAAATAC   680
      G  C  C  TC T     C  C  C     C  C  C
```

FIG. 13A

```
 681  GTATCAAACTGCGTTTAGAGGGTTAAACACCCGTTTACAC   720
      T     G     C   C T  AC C  T  TA GC T

 721  GATATGTTAGAATTTAGAACATATATGTTTTTAAATGTAT   760
        C   C T  G  C  G  C  C     CC T  C  G

 761  TTGAATATGTATCCATTTGGTCATTGTTTAAATATCAGAG   800
          G  C  CAG      AGTC  C  C  G  C

 801  TCTTATGGTATCTTCTGGCGCTAATTTATATGCTAGCGGT   840
      CT G     G  C     A  C   C C  C  CTCT  C

 841  AGTGGACCACAGCAGACACAATCATTTACAGCACAAAACT   880
                    A  T  GAGC  C     T  G

 881  GGCCATTTTTATATTCTCTTTTCCAAGTTAATTCGAATTA   920
             C  G   AGCT G        C  C  C  C

 921  TATATTATCTGGTATTAGTGGTACTAGGCTTTCTATTACC   960
      C  TC CAG      CTC   G  C  A  C  C  A

 961  TTCCCTAATATTGGTGGTTTACCGGGTAGTACTACAACTC   1000
        T  C  C        AC T  A  CTCC        C

1001  ATTCATTGAATAGTGCCAGGGTTAATTATAGCGGAGGAGT   1040
        AGCC T  CTC      A  G  C  C  T     T

1041  TTCATCTGGTCTCATAGGGGCGACTAATCTCAATCACAAC   1080
      CAGC     AT G  T  T  A     CT G  C

1081  TTTAATTGCAGCACGGTCCTCCCTCCTTTATCAACACCAT   1120
        C      TC   C   T G  A   C GAGC     G

1121  TTGTTAGAAGTTGGCTGGATTCAGGTACAGATCGAGAGGG   1160
          G  GTCC     T  CAGC     T     C  A

1161  CGTTGCTACCTCTACGAATTGGCAGACAGAATCCTTTCAA   1200
      A              A  C     A  C  G     C

1201  ACAACTTTAAGTTTAAGGTGTGGTGCTTTTTCAGCCCGTG   1240
        C   C T  CC TC        A     C  T  A

1241  GAAATTCAAACTATTTCCCAGATTATTTTATCCGTAATAT   1280
       G           C  T     C  C  C  TA G  C

1281  TTCTGGGGTTCCTTTAGTTATTAGAAACGAAGATCTAACA   1320
      C     T      C C  C  C  G  T     C  C  C

1321  AGACCGTTACACTATAACCAAATAAGAAATATAGAAAGTC   1360
      C T  AC T  T  C     G  T  G  C  C  GTC

1361  CTTCGGGAACACCTGGTGGAGCACGGGCCTATTTGGTATC   1400
       A  C  T  T  A  A  T   A A  T  CC C  G
```

FIG. 13B

```
               .         .         .         .
1401  TGTGCATAACAGAAAAAATAATATCTATGCCGCTAATGAA  1440
         C        G  G  C  C     C  T  C  C  G
               .         .         .         .
1441  AATGGTACTATGATCCATTTGGCGCCAGAAGATTATACAG  1480
           C  C     T  CC T  A           C  T
               .         .         .         .
1481  GATTTACTATATCGCCAATACATGCCACTCAAGTGAATAA  1520
          C  C  C  T     C     T  C        C
               .         .         .         .
1521  TCAAACTCGAACATTTATTTCTGAAAAATTTGGAAATCAA  1560
         G  A  C  C  C  C  C     G  C
               .         .         .         .
1561  GGTGATTCCTTAAGATTTGAACAAAGCAACACGACAGCTC  1600
           C     G  G  C  G  TC       T  C   A
               .         .         .         .
1601  GTTATACGCTTAGAGGGAATGGAAATAGTTACAATCTTTA  1640
       G  C  TT G     C        C  C     C
               .         .         .         .
1641  TTTAAGAGTATCTTCAATAGGAAATTCAACTATTCGAGTT  1680
      C  G     TAGC  C  T  T  C  C  C  C  T
               .         .         .         .
1681  ACTATAAACGGTAGAGTTTATACTGTTTCAAATGTTAATA  1720
        C  C     AC T     C  A  C  T     G  C
               .         .         .         .
1721  CCACTACAAATAACGATGGAGTTAATGATAATGGAGCTCG  1760
       T  A  G  C  T     C     C  C  C     CA
               .         .         .         .
1761  TTTTTCAGATATTAATATCGGTAATATAGTAGCAAGTGAT  1800
      A  CAGC  C  C  C  T  C  C  C  G  CTC   C
               .         .         .         .
1801  AATACTAATGTAACGCTAGATATAAATGTGACATTAAACT  1840
        C     C  T  TT G  C  C        CC C  T
               .         .         .         .
1841  CCGGTACTCCATTTGATCTCATGAATATTATGTTTGTGCC  1880
       T  A                    C  C
               .         .
1881  AACTAATCTTCCACCACTTTAT  1902
            C  C  T   T G  C
```

FIG. 13C

```
  1 ATGGAGGAAAATAATCAAAATCAATGCATACCTTACAATT  40
            G  C  C     C        T  A     C

 41 GTTTAAGTAATCCTGAAGAAGTACTTTTGGATGGAGAACG  80
     C  G     C  A     G   T GC T

 81 GATATCAACTGGTAATTCATCAATTGATATTTCTCTGTCA  120
    C  T     C     C  T  C  C  C  C  CT    C

121 CTTGTTCAGTTTCTGGTATCTAACTTTGTACCAGGGGGAG  160
    T G  C           CAGC     C  G     T  T

161 GATTTTTAGTTGGATTAATAGATTTTGTATGGGGAATAGT  200
     G  CC T  C   C    T  C  C  C     T  C

201 TGGCCCTTCTCAATGGGATGCATTTCTAGTACAAATTGAA  240
       T  A                 C  G  G        G

241 CAATTAATTAATGAAAGAATAGCTGAATTTGCTAGGAATG  280
      G  G  C  C  G  G  C     G  C  C     C

281 CTGCTATTGCTAATTTAGAAGGATTAGGAAACAATTTCAA  320
        C  C     C  G        G  C  T  C

321 TATATATGTGGAAGCATTTAAAGAATGGGAAGAAGATCCT  360
    C  C        G  C  C     G        G  C

361 AATAATCCAGAAACCAGGACCAGAGTAATTGATCGCTTTC  400
         C     G   C C  T  G  G  C  CA A  CA

401 GTATACTTGATGGGCTACTTGAAAGGACATTCCTTCGTT  440
     A  CT G  C  C  CT G  G  A  T  C  A  C

441 TCGAATTTCTGGATTTGAAGTACCCCTTTTATCCGTTTAT  480
    CA    C     C  C     T  T  C  G     G  C

481 GCTCAAGCGGCCAATCTGCATCTAGCTATATTAAGAGATT  520
            A  T     T  C  C     CC TC    CA

521 CTGTAATTTTTGGAGAAAGATGGGGATTGACAACGATAAA  560
    G   C  C     G     G           C  T  C

561 TGTCAATGAAAACTATAATAGACTAATTAGGCATATTGAT  600
    C        G  T  C  C     T  C     C     C

601 GAATATGCTGATCACTGTGCAAATACGTATAATCGGGGAT  640
      G  C  C  C        T  C  C  C  C  T  C

641 TAAATAATTTACCGAAATCTACGTATCAAGATTGGATAAC  680
     G  C   C C  T  G     T              T

681 ATATAATCGATTACGGAGAGACTTAACATTGACTGTATTA  720
    C  C  CA G  GA          G  CC C  A  T  G
```

FIG. 14A

```
               .         .         .         .
 721  GATATCGCCGCTTTCTTTCCAAACTATGACAATAGGAGAT   760
        C  T  A        C  G           C
               .         .         .         .
 761  ATCCAATTCAGCCAGTTGGTCAACTAACAAGGGAAGTTTA   800
       C  T  C  A     G        T  C  A     C
               .         .         .         .
 801  TACGGACCCATTAATTAATTTTAATCCACAGTTACAGTCT   840
         T      C T     C  C  C  T     G  AAG
               .         .         .         .
 841  GTAGCTCAATTACCTACTTTTAACGTTATGGAGAGCAGCC   880
        C  C   C T  C  A  C     C      TC
               .         .         .         .
 881  GAATTAGAAATCCTCATTTATTTGATATATTGAATAATCT   920
       T  C  G  C  A  C  G     C  C     C  C
               .         .         .         .
 921  TACAATCTTTACGGATTGGTTTAGTGTTGGACGCAATTTT   960
         T     C  C        C  C     G  T  C  C
               .         .         .         .
 961  TATTGGGGAGGACATCGAGTAATATCTAGCCTTATAGGAG   1000
              T     CA G  C  C  CTCT     T
               .         .         .         .
1001  GTGGTAACATAACATCTCCTATATATGGAAGAGAGGCGAA   1040
          G     T  C        C      C T     A
               .         .         .         .
1041  CCAGGAGCCTCCAAGATCCTTTACTTTTAATGGACCGGTA   1080
               A   C TAGT  C  C  C  C  T  A  C
               .         .         .         .
1081  TTTAGGACTTTATCAAATCCTACTTTACGATTATTACAGC   1120
        C  A  C  G  T  C     C  GA    GC C
               .         .         .         .
1121  AACCTTGGCCAGCGCCACCATTTAATTTACGTGGTGTTGA   1160
                   T     T  C  CC TA A
               .         .         .         .
1161  AGGAGTAGAATTTTCTACACCTACAAATAGCTTTACGTAT   1200
      G  C  T  G  C     T     C CTC    C  T  C
               .         .         .         .
1201  CGAGGAAGAGGTACGGTTGATTCTTTAACTGAATTACCGC   1240
      A    T     A  C        C  G  C   C C  A
               .         .         .         .
1241  CTGAGGATAATAGTGTGCCACCTCGCGAAGGATATAGTCA   1280
       A     C     C        CA G     C  CTCC
               .         .         .         .
1281  TCGTTTATGTCATGCAACTTTTGTTCAAAGATCTGGAACA   1320
      CA G  G  C  C     C  C  G  GC T  C     T
               .         .         .         .
1321  CCTTTTTTAACAACTGGTGTAGTATTTTCTTGGACCGATC   1360
        A  CC C  T  A  A  T  G  C  A     T
               .         .         .         .
1361  GTAGTGCAACTCTTACAAATACAATTGATCCAGAGAGAAT   1400
             T     C  T     C        C     G
```

FIG. 14B

```
1401  TAATCAAATACCTTTAGTGAAAGGATTTAGAGTTTGGGGG  1440
      C        C  A  G  C  G  T  CC T  G     A

1441  GGCACCTCTGTCATTACAGGACCAGGATTTACAGGAGGGG  1480
        A  T        C           C  C        T

1481  ATATCCTTCGAAGAAATACCTTTGGTGATTTTGTATCTCT  1520
          T   A       C  T     C  C     GAGC

1521  ACAAGTCAATATTAATTCACCAATTACCCAAAGATACCGT  1560
      C     T  C  C  C  T        T        T

1561  TTAAGATTTCGTTACGCTTCCAGTAGGGATGCACGAGTTA  1600
      C C  G           A  TTCCC T  C  TA    C

1601  TAGTATTAACAGGAGCGGCATCCACAGGAGTGGGAGGCCA  1640
       C  GC C  C  C  A  T  T  C  T  C  T  A

1641  AGTTAGTGTAAATATGCCTCTTCAGAAAACTATGGAAATA  1680
         CTCC  G  C     A  C     G        G  C

1681  GGGGAGAACTTAACATCTAGAACATTTAGATATACCGATT  1720
        C        G     C  G  C  C     C     C

1721  TTAGTAATCCTTTTTCATTTAGAGCTAATCCAGATATAAT  1760
       CTC   C     CAGT  CC T  C  C  T  C  C

1761  TGGGATAAGTGAACAACCTCTATTTGGTGCAGGTTCTATT  1800
         C  T  C           C     A  T   AGC  C

1801  AGTAGCGGTGAACTTTATATAGATAAAATTGAAATTATTC  1840
      TCATCT  C   T G  C  T  C  G     G  C

1841  TAGCAGATGCAACATTTGAAGCAGAATCTGATTTAGAAAG  1880
       T  C  C  T  CC C  G  T  G ACA CC T  G

1881  AGCACAAAAGGCGGTGAATGCCCTGTTTACTTCTTCCAAT  1920
         C  G     T     C     C     C  CA

1921  CAAATCGGGTTAAAAACCGATGTGACGGATTATCATATTG  1960
        GC T  C  G     TA C  T  T  C     C

1961  ATCAAGTATCCAATTTAGTGGATTGTTTATCAGATGAATT  2000
       C     G     C  G  CACC ACC TAGC     G

2001  TTGTCTGGATGAAAAGCGAGAATTGTCCGAGAAAGTCAAA  2040
      C  C  C  C  G     T   C C           T

2041  CATGCGAAGCGACTCAGTGATGAGCGGAATTTACTTCAAG  2080
        C  C     T     C  C   A     C CT G

2081  ATCCAAACTTCAGAGGGATCAATAGACAACCAGACCGTGG  2120
       CT C       A  AC     C  G  G     A
```

FIG. 14C

```
                 .         .         .         .
2121    CTGGAGAGGAAGTACAGATATTACCATCCAAGGAGGAGAT    2160
        T   G T     C  C GG  C              C  C
                 .         .         .         .
2161    GACGTATTCAAAGAGAATTACGTCACACTACCGGGTACCG    2200
          T  G     G     C        C CT  C  A  TT
                 .         .         .         .
2201    TTGATGAGTGCTATCCAACGTATTTATATCAGAAAATAGA    2240
         C  C        C  T  C  C  G  C     G  C
                 .         .         .         .
2241    TGAGTCGAAATTAAAAGCTTATACCCGTTATGAATTAAGA    2280
              C   C C     C TC   A G   C  C T
                 .         .         .         .
2281    GGGTATATCGAAGATAGTCAAGACTTAGAAATCTATTTGA    2320
          C  C        C  C      C T        C C
                 .         .         .         .
2321    TCCGTTACAATGCAAAACACGAAATAGTAAATGTGCCAGG    2360
          A G        C  G     G CC  G     C
                 .         .         .         .
2361    CACGGGTTCCTTATGGCCGCTTTCAGCCCAAATGCCAATC    2400
        T  T      C C     A     T      TCT  C  T
                 .         .         .         .
2401    GGAAAGTGTGGAGAACCGAATCGATGCGCGCCACACCTTG    2440
          G           G  T  CA       T
                 .         .         .         .
2441    AATGGAATCCTGATCTAGATTGTTCCTGCAGAGACGGGGA    2480
         G           CT G  C  C        G  T  C
                 .         .         .         .
2481    AAAATGTGCACATCATTCCCATCATTTCACCTTGGATATT    2520
        G  G     C  C     T     C   T       C  C
                 .         .         .         .
2521    GATGTTGGATGTACAGACTTAAATGAGGACTTAGGTGTAT    2560
             G        T   C G         C C  A  C
                 .         .         .         .
2561    GGGTGATATTCAAGATTAAGACGCAAGATGGCCATGCAAG    2600
            C  C        C     C     C  A  C
                 .         .         .         .
2601    ACTAGGGAATCTAGAGTTTCTCGAAGAGAAACCATTATTA    2640
           T  C  C  T                       GG C
                 .         .         .         .
2641    GGGGAAGCACTAGCTCGTGTGAAAAGAGCGGAGAAGAAGT    2680
          T     T  C           G     A
                 .         .         .         .
2681    GGAGAGACAAACGAGAGAAACTGCAGTTGGAAACAAATAT    2720
            G        T        CG A G      T  C
                 .         .         .         .
2721    TGTTTATAAAGAGGCAAAAGAATCTGTAGATGCTTTATTT    2760
        C     C  G     C     G  C  G        G  C
                 .         .         .         .
2761    GTAAACTCTCAATATGATAGATTACAAGTGGATACGAACA    2800
          G     C         CAG  G    CC  C  C
                 .         .         .         .
2801    TCGCCATGATTCATGCGGCAGATAAACGCGTTCATAGAAT    2840
                  C  C  C     C     T  G  C  C
```

FIG. 14D

```
2841  CCGGGAAGCGTATCTGCCAGAGTTGTCTGTGATTCCAGGT   2880
      T  T  G  T  CT    T        C     C  T

2881  GTCAATGCGGCCATTTCGAAGAATTAGAGGGACGTATTT   2920
        G  C  T     C     G   C T           C

2921  TTACAGCGTATTCCTTATATGATGCGAGAAATGTCATTAA   2960
          C  A TC     G  C     C     C     C

2961  AAATGGCGATTTCAATAATGGCTTATTATGCTGGAACGTG   3000
      G  C  T  C     C      C CAGC        T

3001  AAAGGTCATGTAGATGTAGAAGAGCAAAACAACCACCGTT   3040
                 G  C  G  G  A  G     T  G

3041  CGGTCCTTGTTATCCCAGAATGGAGGCAGAAGTGTCACA   3080
       C     G   G G  T  G     A  T        C

3081  AGAGGTTCGTGTCTGTCCAGGTCGTGGCTATATCCTTCGT   3120
             A A            A A     C  T  C

3121  GTCACAGCATATAAAGAGGGATATGGAGAGGGCTGCGTAA   3160
        G  C  T  C  G        C  T     T     G

3161  CGATCCATGAGATCGAAGACAATACAGACGAACTGAAATT   3200
       C     C        GA    C  C     G  T  G

3201  CAGCAACTGTGTAGAAGAGGAAGTATATCCAAACAACACA   3240
       TC      C  C  G  A   A C     C        C

3241  GTAACGTGTAATAATTATACTGGGACTCAAGAAGAATATG   3280
        T  T  C  CG C  C    T  A   G     G  C

3281  AGGGTACGTACACTTCTCGTAATCAAGGATATGACGAAGC   3320
      GA   G C      AGC     CAG   T  CA

3321  CTATGGTAATAACCCTTCCGTACCAGCTGATTACGCTTCA   3360
      TCC TCXXXXXXXXXXXX   T  T     C  T  C  C

3361  GTCTATGAAGAAAAATCGTATACAGATGGACGAAGAGAGA   3400
        G  C  G  G     C  C        CA  C T

3401  ATCCTTGTGAATCTAACAGAGGCTATGGGGATTACACACC   3440
       C     C  G TC        T  CA    C

3441  ACTACCGGCTGGTTATGTAACAAAGGATTTAGAGTACTTC   3480
         T  A T   C     T  C     GC T        T

3481  CCAGAGACCGATAAGGTATGGATTGAGATCGGAGAAACAG   3520
        T        C  A  G     C        T     C

3521  AAGGAACATTCATCGTGGATAGCGTGGAATTACTCCTTAT   3560
       G     C           C        GC T   T G

3561  GGAGGAA   3567
```

FIG. 14E

```
   1  AGATCTAGAGGTAATTGTTATGAGTACTGTCGTGGTTAAG  40
                    GATC
  41  GGAAACGTCAACGGTGGTGTACAACAACCTAGAAGGAGGA  80
              G           T                 A
  81  GAAGGCAATCCCTTCGCAGGAGGGCTAACAGAGTACAGCC  120
                      T     A           T
 121  AGTGGTTATGGTCACTGCTCCTGGCGAACCCAGGAGGAGG  160
                              GC    A  A     A
 161  AGACGCAGAAGAGGAGGCAATCGCAGGTCAAGAAGAACTG  200
         A G           T        A
 201  GAGTTCCCAGGGGAAGGGGCTCAAGCGAGACATTCGTGTT  240
                A     A  T
 241  TACAAAGGACAACCTCGTGGGCAACTCCCAAGGAAGTTTC  280

 281  ACCTTCGGACCAAGTGTATCAGACTGTCCAGCATTCAAGG  320
                       T
 321  ATGGAATACTCAAGGCCTACCATGAGTACAAGATCACAAG  360
                      T
 361  TATCCTTCTTCAGTTCGTCAGCGAGGCCTCTTCCACCTCA  400
          T G                                T
 401  CCAGGATCCATCGCTTATGAGTTGGACCCACATTGCAAAG  440
           C                 A  T
 441  TATCATCCCTCCAGTCCTACGTCAACAAGTTCCAAATCAC  480
       T
 481  AAAGGGAGGAGCTAAGACCTATCAAGCTAGGATGATCAAC  520
            T  T                  C T
 521  GGAGTAGAATGGCACGATTCATCTGAGGATCAGTGCAGGA  560
           T              T                 A
 561  TACTTTGGAAAGGAAGTGGAAAATCTTCAGACCCAGCAGG  600
       C             A      G        T     T
 601  ATCTTTCAGAGTCACCATCAGAGTGGCTCTTCAAAACCCC  640
                  T           T              A
 641  AAGTAATAGACTCCGGATCAGAGCCTGGTCCAAGCCCACA  680
                A T
```

FIG. 16A

```
681   ACCAACACCCACTCCAACTCCCCAAAAGCATGAGCGATTT   720

721   ATTGCTTACGTCGGCATACCTATGCTGACCATTCAAGAAT   760

761   TC  762
```

SYNTHETIC PLANT GENES AND METHOD FOR PREPARATION

This application is a Divisional of U.S. patent application Ser. No. 07/959,506, filed on Oct. 9, 1992, now U.S. Pat. No. 5,500,365, which is a File Wrapper Continuation of U.S. patent application Ser. No. 07/476,661, filed Feb. 12, 1990, abandoned, which is a Continuation-in-part of U.S. patent application Ser. No. 07/315,355 filed Feb. 24, 1989, abandoned.

BACKGROUND OF THE INVENTION

The present invention relates to genetic engineering and more particularly to plant transformation in which a plant is transformed to express a heterologous gene.

Although great progress has been made in recent years with respect to transgenic plants which express foreign proteins such as herbicide resistant enzymes and viral coat proteins, very little is known about the major factors affecting expression of foreign genes in plants. Several potential factors could be responsible in varying degrees for the level of protein expression from a particular coding sequence. The level of a particular mRNA in the cell is certainly a critical factor.

The potential causes of low steady state levels of mRNA due to the nature of the coding sequence are many. First, full length RNA synthesis might not occur at a high frequency. This could, for example, be caused by the premature termination of RNA during transcription or due to unexpected mRNA processing during transcription. Second, full length RNA could be produced but then processed (splicing, polyA addition) in the nucleus in a fashion that creates a nonfunctional mRNA. If the RNA is properly synthesized, terminated and polyadenylated, it then can move to the cytoplasm for translation. In the cytoplasm, mRNAs have distinct half lives that are determined by their sequences and by the cell type in which they are expressed. Some RNAs are very short-lived and some are much more long-lived. In addition, there is an effect, whose magnitude is uncertain, of translational efficiency on mRNA half-life. In addition, every RNA molecule folds into a particular structure, or perhaps family of structures, which is determined by its sequence. The particular structure of any RNA might lead to greater or lesser stability in the cytoplasm. Structure per se is probably also a determinant of mRNA processing in the nucleus. Unfortunately, it is impossible to predict, and nearly impossible to determine, the structure of any RNA (except for tRNA) in vitro or in vivo. However, it is likely that dramatically changing the sequence of an RNA will have a large effect on its folded structure. It is likely that structure per se or particular structural features also have a role in determining RNA stability.

Some particular sequences and signals have been identified in RNAs that have the potential for having a specific effect on RNA stability. This section summarizes what is known about these sequences and signals. These identified sequences often are A+T rich, and thus are more likely to occur in an A+T rich coding sequence such as a B.t. gene. The sequence motif ATTTA (or AUUUA as it appears in RNA) has been implicated as a destabilizing sequence in mammalian cell mRNA (Shaw and Kamen, 1986). No analysis of the function of this sequence in plants has been done. Many short lived mRNAs have A+T rich 3' untranslated regions, and these regions often have the ATTTA sequence, sometimes present in multiple copies or as multimers (e.g., ATTTATTTA . . . ). Shaw and Kamen showed that the transfer of the 3' end of an unstable mRNA to a stable RNA (globin or VA1) decreased the stable RNA's half life dramatically. They further showed that a pentamer of ATTTA had a profound destabilizing effect on a stable message, and that this signal could exert its effect whether it was located at the 3' end or within the coding sequence. However, the number of ATTTA sequences and/or the sequence context in which they occur also appear to be important in determining whether they function as destabilizing sequences. Shaw and Kamen showed that a trimer of ATTTA had much less effect than a pentamer on mRNA stability and a dimer or a monomer had no effect on stability (Shaw and Kamen, 1987). Note that multimers of ATTTA such as a pentamer automatically create an A+T rich region. This was shown to be a cytoplasmic effect, not nuclear. In other unstable mRNAs, the ATTTA sequence may be present in only a single copy, but it is often contained in an A+T rich region. From the animal cell data collected to date, it appears that ATTTA at least in some contexts is important in stability, but it is not yet possible to predict which occurrences of ATTTA are destabilizing elements or whether any of these effects are likely to be seen in plants.

Some studies on mRNA degradation in animal cells also indicate that RNA degradation may begin in some cases with nucleotlytic attack in A+T rich regions. It is not clear if these cleavages occur at ATTTA sequences. There are also examples of mRNAs that have differential stability depending on the cell type in which they are expressed or on the stage within the cell cycle at which they are expressed. For example, histone mRNAs are stable during DNA synthesis but unstable if DNA synthesis is disrupted. The 3' end of some histone mRNAs seems to be responsible for this effect (Pandey and Marzluff, 1987). It does not appear to be mediated by ATTTA, nor is it clear what controls the differential stability of this mRNA. Another example is the differential stability of IgG mRNA in B lymphocytes during B cell maturation (Genovese and Milcarek, 1988). A final example is the instability of a mutant beta-thallesemic globin mRNA. In bone marrow cells, where this gene is normally expressed, the mutant mRNA is unstable, while the wild-type mRNA is stable. When the mutant gene is expressed in HeLa or L cells in vitro, the mutant mRNA shows no instability (Lim et al., 1988). These examples all provide evidence that mRNA stability can be mediated by cell type or cell cycle specific factors. Furthermore this type of instability is not yet associated with specific sequences. Given these uncertainties, it is not possible to predict which RNAs are likely to be unstable in a given cell. In addition, even the ATTTA motif may act differentially depending on the nature of the cell in which the RNA is present. Shaw and Kamen (1987) have reported that activation of protein kinase C can block degradation mediated by ATTTA.

The addition of a polyadenylate string to the 3' end is common to most eucaryotic mRNAs, both plant and animal. The currently accepted view of polyA addition is that the nascent transcript extends beyond the mature 3' terminus. Contained within this transcript are signals for polyadenylation and proper 3' end formation. This processing at the 3' end involves cleavage of the mRNA and addition of polyA to the mature 3' end. By searching for consensus sequences near the polyA tract in both plant and animal mRNAs, it has been possible to identify consensus sequences that apparently are involved in polyA addition and 3' end cleavage. The same consensus sequences seem to be important to both of these processes. These signals are typically a variation on the sequence AATAAA. In animal cells, some variants of this sequence that are functional have been identified; in plant cells there seems to be an extended range of functional sequences (Wickens and Stephenson, 1984; Dean et al., 1986). Because all of these consensus sequences are variations on AATAAA, they all are A+T rich sequences. This sequence is typically found 15 to 20 bp before the polyA tract in a mature mRNA. Experiments in animal cells indicate that this sequence is involved in both polyA addition and 3' maturation. Site directed mutations in this sequence can disrupt these functions (Conway and Wickens, 1988; Wickens et al., 1987). However, it has also been observed that sequences up to 50 to 100 bp 3' to the putative polyA signal are also required; i.e., a gene that has a normal AATAAA but has been replaced or disrupted downstream does not get properly polyadenylated (Gil and Proudfoot, 1984; Sadofsky and Alwine, 1984; McDevitt et al., 1984). That is, the polyA signal itself is not sufficient for complete and proper processing. It is not yet known what specific downstream sequences are required in addition to the polyA signal, or if there is a specific sequence that has this function. Therefore, sequence analysis can only identify potential polyA signals.

In naturally occurring mRNAs that are normally polyadenylated, it has been observed that disruption of this process, either by altering the polyA signal or other sequences in the mRNA, profound effects can be obtained in the level of functional mRNA. This has been observed in several naturally occurring mRNAs, with results that are gene specific so far. There are no general rules that can be derived yet from the study of mutants of these natural genes, and no rules that can be applied to heterologous genes. Below are four examples:

1. In a globin gene, absence of a proper polyA site leads to improper termination of transcription. It is likely, but not proven, that the improperly terminated RNA is nonfunctional and unstable (Proudfoot et al., 1987).

2. In a globin gene, absence of a functional polyA signal can lead to a 100-fold decrease in the level of mRNA accumulation (Proudfoot et al., 1987).

3. A globin gene polyA site was placed into the 3' ends of two different histone genes. The histone genes contain a secondary structure (stem-loop) near their 3' ends. The amount of properly polyadenylated histone mRNA produced from these chimeras decreased as the distance between the stem-loop and the polyA site increased. Also, the two histone genes produced greatly different levels of properly polyadenylated mRNA. This suggests an interaction between the polyA site and other sequences on the mRNA that can modulate mRNA accumulation (Pandy and Marzluff, 1987).

4. The soybean leghemoglobin gene has been cloned into HeLa cells, and it has been determined that this plant gene contains a "cryptic" polyadenylation signal that is active in animal cells, but is not utilized in plant cells. This leads to the production of a new polyadenylated mRNA that is nonfunctional. This again shows that analysis of a gene in one cell type cannot predict its behavior in alternative cell types (Wiebauer et al., 1988).

From these examples, it is clear that in natural mRNAs proper polyadenylation is important in mRNA accumulation, and that disruption of this process can effect mRNA levels significantly. However, insufficient knowledge exists to predict the effect of changes in a normal gene. In a heterologous gene, where we do not know if the putative polyA sites (consensus sequences) are functional, it is even harder to predict the consequences. However, it is possible that the putative sites identified are disfunctional. That is, these sites may not act as proper polyA sites, but instead function as aberrant sites that give rise to unstable mRNAs.

In animal cell systems, AATAAA is by far the most common signal identified in mRNAs upstream of the polyA, but at least four variants have also been found (Wickens and Stephenson, 1984). In plants, not nearly so much analysis has been done, but it is clear that multiple sequences similar to AATAAA can be used. The plant sites below called major or minor refer only to the study of Dean et al. (1986) which analyzed only three types of plant gene. The designation of polyadenylation sites as major or minor refers only to the frequency of their occurrence as functional sites in naturally occurring genes that have been analyzed. In the case of plants this is a very limited database. It is hard to predict with any certainty that a site designated major or minor is more or less likely to function partially or completely when found in a heterologous gene such as B.t.

| | | |
|---|---|---|
| PA | AATAAA | Major consensus site |
| P1A | AATAAT | Major plant site |
| P2A | AACCAA | Minor plant site |
| P3A | ATATAA | " |
| P4A | AATCAA | " |
| P5A | ATACTA | " |
| P6A | ATAAAA | " |
| P7A | ATGAAA | " |
| P8A | AAGCAT | " |
| P9A | ATTAAT | " |
| P10A | ATACAT | " |
| P11A | AAAATA | " |
| P12A | ATTAAA | Minor animal site |
| P13A | AATTAA | " |
| P14A | AATACA | " |
| P15A | CATAAA | " |

Another type of RNA processing that occurs in the nucleus is intron splicing. Nearly all of the work on intron processing has been done in animal cells, but some data is emerging from plants. Intron processing depends on proper 5' and 3' splice junction sequences. Consensus sequences for these junctions have been derived for both animal and plant mRNAs, but only a few nucleotides are known to be invariant. Therefore, it is hard to predict with any certainty whether a putative splice junction is functional or partially functional based solely on sequence analysis. In particular, the only invariant nucleotides are GT at the 5' end of the intron and AG at the 3' end of the intron. In plants, at every nearby position, either within the intron or in the exon flanking the intron, all four nucleotides can be found, although some positions show some nucleotide preference (Brown, 1986; Hanley and Schuler, 1988).

A plant intron has been moved from a patatin gene into a GUS gene. To do this, site directed mutagenesis was performed to introduce new restriction sites, and this mutagenesis changed several nucleotides in the intron and exon sequences flanking the GT and AG. This intron still functioned properly, indicating the importance of the GT and AG and the flexibility at other nucleotide positions. There are of course many occurrences of GT and AG in all genes that do not function as intron splice junctions, so there must be some other sequence or structural features that identify splice junctions. In plants, one such feature appears to be base composition per se. Wiebauer et al. (1988) and Goodall et al. (1988) have analyzed plant introns and exons and found that exons have ~50% A+T while introns have ~70% A+T. Goodall et al. (1988) also created an artificial plant intron that has consensus 5' and 3' splice junctions and a random A+T rich internal sequence. This intron was spliced correctly in plants. When the internal segment was replaced by a G+C rich sequence, splicing efficiency was drastically reduced. These two examples demonstrate that intron recognition in plants may depend on very general features—splice junctions that have a great deal of sequence diversity and A+T richness of the intron itself. This, of course, makes it difficult to predict from sequence alone whether any particular sequence is likely to function as an active or partially active intron for RNA processing.

B.t. genes being A+T rich contain numerous stretches of various lengths that have 70% or greater A+T. The number of such stretches identified by sequence analysis depends on the length of sequence scanned.

As for polyadenylation described above, there are complications in predicting what sequences might be utilized as splice sites in any given gene. First, many naturally occurring genes have alternative splicing pathways that create alternative combinations of exons in the final mRNA (Gallega and Nadal-Ginard, 1988; Helfman and Ricci, 1988; Tsurushita and Korn, 1989). That is, some splice junctions are apparently recognized under some circumstances or in certain cell types, but not in others. The rules governing this are not understood. In addition, there can be an interaction between processing paths such that utilization of a particular polyadenylation site can interfere with splicing at a nearby splice site and vice versa (Adami and Nevins, 1988; Brady and Wold, 1988; Marzluff and Pandey, 1988). Again no predictive rules are available. Also, sequence changes in a gene can drastically alter the utilization of particular splice junctions. For example, in a bovine growth hormone gene, small deletions in an exon a few hundred bases downstream of an intron cause the splicing efficiency of the intron to drop from greater than 95% to less than 2% (essentially nonfunctional). Other deletions however have essentially no effect (Hampson and Rottman, 1988). Finally, a variety of in vitro and in vivo experiments indicate that mutations that disrupt normal splicing lead to rapid degradation of the RNA in the nucleus. Splicing is a multistep process in the nucleus and mutations in normal splicing can lead to blockades in the process at a variety of steps. Any of these blockades can then lead to an abnormal and unstable RNA. Studies of mutants of normally processed (polyadenylation and splicing) genes are relevant to the study of heterologous genes such as B.t. B.t. genes might contain functional signals that lead to the production of aberrant nonfunctional mRNAs, and these mRNAs are likely to be unstable. But the B.t. genes are perhaps even more likely to contain signals that are analogous to mutant signals in a natural gene. As shown above these mutant signals are very likely to cause defects in the processing pathways whose consequence is to produce unstable mRNAs.

It is not known with any certainty what signals RNA transcription termination in plant or animal cells. Some studies on animal genes that indicate that stretches of sequence rich in T cause termination by calf thymus RNA polymerase II in vitro. These studies have shown that the 3' ends of in vitro terminated transcripts often lie within runs of T such as T5, T6 or T7. Other identified sites have not been composed solely of T, but have had one or more other nucleotides as well. Termination has been found to occur within the sequences TATTTTTT, ATTCTC, TTCTT (Dedrick et al., 1987; Reines et al., 1987). In the case of these latter two, the context in which the sequence is found has been C+T rich as well. It is not known if this is essential. Other studies have implicated stretches of A as potential transcriptional terminators. An interesting example from SV40 illustrates the uncertainty in defining terminators based on sequence alone. One potential terminator in SV40 was identified as being A rich and having a region of dyad symmetry (potential stem-loop) 5' to the A rich stretch. However, a second terminator identified experimentally downstream in the same gene was not A rich and included no potential secondary structure (Kessler et al., 1988). Of course, due to the A+T content of B.t. genes, they are rich in runs of A or T that could act as terminators. The importance of termination to stability of the mRNA is shown by the globin gene example described above. Absence of a normal polyA site leads to a failure in proper termination with a consequent decrease in mRNA.

There is also an effect on mRNA stability due the translation of the mRNA. Premature translational termination in human triose phosphate isomerase leads to instability of the mRNA (Daar et al., 1988). Another example is the beta-thallesemic globin mRNA described above that is specifically unstable in bone marrow cells (Lim et al., 1988). The defect in this mutant gene is a single base pair deletion at codon 44 that leads to translational termination (a nonsense codon) at codon 60. Compared to properly translated normal globin mRNA, this mutant RNA is very unstable. These results indicate that an improperly translated mRNA is unstable. Other work in yeast indicates that proper but poor translation can have an effect on mRNA levels. A heterologous gene was modified to convert certain codons to more yeast preferred codons. An overall 10-fold increase in protein production was achieved, but there was also about a 3-fold increase in mRNA Hoekema et al., 1987). This indicates that more efficient translation can lead to greater mRNA stability, and that the effect of codon usage can be at the RNA level as well as the translational level. It is not clear from codon usage studies which codons lead to poor translation, or how this is coupled to mRNA stability.

Therefore, it is an object of the present invention to provide a method for preparing synthetic plant genes which express their respective proteins at relatively high levels when compared to wild-type genes. It is yet another object of the present invention to provide synthetic plant genes which express the crystal protein toxin of *Bacillus thuringiensis* at relatively high levels.

BRIEF DESCRIPTION OF THE DRAWINGS

FIGS. 2A-2C illustrate a comparison of the changes in the modified B.t.k. HD-1 sequence of Example 1 (lower line (SEQ ID NO:1)) versus the wild-type sequence of B.t.k. HD-1 (Cry1Ab) which encodes the crystal protein toxin (upper line (SEQ ID NO:2)).

FIGS. 3A-3C illustrate a comparison of the changes in the synthetic B.t.k. HD-1 sequence of Example 2 (lower line (SEQ ID NO:3)) versus the wild-type sequence of B.t.k. HD-1 (Cry1Ab) which encodes the crystal protein toxin (upper line (SEQ ID NO:4)).

FIGS. 4A-4C illustrate a comparison of the changes in the synthetic B.t.k. HD-73 (Cry1Ac/Cry1Ab hybrid) sequence of Example 3 (lower line (SEQ ID NO:5)) versus the wild-type sequence of B.t.k. HD-73 (upper line (SEQ ID NO:6)).

FIGS. 8A-8C illustrate a comparison of the changes in the synthetic truncated B.t.k. HD-73 gene (Amino acids 29-615 with an N-terminal Met-Ala) of Example 3 (lower line (SEQ ID NO:7)) versus the wild-type sequence of B.t.k. HD-73 (upper line (SEQ ID NO:8)).

FIGS. 9A-9E illustrate a comparison of the changes in the synthetic/wild-type full length B.t.k. HD-73 sequence of Example 3 (lower line (SEQ ID NO:9)) versus the wild-type full-length sequence of B.t.k. HD-73 (upper line (SEQ ID NO:10)).

FIGS. 10A-10E illustrate a comparison of the changes in the synthetic/modified full length B.t.k. HD-73 sequence of Example 3 (lower line (SEQ ID NO:11)) versus the wild-type full-length sequence of B.t.k. HD-73 (upper line (SEQ ID NO:10)).

FIGS. 11A-11E illustrate a comparison of the changes in the fully synthetic full-length B.t.k. HD-73 sequence of Example 3 (lower line (SEQ ID NO:12)) versus the wild-type full-length sequence of B.t.k. HD-73 (upper line (SEQ ID NO:10)).

FIGS. 12A-12C illustrate a comparison of the changes in the synthetic B.t.t. sequence of Example 5 (lower line (SEQ ID NO:14)) versus the wild-type sequence of B.t.t. which encodes the crystal protein toxin (Cry3Aa) (upper line (SEQ ID NO:15)).

FIGS. 13A-13C illustrate a comparison of the changes in the synthetic B.t. P2 sequence of Example 6 (lower line (SEQ ID NO:16)) versus the wild-type sequence of B.t.k. HD-1 which encodes the P2 protein toxin (Cry2Aa) (upper line (SEQ ID NO:17)).

FIGS. 14A-14E illustrate a comparison of the changes in the synthetic *B.t. entomocidus* sequence of Example 7 (lower line (SEQ ID NO:18)) versus the wild-type sequence of *B.t. entomocidus* which encodes the Btent protein toxin (Cry1Ca) (upper line (SEQ ID NO:19)).

FIGS. 16A-16B illustrate a comparison of the changes in the synthetic potato leaf roll virus (PLRV) coat protein sequence of Example 9 (lower line (SEQ ID NO:20)) versus the wild-type coat protein sequence of PLRV (upper line (SEQ ID NO:21)).

STATEMENT OF THE INVENTION

Figure 1A:
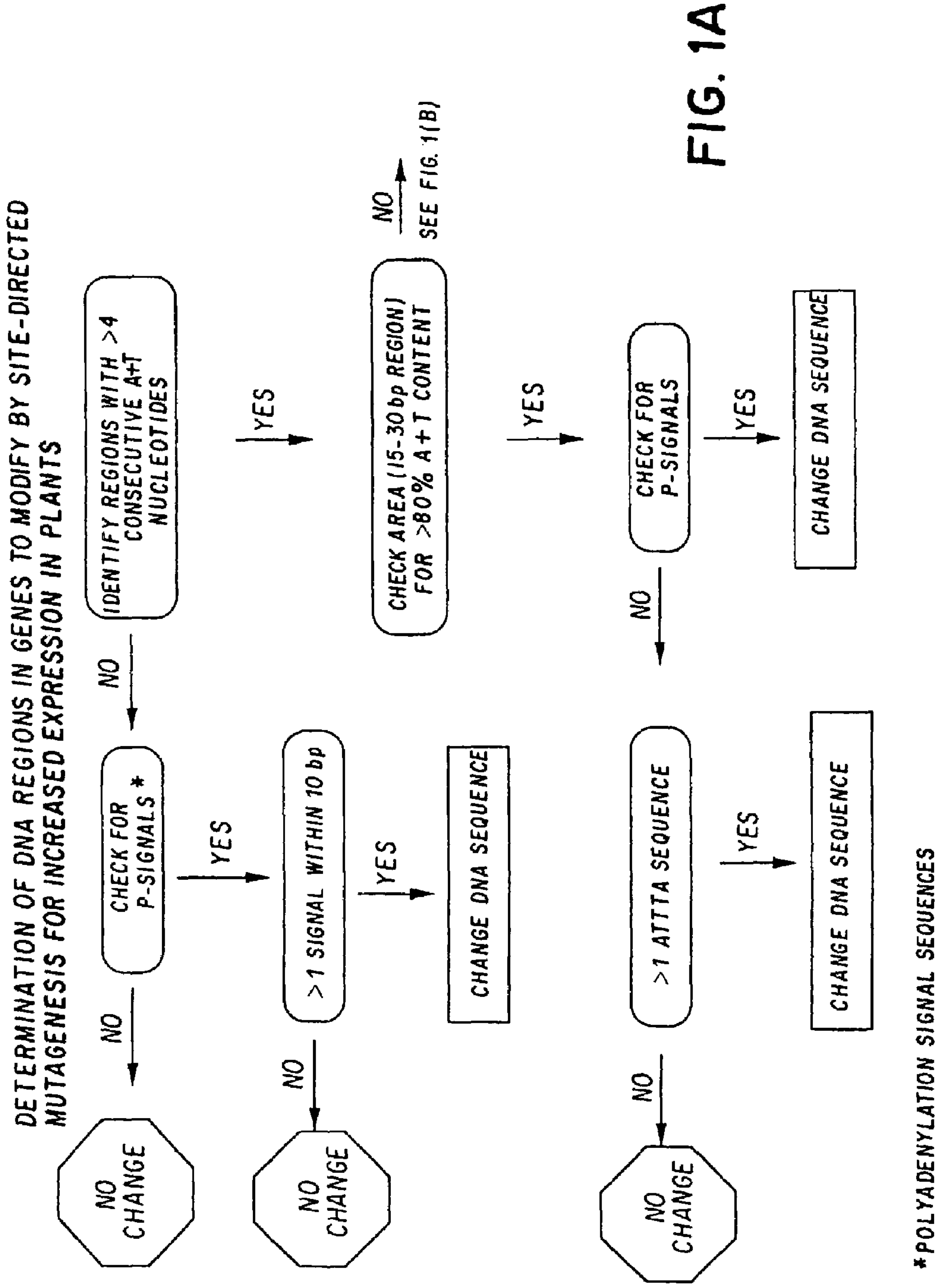
FIGS. 1A and 1B illustrate the steps employed in modifying a wild-type gene to increase expression efficiency in plants.

The present invention provides a method for preparing synthetic plant genes which genes express their protein product at levels significantly higher than the wild-type genes which were commonly employed in plant transformation heretofore. In another aspect, the present invention also provides novel synthetic plant genes which encode non-plant proteins.

For brevity and clarity of description, the present invention will be primarily described with respect to the preparation of synthetic plant genes which encode the crystal protein toxin of *Bacillus thuringiensis* (B.t.). Suitable B.t. subspecies include, but are not limited to, *B.t. kurstaki* HD-1, *B.t. kurstaki* HD-73, *B.t. sotto, B.t. berliner, B.t. thuringiensis, B.t. tolworthi, B.t. dendrolimus, B.t. alesti, B.t. galleriae, B.t. aizawai, B.t. subtoxicus, B.t. entomocidus, B.t. tenebrionis* and *B.t. san diego*. However, those skilled in the art will recognize and it should be understood that the present method may be used to prepare synthetic plant genes which encode non-plant proteins other than the crystal protein toxin of B.t. as well as plant proteins (see for instance, Example 9).

The expression of B.t. genes in plants is problematic. Although the expression of B.t. genes in plants at insecticidal levels has been reported, this accomplishment has not been straightforward. In particular, the expression of a full-length lepidopteran specific B.t. gene (comprising DNA from a B.t.k. isolate) has been reported to be unsuccessful in yielding insecticidal levels of expression in some plant species (Vaeck et al., 1987 and Barton et al., 1987).

It has been reported that expression of the full-length gene from B.t.k. HD-1 was detectable in tomato plants but that truncated genes led to a higher frequency of insecticidal plants with an overall higher level of expression. Truncated genes of *B.t. berliner* also led to a higher frequency of insecticidal plants in tobacco (Vaeck et al., 1987). On the other hand, insecticidal plants were provided from lettuce transformants using a full-length gene.

It has also been reported that the full length gene from B.t.k. HD-73 gave some insecticidal effect in tobacco (Adang et al., 1987). However, the B.t. mRNA detected in these plants was only 1.7 kb compared to the expected 3.7 kb indicating improper expression of the gene. It was suggested that this truncated mRNA was too short to encode a functional truncated toxin, but there must have been a low level of longer mRNA in some plants or no insecticidal activity would have been observed. Others have reported in a publication that they observed a large amount of shorter than expected mRNA from a truncated B.t.k. gene, but some mRNA of the expected size was also observed. In fact, it was suggested that expression of the full length gene is toxic to tobacco callus (Barton et al., 1987). The above illustrates that lepidopteran type B.t. genes are poorly expressed in plants compared to other chimeric genes previously expressed from the same promoter cassettes.

The expression of B.t.t. in tomato and potato is at levels similar to that of B.t.k. (i.e., poor). B.t.t. and B.t.k. genes share only limited sequence homology, but they share many common features in terms of base composition and the presence of particular A+T rich elements.

All reports in the field have noted the lower than expected expression of B.t. genes in plants. In general, insecticidal efficacy has been measured using insects very sensitive to B.t. toxin such as tobacco hornworm. Although it has been possible to obtain plants totally protected against tobacco hornworm, it is important to note that hornworm is up to 500 fold more sensitive to B.t. toxin than some agronomically important insect pests such as beet armyworm. It is therefore of interest to obtain transgenic plants that are protected against all important lepidopteran pests (or against Colorado potato beetle in the case of *B.t. tenebrionis*), and in addition to have a level of B.t. expression that provides an additional safety margin over and above the efficacious protection level. It is also important to devise plant genes which function reproducibly from species to species, so that insect resistant plants can be obtained in a predictable fashion.

In order to achieve these goals, it is important to understand the nature of the poorer than expected expression of B.t. genes in plants. The level of stable B.t. mRNA in plants is much lower than expected. That is, compared to other coding sequences driven by the same promoter, the level of B.t. mRNA measured by Northern analysis or nuclease protection experiments is much lower. For example, tomato plant 337 (Fischhoff et al., 1987) was selected as the best expressing plant with pMON9711 which contains the B.t.k. HD-1 KpnI fragment driven by the CaMV 35S promoter and contains the NOS-NPTII-NOS selectable marker gene. In this plant the level of B.t. mRNA is between 100 to 1000 fold lower than the level of NPTII mRNA, even though the 35S promoter is approximately 50-fold stronger than the NOS promoter (Sanders et al., 1987).

The level of B.t. toxin protein detected in plants is consistent with the low level of B.t. mRNA. Moreover, the insecticidal efficacy of the transgenic plants correlates with the B.t. protein level indicating that the toxin protein produced in plants is biologically active. Therefore, the low level of B.t. toxin expression may be the result of the low levels of B.t. mRNA.

Messenger RNA levels are determined by the rate of synthesis and rate of degradation. It is the balance between these two that determines the steady state level of mRNA. The rate of synthesis has been maximized by the use of the CaMV 35S promoter, a strong constitutive plant expressible promoter. The use of other plant promoters such as nopaline synthase (NOS), mannopine synthase (MAS) and ribulose bisphosphatecarboxylase small subunit (RUBISCO) have not led to dramatic changes in the levels of B.t. toxin protein expression indicating that the effects determining B.t. toxin protein levels are promoter independent. These data imply that the coding sequences of DNA genes encoding B.t. toxin proteins are somehow responsible for the poor expression level, and that this effect is manifested by a low level of accumulated stable mRNA.

Lower than expected levels of mRNA have been observed with four different lepidopteran specific genes (two from B.t.k. HD-1*; B.t. berliner* and B.t.k. HD-73) as well as the gene from the coleopteran specific *B.t. tenebrionis*. It appears that for lepidopteran type B.t. genes these effects are manifest more strongly in the full length coding sequences than in the truncated coding sequences. These effects are seen across plant species although their magnitude seems greater in some plant species such as tobacco.

The nature of the coding sequences of B.t. genes distinguishes them from plant genes as well as many other heterologous genes expressed in plants. In particular, B.t. genes are very rich (~62%) in adenine (A) and thymine (T) while plant genes and most bacterial genes which have been expressed in plants are on the order of 45-55% A+T. The A+T content of the genomes (and thus the genes) of any organism are features of that organism and reflect its evolutionary history. While within any one organism genes have similar A+T content, the A+T content can vary tremendously from organism to organism. For example, some *Bacillus* species have among the most A+T rich genomes while some *Steptomyces* species are among the least A+T rich genomes (~30 to 35% A+T).

Due to the degeneracy of the genetic code and the limited number of codon choices for any amino acid, most of the "excess" A+T of the structural coding sequences of some *Bacillus* species are found in the third position of the codons. That is, genes of some *Bacillus* species have A or T as the third nucleotide in many codons. Thus A+T content in part can determine codon usage bias. In addition, it is clear that genes evolve for maximum function in the organism in which they evolve. This means that particular nucleotide sequences found in a gene from one organism, where they may play no role except to code for a particular stretch of amino acids, have the potential to be recognized as gene control elements in another organism (such as transcriptional promoters or terminators, polyA addition sites, intron splice sites, or specific mRNA degradation signals). It is perhaps surprising that such misread signals are not a more common feature of heterologous gene expression, but this can be explained in part by the relatively homogeneous A+T content (~50%) of many organisms. This A+T content plus the nature of the genetic code put clear constraints on the likelihood of occurrence of any particular oligonucleotide sequence. Thus, a gene from *E. coli* with a 50% A+T content is much less likely to contain any particular A+T rich segment than a gene from *B. thuringiensis*.

As described above, the expression of B.t. toxin protein in plants has been problematic. Although the observations made in other systems described above offer the hope of a means to elevate the expression level of B.t. toxin proteins in plants, the success obtained by the present method is quite unexpected. Indeed, inasmuch as it has been recently reported that expression of the full-length B.t.k. toxin protein in tobacco makes callus tissue necrotic (Barton et al., 1987); one would reasonably expect that high level expression of B.t. toxin protein to be unattainable due to the reported toxicity effects.

In its most rigorous application, the method of the present invention involves the modification of an existing structural coding sequence ("structural gene") which codes for a particular protein by removal of ATTTA sequences and putative polyadenylation signals by site directed mutagenesis of the DNA comprising the structural gene. It is most preferred that substantially all the polyadenylation signals and ATTTA sequences are removed although enhanced expression levels are observed with only partial removal of either of the above identified sequences. Alternately if a synthetic gene is prepared which codes for the expression of the subject protein, codons are selected to avoid the ATTTA sequence and putative polyadenylation signals. For purposes of the present invention putative polyadenylation signals include, but are not necessarily limited to, AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA and CATAAA. In replacing the ATTTA sequences and polyadenylation signals, codons are preferably utilized which avoid the codons which are rarely found in plant genomes.

Figure 1B:
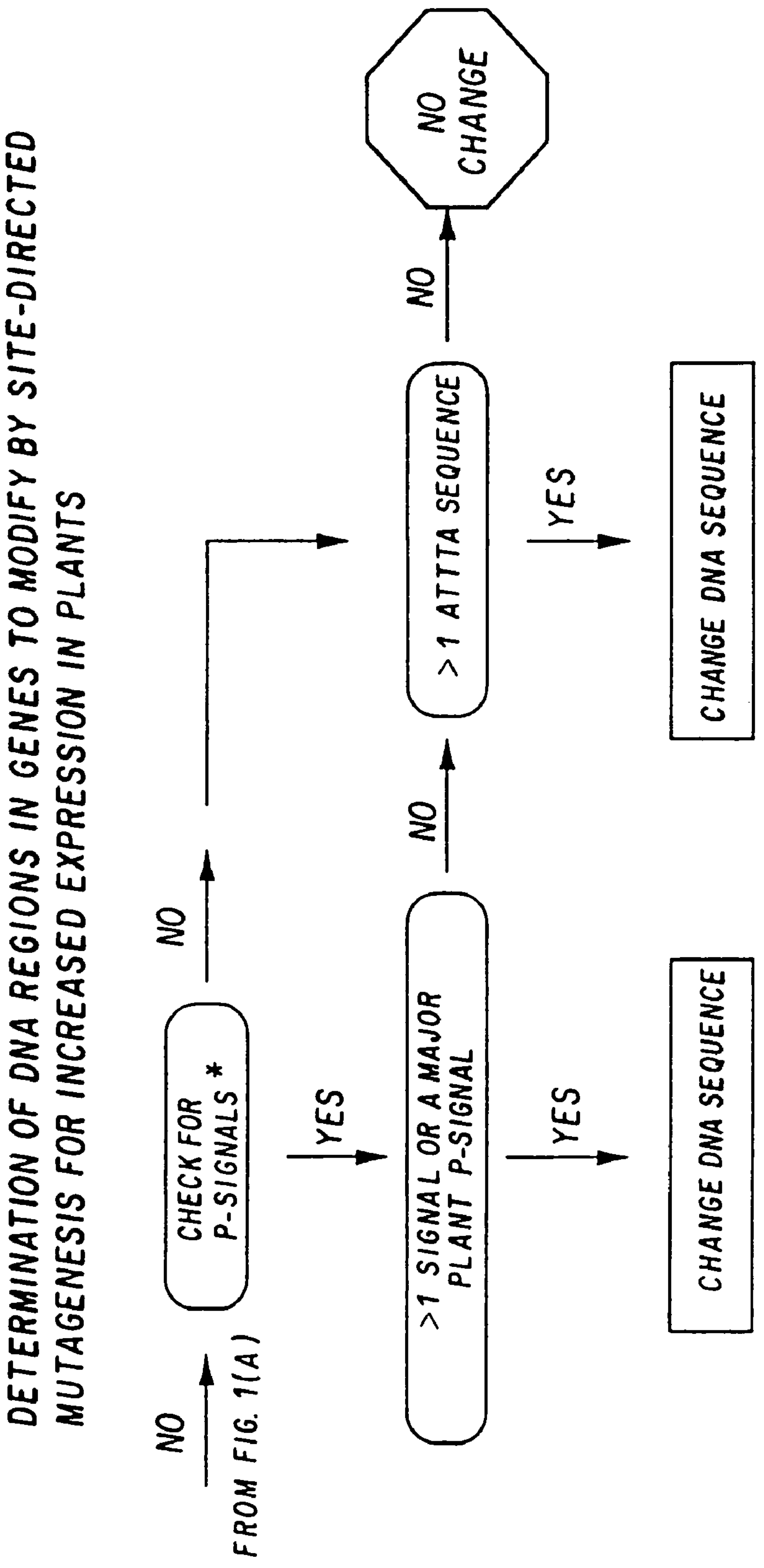

Another embodiment of the present invention, represented in the flow diagram of FIG. 1, employs a method for the modification of an existing structural gene or alternately the de novo synthesis of a structural gene which method is somewhat less rigorous than the method first described above. Referring to FIG. 1, the selected DNA sequence is scanned to identify regions with greater than four consecutive adenine (A) or thymine (T) nucleotides. The A+T regions are scanned for potential plant polyadenylation signals. Although the absence of five or more consecutive A or T nucleotides eliminates most plant polyadenylation signals, if there are more than one of the minor polyadenylation signals identified within ten nucleotides of each other, then the nucleotide sequence of this region is preferably altered to remove these signals while maintaining the original encoded amino acid sequence.

The second step is to consider the 15 to 30 nucleotide regions surrounding the A+T rich region identified in step one. If the A+T content of the surrounding region is less than 80%, the region should be examined for polyadenylation signals. Alteration of the region based on polyadenylation signals is dependent upon (1) the number of polyadenylation signals present and (2) presence of a major plant polyadenylation signal.

The extended region is examined for the presence of plant polyadenylation signals. The polyadenylation signals are removed by site-directed mutagenesis of the DNA sequence. The extended region is also examined for multiple copies of the ATTTA sequence which are also removed by mutagenesis.

It is also preferred that regions comprising many consecutive A+T bases or G+C bases are disrupted since these regions are predicted to have a higher likelihood to form hairpin structure due to self-complementarity. Therefore, insertion of heterogeneous base pairs would reduce the likelihood of self-complementary secondary structure formation which are known to inhibit transcription and/or translation in some organisms. In most cases, the adverse effects may be minimized by using sequences which do not contain more than five consecutive A+T or G+C.

A Synthetic Oligonucleotides for Mutagenesis

The oligonucleotides used in the mutagenesis are designed to maintain the proper amino acid sequence and reading frame and preferably to not introduce common restriction sites such as BglII, HindIII, SacI, KpnI, EcoRI, NcoI, PstI and SalI into the modified gene. These restriction sites are found in multilinker insertion sites of cloning vectors such as plasmids pUC118 and pMON7258. Of course, the introduction of new polyadenylation signals, ATTTA sequences or consecutive stretches of more than five A+T or G+C, should also be avoided. The preferred size for the oligonucleotides is around 40-50 bases, but fragments ranging from 18 to 100 bases have been utilized. In most cases, a minimum of 5 to 8 base pairs of homology to the template DNA on both ends of the synthesized fragment are maintained to insure proper hybridization of the primer to the template. The oligonucleotides should avoid sequences longer than five base pairs A+T or G+C. Codons used in the replacement of wild-type codons should preferably avoid the TA or CG doublet wherever possible. Codons are selected from a plant preferred codon table (such as Table I below) so as to avoid codons which are rarely found in plant genomes, and efforts should be made to select codons to preferably adjust the G+C content to about 50%.

TABLE I

Preferred Codon Usage in Plants

| Amino Acid | Codon | Percent Usage in Plants |
|---|---|---|
| ARG | CGA | 7 |
| | CGC | 11 |
| | CGG | 5 |
| | CGU | 25 |
| | AGA | 29 |
| | AGG | 23 |
| LEU | CUA | 8 |
| | CUC | 20 |
| | CUG | 10 |
| | CUU | 28 |
| | UUA | 5 |
| | UUG | 30 |
| SER | UCA | 14 |
| | UCC | 26 |
| | UCG | 3 |
| | UCU | 21 |
| | AGC | 21 |
| | AGU | 15 |
| THR | ACA | 21 |
| | ACC | 41 |
| | ACG | 7 |
| | ACU | 31 |
| PRO | CCA | 45 |
| | CCC | 19 |
| | CCG | 9 |
| | CCU | 26 |
| ALA | GCA | 23 |
| | GCC | 32 |
| | GCG | 3 |
| | GCU | 41 |
| GLY | GGA | 32 |
| | GGC | 20 |
| | GGG | 11 |
| | GGU | 37 |
| ILE | AUA | 12 |
| | AUC | 45 |
| | AUU | 43 |

TABLE I-continued

Preferred Codon Usage in Plants

| Amino Acid | Codon | Percent Usage in Plants |
|---|---|---|
| VAL | GUA | 9 |
| | GUC | 20 |
| | GUG | 28 |
| | GUU | 43 |
| LYS | AAA | 36 |
| | AAG | 64 |
| ASN | AAC | 72 |
| | AAU | 28 |
| GLN | CAA | 64 |
| | CAG | 36 |
| HIS | CAC | 65 |
| | CAU | 35 |
| GLU | GAA | 48 |
| | GAG | 52 |
| ASP | GAC | 48 |
| | GAU | 52 |
| TYR | UAC | 68 |
| | UAU | 32 |
| CYS | UGC | 78 |
| | UGU | 22 |
| PHE | UUC | 56 |
| | UUU | 44 |
| MET | AUG | 100 |
| TRP | UGG | 100 |

Regions with many consecutive A+T bases or G+C bases are predicted to have a higher likelihood to form hairpin structures due to self-complementarity. Disruption of these regions by the insertion of heterogeneous base pairs is preferred and should reduce the likelihood of the formation of self-complementary secondary structures such as hairpins which are known in some organisms to inhibit transcription (transcriptional terminators) and translation (attenuators). However, it is difficult to predict the biological effect of a potential hairpin forming region.

It is evident to those skilled in the art that while the above description is directed toward the modification of the DNA sequences of wild-type genes, the present method can be used to construct a completely synthetic gene for a given amino acid sequence. Regions with five or more consecutive A+T or G+C nucleotides should be avoided. Codons should be selected avoiding the TA and CG doublets in codons whenever possible. Codon usage can be normalized against a plant preferred codon usage table (such as Table I) and the G+C content preferably adjusted to about 50%. The resulting sequence should be examined to ensure that there are minimal putative plant polyadenylation signals and ATTTA sequences. Restriction sites found in commonly used cloning vectors are also preferably avoided. However, placement of several unique restriction sites throughout the gene is useful for analysis of gene expression or construction of gene variants.

Plant Gene Construction

The expression of a plant gene which exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region which adds polyadenylate nucleotides to the 3' end of the RNA. Transcription of DNA into mRNA is regulated by a region of DNA usually referred to as the "promoter." The promoter region contains a sequence of bases that signals RNA polymerase to associate with the DNA and to initiate the transcription of mRNA using one of the DNA strands as a template to make a corresponding strand of RNA.

A number of promoters which are active in plant cells have been described in the literature. These include the nopaline synthase (NOS) and octopine synthase (OCS) promoters (which are carried on tumor-inducing plasmids of *Agrobacterium tumefaciens*), the Cauliflower Mosaic Virus (CaMV) 19S and 35S promoters, the light-inducible promoter from the small subunit of ribulose bis-phosphate carboxylase (ssRUBISCO, a very abundant plant polypeptide) and the mannopine synthase (MAS) promoter (Velten et al. 1984 and Velten & Schell, 1985). All of these promoters have been used to create various types of DNA constructs which have been expressed in plants (see e.g., PCT publication WO84/02913 (Rogers et al., Monsanto).

Promoters which are known or are found to cause transcription of RNA in plant cells can be used in the present invention. Such promoters may be obtained from plants or plant viruses and include, but are not limited to, the CaMV35S promoter and promoters isolated from plant genes such as ssRUBISCO genes. As described below, it is preferred that the particular promoter selected should be capable of causing sufficient expression to result in the production of an effective amount of protein.

The promoters used in the DNA constructs (i.e. chimeric plant genes) of the present invention may be modified, if desired, to affect their control characteristics. For example, the CaMV35S promoter may be ligated to the portion of the ssRUBISCO gene that represses the expression of ssRUBISCO in the absence of light, to create a promoter which is active in leaves but not in roots. The resulting chimeric promoter may be used as described herein. For purposes of this description, the phrase "CaMV35S" promoter thus includes variations of CaMV35S promoter, e.g., promoters derived by means of ligation with operator regions, random or controlled mutagenesis, etc. Furthermore, the promoters may be altered to contain multiple "enhancer sequences" to assist in elevating gene expression.

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNA's, from suitable eukaryotic genes, or from a synthetic gene sequence. The present invention is not limited to constructs, as presented in the following examples. Rather, the non-translated leader sequence can be part of the 5' end of the non-translated region of the coding sequence for the virus coat protein, or part of the promoter sequence, or can be derived from an unrelated promoter or coding sequence. In any case, it is preferred that the sequence flanking the initiation site conform to the translational consensus sequence rules for enhanced translation initiation reported by Kozak (1984).

The DNA construct of the present invention also contains a modified or fully-synthetic structural coding sequence which has been changed to enhance the performance of the gene in plants. In a particular embodiment of the present invention the enhancement method has been applied to design modified and fully synthetic genes encoding the crystal toxin protein of *Bacillus thuringiensis*. The structural genes of the present invention may optionally encode a fusion protein comprising an amino-terminal chloroplast transit peptide or secretory signal sequence (see for instance, Examples 10 and 11).

The DNA construct also contains a 3' non-translated region. The 3' non-translated region contains a polyadenylation signal which functions in plants to cause the addition of polyadenylate nucleotides to the 3' end of the viral RNA. Examples of suitable 3' regions are (1) the 3' transcribed, non-translated regions containing the polyadenylation signal of *Agrobacterium* tumor-inducing (Ti) plasmid genes, such as the nopaline synthase (NOS) gene, and (2) plant genes like the soybean storage protein (7S) genes and the small subunit of the RuBP carboxylase (E9) gene. An example of a preferred 3' region is that from the 7S gene, described in greater detail in the examples below.

Plant Transformation

A chimeric plant gene containing a structural coding sequence of the present invention can be inserted into the genome of a plant by any suitable method. Suitable plants for use in the practice of the present invention include, but are not limited to, soybean, cotton, alfalfa, oilseed rape, flax, tomato, sugarbeet, sunflower, potato, tobacco, maize, rice and wheat. Suitable plant transformation vectors include those derived from a Ti plasmid of *Agrobacterium tumefaciens*, as well as those disclosed, e.g., by Herrera-Estrella (1983), Bevan (1983), Klee (1985) and EPO publication 120,516 (Schilperoort et al.). In addition to plant transformation vectors derived from the Ti or root-inducing (Ri) plasmids of *Agrobacterium*, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen.

Figure 5:
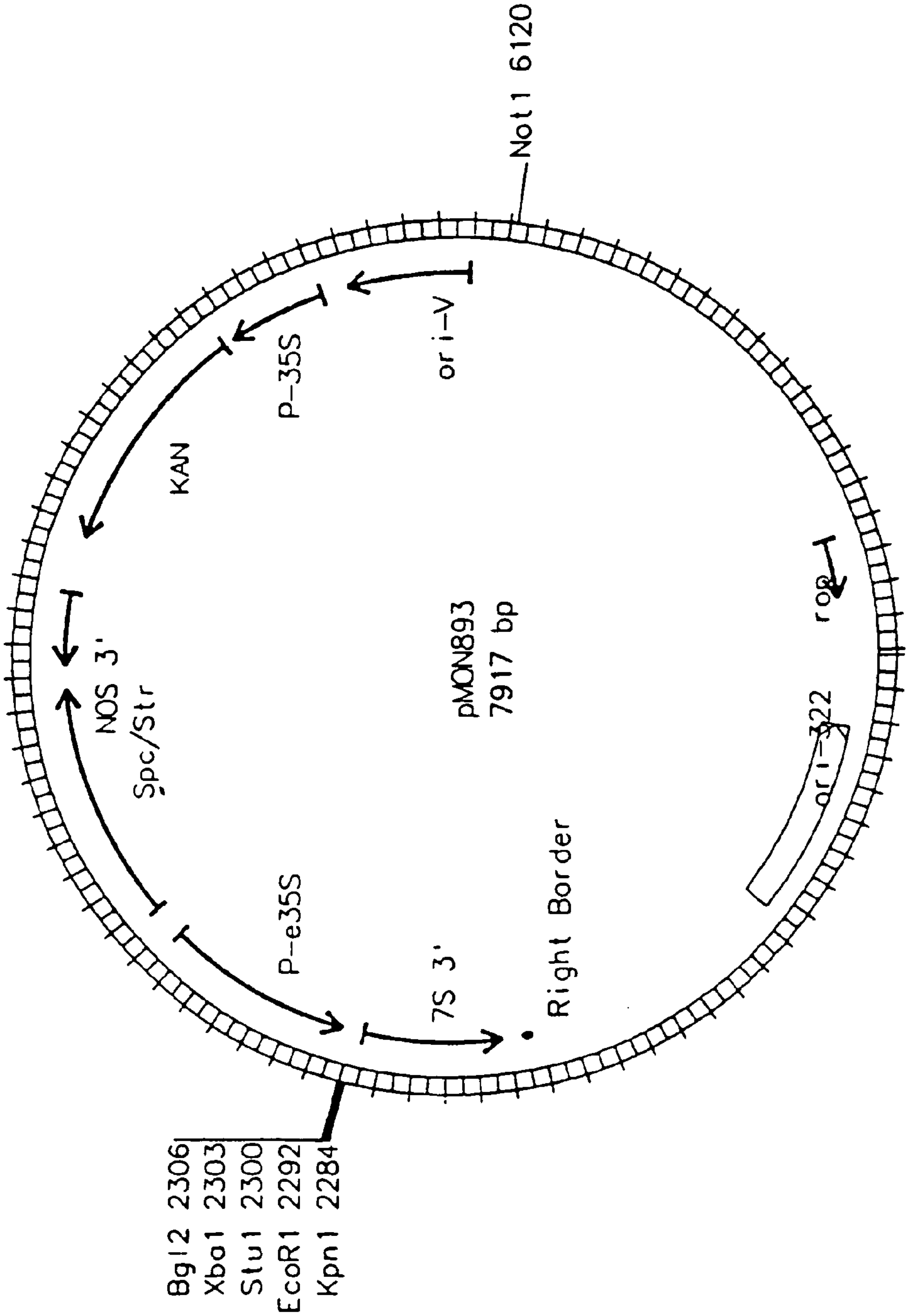
FIG. 5 represents a plasmid map of intermediate plant transformation vector cassette pMON893.

A particularly useful Ti plasmid cassette vector for transformation of dicotyledonous plants is shown in FIG. 5. Referring to FIG. 5, the expression cassette pMON893 consists of the enhanced CaMV35S promoter (EN 35S) and the 3' end including polyadenylation signals from a soybean gene encoding the alpha-prime subunit of beta-conglycinin. Between these two elements is a multilinker containing multiple restriction sites for the insertion of genes.

The enhanced CaMV35S promoter was constructed as follows. A fragment of the CaMV35S promoter extending between position −343 and +9 was previously constructed in pUC13 by Odell et al. (1985). This segment contains a region identified by Odell et al. (1985) as being necessary for maximal expression of the CaMV35S promoter. It was excised as a ClaI-HindIII fragment, made blunt ended with DNA polymerase I (Klenow fragment) and inserted into the HincII site of pUC18. This upstream region of the 35S promoter was excised from this plasmid as a HindIII-EcoRV fragment (extending from −343 to −90) and inserted into the same plasmid between the HindIII and PstI sites. The enhanced CaMV35S promoter thus contains a duplication of sequences between −343 and −90 (Kay et al., 1987).

The 3' end of the 7S gene is derived from the 7S gene contained on the clone designated 17.1 (Schuler et al., 1982). This 3' end fragment, which includes the polyadenylation signals, extends from an AvaII site located about 30 bp upstream of the termination codon for the beta-conglycinin gene in clone 17.1 to an EcoRI site located about 450 bp downstream of this termination codon.

The remainder of pMON893 contains a segment of pBR322 which provides an origin of replication in *E. coli* and a region for homologous recombination with the disarmed T-DNA in *Agrobacterium* strain ACO (described below); the oriV region from the broad host range plasmid RK1; the streptomycin/spectinomycin resistance gene from Tn7; and a chimeric NPTII gene, containing the CaMV35S promoter and the nopaline synthase (NOS) 3' end, which provides kanamycin resistance in transformed plant cells.

Figure 6:
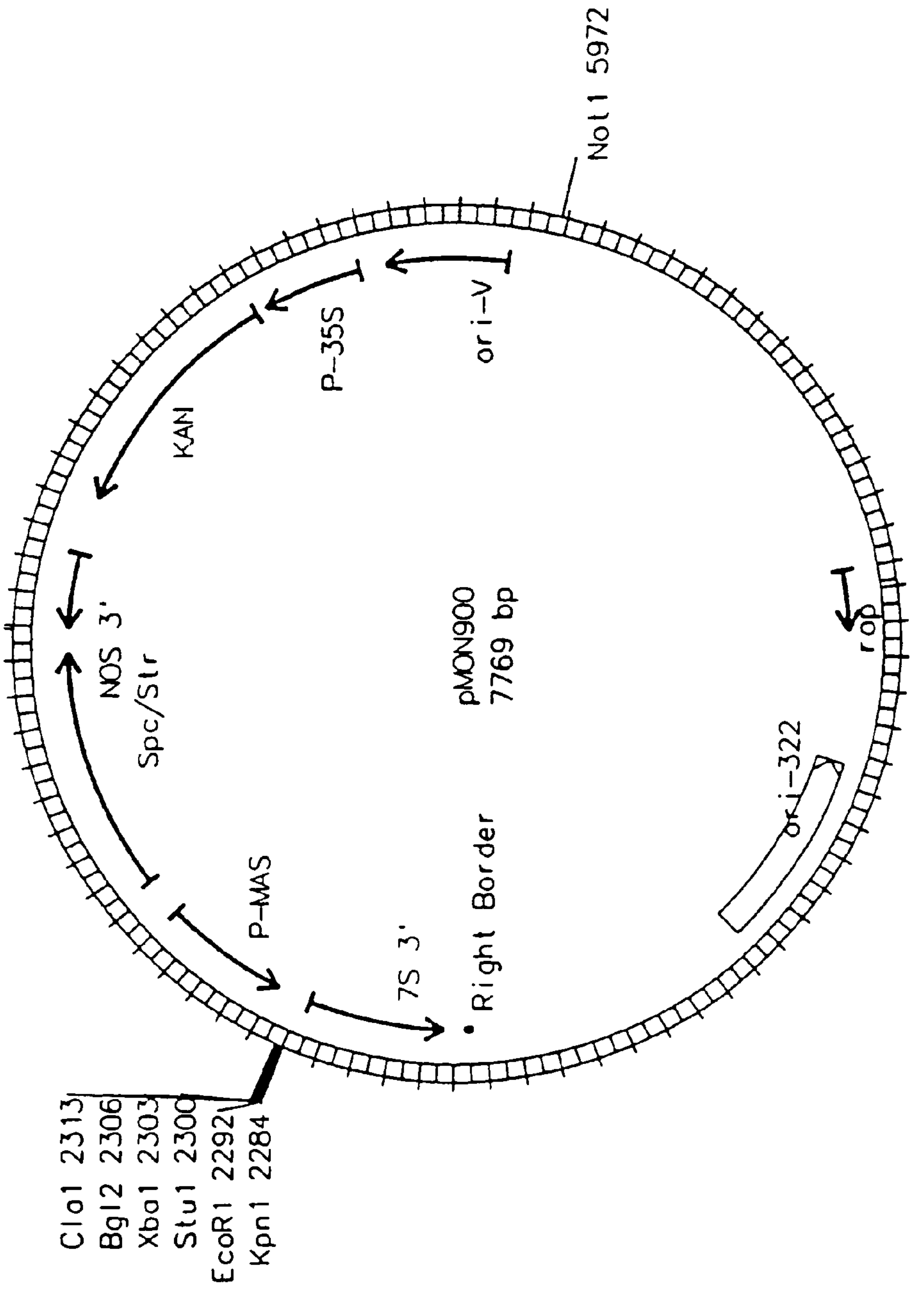
FIG. 6 represents a plasmid map of intermediate plant transformation vector cassette pMON900.

Referring to FIG. 6, transformation vector plasmid pMON900 is a derivative of pMON893. The enhanced CaMV35S promoter of pMON893 has been replaced with the 1.5 kb mannopine synthase (MAS) promoter (Velten et al. 1984). The other segments are the same as plasmid pMON893. After incorporation of a DNA construct into plasmid vector pMON893 or pMON900, the intermediate vector is introduced into *A. tumefaciens* strain ACO which contains a disarmed Ti plasmid. Cointegrate Ti plasmid vectors are selected and used to transform dicotyledonous plants.

Figure 7:
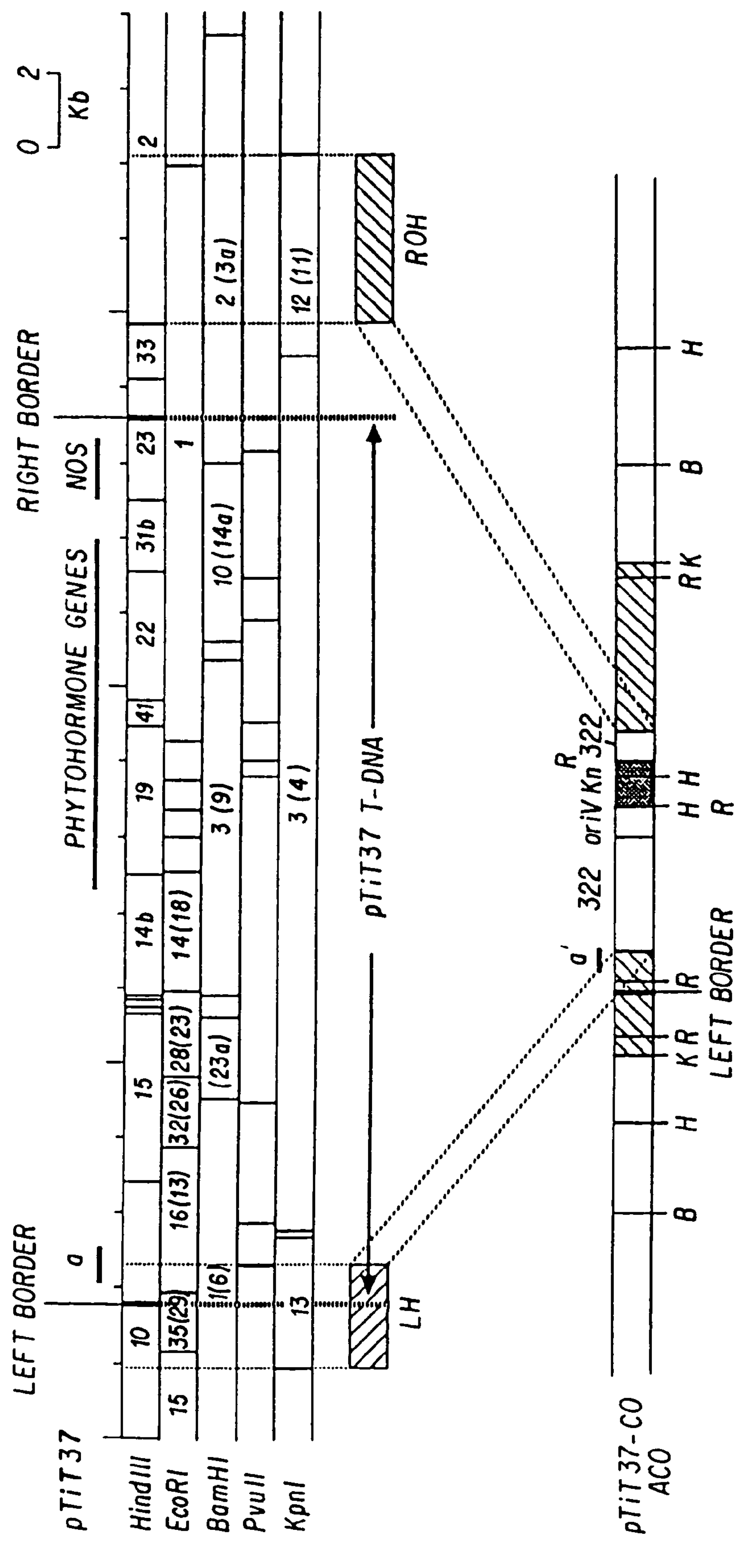
FIG. 7 represents a map for the disarmed T-DNA of *A. tumefaciens* ACO.

Referring to FIG. 7, *A. tumefaciens* ACO is a disarmed strain similar to pTiB6SE described by Fraley et al. (1985). For construction of ACO the starting *Agrobacterium* strain was the strain A208 which contains a nopaline-type Ti plasmid. The Ti plasmid was disarmed in a manner similar to that described by Fraley et al. (1985) so that essentially all of the native T-DNA was removed except for the left border and a few hundred base pairs of T-DNA inside the left border. The remainder of the T-DNA extending to a point just beyond the right border was replaced with a novel piece of DNA including (from left to right) a segment of pBR322, the oriV region from plasmid RK2, and the kanamycin resistance gene from Tn601. The pBR322 and oriV segments are similar to the segments in pMON893 and provide a region of homology for cointegrate formation.

The following examples are provided to better elucidate the practice of the present invention and should not be interpreted in any way to limit the scope of the present invention. Those skilled in the art will recognize that various modifications, truncations etc. can be made to the methods and genes described herein while not departing from the spirit and scope of the present invention.

EXAMPLE 1

Modified B.t.k. HD-1 Gene

Referring to FIG. 2, the wild-type B.t.k. HD-1 gene is known to be expressed poorly in plants as a full length gene or as a truncated gene. The G+C content of the B.t.k. gene is low (37%) containing many A+T rich regions, potential polyadenylation sites (18 sites; see Table II for the list of sequences) and numerous ATTTA sequences.

TABLE II

List of Sequences of the Potential Polyadenylation Signals

| | |
|---|---|
| AATAAA* | AAGCAT |
| AATAAT* | ATTAAT |
| AACCAA | ATACAT |
| ATATAA | AAAATA |
| AATCAA | ATTAAA** |
| ATACTA | AATTAA** |
| ATAAAA | AATACA** |
| ATGAAA | CATAAA** |

*indicates a potential major plant polyadenylation site.
**indicates a potential minor animal polyadenylation site.
All others are potential minor plant polyadenylation sites.

Table III lists the synthetic oligonucleotides designed and synthesized for the site-directed mutagenesis of the B.t.k. HD-1 gene.

TABLE III

Mutagenesis Primers for B.t.k. HD-1 Gene

| Primer | Length (bp) | Sequence |
|---|---|---|
| BTK185 (SEQ ID NO: 22) | 18 | TCCCCAGATA ATATCAAC |
| BTK240 (SEQ ID NO:23) | 48 | GGCTTGATTC CTAGCGAACT CTTCGATTCT CTGGTTGATG AGCTGTTC |
| BTK462 (SEQ ID NO:24) | 54 | CAAAACTGAG AGGTGGAGGT TGGCAGCTTG AACGTACACG GAGAGGAGAGGAAC |
| BTK669 (SEQ ID NO:25) | 48 | AGTTAGTGTA AGCTCTCTTC TGAACTGGTT GTACCTGATC CAATCTCT |
| BTK930 (SEQ ID NO:26) | 39 | AGCCATGATC TGGTGACCGG ACCAGTAGTA TTCTCCTCT |
| BTK1110 (SEQ ID NO:27) | 32 | AGTTGTTGGT TGTTGATCCC GATGTTAAAA GG |
| BTK1380A (SEQ ID NO:28) | 37 | GTGATGAAGG GATGATGTTG TTGAACTCAG CACTACG |
| BTK1380T (SEQ ID NO:29) | 100 | CAGAAGTTCC AGAGCCAAGA TTAGTAGACT TGGTGAGTGG GATTTGGGTG ATTTGTGATG AAGGGATGAT GTTGTTGAAC TCAGCACTAC GATGTATCCA |
| BTK1600 (SEQ ID NO:30) | 27 | TGATGTGTGG AACTGAAGGT TTGTGGT |

The B.t.k. HD-1 gene (BglII fragment from pMON9921 encoding amino acids 29-607 with a Met-Ala at the N-terminus) was cloned into pMON7258 (pUC118 derivative which contains a BglII site in the multilinker cloning region) at the BglII site resulting in pMON5342. The orientation of the B.t.k. gene was chosen so that the opposite strand (negative strand) was synthesized in filamentous phage particles for the mutagenesis. The procedure of Kunkle (1985) was used for the mutagenesis using plasmid pMON5342 as starting material.

The regions for mutagenesis were selected in the following manner. All regions of the DNA sequence of the B.t.k. gene were identified which contained five or more consecutive base pairs which were A or T. These were ranked in terms of length and highest percentage of A+T in the surrounding sequence over a 20-30 base pair region. The DNA was then analyzed for regions which might contain polyadenylation sites (see Table II above) or ATTTA sequences. Oligonucleotides were designed which maximized the elimination of A+T consecutive regions which contained one or more polyadenylation sites or ATTTA sequences. Two potential plant polyadenylation sites were rated more critical (see Table II) based on published reports. Codons were selected which increased G+C content, did not generate restriction sites for enzymes useful for cloning and assembly of the modified gene (BamHI, BglII, SacI, NcoI, EcoRV) and did not contain the doublets TA or GC which have been reported to be infrequently found in codons in plants. The oligonucleotides were at least 18 bp long ranging up to 100 base pairs and contained at least 5-8 base pairs of direct homology to native sequences at the ends of the fragments for efficient hybridization and priming in site-directed mutagenesis reactions. FIG. 2 compares the wild-type B.t.k. HD-1 gene sequence (cry1Ab: SEQ ID NO:2) with the sequence which resulted from the modifications by site-directed mutagenesis (SEQ ID NO:1).

The end result of these changes was to increase the G+C content of B.t.k. gene from 37% to 41% while also decreasing the potential plant polyadenylation sites from 18 to 7 and decreasing the ATTTA regions from 13 to 7. Specifically, the mutagenesis changes from amino (5') terminus to the carboxy (3') terminus are as follows:

BTK185 (SEQ ID NO:22) is an 18-mer used to eliminate a plant polyadenylation site in the midst of a nine base pair region of A+T.

BTK240 (SEQ ID NO:23) is a 48-mer. Seven base pairs were changed by this oligonucleotide to eliminate three potential polyadenylation sites (2 AACCAA, 1 AATTAA). Another region close to the region altered by BTK240, starting at bp 312, had a high A+T content (13 of 15 base pairs) and an ATTTA region. However, it did not contain a potential polyadenylation site and its longest string of uninterrupted A+T was seven base pairs.

BTK462 (SEQ ID NO:24) is a 54-mer introducing 13 base pair changes. The first six changes were to reduce the A+T richness of the gene by replacing wild-type codons with codons containing G and C while avoiding the CG doublet. The next seven changes made by BTK462 were used to eliminate an A+T rich region (13 of 14 base pairs were A or T) containing two ATTTA regions.

BTK669 (SEQ ID NO:25) is a 48-mer making nine individual base pair changes eliminating three possible polyadenylation sites (ATATAA, AATCAA, and AATTAA) and a single ATTTA site.

BTK930 (SEQ ID NO:26) is a 39-mer designed to increase the G+C content and to eliminate a potential polyadenylation site (AATAAT—a major site). This region did contain a nine base pair region of consecutive A+T sequence. One of the base pair changes was a G to A because a G at this position would have created a G+C rich region (CCGG(G)C). Since sequencing reactions indicate that there can be difficulties generating sequence through G+C consecutive bases, it was thought to be prudent to avoid generating potentially problematic regions even if they were problematic only in vitro.

BTK1110 (SEQ ID NO:27) is a 32-mer designed to introduce five changes in the wild-type gene. One potential site (AATAAT—a major site) was eliminated in the midst of an A+T rich region (19 of 22 base pairs).

BTK1380A (SEQ ID NO:28) and BTK1380T (SEQ ID NO:29) are responsible for 14 individual base pair changes. The first region (1380A) has 17 consecutive A+T base pairs. In this region is an ATTTA and a potential polyadenylation site (AATAAT). The 100-mer (1380T) contains all the changes dictated by 1380A. The large size of this primer was in part an experiment to determine if it was feasible to utilize large oligonucleotides for mutagenesis (over 60 bases in length). A second consideration was that the 100-mer was used to mutagenize a template which had previously been mutagenized by 1380A. The original primer ordered to mutagenize the region downstream and adjacent to 1380A did not anneal efficiently to the desired site as indicated by an inability to obtain clean sequence utilizing the primer. The large region of homology of 1380T did assure proper annealing. The extended size of 1380T was more of a convenience rather than a necessity. The second region adjacent to 1380A covered by 1380T has a high A+T content (22 of 29 bases are A or T).

BTK1600 (SEQ ID NO:30) is a 27-mer responsible for five individual base pair changes. An ATTTA region and a plant polyadenylation site were identified and the appropriate changes engineered.

A total of 62 bases were changed by site-directed mutagenesis. The G+C content increased by 55 base pairs, the potential polyadenylation sites were reduced from 18 to seven and the ATTTA sequences decreased from 13 to seven. The changes in the DNA sequence resulted in changes in 55 of the 579 codons in the truncated B.t.k. gene in pMON5342 (approximately 9.5%).

Referring to Table IV modified B.t.k. HD-1 genes were constructed that contained all of the above modifications (pMON5370) or various subsets of individual modifications. These genes were inserted into pMON893 for plant transformation and tobacco plants containing these genes were analyzed. The analysis of tobacco plants with the individual modifications was undertaken for several reasons. Expression of the wild type truncated gene in tobacco is very poor, resulting in infrequent identification of plants toxic to THW. Toxicity is defined by leaf feeding assays as at least 60% mortality of tobacco hornworm neonate larvae with a damage rating of 1 or less (scale is 0 to 4; 0 is equivalent to total protection, 4 total damage). The modified HD-1 gene (pMON5370) shows a large increase in expression (estimated to be approximately 100-fold; see Table VII) in tobacco. Therefore, increases in expression of the wild-type gene due to individual modifications would be apparently a large increase in the frequency of toxic tobacco plants and the presence of detectable B.t.k. protein. Results are shown in the following table:

TABLE IV

Relative effects of Regional Modifications within the B.t.k. Gene

| Construct | Position Modified | # of Plants | # of Toxic Plants |
|---|---|---|---|
| pMON5370 | 185, 240, 669, 930, 1110, 1380a + b, 1600 | 38 | 22 |
| pMON10707 | 185, 240, 462, 669 | 48 | 19 |
| pMON10706 | 930, 1110, 1380a + b, 1600 | 43 | 1 |
| pMON10539 | 185 | 55 | 2 |
| pMON10537 | 240 | 57 | 17 |
| pMON10540 | 185, 240 | 88 | 23 |
| pMON10705 | 462 | 47 | 1 |

The effects of each individual oligonucleotides' changes on expression did reveal some overall trends. Six different constructs were generated which were designed to identify the key regions. The nine different oligonucleotides were divided in half by their position on the gene. Changes in the N-terminal half were incorporated into pMON10707 (185, 240, 462,669). C-terminal half changes were incorporated into pMON10706 (930,1110,1380a+b,1600). The results of analysis of plants with these two constructs indicate that pMON10707 produces a substantial number of toxic plants (19 of 48). Protein from these plants is detectable by ELISA analysis. pMON10706 plants were rarely identified as insecticidal (1 of 43) and the levels of B.t.k. were barely detectable by immunological analysis. Investigation of the N-terminal changes in greater detail was done with 4 pMON constructs; 10539 (185 alone), 10537 (240 alone), 10540 (185 and 240) and 10705 (462 alone). The results indicate that the presence of the changes in 240 were required to generate a substantial number of toxic plants (pMON10540; 23 of 88, pMON10537; 17 of 57). The absence of the 240 changes resulted in a low frequency of toxic plants with low B.t.k. protein levels, identical to results with the wild type gene. These results indicate that the changes in 240 are responsible for a substantial increase in B.t.k. expression levels over an analogous wild-type construct in tobacco. Changes in additional regions (185,462,669) in conjunction with 240 may result in increases in B.t.k. expression (>2 fold). However, changes at the 240 region of the N-terminal portion of the gene do result in dramatic increases in expression.

Despite the importance of the alteration of the 240 region in expression of modified genes, increased expression can be achieved by alteration of other regions. Hybrid genes, part wild-type, part synthetic, were generated to determine the effects of synthetic gene segments on the levels of B.t.k. expression. A hybrid gene was generated with a synthetic N-terminal third (base pair 1 to 590 of FIG. 2: to the XbaI site) with the C-terminal wild type B.t.k. HD-1 (pMON5378) Plants transformed with this vector were as toxic as plants transformed with the modified HD-1 gene (pMON5370). This is consistent with the alteration of the 240 region. However, pMON10538, a hybrid with a wild-type N-terminal third (wild type gene for the first 600 base pairs, to the second XbaI site) and a synthetic C-terminal last two-thirds (base pair 590 to 1845 of FIG. 3 was used to transform tobacco and resulted in a dramatic increase in expression. The levels of expression do not appear to be as high as those seen with the synthetic gene, but are comparable to the modified gene levels. These results indicate that modification of the 240 segment is not essential to increased expression since pMON10538 has an intact 240 region. A fully synthetic gene is, in most cases, superior for expression levels of B.t.k. (See Example 2.)

EXAMPLE 2

Fully Synthetic B.t.k. HD-1 Gene

A synthetic B.t.k. HD-1 gene was designed using the preferred plant codons listed in Table V below. Table V lists the codons and frequency of use in plant genes of dicotyledonous plants compared to the frequency of their use in the wild type B.t.k. HD-1 gene (amino acids 1-615) and the synthetic gene of this example. The total number of each amino acid in this segment of the gene is listed in the parenthesis under the amino acid designated.

TABLE V

Codon in Usage Synthetic B.t.k. HD-1 Gene

| Amino Acid | Codon | Percent Usage in Plants/Wt B.t.k./Syn | | |
|---|---|---|---|---|
| ARG (43) | CGA | 7 | 11 | 2 |
| | CGC | 11 | 5 | 5 |
| | CGG | 5 | 2 | 0 |
| | CGU | 25 | 14 | 27 |
| | AGA | 29 | 55 | 41 |
| | AGG | 23 | 14 | 25 |
| LEU (49) | CUA | 8 | 16 | 4 |
| | CUC | 20 | 0 | 20 |
| | CUG | 10 | 2 | 6 |
| | CUU | 28 | 22 | 24 |
| | UUA | 5 | 50 | 0 |
| | UUG | 30 | 10 | 45 |
| SER (64) | UCA | 14 | 27 | 5 |
| | UCC | 26 | 9 | 28 |
| | UCG | 3 | 8 | 0 |
| | UCU | 21 | 19 | 31 |
| | AGC | 21 | 6 | 32 |
| | AGU | 15 | 31 | 5 |
| THR (42) | ACA | 21 | 31 | 14 |
| | ACC | 41 | 19 | 53 |
| | ACG | 7 | 14 | 0 |
| | ACU | 31 | 36 | 33 |
| PRO (34) | CCA | 45 | 35 | 53 |
| | CCC | 19 | 6 | 12 |
| | CCG | 9 | 21 | 3 |
| | CCU | 26 | 38 | 32 |

TABLE V-continued

Codon in Usage Synthetic B.t.k. HD-1 Gene

| Amino Acid | Codon | Percent Usage in Plants/Wt B.t.k./Syn | | |
|---|---|---|---|---|
| ALA (31) | GCA | 23 | 38 | 26 |
| | GCC | 32 | 9 | 29 |
| | GCG | 3 | 3 | 0 |
| | GCU | 41 | 50 | 45 |
| GLY (46) | GGA | 32 | 52 | 45 |
| | GGC | 20 | 17 | 15 |
| | GGG | 11 | 15 | 6 |
| | GGU | 37 | 15 | 34 |
| ILE (46) | AUA | 12 | 39 | 2 |
| | AUC | 45 | 11 | 67 |
| | AUU | 43 | 50 | 30 |
| VAL (38) | GUA | 9 | 45 | 3 |
| | GUC | 20 | 5 | 16 |
| | GUG | 28 | 11 | 37 |
| | GUU | 43 | 39 | 45 |
| LYS (3) | AAA | 36 | 100 | 33 |
| | AAG | 64 | 0 | 67 |
| ASN (44) | AAC | 72 | 27 | 80 |
| | AAU | 28 | 73 | 20 |
| GLN (31) | CAA | 64 | 77 | 61 |
| | CAG | 36 | 23 | 39 |
| HIS (10) | CAC | 65 | 0 | 80 |
| | CAU | 35 | 100 | 20 |
| GLU (30) | GAA | 48 | 87 | 50 |
| | GAG | 52 | 13 | 50 |
| ASP (23) | GAC | 48 | 17 | 65 |
| | GAU | 52 | 83 | 35 |
| TYR (25) | UAC | 68 | 20 | 72 |
| | UAU | 32 | 80 | 28 |
| CYS (2) | UGC | 78 | 50 | 100 |
| | UGU | 22 | 50 | 0 |
| PHE (36) | UUC | 56 | 17 | 83 |
| | UUU | 44 | 83 | 17 |
| MET (9) | AUG | 100 | 100 | 100 |
| TRP (9) | UGG | 100 | 100 | 100 |

The resulting synthetic gene lacks ATTTA sequences, contains only one potential polyadenylation site and has a G+C content of 48.5%. FIG. 3 is a comparison of the wild-type HD-1 sequence to the synthetic gene sequence for amino acids 1-615. There is approximately 77% DNA homology between the synthetic gene and the wild-type gene and 356 of the 615 codons have been changed (approximately 60%).

EXAMPLE 3

Synthetic B.t.k. HD-73 Gene

The crystal protein toxin from B.t.k. HD-73 exhibits a higher unit activity against some important agricultural pests. The toxin protein of HD-1 and HD-73 exhibit substantial homology (~90%) in the N-terminal 450 amino acids, but differ substantially in the amino acid region 451-615. Fusion proteins comprising amino acids 1-450 of HD-1 and 451-615 of HD-73 exhibit the insecticidal properties of the wild-type HD-73. The strategy employed was to use the 5'-two thirds of the synthetic HD-1 gene (first 1350 bases, up to the SacI site) and to dramatically modify the final 590 bases (through amino acid 645) of the HD-73 in a manner consistent with the algorithm used to design the synthetic HD-1 gene. Table VI below lists the oligonucleotides used to modify the HD-73 gene in the order used in the gene from 5' to 3' end. Nine oligonucleotides were used in a 590 base pair region, each nucleotide ranging in size from 33 to 60 bases. The only regions left unchanged were areas where there were no long consecutive strings of A or T bases (longer than six). All polyadenylation sites and ATTTA sites were eliminated.

TABLE VI

Mutagenesis Primers for B.t.k. HD-73

| Primer | Length (bp) | Sequence |
|---|---|---|
| 73K1363 (SEQ ID NO:31) | 51 | AATACTATCG GATGCGATGA TGTTGTTGAA CTCAGCACTA CGGTGTATCC A |
| 73K1437 (SEQ ID NO:32) | 33 | TCCTGAAATG ACAGAACCGT TGAAGAGAAA GTT |
| 73K1471 (SEQ ID NO:33) | 48 | ATTTCCACTG CTGTTGAGTC TAACGAGGTC TCCACCAGTG AATCCTGG |
| 73K1561 (SEQ ID NO:34) | 61 | GTGAATAGGG GTCACAGAAG CATACCTCAC ACGAACTCTA TATCTGGTAG ATGTTGGATG G |
| 73K1642 (SEQ ID NO:35) | 33 | TGTAGCTGGA ACTGTATTGG AGAAGATGGA TGA |
| 73K1675 (SEQ ID NO:36) | 48 | TTCAAAGTAA CCGAAATCGC TGGATTGGAG ATTATCCAAG GAGGTAGC |
| 73K1741 (SEQ ID NO:37) | 39 | ACTAAAGTTT CTAACACCCA CGATGTTACC GAGTGAAGA |
| 73K1797 (SEQ ID NO:38) | 36 | AACTGGAATG AACTCGAATC TGTCGATAAT CACTCC |
| 73KTERM (SEQ ID NO:39) | 54 | GGACACTAGA TCTTAGTGAT AATCGGTCAC ATTTGTCTTG AGTCCAAGCT GGTT |

The resulting gene has two potential polyadenylation sites (compared to 18 in the WT) and no ATTTA sequence (12 in the WT). The G+C content has increased from 37% to 48%. A total of 59 individual base pair changes were made using the primers in Table VI. Overall, there is 90% DNA homology between the region of the HD-73 gene modified by site directed mutagenesis and the wild-type sequence of the analogous region of HD-73. The synthetic HD-73 is a hybrid of the first 1360 bases from the synthetic HD-1 and the next 590 bases or so modified HD-73 sequence. FIG. 4 is a comparison of the above-described synthetic B.t.k. HD-73 and the wild-type B.t.k. HD-73 encoding amino acids 1-645. In the modified region of the HD-73 gene 44 of the 170 codons (25%) were changed as a result of the site-directed mutagenesis changes resulting from the oligonucleotides found in Table VI. Overall, approximately 50% of the codons in the synthetic B.t.k. HD-73 differ from the analogous segment of the wild-type and HD-73 gene.

A one base pair deletion in the synthetic HD-73 gene was detected in the course of sequencing the 3' end at base pair 1890. This results in a frame-shift mutation at amino acid 625 with a premature stop codon at amino acid 640 (pMON5379). Table VII below compares the codon usage of the wild-type gene of B.t.k. HD-73 versus the synthetic gene of this example for amino acids 451-645 and codon usage of naturally occurring genes of dicotyledonous plants. The total number of each amino acid encoded in this segment of the gene is found in the parentheses under the amino acid designation.

TABLE VII

Codon Usage in Synthetic B.t.k. HD-73 Gene

| Amino Acid | Codon | Percent Usage in Plants/Wt HD-73/Syn | | |
|---|---|---|---|---|
| ARG (10) | CGA | 7 | 10 | 0 |
| | CGC | 11 | 0 | 8 |
| | CGG | 5 | 10 | 0 |
| | CGU | 25 | 20 | 23 |
| | AGA | 29 | 60 | 62 |
| | AGG | 23 | 0 | 8 |
| LEU (12) | CUA | 8 | 25 | 8 |
| | CUC | 20 | 17 | 58 |
| | CUG | 10 | 17 | 8 |
| | CUU | 28 | 8 | 0 |
| | UUA | 5 | 33 | 8 |
| | UUG | 30 | 0 | 17 |
| SER (21) | UCA | 14 | 24 | 18 |
| | UCC | 26 | 10 | 27 |
| | UCG | 3 | 10 | 0 |
| | UCU | 21 | 24 | 18 |
| | AGC | 21 | 0 | 14 |
| | AGU | 15 | 33 | 23 |
| THR (15) | ACA | 21 | 47 | 38 |
| | ACC | 41 | 13 | 31 |
| | ACG | 7 | 13 | 0 |
| | ACU | 31 | 27 | 31 |
| PRO (7) | CCA | 45 | 71 | 71 |
| | CCC | 19 | 0 | 0 |
| | CCG | 9 | 14 | 0 |
| | CCU | 26 | 14 | 29 |
| ALA (14) | GCA | 23 | 29 | 31 |
| | GCC | 32 | 7 | 8 |
| | GCG | 3 | 21 | 15 |
| | GCU | 41 | 43 | 46 |
| GLY (15) | GGA | 32 | 33 | 43 |
| | GGC | 20 | 0 | 0 |
| | GGG | 11 | 27 | 14 |
| | GGU | 37 | 40 | 43 |
| ILE (15) | AUA | 12 | 33 | 7 |
| | AUC | 45 | 7 | 40 |
| | AUU | 43 | 60 | 53 |
| VAL (15) | GUA | 9 | 40 | 7 |
| | GUC | 20 | 0 | 7 |
| | GUG | 28 | 20 | 36 |
| | GUU | 43 | 40 | 50 |
| LYS (3) | AAA | 36 | 67 | 100 |
| | AAG | 64 | 33 | 0 |
| ASN (20) | AAC | 72 | 20 | 53 |
| | AAU | 28 | 80 | 47 |
| GLN (5) | CAA | 64 | 60 | 67 |
| | CAG | 36 | 40 | 33 |
| HIS (3) | CAC | 65 | 67 | 100 |
| | CAU | 35 | 33 | 0 |
| GLU (7) | GAA | 48 | 86 | 57 |
| | GAG | 52 | 14 | 43 |
| ASP (5) | GAC | 48 | 40 | 50 |
| | GAU | 52 | 60 | 50 |
| TYR (5) | UAC | 68 | 0 | 20 |
| | UAU | 32 | 100 | 80 |
| CYS (0) | UGC | 78 | 0 | 0 |
| | UGU | 22 | 0 | 0 |
| PHE (13) | UUC | 56 | 8 | 67 |
| | UUU | 44 | 92 | 33 |
| MET (2) | AUG | 100 | 100 | 100 |
| TRP (2) | UGG | 100 | 100 | 100 |

Another truncated synthetic HD-73 gene was constructed. The sequence of this synthetic HD-73 gene is identical to that of the above synthetic HD-73 gene in the region in which they overlap (amino acids 29-615), and it also encodes Met-Ala at the N-terminus. FIG. 8 shows a comparison of this truncated synthetic HD-73 gene with the N-terminal Met-Ala versus the wild-type HD-73 gene.

While the previous examples have been directed at the preparation of synthetic and modified genes encoding truncated B.t.k. proteins, synthetic or modified genes can also be prepared which encode full length toxin proteins.

One full length B.t.k. gene consists of the synthetic HD-73 sequence of FIG. 4 from nucleotide 1-1845 plus wild-type HD-73 sequence encoding amino acids 616 to the C-terminus of the native protein. FIG. 9 shows a comparison of this synthetic/wild-type full length HD-73 gene versus the wild-type full length HD-73 gene.

Another full length B.t.k. gene consists of the synthetic HD-73 sequence of FIG. 4 from nucleotide 1-1845 plus a modified HD-73 sequence ending amino acids 616 to the C-terminus of the native protein. The C-terminal portion has been modified by site-directed mutagenesis to remove putative polyadenylation signals and ATTTA sequences according to the algorithm of FIG. 1. FIG. 10 shows a comparison of this synthetic/modified full length HD-73 gene versus the wild-type full length HD-73 gene.

Another full length B.t.k. gene consists of a fully synthetic HD-73 sequence which incorporates the synthetic HD-73 sequence of FIG. 4 from nucleotide 1-1845 plus a synthetic sequence encoding amino acids 616 to the C-terminus of the native protein. The C-terminal synthetic portion has been designed to eliminate putative polyadenylation signals and ATTTA sequences and to include plant preferred codons. FIG. 11 shows a comparison of this fully synthetic full length HD-73 gene versus the wild-type full length HD-73 gene.

Alternatively, another full length B.t.k. gene consists of a fully synthetic sequence comprising base pairs 1-1830 of B.t.k. HD-1 (FIG. 3) and base pairs 1834-3534 of B.t.k. HD-73 (FIG. 11).

EXAMPLE 4

Expression of Modified and Synthetic B.t.k. HD-1 and Synthetic HD-73

A number of plant transformation vectors for the expression of B.t.k. genes were constructed by incorporating the structural coding sequences of the previously described genes into plant transformation cassette vector pMON893. The respective intermediate transformation vector is inserted into a suitable disarmed *Agrobacterium* vector such as *A. tumefaciens* ACO, supra. Tissue explants are cocultured with the disarmed *Agrobacterium* vector and plants regenerated under selection for kanamycin resistance using known protocols: tobacco (Horsch et al., 1985); tomato (McCormick et al., 1986) and cotton (Trolinder et al., 1987).

a) Tobacco.

The level of B.t.k. HD-1 protein in transgenic tobacco plants containing pMON9921 (wild type truncated), pMON5370 (modified HD-1, Example 1, FIG. 2) and pMON5377 (synthetic HD-1, Example 2, FIG. 3) were analyzed by Western analysis. Leaf tissue was frozen in liquid nitrogen, ground to a fine powder and then ground in a 1:2 (wt:volume) of SDS-PAGE sample buffer. Samples were frozen on dry ice, then incubated for 10 minutes in a boiling water bath and microfuged for 10 minutes. The protein concentration of the supernatant was determined by the method of Bradford (Anal. Biochem. 72:248-254). Fifty ug of protein was run per lane on 9% SDS-PAGE gels, the protein transferred to nitrocellulose and the B.t.k. HD-1 protein visualized using antibodies produced against B.t.k. HD-1 protein as the primary antibody and alkaline phosphatase conjugated second antibody as described by the manufacturer (Promega, Madison, Wis.). Purified HD-1 tryptic fragment was used as the control. Whereas the B.t.k. protein from tobacco plants containing pMON9921 was below the level of detection, the B.t.k. protein from plants containing the modified (pMON5370) and synthetic (pMON5377) genes was easily detected. The B.t.k. protein from plants containing pMON9921 remained undetectable, even with 10 fold longer incubation times. The relative levels of B.t.k. HD-1 protein in these plants is estimated in Table VIII. Because the protein from plants containing pMON9921 was not observed, the level of protein in these plants was estimated from the relative mRNA levels (see below). Plants containing the modified gene (pMON5370) expressed approximately 100 fold more B.t.k. protein than plants containing the wild-type gene (pMON9921). Plants containing the fully synthetic B.t.k. HD-1 gene (pMON5377) expressed approximately five fold more protein than plants containing the modified gene. The modified gene contributes the majority of the increase in B.t.k. expression observed. The plants used to generate the above data are the best representatives from each construct based either on a tobacco hornworm bioassay or on data derived from previous Western analysis.

TABLE VIII

Expression of B.t.k. HD-1 Protein in Transgenic Tobacco

| Gene Description | Vector | B.t.k. Protein* Concentration | Fold Increase in B.t.k. Expression |
|---|---|---|---|
| Wild type | pMON9921 | 10 | 1 |
| Modified | pMON5370 | 1000 | 100 |
| Synthetic | pMON5377 | 5000 | 500 |

*B.t.k. protein concentrations are expressed in ng/mg of total soluble protein. The level of B.t.k. protein for plants containing the wild type gene are estimated from mRNA levels.

Plants containing these genes were tested for bioactivity to determine whether the increased quantities of protein observed by Western analysis result in a corresponding increase in bioactivity. Leaves from the same plants used for the Western data in Table 1 were tested for bioactivity against two insects. A detached leaf bioassay was first done using tobacco hornworm, an extremely sensitive lepidopteran insect. Leaves from all three transgenic tobacco plants were totally protected and 100% mortality of tobacco hornworm observed (see Table IX below). A much less sensitive insect, beet armyworm, was then used in another detached leaf bioassay. Beet armyworm is approximately 500 fold less sensitive to B.t.k. HD-1 protein than tobacco hornworm. The difference in sensitivity of these two insects was determined using purified HD-1 protein in a diet incorporation assay (see below). Plants containing the wild-type gene (pMON9921) showed only minimal protection against beet armyworm, whereas plants containing the modified gene showed almost complete protection and plants containing the fully synthetic gene were totally protected against beet armyworm damage. The results of these bioassays confirm the levels of B.t.k. HD-1 expression observed in the Western analysis and demonstrates that the increased levels of B.t.k. HD-1 protein correlates with increased insecticidal activity.

TABLE IX

Protection of Tobacco Plants from Tobacco Hornworm and Beet Armyworm

| Gene Description | Vector | Tobacco Hornworm Damage* | Beet Armyworm Damage* |
|---|---|---|---|
| None | None | NL | NL |
| Wild type | pMON9921 | 0 | 3 |
| Modified | pMON5370 | 0 | 1 |
| Synthetic | pMON5377 | 0 | 0 |

*Extent of insect damage was rated: 0, no damage; 1, slight; 2, moderate; 3, severe; or NL, no leaf left.

The bioactivity of the B.t.k. HD-1 protein produced by these transgenic plants was further investigated to more accurately quantitate the relative activities. Leaf tissue from tobacco plants containing the wild-type, modified and synthetic genes were ground in 100 mM sodium carbonate buffer, pH 10 at a 1:2 (wt:vol) ratio. Particulate material was removed by centrifugation. The supernatant was incorporated into a synthetic diet similar to that described by Marrone et al. (1985). The diet medium was prepared the day of the test with the plant extract solutions incorporated in place of the 20% water component. One ml of the diet was aliquoted into 96 well plates.

After the diet dried, one neonate tobacco budworm larva was added to each well. Sixteen insects were tested with each plant sample. The plants were incubated at 27° C. After seven days, the larvae from each treatment were combined and weighed on an analytical balance. The average weight per insect was calculated and compared to a standard curve relating B.t.k. protein concentrations to average larval weight. Insect weight was inversely proportional (in a logarithmic manner) to the relative increase in B.t.k. protein concentration. The amount of B.t.k. HD-1 protein, based on the extent of larval growth inhibition was determined for two different plants containing each of the three genes. The specific activity (ng of B.t.k. HD-1 per mg of plant protein) was determined for each plant. Plants containing the modified HD-1 gene (pMON5370) averaged approximately 1400 ng (1200 and 1600 ng) of B.t.k. HD-1 per mg of plant extract protein. This value compares closely with the 1000 ng of B.t.k. HD-1 protein per mg of plant extract protein as determined by Western analysis (Table I). B.t.k. HD-1 concentrations for the plants containing the synthetic HD-1 gene averaged approximately 8200 ng (7200 and 9200 ng) of B.t.k. HD-1 protein per mg of plant extract protein. This number compares well to the 5000 ng of HD-1 protein per mg of plant extract protein estimated by Western analysis. Likewise, plants containing the synthetic gene showed approximately a six-fold higher specific activity than the corresponding plants containing the modified gene for these bioassays. In the Western analysis the ratio was approximately 10 fold, again both are in good agreement. The level of B.t.k. protein in plants containing the wild-type HD-1 gene (pMON9921) was too low to give a significant decrease in larval weight and hence was below a level that could be quantitated in this assay. In conclusion, the levels of B.t.k. HD-1 protein determined by both the bioassays and the Western analysis for these plants containing the modified and synthetic genes agree, which demonstrates that the B.t.k. HD-1 protein produced by these plants is biologically active.

The levels of mRNA were determined in the plants containing the wild-type B.t.k. HD-1 gene (pMON9921) and the modified gene (pMON5370) to establish whether the increased levels of protein production result from increased transcription or translation. mRNA from plants containing the synthetic gene could not be analyzed directly with the same DNA probe as used for the wild-type and modified genes because of the numerous changes made in the coding sequence. mRNA was isolated and hybridized with a single-stranded DNA probe homologous to approximately the 5' 90 bp of the wild-type or modified gene coding sequences. The hybrids were digested with S1 nuclease and the protected probe fragments analyzed by gel electrophoresis. Because the procedure used a large excess of probe and long hybridization time, the amount of protected probe is proportional to the amount of B.t.k. mRNA present in the sample. Two plants expressing the modified gene (pMON5370) were found to produce up to ten-fold more RNA than a plant expressing the wild-type gene (pMON9921).

The increased mRNA level from the modified gene is consistent with the result expected from the modifications introduced into this gene. However, this 10 fold increase in mRNA with the modified gene compared to the wild-type gene is in contrast to the 100 fold increase in B.t.k. protein from these genes in tobacco plants. If the two mRNAs were equally well translated then a 10 fold increase in stable mRNA would be expected to yield a 10 fold increase in protein. The higher increase in protein indicates that the modified gene mRNA is translated at about a 10 fold higher efficiency than wild-type. Thus, about half of the total effect on gene expression can be explained by changes in mRNA levels and about half to changes in translational efficiency. This increase in translational efficiency is striking in that only about 9.5% of the codons have been changed in the modified gene; that is, this effect is clearly not due to wholesale codon usage changes. The increased translational efficiency could be due to changes in mRNA secondary structure that affect translation or to the removal of specific translational blockades due to specific codons that were changed.

The increased expression seen with the synthetic HD-1 gene was also seen with a synthetic HD-73 gene in tobacco. B.t.k. HD-73 was undetected in extracts of tobacco plants containing the wild-type truncated HD-73 gene (pMON5367), whereas B.t.k. HD-73 protein was easily detected in extracts from tobacco plants containing the synthetic HD-73 gene of FIG. 4 (pMON5383). Approximately 1000 ng of B.t.k. HD-73 protein was detected per mg of total soluble plant protein.

As described in Example 3 above, the B.t.k. HD-73 protein encoded in pMON5383 contains a small C-terminal extension of amino acids not encoded in the wild-type HD-73 protein. These extra amino acids had no effect on insect toxicity or on increased plant expression. A second synthetic HD-73 gene was constructed as described in Example 3 (FIG. 8) and used to transform tobacco (pMON5390). Analysis of plants containing pMON5390 showed that this gene was expressed at levels comparable to that of pMON5383 and that these plants had similar insecticidal efficacy.

In tobacco plants the synthetic HD-1 gene was expressed at approximately a 5-fold higher level than the synthetic HD-73 gene. However, this synthetic HD-73 gene still was expressed at least 100-fold better than the wild-type HD-73 gene. The HD-73 protein is approximately 5-fold more toxic to many insect pests than the HD-1 protein, so both synthetic HD-1 and HD-73 genes provide approximately comparable insecticidal efficacy in tobacco.

The full length B.t.k. HD-73 genes described in Example 3 were also incorporated into the plant transformation vector pMON893 so that they were expressed from the En 35S promoter. The synthetic/wild-type full length HD-73 gene of FIG. 9 was incorporated into pMON893 to create pMON10506. The synthetic/modified full length HD-73 gene of FIG. 10 was incorporated into pMON893 to create pMON10526. The fully synthetic HD-73 gene of FIG. 11 was incorporated into pMON893 to create pMON10518. These vectors were used to obtain transformed tobacco plants, and the plants were analyzed for insecticidal efficacy and for B.t.k. HD-73 protein levels by Western blot or ELISA immunoassay.

Tobacco plants containing all three of these full length B.t.k. genes produced detectable B.t.k. protein and showed 100% mortality of tobacco hornworm. This result is surprising in light of previous reported attempts to express the full length B.t.k. genes in transgenic plants. Vaeck et al. (1987) reported that a full length *B.t.k. berliner* gene similar to our HD-1 gene could not be detectably expressed in tobacco. Barton et al. (1987) reported a similar result for another full length gene from B.t.k. HD-1 (the so called 4.5 kb gene), and further indicated that tobacco callus containing this gene became necrotic, indicating that the full length gene product was toxic to plant cells. Fischhoff et al. (1987) reported that the full length B.t.k. HD-1 gene in tomato was poorly expressed compared to a truncated gene, and no plants that were fully toxic to tobacco hornworm could be recovered. All three of the above reports indicated much higher expression levels and recovery of toxic plants if the respective B.t.k. genes were truncated. Adang et al. reported that the full length HD-73 gene yielded a few tobacco plants with some biological activity (none were highly toxic) against hornworm and barely detectable B.t.k. protein. It was also noted by them that the major B.t.k. mRNA in these plants was a truncated 1.7 kb species that would not encode a functional toxin. This indicated improper expression of the gene in tobacco. In contrast to all of these reports, the three full length B.t.k. HD-73 genes described above all lead to relatively high levels of protein and high levels of insect toxicity.

B.t.k. protein and mRNA levels in tobacco plants are shown in Table X for these three vectors. As can be seen from the table, the synthetic/wild-type gene (pMON10506) produces B.t.k. protein as about 0.01% of total soluble protein; the synthetic/modified gene produces B.t.k. as about 0.02% of total soluble protein; and the fully synthetic gene produces B.t.k. as about 0.2% of total soluble protein. B.t.k. mRNA was analyzed in these plants by Northern blot analysis using the common 5' synthetic half of the genes as a probe. As shown in Table X, the increased protein levels can largely be attributed to increased mRNA levels. Compared to the truncated modified and synthetic genes, this could indicate that the major contributors to increased translational efficiency are in the 51 half of the gene while the 3' half of the gene contains mostly determinants of mRNA stability. The increased protein levels also indicate that increasing the amount of the full length gene that is synthetic or modified increases B.t.k. protein levels. Compared to the truncated synthetic B.t.k. HD-73 genes (pMON5383 or pMON5390), the fully synthetic gene (pMON10518) produces as much or slightly more B.t.k. protein demonstrating that the full length genes are capable of being expressed at high levels in plants. These tobacco plants with high levels of full length HD-73 protein show no evidence of abnormality and are fully fertile. The B.t.k. protein levels in these plants also produce the expected levels of insect toxicity based on feeding studies with beet armyworm or diet incorporation assays of plant extracts with tobacco budworm. The B.t.k. protein detected by Western blot analysis in these tobacco plants often contains a varying amount of protein of about 80 kDa which is apparently a proteolytic fragment of the full length protein. The C-terminal half of the full length protein is known to be proteolytically sensitive, and similar proteolytic fragments are seen from the full length gene in *E. coli* and B.t. itself. These fragments are fully insecticidal. The Northern analysis indicated that essentially all of the mRNA from these full length genes was of the expected full length size. There is no evidence of truncated mRNAs that could give rise to the 80 kDa protein fragment. In addition, it is possible that the fragment is not present in intact plant cells and is merely due to proteolysis during extraction for immunoassay.

TABLE X

Full Length B.t.k. HD-73 Protein and mRNA Levels in Transgenic Tobacco Plants

| Gene description | Vector | B.t.k. protein concentration | Relative B.t.k. mRNA level |
|---|---|---|---|
| Synthetic/wild type | pMON10506 | >100 | 0.5 |
| Synthetic/modified | pMON10526 | 400 | 1 |
| Fully synthetic | pMON10518 | >2000 | 40 |

Thus, there is no serious impediment to producing high levels of B.t.k. HD-73 protein in plants from synthetic genes, and this is expected to be true of other full length lepidopteran active genes such as B.t.k. HD-1 or *B.t. entomocidus*. The fully synthetic B.t.k. HD-1 gene of Example 3 has been assembled in plant transformation vectors such as pMON893.

The fully synthetic gene in pMON10518 was also utilized in another plant vector and analyzed in tobacco plants. Although the CaMV35S promoter is generally a high level constitutive promoter in most plant tissues, the expression level of genes driven the CaMV35S promoter is low in floral tissue relative to the levels seen in leaf tissue. Because the economically important targets damaged by some insects are the floral parts or derived from floral parts (e.g., cotton squares and bolls, tobacco buds, tomato buds and fruit), it may be advantageous to increase the expression of B.t. protein in these tissues over that obtained with the CaMV35S promoter.

The 35S promoter of Figwort Mosaic Virus (FMV) is analogous to the CaMV35S promoter. This promoter has been isolated and engineered into a plant transformation vector analogous to pMON893. Relative to the CaMV promoter, the FMV 35S promoter is highly expressed in the floral tissue, while still providing similar high levels of gene expression in other tissues such as leaf. A plant transformation vector, pMON10517, was constructed in which the full length synthetic B.t.k. HD-73 gene of FIG. 11 was driven by the FMV 35S promoter. This vector is identical to pMON10518 of Example 3 except that the FMV promoter is substituted for the CaMV promoter. Tobacco plants transformed with pMON10517 and pMON10518 were obtained and compared for expression of the B.t.k. protein by Western blot or ELISA immunoassay in leaf and floral tissue. This analysis showed that pMON10517 containing the FMV promoter expressed the full length HD-73 protein at higher levels in floral tissue than pMON10518 containing the CaMV promoter. Expression of the full length B.t.k. HD-73 protein from pMON10517 in leaf tissue is comparable to that seen with the most highly expressing plants containing pMON10518. However, when floral tissue was analyzed, tobacco plants containing pMON10518 that had high levels of B.t.k. protein in leaf tissue did not have detectable B.t.k. protein in the flowers. On the other hand, flowers of tobacco plants containing pMON10517 had levels of B.t.k. protein nearly as high as the levels in leaves at approximately 0.05% of total soluble protein. This analysis showed that the FMV promoter could be used to produce relatively high levels of B.t.k. protein in floral tissue compared to the CaMV promoter.

b) Tomato.

The wild-type, modified and synthetic B.t.k. HD-1 genes tested in tobacco were introduced into other plants to demonstrate the broad utility of this invention. Transgenic tomatoes were produced which contain these three genes. Data show that the increased expression observed with the modified and synthetic gene in tobacco also extends to tomato. Whereas the B.t.k. HD-1 protein is only barely detectable in plants containing the wild type HD-1 gene (pMON9921), B.t.k. HD-1 was readily detected and the levels determined for plants containing the modified (pMON5370) or synthetic (pMON5377) genes. Expression levels for the plants containing the wild-type, modified and synthetic HD-1 genes were approximately 10, 100 and 500 ng per mg of total plant extract see Table XI below). The increase in B.t.k. HD-1 protein for the modified gene accounted for the majority of increase observed; 10 fold higher than the plants containing the wild-type gene, compared to only an additional five-fold increase for plants containing the synthetic gene. Again the site-directed changes made in the modified gene are the major contributors to the increased expression of B.t.k. HD-1.

TABLE XI

B.t.k. HD-1 Expression in Transgenic Tomato Plants

| Gene Description | Vector | B.t.k. Protein* Concentration | Fold Increase in B.t.k. Expression |
|---|---|---|---|
| Wild type | pMON9921 | 10 | 1 |
| Modified | pMON5370 | 100 | 10 |
| Synthetic | pMON5377 | 500 | 50 |

*B.t.k. HD-1 protein concentrations are expressed in ng/mg of total soluble plant protein. Data for plants containing the wild-type gene are estimates from mRNA levels and protein levels determined by ELISA.

These differences in B.t.k. HD-1 expression were confirmed with bioassays against tobacco hornworm and beet armyworm. Leaves from tomato plants containing each of these genes controlled tobacco hornworm damage and produced 100% mortality. With beet armyworm, leaves from plants containing the wild-type HD-1 gene (pMON9921) showed significant damage, leaves from plants containing the modified gene (pMON5370) showed less damage and leaves from plants containing the synthetic gene (pMON5377) were completely protected (see Table XII below).

TABLE XII

Protection of Tomato Plants from Tobacco Hornworm and Beet Armyworm

| Gene Description | Vector | Tobacco Hornworm Damage* | Beet Armyworm Damage* |
|---|---|---|---|
| None | None | NL | NL |
| Wild type | pMON9921 | 0 | 3 |
| Modified | pMON5370 | 0 | 1 |
| Synthetic | pMON5377 | 0 | 0 |

*Damage was rated as shown in Table IX.

The generality of the synthetic gene approach was extended in tomato with a synthetic B.t.k. HD-73 gene.

In tomato, extracts from plants containing the wild-type truncated HD-73 gene (pMON5367) showed no detectable HD-73 protein. Extracts from plants containing the synthetic HD-73 gene (pMON5383) showed high levels of B.t.k. HD-73 protein, approximately 2000 ng per mg of plant extract protein. These data clearly demonstrate that the changes made in the synthetic HD-73 gene lead to dramatic increases in the expression of the HD-73 protein in tomato as well as in tobacco In contrast to tobacco, the synthetic HD-73 gene in tomato is expressed at approximately 4-fold to 5-fold higher levels than the synthetic HD-1 gene. Because the HD-73 protein is about 5-fold more active than the HD-1 protein against many insect pests including *Heliothis* species, the increased expression of synthetic HD-73 compared to synthetic HD-1 corresponds to about a 25-fold increased insecticidal efficacy in tomato.

In order to determine the mechanisms involved in the increased expression of modified and synthetic B.t.k. HD-1 genes in tomato, S1 nuclease analysis of mRNA levels from transformed tomato plants was performed. As indicated above, a similar analysis had been performed with tobacco plants, and this analysis showed that the modified gene produced up to 10-fold more mRNA than the wild-type gene. The analysis in tomato utilized a different DNA probe that allowed the analysis of wild-type (pMON9921), modified (pMON5370) and synthetic (pMON5377) HD-1 genes with the same probe. This probe was derived from the 5' untranslated region of the CaMV35S promoter in pMON893 that was common to all three of these vectors (pMON9921, pMON5370 and pMON5377). This S1 analysis indicated that B.t.k. mRNA levels from the modified gene were 3 to 5 fold higher than for the wild-type gene, and that mRNA levels for the synthetic gene were about 2 to 3 fold higher than for the modified gene. Three independent transformants were analyzed for each gene. Compared to the fold increases in B.t.k. HD-1 protein from these genes in tomato shown in Table XI, these mRNA increases can explain about half of the total protein increase as was seen in tobacco for the wild-type and modified genes. For tomato the total mRNA increase from wild-type to synthetic is about 6 to 15 fold compared to a protein increase of about 50 fold. This result is similar to that seen for tobacco in comparing the wild-type and modified genes, and it extends to the synthetic gene as well. That is, about half of the total fold increase in B.t.k. protein from wild-type to modified genes can be explained by mRNA increases and about half to enhanced translational efficiency. The same is also true in comparing the modified gene to the synthetic gene. Although there is an additional increase in RNA levels, this mRNA increase can explain only about half of the total protein increase.

The full length B.t.k. genes described above were also used to transform tomato plants and these plants were analyzed for B.t.k. protein and insecticidal efficacy. The results of this analysis are shown in Table XIII. Plants containing the synthetic/wild-type gene (pMON10506) produce the B.t.k. HD-73 protein at levels of about 0.01% of their total soluble protein. Plants containing the synthetic/modified gene (pMON10526) produce about 0.04% B.t.k. protein, and plants containing the fully synthetic gene (pMON10518) produce about 0.2% B.t.k. protein. These results are very similar to the tobacco plant results for the same genes. mRNA levels estimated by Northern blot analysis in tomato also increase in parallel with the protein level increase. As for tobacco with these three genes, most of the protein increase can be attributed to increased mRNA with a small component of translational efficiency increase indicated for the fully synthetic gene. The highest levels of full length B.t.k. protein (from pMON10518) are comparable to or just slightly lower than the highest levels observed for the truncated HD-73 genes (pMON5383 and pMON5390). Tomato plants expressing these full length genes have the insecticidal activity expected for the observed protein levels as determined by feeding assays with beet armyworm or by diet incorporation of plant extracts with tobacco hornworm.

TABLE XIII

Full Length B.t.k. HD-73 Protein and mRNA Levels in Transgenic Tomato Plants

| Gene description | Vector | B.t.k. protein concentration | Relative B.t.k. mRNA level |
|---|---|---|---|
| Synthetic/wild type | pMON10506 | 100 | 1 |
| Synthetic/modified | pMON10526 | 400 | 2-4 |
| Fully synthetic | pMON10518 | 2000 | 10 |

c) Cotton.

The generality of the increased expression of B.t.k. HD-1 and B.t.k. HD-73 by use of the modified and synthetic genes was extended to cotton. Transgenic calli were produced which contain the wild type (pMON9921) and the synthetic HD-1 (pMON5377) genes. Here again the B.t.k. HD-1 protein produced from calli containing the wild-type gene was not detected, whereas calli containing the synthetic HD-1 gene expressed the HD-1 protein at easily detectable levels. The HD-1 protein was produced at approximately 1000 ng/mg of plant calli extract protein. Again, to ensure that the protein produced by the transgenic cotton calli was biologically active and that the increased expression observed with the synthetic gene translated to increased biological activity, extracts of cotton calli were made in similar manner as described for tobacco plants, except that the calli was first dried between Whatman filter paper to remove as much of the water as possible. The dried calli were then ground in liquid nitrogen and ground in 100 mM sodium carbonate buffer, pH 10. Approximately 0.5 ml aliquots of this material was applied to tomato leaves with a paint brush. After the leaf dried, five tobacco hornworm larvae were applied to each of two leaf samples. Leaves painted with extract from control calli were completely destroyed. Leaves painted with extract from calli containing the wild-type HD-1 gene (pMON9921) showed severe damage. Leaves painted with extract from calli containing the synthetic HD-1 gene (pMON5377) showed no damage (see Table XIV below).

TABLE XIV

Protection against Tobacco Hornworm by Tomato Leaves Painted with Extracts Prepared from Cotton Calli Containing a Control, the WildType B.t.k. HD-1 Gene, Synthetic HD-1 Gene or Synthetic HD-73 Gene

| Gene Description | Vector | Tobacco Hornworm Damage* |
|---|---|---|
| Control | Control | NL |
| Wild type HD-1 | pMON9921 | 3 |
| Synthetic HD-1 | pMON5377 | 0 |
| Synthetic HD-73 | pMON5383 | 0 |

*Damage was rated as shown in Table VIII.

Cotton calli were also produced containing another synthetic gene, a gene encoding B.t.k. HD-73. The preparation of this gene is described in Example 3. Calli containing the synthetic HD-73 gene produced the corresponding HD-73 protein at even higher levels than the calli which contained the synthetic HD-1 gene. Extracts made from calli containing the HD-73 synthetic gene (pMON5383) showed complete control of tobacco hornworm when painted onto tomato leaves as described above for extracts containing the HD-1 protein. (See Table XIV).

Transgenic cotton plants containing the synthetic B.t.k. HD-1 gene (pMON5377) or the synthetic B.t.k. HD-73 gene (pMON5383) have also been examined. These plants produce the HD-1 or HD-73 proteins at levels comparable to that seen in cotton callus with the same genes and comparable to tomato and tobacco plants with these genes. For either synthetic truncated HD-1 or HD-73 genes, cotton plants expressing B.t.k. protein at 1000 to 2000 ng/mg total protein (0.1% to 0.2%) were recovered at a high frequency. Insect feeding assays were performed with leaves from cotton plants expressing the synthetic HD-1 or HD-73 genes. These leaves showed no damage (rating of 0) when challenged with larvae of cabbage looper (*Trichoplusia ni*), and only slight damage when challenged with larvae of beet armyworm (*Spodoptera exigua*). Damage ratings are as defined in Table VIII above. This demonstrated that cotton plants as well as calli expressed the synthetic HD-1 or HD-73 genes at high levels and that those plants were protected from damage by Lepidopteran insect larvae.

Transgenic cotton plants containing either the synthetic truncated HD-1 gene (pMON5377) or the synthetic truncated HD-73 gene (pMON5383) were also assessed for protection against cotton bollworm at the whole plant level in the greenhouse. This is a more realistic test of the ability of these plants to produce an agriculturally acceptable level of control. The cotton bollworm (*Heliothis zea*) is a major pest of cotton that produces economic damage by destroying terminals, squares and bolls, and protection of these fruiting bodies as well as the leaf tissue will be important for effective insect control and adequate crop protection. To test the protection afforded to whole plants, R1 progeny of cotton plants expressing high levels of either B.t.k. HD-1 (pMON5377) or B.t.k. HD-73 (pMON5383) were assayed by applying 10-15 eggs of cotton bollworm per boll or square to the 20 uppermost squares or bolls on each plant. At least 12 plants were analyzed per treatment. The hatch rate of the eggs was approximately 70%. This corresponds to very high insect pressure compared to numbers of larvae per plant seen under typical field conditions. Under these conditions 100% of the bolls on control cotton plants were destroyed by insect damage. For the transgenics, significant boll protection was observed. Plants containing pMON5377 (HD-1) had 70-75% of the bolls survive the intense pressure of this assay. Plants containing pMON5383 (HD-73) had 80% to 90% boll protection. This is likely to be a consequence of the higher activity of HD-73 protein against cotton bollworm compared to HD-1 protein. In cases where the transgenic plants were damaged by the insects, the surviving larvae were delayed in their development by at least one instar.

Therefore, the increased expression obtained with the modified and synthetic genes is not limited to any one crop; tobacco, tomato and cotton calli and cotton plants all showed drastic increases in B.t.k. expression when the plants/calli were produced containing the modified or synthetic genes. Likewise, the utility of changes made to produce the modified and synthetic B.t.k. HD-1 gene is not limited to the HD-1 gene. The synthetic HD-73 gene in all three species also showed drastic increases in expression.

In summary, it has been demonstrated that: (1) the genetic changes made in the HD-1 modified gene lead to very significant increases in B.t.k. HD-1 expression; (2) production of a totally synthetic gene lead to a further five-fold increase in B.t.k. HD-1 expression; (3) the changes incorporated into the modified HD-1 gene accounted for the majority of the increased B.t.k. expression observed with the synthetic gene; (4) the increased expression was demonstrated in three different plants—tobacco plants, tomato plants and cotton calli and cotton plants; (5) the increased expression as observed by Western analysis also correlated with similar increases in bioactivity, showing that the B.t.k. HD-1 proteins produced were comparably active; (6) when the method of the present invention used to design the synthetic HD-1 gene was employed to design a synthetic HD-73 gene it also was expressed at much higher levels in tobacco, tomato and cotton than the wild-type equivalent gene with consequent increases in bioactivity; (7) a fully synthetic full length B.t.k. gene was expressed at levels comparable to synthetic truncated genes.

EXAMPLE 5

Synthetic *B.t. tenebrionis* Gene in Tobacco, Tomato and Potato

Referring to FIG. 12, a synthetic gene encoding a Coleopteran active toxin is prepared by making the indicated changes in the wild-type gene of *B.t. tenebrionis* or de novo synthesis of the synthetic structural gene. The synthetic gene is inserted into an intermediate plant transformation vector such as pMON893: Plasmid pMON893 containing the synthetic B.t.t. gene is then inserted into a suitable disarmed *Agrobacterium* strain such as *A. tumefaciens* ACO.

Transformation and Regeneration of Potato

Sterile shoot cultures of Russet Burbank are maintained in vials containing 10 ml of PM medium (Murashige and Skoog (MS) inorganic salts, 30 g/l sucrose, 0.17 g/l $NaH_2PO_4H_2O$, 0.4 mg/l thiamine-HCl, and 100 mg/l myo-inositol, solidified with 1 g/l Gelrite at pH 6.0). When shoots reached approximately 5 cm in length, stem internode segments of 7-10 mm are excised and smeared at the cut ends with a disarmed *Agrobacterium tumefaciens* vector containing the synthetic B.t.t. gene from a four day old plate culture. The stem explants are co-cultured for three days at 23Ec on a sterile filter paper placed over 1.5 ml of a tobacco cell feeder layer overlaid on 1/10 P medium (1/10 strength MS inorganic salts and organic addenda without casein as in Jarret et al. (1980), 30 g/l sucrose and 8.0 g/l agar). Following co-culture the explants are transferred to full strength P-1 medium for callus induction, composed of MS inorganic salts, organic additions as in Jarret et al. (1980) with the exception of casein, 3.0 mg/l benzyladenine (BA), and 0.01 mg/l naphthaleneacetic acid (NAA) (Jarret, et al., 1980). Carbenicillin (500 mg/l) is included to inhibit bacterial growth, and 100 mg/l kanamycin is added to select for transformed cells. After four weeks the explants are transferred to medium of the same composition but with 0.3 mg/l gibberellic acid (GA3) replacing the BA and NAA (Jarret et al., 1981) to promote shoot formation. Shoots begin to develop approximately two weeks after transfer to shoot induction medium; these are excised and transferred to vials of PM medium for rooting. Shoots are tested for kanamycin resistance conferred by the enzyme neomycin phosphotransferase II, by placing a section of the stem onto callus induction medium containing MS organic and inorganic salts, 30 g/l sucrose, 2.25 mg/l BA, 0.186 mg/l NAA, 10 mg/l GA3 (Webb, et al., 1983) and 200 mg/l kanamycin to select for transformed cells.

The synthetic B.t.t. gene described in FIG. 12, was placed into a plant expression vector as described in example 5. The plasmid has the following characteristics; a synthetic BglII fragment having approximately 1800 base pairs was inserted into pMON893 in such a manner that the enhanced 35S promoter would express the B.t.t. gene. This construct, pMON1982, was used to transform both tobacco and tomato. Tobacco plants, selected as kanamycin resistant plants were screened with rabbit anti-B.t.t. antibody. Cross-reactive material was detected at levels predicted to be suitable to cause mortality to CPB. These target insects will not feed on tobacco, but the transgenic tobacco plants do demonstrate that the synthetic gene does improve expression of this protein to detectable levels.

Tomato plants with the pMON1982 construct were determined to produce B.t.t. protein at levels insecticidal to CPB. In initial studies, the leaves of four plants (5190, 5225, 5328 and 5133) showed little or no damage when exposed to CPB larvae (damage rating of 0-1 on a scale of 0 to 4 with 4 as no leaf remaining). Under these conditions the control leaves were completely eaten. Immunological analysis of these plants confirmed the presence of material cross-reactive with anti-B.t.t. antibody. Levels of protein expression in these plants were estimated at approximately 1 to 5 ng of B.t.t. protein in 50 ug of total extractable protein. A total of 17 tomato plants (17 of 65 tested) have been identified which demonstrate protection of leaf tissue from CPB (rating of 0 or 1) and show good insect mortality.

Results similar to those seen in tobacco and tomato with pMON1982 were seen with pMON1984 in the same plant species. pMON1984 is identical to pMON1982 except that the synthetic protease inhibitor (CMTI) is fused upstream of the native proteolytic cleavage site. Levels of expression in tobacco were estimated to be similar to pMON1982, between 10-15 ng per 50 ug of total soluble protein.

Tomato plants expressing pMON1984 have been identified which protect the leaves from ingestion by CPB. The damage rating was 0 with 100% insect mortality.

Potato was transformed as described in example 5 with a vector similar to pMON1982 containing the enhanced CaMV35S/synthetic B.t.t. gene. Leaves of potato plants transformed with this vector, were screened by CPB insect bioassay. Of the 35 plants tested, leaves from 4 plants, 16a, 13c, 13d, and 23a were totally protected when challenged. Insect bioassays with leaves from three other plants, 13e, 1a, and 13b, recorded damage levels of 1 on a scale of 0 to 4 with 4 being total devestation of the leaf material. Immunological analysis confirmed the presence of B.t.t. cross-reactive material in the leaf tissue. The level of B.t.t. protein in leaf tissue of plant 16a (damage rating of 0) was estimated at 20-50 ng of B.t.t. protein/50 ug of total soluble protein. The levels of B.t.t. protein seen in 16a tissue was consistent with its biological activity. Immunological analysis of 13e and 13b (tissue which scored 1 in damage rating) reveal less protein (5-10 ng/50 ug of total soluble protein) than in plant 16a. Cuttings of plant 16a were challenged with 50 to 200 eggs of CPB in a whole plant assay. Under these conditions 16a showed no damage and 100% mortality of insects while control potato plants were heavily damaged.

EXAMPLE 6

Synthetic B.t.k. P2 Protein Gene

The P2 protein is a distinct insecticidal protein produced by some strains of B.t. including B.t.k. HD-1. It is characterized by its activity against both lepidopteran and dipteran insects (Yamamoto and Iizuka, 1983). Genes encoding the P2 protein have been isolated and characterized (Donovan et al., 1988). The P2 proteins encoded by these genes are approximately 600 amino acids in length. These proteins share only limited homology with the lepidopteran specific P1 type proteins, such as the B.t.k. HD-1 and HD-73 proteins described in previous examples.

The P2 proteins have substantial activity against a variety of lepidopteran larvae including cabbage looper, tobacco hornworm and tobacco budworm. Because they are active against agronomically important insect pests, the P2 proteins are a desirable candidate in the production of insect tolerant transgenic plants either alone or in combination with the other B.t. toxins described in the above examples. In some plants, expression of the P2 protein alone might be sufficient to provide protection against damaging insects. In addition, the P2 proteins might provide protection against agronomically important dipteran pests. In other cases, expression of P2 together with the B.t.k. HD-1 or HD-73 protein might be preferred. The P2 proteins should provide at least an additive level of insecticidal activity when combined with the crystal protein toxin of B.t.k. HD-1 or HD-73, and the combination may even provide a synergistic activity. Although the mode of action of the P2 protein is unknown, its distinct amino acid sequence suggests that it functions differently from the B.t.k. HD-1 and HD-73 type of proteins. Production of two insect tolerance proteins with different modes of action in the same plant would minimize the potential for development of insect resistance to B.t. proteins in plants. The lack of substantial DNA homology between P2 genes and the HD-1 and HD-73 genes minimizes the potential for recombination between multiple insect tolerance genes in the plant chromosome.

The genes encoding the P2 protein although distinct in sequence from the B.t.k. HD-1 and HD-73 genes share many common features with these genes. In particular, the P2 protein genes have a high A+T content (65%), multiple potential polyadenylation signal sequences (26) and numerous ATTTA sequences (10). Because of its overall similarity to the poorly expressed wild-type B.t.k. HD-1 and HD-73 genes, the same problems are expected in expression of the wild-type P2 gene as were encountered with the previous examples. Based on the above-described method for designing the synthetic B.t. genes, a synthetic P2 gene has been designed which gene should be expressed at adequate levels for protection in plants. A comparison of the wild-type and synthetic P2 genes is shown in FIG. 13.

EXAMPLE 7

Synthetic *B.t. Entomocidus* Gene

The *B.t. entomocidus* ("Btent") protein is a distinct insecticidal protein produced by some strains of B.t. bacteria. It is characterized by its high level of activity against some lepidopterans that are relatively insensitive to B.t.k. HD-1 and HD-73 such as *Spodoptera* species including beet armyworm (Visser et al., 1988). Genes encoding the Btent protein have been isolated and characterized (Honee et al, 1988). The Btent proteins encoded by these genes are approximately the same length as B.t.k. HD-1 and HD-73. These proteins share only 68% amino acid homology with the B.t.k. HD-1 and HD-73 proteins. It is likely that only the N-terminal half of the Btent protein is required for insecticidal activity as is the case for HD-1 and HD-73. Over the first 625 amino acids, Btent shares only 38% amino acid homology with HD-1 and HD-73.

Because of their higher activity against *Spodoptera* species that are relatively insensitive to HD-1 and HD-73, the Btent proteins are a desirable candidate for the production of insect tolerant transgenic plants either alone or in combination with the other B.t. toxins described in the above examples. In some plants production of Btent alone might be sufficient to control the agronomically important pests. In other plants, the production of two distinct insect tolerance proteins would provide protection against a wider array of insects. Against those insects where both proteins are active, the combination of the B.t.k. HD-1 or HD-73 type protein plus the Btent protein should provide at least additive insecticidal efficacy, and may even provide a synergistic activity. In addition, because of its distinct amino acid sequence, the Btent protein may have a different mode of action than HD-1 or HD-73. Production of two insecticidal proteins in the same plant with different modes of action would minimize the potential for development of insect resistance to B.t. proteins in plants. The relative lack of DNA sequence homology with the B.t.k. type genes minimizes the potential for recombination between multiple insect tolerance genes in the plant chromosome.

The genes encoding the Btent protein although distinct in sequence from the B.t.k. HD-1 and HD-73 genes share many common features with these genes. In particular, the Btent protein genes have a high A+T content (62%), multiple potential polyadenylation signal sequences (39 in the full length coding sequence and 27 in the first 1875 nucleotides that is likely to encode the active toxic fragment) and numerous ATTTA sequences (16 in the full length coding sequence and 12 in the first 1875 nucleotides). Because of its overall similarity to the poorly expressed wild type B.t.k. HD-1 and HD-73 genes, the wild-type Btent genes are expected to exhibit similar problems in expression as were encountered with the wild-type HD-1 and HD-73 genes. Based on the above-described method used for designing the other synthetic B.t. genes, a synthetic Btent gene has been designed which gene should be expressed at adequate levels for protection in plants. A comparison of the wild type and synthetic Btent genes is shown in FIG. 14.

EXAMPLE 8

Synthetic B.t.k. Genes for Expression in Corn

High level expression of heterologous genes in corn cells has been shown to be enhanced by the presence of a corn gene intron (Callis et al., 1987). Typically these introns have been located in the 5' untranslated region of the chimeric gene. It has been shown that the CaMV35S promoter and the NOS 3' end function efficiently in the expression of heterologous genes in corn cells (Fromm et al., 1986).

Figure 15:
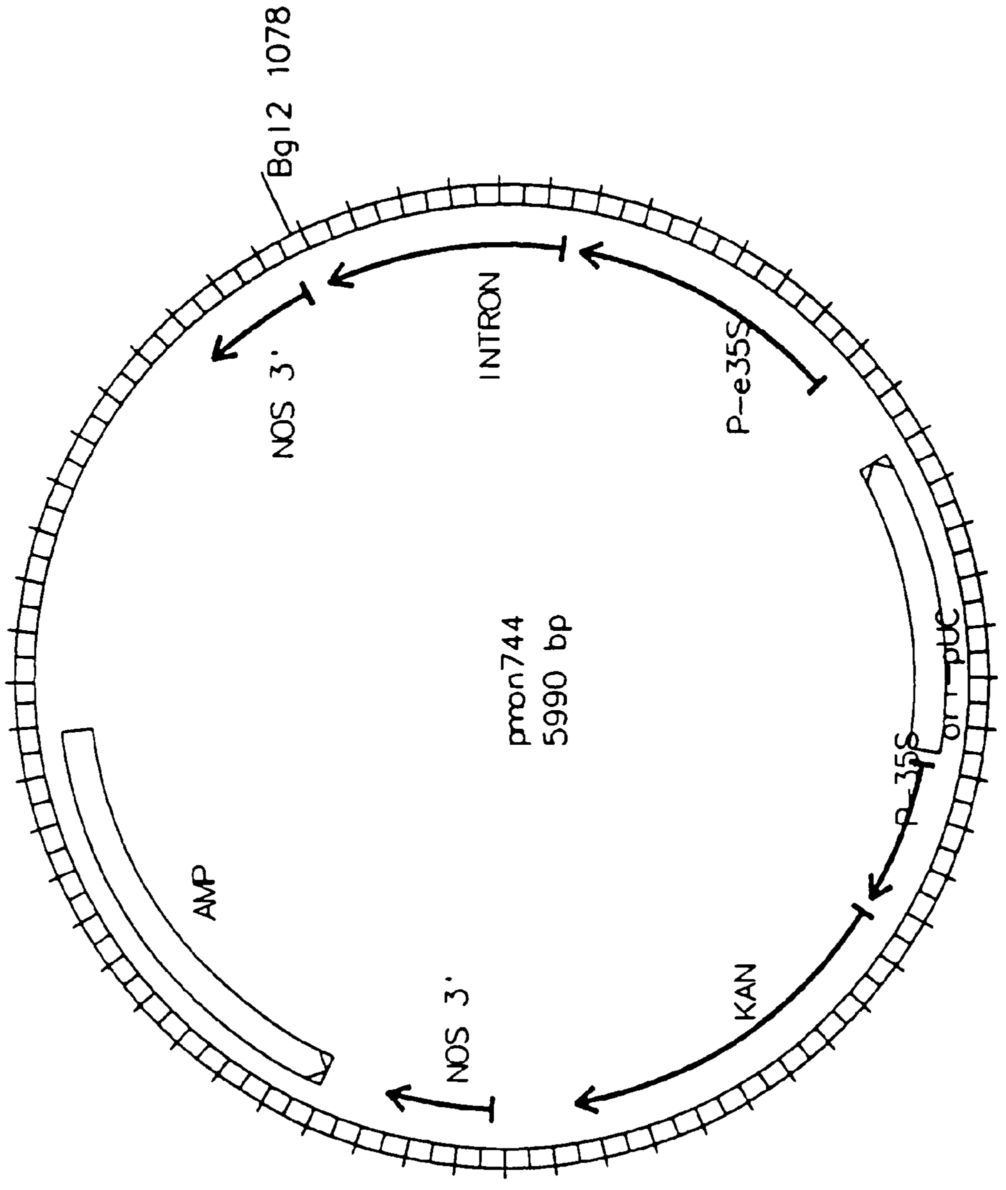
FIG. 15 illustrates a plasmid map for plant expression cassette vector pMON744.

Referring to FIG. 15, a plant expression cassette vector (pMON744) was constructed that contains these sequences. Specifically the expression cassette contains the enhanced CaMV 35S promoter followed by intron 1 of the corn Adh1 gene (Callis et al., 1987). This is followed by a multilinker cloning site for insertion of coding sequences; this multilinker contains a BglII site among others. Following the multilinker is the NOS 3' end. pMON744 also contains the selectable marker gene 35S/NPTII/NOS 3' for kanamycin selection of transgenic corn cells. In addition, pMON744 has an *E. coli* origin of replication and an ampicillin resistance gene for selection of the plasmid in *E. coli.*

Five B.t.k. coding sequences described in the previous examples were inserted into the BglII site of pMON744 for corn cell expression of B.t.k. The coding sequences inserted and resulting vectors were:

1. Wild type B.t.k. HD-1 from pMON9921 to make pMON8652.

2. Modified B.t.k. HD-1 from pMON5370 to make pMON8642.

3. Synthetic B.t.k. HD-1 from pMON5377 to make pMON8643.

4. Synthetic B.t.k. HD-73 from pMON5390 to make pMON8644.

5. Synthetic full length B.t.k. HD-73 from pMON10518 to make pMON10902.

pMON8652 (wild-type B.t.k. HD-1) was used to transform corn cell protoplasts and stably transformed kanamycin resistant callus was isolated. B.t.k. mRNA in the corn cells was analyzed by nuclease S1 protection and found to be present at a level comparable to that seen with the same wild-type coding sequence (pMON9921) in transgenic tomato plants.

pMON8652 and pMON8642 (modified HD-1) were used to transform corn cell protoplasts in a transient expression system. The level of B.t.k. mRNA was analyzed by nuclease S1 protection. The modified HD-1 gave rise to a several fold increase in B.t.k. mRNA compared to the wild-type coding sequence in the transiently transformed corn cells. This indicated that the modifications introduced into the B.t.k. HD-1 gene are capable of enhancing B.t.k. expression in monocot cells as was demonstrated for dicot plants and cells.

pMON8642 (modified HD-1) and pMON8643 (synthetic HD-1) were used to transform Black Mexican Sweet (BMS) corn cell protoplasts by PEG-mediated DNA uptake, and stably transformed corn callus was selected by growth on kanamycin containing plant growth medium. Individual callus colonies that were derived from single transformed cells were isolated and propagated separately on kanamycin containing medium.

To assess the expression of the B.t.k. genes in these cells, callus samples were tested for insect toxicity by bioassay against tobacco hornworm larvae. For each vector, 96 callus lines were tested by bioassay. Portions of each callus were placed on sterile water agar plates, and five neonate tobacco hornworm larvae were added and allowed to feed for 4 days. For pMON8643, 100% of the larvae died after feeding on 15 of the 96 calli and these calli showed little feeding damage. For pMON8642, only 1 of the 96 calli was toxic to the larvae. This showed that the B.t.k. gene was being expressed in these samples at insecticidal levels. The observation that significantly more calli containing pMON8643 were toxic than for pMON8642 showed that significantly higher levels of expression were obtained when the synthetic HD-1 coding sequence was contained in corn cells than when the modified HD-1 coding sequence was used, similar to the previous examples with dicot plants. A semiquantitative immunoassay showed that the pMON8643 toxic samples had significantly higher B.t.k. protein levels than the pMON8642 toxic sample.

The 16 callus samples that were toxic to tobacco hornworm were also tested for activity against European corn borer. European corn borer is approximately 40-fold less sensitive to the HD-1 gene product than is tobacco hornworm. Larvae of European corn borer were applied to the callus samples and allowed to feed for 4 days. Two of the 16 calli tested, both of which contained pMON8643 (synthetic HD-1), were toxic to European corn borer larvae.

To assess the expression of the B.t.k. genes in differentiated corn tissue, another method of DNA delivery was used. Young leaves were excised from corn plants, and DNA samples were delivered into the leaf tissue by microprojectile bombardment. In this system, the DNA on the microprojectiles is transiently expressed in the leaf cells after bombardment. Three DNA samples were used, and each DNA was tested in triplicate.

1. pMON744, the corn expression vector with no B.t.k. gene.

2. pMON8643 (synthetic HD-1).

3. pMON752, a corn expression vector for the GUS gene, no B.t.k. gene.

The leaves were incubated at room temperature for 24 hours. The pMON752 samples were stained with a substrate that allows visual detection of the GUS gene product. This analysis showed that over one hundred spots in each sample were expressing the GUS product and the triplicate samples showed very similar levels of GUS expression. For the pMON744 and pMON8643 samples 5 larvae of tobacco hornworm were added to each leaf and allowed to feed for 48 hours. All three samples bombarded with pMON744 showed extensive feeding damage and no larval mortality. All three samples bombarded with pMON8643 showed no evidence of feeding damage and 100% larval mortality. The samples were also assayed for the presence of B.t.k. protein by a qualitative immunoassay. All of the pMON8643 samples had detectable B.t.k. protein. These results demonstrated that the synthetic B.t.k. gene was expressed in differentiated corn plant tissue at insecticidal levels.

EXAMPLE 9

Synthetic Potato Leaf Roll Virus Coat Protein Gene

Expression in plants of the coat protein genes from a variety of plant viruses has proven to be an effective method of engineering resistance to these viruses. In order to achieve virus resistance, it is important to express the viral coat protein at an effective level. For many plant virus coat protein genes, this has not proved to be a problem. However, for the coat protein gene from potato leaf roll virus (PLRV), expression of the coat protein has been observed to be low relative to other coat protein genes, and this lower level of protein has not led to optimal resistance to PLRV.

The gene for PLRV coat protein is shown in FIG. 16. Referring to FIG. 16, the upper line of sequence shows the gene as it was originally engineered for plant expression in vector pMON893. The gene was contained on a 749 nucleotide BglII-EcoRI fragment with the coding sequence contained between nucleotides 20 and 643. This fragment also contained 19 nucleotides of 5' noncoding sequence and 104 nucleotides of 3' noncoding sequence. This PLRV coat protein gene was relatively poorly expressed in plants compared to other viral coat protein genes.

A synthetic gene was designed to improve plant expression of the PLRV coat protein. Referring again to FIG. 16, the changes made in the synthetic PLRV gene are shown in the lower line. This gene was designed to encode exactly the same protein as the naturally occurring gene. Note that the beginning of the synthetic gene is at nucleotide 14 and the end of the sequence is at nucleotide 654. The coding sequence for the synthetic gene is from nucleotide 20 to 643 of the figure. The changes indicated just upstream and downstream of these endpoints serve only to introduce convenient restriction sites just outside the coding sequence. Thus the size of the synthetic gene is 641 nucleotides which is smaller than the naturally occurring gene. The synthetic gene is smaller because substantially all of the noncoding sequence at both the 5' and 3' ends, except for segments encoding the BglII and EcoRI restriction sites has been removed.

The synthetic gene differs from the naturally occurring gene in two main respects. First, 41 individual codons within the coding sequence have been changed to remove nearly all codons for a given amino acid that constitute less than about 15% of the codons for that amino acid in a survey of dicot plant genes. Second, the 5' and 3' noncoding sequences of the original gene have been removed. Although not strictly conforming to the algorithm described in FIG. 1, a few of the codon changes and especially the removal of the long 3' noncoding region is consistent with this algorithm.

The original PLRV sequence contains two potential plant polyadenylation signals (AACCAA and AAGCAT) and both of these occur in the 3' noncoding sequence that has been removed in the synthetic gene. The original PLRV gene also contains one ATTTA sequence. This is also contained in the 3' noncoding sequence, and is in the midst of the longest stretch of uninterrupted A+T in the gene (a stretch of 7 A+T nucleotides). This sequence was removed in the synthetic gene. Thus, sequences that the algorithm of FIG. 1 targets for change have been changed in the synthetic PLRV coat protein gene by removal of the 3' noncoding segment. Within the coding sequence, codon changes were also made to remove three other regions of sequence described above. In particular, two regions of 5 consecutive A+T and one region of 5 consecutive G+C within the coding sequence have been removed in the synthetic gene.

The synthetic PLRV coat protein gene is cloned in a plant transformation vector such as pMON893 and used to transform potato plants as described above. These plants express the PLRV coat protein at higher levels than achieved with the naturally occurring gene, and these plants exhibit increased resistance to infection by PLRV.

EXAMPLE 10

Expression of Synthetic B.t. Genes with RUBISCO Small Subunit Promoters and Chloroplast Transit Peptides The genes in plants encoding the small subunit of RUBISCO (SSU) are often highly expressed, light regulated and sometimes show tissue specificity. These expression properties are largely due to the promoter sequences of these genes. It has been possible to use SSU promoters to express heterologous genes in transformed plants. Typically a plant will contain multiple SSU genes, and the expression levels and tissue specificity of different SSU genes will be different. The SSU proteins are encoded in the nucleus and synthesized in the cytoplasm as precursors that contain an N-terminal extension known as the chloroplast transit peptide (CTP). The CTP directs the precursor to the chloroplast and promotes the uptake of the SSU protein into the chloroplast. In this process, the CTP is cleaved from the SSU protein. These CTP sequences have been used to direct heterologous proteins into chloroplasts of transformed plants.

The SSU promoters might have several advantages for expression of B.t.k. genes in plants. Some SSU promoters are very highly expressed and could give rise to expression levels as high or higher than those observed with the CaMV35S promoter. The tissue distribution of expression from SSU promoters is different from that of the CaMV35S promoter, so for control of some insect pests, it may be advantageous to direct the expression of B.t.k. to those cells in which SSU is most highly expressed. For example, although relatively constitutive, in the leaf the CaMV35S promoter is more highly expressed in vascular tissue than in some other parts of the leaf, while most SSU promoters are most highly expressed in the mesophyll cells of the leaf. Some SSU promoters also are more highly tissue specific, so it could be possible to utilize a specific SSU promoter to express B.t.k. in only a subset of plant tissues, if for example B.t. expression in certain cells was found to be deleterious to those cells. For example, for control of Colorado potato beetle in potato, it may be advantageous to use SSU promoters to direct B.t.t. expression to the leaves but not to the edible tubers.

Utilizing SSU CTP sequences to localize B.t. proteins to the chloroplast might also be advantageous. Localization of the B.t. to the chloroplast could protect the protein from proteases found in the cytoplasm. This could stabilize the B.t. protein and lead to higher levels of accumulation of active protein. B.t. genes containing the CTP could be used in combination with the SSU promoter or with other promoters such as CaMV35S.

A variety of plant transformation vectors were constructed for the expression of B.t.k. genes utilizing SSU promoters and SSU CTPs. The promoters and CTPs utilized were from the petunia SSU11a gene described by Tumer et al. (1986) and from the *Arabidopsis* ats1A gene (an SSU gene) described by Krebbers et al. (1988) and by Elionor et al. (1989). The petunia SSU11a promoter was contained on a DNA fragment that extended approximately 800 bp upstream of the SSU coding sequence. The *Arabidopsis* ats1A promoter was contained on a DNA fragment that extended approximately 1.8 kb upstream of the SSU coding sequence. At the upstream end convenient sites from the multilinker of pUC18 were used to move these promoters into plant transformation vectors such as pMON893. These promoter fragments extended to the start of the SSU coding sequence at which point an NcoI restriction site was engineered to allow insertion of the B.t. coding sequence, replacing the SSU coding sequence.

When SSU promoters were used in combination with their CTP, the DNA fragments extended through the coding sequence of the CTP and a small portion of the mature SSU coding sequence at which point an NcoI restriction site was engineered by standard techniques to allow the in frame fusion of B.t. coding sequences with the CTP. In particular, for the petunia SSU11a CTP, B.t. coding sequences were fused to the SSU sequence after amino acid 8 of the mature SSU sequence at which point the NcoI site was placed. The 8 amino acids of mature SSU sequence were included because preliminary in vitro chloroplast uptake experiments indicated that uptake was of B.t.k. was observed only if this segment of mature SSU was included. For the *Arabidopsis* ats1A CTP, the complete CTP was included plus 24 amino acids of mature SSU sequence plus the sequence gly-gly-arg-val-asn-cys-met-gln-ala-met (SEQ ID NO:40), terminating in an NcoI site for B.t. fusion. This short sequence reiterates the native SSU CTP cleavage site (between the cys and met) plus a short segment surrounding the cleavage site. This sequence was included in order to insure proper uptake into chloroplasts. B.t. coding sequences were fused to this ats1A CTP after the met codon. In vitro uptake experiments with this CTP construction and other (non-B.t.) coding sequences showed that this CTP did target proteins to the chloroplast.

When CTPs were used in combination with the CaMV 35S promoter, the same CTP segments were used. They were excised just upstream of the ATG start sites of the CTP by engineering of BglII sites, and placed downstream of the CaMV35S promoter in pMON893, as BglII to NcoI fragments. B.t. coding sequences were fused as described above.

The wild type B.t.k. HD-1 coding sequence of pMON9921 (see FIG. 1) was fused to the ats1A promoter to make pMON1925 or the ats1A promoter plus CTP to make pMON1921. These vectors were used to transform tobacco plants, and the plants were screened for activity against tobacco hornworm. No toxic plants were recovered. This is surprising in light of the fact that toxic plants could be recovered, albeit at a low frequency, after transformation with pMON9921 in which the B.t.k. coding sequence was expressed from the enhanced CaMV35S, promoter in pMON893, and in light of the fact that Elionor et al. (1989) report that the ats1A promoter itself is comparable in strength to the CaMV35S promoter and approximately 10-fold stronger when the CTP sequence is included. At least for the wild-type B.t.k. HD-1 coding sequence, this does not appear to be the case.

A variety of plant transformation vectors were constructed utilizing either the truncated synthetic HD-73 coding sequence of FIG. 4 or the full length B.t.k. HD-73 coding sequence of FIG. 11. These are listed in the table below.

TABLE XV

Gene Constructs with CTPs

| Vector | Promoter | CTP | B.t.k. HD-73 Coding Sequence |
|---|---|---|---|
| pMON10806 | En 35S | ats1A | truncated |
| pMON10814 | En35S | SSU11a | full length |
| pMON10811 | SSU11a | SSU11a | truncated |
| pMON10819 | SSU11a | none | truncated |
| pMON10815 | ats1A | none | truncated |
| pMON10817 | ats1A | ats1A | truncated |
| pMON10821 | En 35S | ats1A | truncated |
| pMON10822 | En 35S | ats1A | full length |
| pMON10838 | SSU11a | SSU11a | full length |
| pMON10839 | ats1A | ats1A | full length |

All of the above vectors were used to transform tobacco plants. For all of the vectors containing truncated B.t.k. genes, leaf tissue from these plants has been analyzed for toxicity to insects and B.t.k. protein levels by immunoassay. pMON10806, 10811, 10819 and 10821 produce levels of B.t.k. protein comparable to pMON5383 and pMON5390 which contain synthetic B.t.k. HD-73 coding sequences driven by the 35S promoter itself with no CTP. These plants also have the insecticidal activity expected for the B.t.k. protein levels detected. For pMON10815 and pMON10817 (containing the ats1A promoter), the level of B.t.k. protein is about 5-fold higher than that found in plants containing pMON5383 or 5390. These plants also have higher insecticidal activity. Plants containing 10815 and 10817 contain up to 1% of their total soluble leaf protein as B.t.k. HD-73. This is the highest level of B.t.k. protein yet obtained with any of the synthetic genes.

This result is surprising in two respects. First, as noted above, the wild type coding sequences fused to the ats1A promoter and CTP did not show any evidence of higher levels of expression than for En 35S, and in fact had lower expression based on the absence of any insecticidal plants. Second, Elionor et al. (1989) show that for two other genes, the ats1A CTP can increase expression from the ats1A promoter by about 10-fold. For the synthetic B.t.k. HD-73 gene, there is no consistent increase seen by including the CTP over and above that seen for the ats1A promoter alone.

Tobacco plants containing the full length synthetic HD-73 fused to the SSU11A CTP and driven by the En 35S promoter produced levels of B.t.k. protein and insecticidal activity comparable to pMON10815 which contains does not include the CTP. In addition, for pMON10815 the B.t.k protein extracted from plants was observed by gel electrophoresis to contain multiple forms less than full length, apparently due the cleavage of the C-terminal portion (not required for toxicity) in the cytoplasm. For pMON10814, the majority of the protein appeared to be intact full length indicating that the protein has been stabilized from proteolysis by targeting to the chloroplast.

EXAMPLE 11

Targeting of B.t. Proteins to the Extracellular Space or Vacuole Through the Use of Signal Peptides The B.t. proteins produced from the synthetic genes described here are localized to the cytoplasm of the plant cell, and this cytoplasmic localization results in plants that are insecticidally effective. It may be advantageous for some purposes to direct the B.t. proteins to other compartments of the plant cell. Localizing B.t. proteins in compartments other than the cytoplasm may result in less exposure of the B.t. proteins to cytoplasmic proteases leading to greater accumulation of the protein yielding enhanced insecticidal activity. Extracellular localization could lead to more efficient exposure of certain insects to the B.t. proteins leading to greater efficacy. If a B.t. protein were found to be deleterious to plant cell function, then localization to a noncytoplasmic compartment could protect these cells from the protein.

In plants as well as other eucaryotes, proteins that are destined to be localized either extracellularly or in several specific compartments are typically synthesized with an N-terminal amino acid extension known as the signal peptide. This signal peptide directs the protein to enter the compartmentalization pathway, and it is typically cleaved from the mature protein as an early step in compartmentalization. For an extracellular protein, the secretory pathway typically involves cotranslational insertion into the endoplasmic reticulum with cleavage of the signal peptide occurring at this stage. The mature protein then passes thru the Golgi body into vesicles that fuse with the plasma membrane thus releasing the protein into the extracellular space. Proteins destined for other compartments follow a similar pathway. For example, proteins that are destined for the endoplasmic reticulum or the Golgi body follow this scheme, but they are specifically retained in the appropriate compartment. In plants, some proteins are also targeted to the vacuole, another membrane bound compartment in the cytoplasm of many plant cells. Vacuole targeted proteins diverge from the above pathway at the Golgi body where they enter vesicles that fuse with the vacuole.

A common feature of this protein targeting is the signal peptide that initiates the compartmentalization process. Fusing a signal peptide to a protein will in many cases lead to the targeting of that protein to the endoplasmic reticulum. The efficiency of this step may depend on the sequence of the mature protein itself as well. The signals that direct a protein to a specific compartment rather than to the extracellular space are not as clearly defined. It appears that many of the signals that direct the protein to specific compartments are contained within the amino acid sequence of the mature protein. This has been shown for some vacuole targeted proteins, but it is not yet possible to define these sequences precisely. It appears that secretion into the extracellular space is the "default" pathway for a protein that contains a signal sequence but no other compartmentalization signals. Thus, a strategy to direct B.t. proteins out of the cytoplasm is to fuse the genes for synthetic B.t. genes to DNA sequences encoding known plant signal peptides. These fusion genes will give rise to B.t. proteins that enter the secretory pathway, and lead to extracellular secretion or targeting to the vacuole or other compartments.

Signal sequences for several plant genes have been described. One such sequence is for the tobacco pathogenesis related protein PR1b described by Cornelissen et al. The PR1b protein is normally localized to the extracellular space. Another type of signal peptide is contained on seed storage proteins of legumes. These proteins are localized to the protein body of seeds, which is a vacuole like compartment found in seeds. A signal peptide DNA sequence for the beta subunit of the 7S storage protein of common bean (*Phaseolus vulgaris*), PvuB has been described by Doyle et al. Based on the published these published sequences, genes were synthesized by chemical synthesis of oligonucleotides that encoded the signal peptides for PR1b and PvuB. The synthetic genes for these signal peptides corresponded exactly to the reported DNA sequences. Just upstream of the translational initiation codon of each signal peptide a BamHI and BglII site were inserted with the BamHI site at the 5' end. This allowed the insertion of the signal peptide encoding segments into the BglII site of pMON893 for expression from the En 35S promoter. In some cases to achieve secretion or compartmentalization of heterologous proteins, it has proved necessary to include some amino acid sequence beyond the normal cleavage site of the signal peptide. This may be necessary to insure proper cleavage of the signal peptide. For PR1b the synthetic DNA sequence also included the first 10 amino acids of mature PR1b. For PvuB the synthetic DNA sequence included the first 13 amino acids of mature PvuB. Both synthetic signal peptide encoding segments ended with NcoI sites to allow fusion in frame to the methionine initiation codon of the synthetic B.t. genes.

Four vectors encoding synthetic B.t.k. HD-73 genes were constructed containing these signal peptides. The synthetic truncated HD-73 gene from pMON5383 was fused with the signal peptide sequence of PvuB and incorporated into pMON893 to create pMON10827. The synthetic truncated HD-73 gene from pMON5383 was also fused with the signal peptide sequence of PR1b to create pMON10824. The full length synthetic HD-73 gene from pMON10518 was fused with the signal peptide sequence of PvuB and incorporated into pMON893 to create pMON10828. The full length synthetic HD-73 gene from pMON10518 was also fused with the signal peptide sequence of PR1b and incorporated into pMON893 to create pMON10825.

These vectors were used to transform tobacco plants and the plants were assayed for expression of the B.t.k. protein by Western blot analysis and for insecticidal efficacy. pMON10824 and pMON10827 produced amounts of B.t.k. protein in leaf comparable to the truncated HD-73 vectors, pMON5383 and pMON5390. pMON10825 and pMON10828 produced full length B.t.k. protein in amounts comparable to pMON10518. In all cases, the plants were insecticidally active against tobacco hornworm.

BIBLIOGRAPHY

Adami, G. and Nevins, J. (1988) RNA Processing, Cold Spring Harbor Laboratory, p. 26.

Adang, et al., *Molecular Strategies for Crop Protection* (1987) pp. 345-353, Alan R. Liss, Inc.

Barton, K. A. et al., *Plant Physiol.* (1987), 85, 1103-1109.

Bevan, M. et al., *Nature* (1983) 304:184.

Brady, H. and Wold, W. (1988), RNA Processing, Cold Spring Harbor Laboratory, p. 224.

Brown, John W., *Nucleic Acids Research* (1986) Vol. 14, No. 24, p. 9549.

Callis, J. Fromm, M. and Walbot, V., *Genes and Develop.* (1987), 1:1183-1200.

Conway, L. and Wickens, M. (1988), RNA Processing, Cold Spring Harbor Laboratory, p. 40.

Cornellssen, B. J. C., et al., *EMBO J.* (1986) Vol. 5, No. 1, 37-40.

Daar, I. O. et al. (1988), RNA Processing, Cold Spring Harbor Laboratory, p. 45.

Dean, C. et al., *Nucleic Acids Research* (1986), Vol. 14, No. 5, p. 2229.

Dedrick, R., et al., *The Journal of Biological Chemistry* (1987), Vol. 262, No. 19, pp. 9098-1106.

Donovan, W. P. et al., *The J. of Biol. Chem.* (1988), Vol. 263, No. 1, pp. 561-567.

Doyle, J. J., et al., *J. Biol. Chem.* (1986), Vol. 261, No. 20, 9228-9236.

Elionor, R. P., et al., *Mol. Gen. Genet.* (1989), 218:78-86.

Fischhoff, D. A. et al., *Bio/Technology* (1987), Vol. 5, p. 807.

Fraley, R. T. et al., *Bio/Technology* (1985) 3:629-635.

Fromm, M., Taylor, L. P. and Walbot, V., *Nature* (1986), 319:791-793.

Gallego, M. E. and Nadal-Ginard B. (1988), RNA Processing, Cold Spring Harbor Laboratory, p. 61.

Genovese, C. and Milcarek, C. (1988), RNA Processing, Cold Spring Harbor Laboratory, p. 62.

Gil, A. and Proudfoot, N.J., *Nature* (1984), Vol. 312, p. 473.

Goodall, G. et al. (1988), RNA Processing, Cold Spring Harbor Laboratory, p. 63.

Gross, et al. (1988), RNA Processing, Cold Spring Harbor Laboratory, p. 128.

Hampson, R. K. and Rottman, F. M. (1988), RNA Processing, Cold Spring Harbor Laboratory, p. 68.

Hanley, Brian A and Schuler, Mary A., *Nucleic Acids Research* (1988), Vol. 16, No. 14, p. 7159.

Helfman, D. M. and Ricci, W. M. (1988), RNA Processing, Cold Spring Harbor Laboratory, p. 219.

Herrera-Estrella, L. et al., *Nature* (1983), 303:209.

Hoekema, A. et al., *Molecular and Cellular Biology* (1987), Vol. 7, pp. 2914-2924.

Honee, G. et al., *Nucleic Acids Research* (1988), Vol. 16, No. 13.

Horsch, R. B. et al., *Science* (1985), 227:1229.

Jarret, R. L. et al., *Physiol. Plant* (1980), 49:177.

Jarret, R. L. et al., *In Vitro* (1981), 17:825.

Kay, R. et al., *Science* (1987), 236:1299-1302.

Kessler, M. et al. (1988), RNA Processing, Cold Spring Harbor Laboratory, p. 85.

Klee, H. J. et al., *Bio/Technology* (1985), 3:637-642.

Kozak, M., *Nature* (1984), 308:241-246.

Krebbers, E., et al., *Plant Molecular Biology* (1988), 11:745-759.

Kunkel, T. A., *Proc. Natl. Acad. Sci. USA* (1985), Vol. 82, pp. 488-492.

Marrone et al., *J. Econ. Entomol.* (1985), 78-290-293.

Marzluff, W. and Pandey, N. (1988), RNA Processing, Cold Spring Harbor Laboratory, p. 244.

McCormick, S. et al., *Plant Cell Reports* (1986), 5:81-84.

McDevitt, M. A. et al., *Cell* (1984), Vol. 37, pp. 993-999.

Murashige, T. and Skoog, F., *Physiol. Plant* (1962), 15:473.

Odell, J. et al., *Nature* (1985), 313:810.

Pandey, N. B. and Marzluff, W. F. (1987), RNA Processing, Cold Spring Harbor Laboratory, p. 133.

Proudfoot, N. J. et al. (1987), RNA Processing, Cold Spring Harbor Laboratory, p. 17.

Reines, D., et al., *J. Mol. Biol.* (1987) 196:299-312.

Sadofsky, M. and Alwine, J. C., *Molecular and Cellular Biology* (1984), Vol. 4, No. 8, pp. 1460-1468.

Sanders, P. R. et al., *Nucleic Acids Research* (1987), Vol. 15, No. 4, p. 1543.

Schuler, M. A. et al., *Nucleic Acids Research* (1982), Vol. 10, No. 24, pp. 8225-8244.
Shaw, G. & Kamen, R., *Cell* (1986), 46:659-667.
Shaw, G. and Kamen, R. (1987), RNA Processing, Cold Spring Harbor Laboratory, p. 220.
Trolinder, N. L. and Goodin, J. R., *Plant Cell Reports* (1987), 6:231-234.
Tsurushita, N. and Korn, L. J. (1987), RNA Processing, Cold Spring Harbor Laboratory, p. 215.
Tumer, N. E., et al., *Nucleic Acids Reg.* (1986), Vol. 14:8, 3325.
Vaeck, M. et al., *Nature* (1987), Vol. 328, p. 33.
Velten et al., *EMBO J.* (1984), 3:2723-2730.
Velten & Schell, *Nucleic Acids Research* (1985), 13:6981-6998.
Visser, B. et al., *Mol. Gen. Genet.* (1988), 212:219-224.
Webb, K. J. et al., *Plant Sci. Letters* (1983), 30:1.
Wickens, M. and Stephenson, P., *Science* (1984), Vol. 226, p. 1045.
Wickens, M. et al. (1987), RNA Processing, Cold Spring Harbor Laboratory, p. 9.
Wiebauer, K. et al., *Molecular and Cellular Biology* (1988), Vol. 8, No. 5, pp. 2042-2051.
Yamamoto, T. and Iizuka, T., *Archives of Biochemistry and Biophysics* (1983), Vol. 227, No. 1, pp. 233-241.

SEQUENCE LISTING

```
<160> NUMBER OF SEQ ID NOS: 40

<210> SEQ ID NO 1
<211> LENGTH: 1743
<212> TYPE: DNA
<213> ORGANISM: Artificial sequence
<220> FEATURE:
<223> OTHER INFORMATION: Synthetic nucleotide sequence encoding Btk HD-1
      insecticidal protein (cry1Ab), described in Example 1, and set
      forth in the lower line of Figure 2

<400> SEQUENCE: 1

atggctatag aaactggtta caccccaatc gatatttcct tgtcgctaac gcaatttctt     60

ttgagtgaat ttgttcccgg tgctggattt gtgttaggac tagttgatat tatctgggga    120

atttttggtc cctctcaatg ggacgcattt cttgtacaaa ttgaacagct catcaaccag    180

agaatcgaag agttcgctag gaatcaagcc atttctagat tagaaggact aagcaatctt    240

tatcaaattt acgcagaatc ttttagagag tgggaagcag atcctactaa tccagcatta    300

agagaagaga tgcgtattca attcaatgac atgaacagtg cccttacaac cgctattcct    360

ctttttgcag ttcaaaatta tcaagttcct ctcctctccg tgtacgttca agctgccaac    420

ctccacctct cagttttgag agatgtttca gtgtttggac aaaggtgggg atttgatgcc    480

gcgactatca atagtcgtta taatgattta actaggctta ttggcaacta tacagatcat    540

gctgtacgct ggtacaatac gggattagag cgtgtatggg gaccggattc tagagattgg    600

atcaggtaca accagttcag aagagagctt acactaactg tattagatat cgtttctcta    660

tttccgaact atgatagtag aacgtatcca attcgaacag tttcccaatt aacaagagaa    720

atttatacaa acccagtatt agaaaatttt gatggtagtt ttcgaggctc ggctcagggc    780

atagaaggaa gtattaggag tccacatttg atggatatac ttaatagtat aaccatctat    840

acggatgctc atagaggaga atactactgg tccggtcacc agatcatggc ttctcctgta    900

gggttttcgg ggccagaatt cacttttccg ctatatggaa ctatgggaaa tgcagctcca    960

caacaacgta ttgttgctca actaggtcag ggcgtgtata gaacattatc gtccacctta   1020

tatagaagac cttttaacat cgggatcaac aaccaacaac tatctgttct tgacgggaca   1080

gaatttgctt atggaacctc ctcaaatttg ccatccgctg tatacagaaa aagcggaacg   1140

gtagattcgc tggatgaaat accgccacag aataacaacg tgccacctag gcaaggattt   1200

agtcatcgat taagccatgt ttcaatgttt cgttcaggct ttagtaatag tagtgtaagt   1260

ataataagag ctcctatgtt ctcttggata catcgtagtg ctgagttcaa caacatcatc   1320

ccttcatcac aaatcaccca aatcccactc accaagtcta ctaatcttgg ctctggaact   1380
```

-continued

```
tctgtcgtta aaggaccagg atttacagga ggagatattc ttcgaagaac ttcacctggc   1440

cagatttcaa ccttaagagt aaatattact gcaccattat cacaaagata tcgggtaaga   1500

attcgctacg cttctaccac aaaccttcag ttccacacat caattgacgg aagacctatt   1560

aatcagggga atttttcagc aactatgagt agtgggagta atttacagtc cggaagcttt   1620

aggactgtag gttttactac tccgtttaac ttttcaaatg gatcaagtgt atttacgtta   1680

agtgctcatg tcttcaattc aggcaatgaa gtttatatag atcgaattga atttgttccg   1740

gca                                                                 1743
```

<210> SEQ ID NO 2
<211> LENGTH: 1743
<212> TYPE: DNA
<213> ORGANISM: Artificial sequence
<220> FEATURE:
<223> OTHER INFORMATION: Native Btk HD-1 nucleotide sequence encoding Btk HD-1 toxin protein (Cry1Ab) from amino acid 29-607 as described in Example 1 & set forth in the upper line of Figure 2, & includes synthetic sequence encoding N-terminal Met-Ala

<400> SEQUENCE: 2

```
atggctatag aaactggtta caccccaatc gatatttcct tgtcgctaac gcaatttctt     60

ttgagtgaat ttgttcccgg tgctggattt gtgttaggac tagttgatat aatatgggga    120

atttttggtc cctctcaatg ggacgcattt cttgtacaaa ttgaacagtt aattaaccaa    180

agaatagaag aattcgctag gaaccaagcc atttctagat tagaaggact aagcaatctt    240

tatcaaattt acgcagaatc ttttagagag tgggaagcag atcctactaa tccagcatta    300

agagaagaga tgcgtattca attcaatgac atgaacagtg cccttacaac cgctattcct    360

ctttttgcag ttcaaaatta tcaagttcct cttttatcag tatatgttca agctgcaaat    420

ttacatttat cagttttgag agatgtttca gtgtttggac aaaggtgggg atttgatgcc    480

gcgactatca atagtcgtta taatgattta actaggctta ttggcaacta tacagatcat    540

gctgtacgct ggtacaatac gggattagag cgtgtatggg gaccggattc tagagattgg    600

ataagatata atcaatttag aagagaatta acactaactg tattagatat cgtttctcta    660

tttccgaact atgatagtag aacgtatcca attcgaacag tttcccaatt aacaagagaa    720

atttatacaa acccagtatt agaaaatttt gatggtagtt ttcgaggctc ggctcagggc    780

atagaaggaa gtattaggag tccacatttg atggatatac ttaatagtat aaccatctat    840

acggatgctc atagaggaga atattattgg tcagggcatc aaataatggc ttctcctgta    900

gggttttcgg ggccagaatt cacttttccg ctatatggaa ctatgggaaa tgcagctcca    960

caacaacgta ttgttgctca actaggtcag ggcgtgtata gaacattatc gtccacctta   1020

tatagaagac cttttaatat agggataaat aatcaacaac tatctgttct tgacgggaca   1080

gaatttgctt atggaacctc ctcaaatttg ccatccgctg tatacagaaa aagcggaacg   1140

gtagattcgc tggatgaaat accgccacag aataacaacg tgccacctag gcaaggattt   1200

agtcatcgat taagccatgt ttcaatgttt cgttcaggct ttagtaatag tagtgtaagt   1260

ataataagag ctcctatgtt ctcttggata catcgtagtg ctgaatttaa taatataatt   1320

ccttcatcac aaattacaca aataccttta acaaaatcta ctaatcttgg ctctggaact   1380

tctgtcgtta aaggaccagg atttacagga ggagatattc ttcgaagaac ttcacctggc   1440

cagatttcaa ccttaagagt aaatattact gcaccattat cacaaagata tcgggtaaga   1500

attcgctacg cttctaccac aaatttacaa ttccatacat caattgacgg aagacctatt   1560
```

-continued

```
aatcagggga atttttcagc aactatgagt agtgggagta atttacagtc cggaagcttt   1620

aggactgtag gttttactac tccgtttaac ttttcaaatg gatcaagtgt atttacgtta   1680

agtgctcatg tcttcaattc aggcaatgaa gtttatatag atcgaattga atttgttccg   1740

gca                                                                 1743
```

<210> SEQ ID NO 3
<211> LENGTH: 1845
<212> TYPE: DNA
<213> ORGANISM: Artificial sequence
<220> FEATURE:
<223> OTHER INFORMATION: Synthetic sequence encoding Btk HD-1 insecticidal toxin protein (Cry1Ab), described in Example 2, and set forth in the lower line of Figure 3

<400> SEQUENCE: 3

```
atggacaaca acccaaacat caacgaatgc attccataca actgcttgag taacccagaa     60

gttgaagtac ttggtggaga acgcattgaa accggttaca ctcccatcga catctccttg    120

tccttgacac agtttctgct cagcgagttc gtgccaggtg ctgggttcgt tctcggacta    180

gttgacatca tctggggtat ctttggtcca tctcaatggg atgcattcct ggtgcaaatt    240

gagcagttga tcaaccagag gatcgaagag ttcgccagga accaggccat ctctaggttg    300

gaaggattga gcaatctcta ccaaatctat gcagagagct tcagagagtg ggaagccgat    360

cctactaacc cagctctccg cgaggaaatg cgtattcaat tcaacgacat gaacagcgcc    420

ttgaccacag ctatcccatt gttcgcagtc cagaactacc aagttcctct cttgtccgtg    480

tacgttcaag cagctaatct tcacctcagc gtgcttcgag acgttagcgt gtttgggcaa    540

aggtggggat tcgatgctgc aaccatcaat agccgttaca acgaccttac taggctgatt    600

ggaaactaca ccgaccacgc tgttcgttgg tacaacactg gcttggagcg tgtctggggt    660

cctgattcta gagattggat tagatacaac cagttcagga gagaattgac cctcacagtt    720

ttggacattg tgtctctctt cccgaactat gactccagaa cctaccctat ccgtacagtg    780

tcccaactta ccagagaaat ctatactaac ccagttcttg agaacttcga cggtagcttc    840

cgtggttctg cccaaggtat cgaaggctcc atcaggagcc cacacttgat ggacatcttg    900

aacagcataa ctatctacac cgatgctcac agaggagagt attactggtc tggacaccag    960

atcatggcct ctccagttgg attcagcggg cccgagttta cctttcctct ctatggaact   1020

atgggaaacg ccgctccaca acaacgtatc gttgctcaac taggtcaggg tgtctacaga   1080

accttgtctt ccaccttgta cagaagaccc ttcaatatcg gtatcaacaa ccagcaactt   1140

tccgttcttg acggaacaga gttcgcctat ggaacctctt ctaacttgcc atccgctgtt   1200

tacagaaaga gcggaaccgt tgattccttg gacgaaatcc caccacagaa caacaatgtg   1260

ccacccaggc aaggattctc ccacaggttg agccacgtgt ccatgttccg ttccggattc   1320

agcaacagtt ccgtgagcat catcagagct cctatgttct catggattca tcgtagtgct   1380

gagttcaaca atatcattcc ttcctctcaa atcacccaaa tcccattgac caagtctact   1440

aaccttggat ctggaacttc tgtcgtgaaa ggaccaggct tcacaggagg tgatattctt   1500

agaagaactt ctcctggcca gattagcacc ctcagagtta acatcactgc accactttct   1560

caaagatatc gtgtcaggat tcgttacgca tctaccacta acttgcaatt ccacacctcc   1620

atcgacggaa ggcctatcaa tcagggtaac ttctccgcaa ccatgtcaag cggcagcaac   1680

ttgcaatccg gcagcttcag aaccgtcggt ttcactactc ctttcaactt ctctaacgga   1740
```

-continued

```
tcaagcgttt tcacccttag cgctcatgtg ttcaattctg gcaatgaagt gtacattgac   1800

cgtattgagt ttgtgcctgc cgaagttacc ttcgaggctg agtac                  1845


<210> SEQ ID NO 4
<211> LENGTH: 1845
<212> TYPE: DNA
<213> ORGANISM: Artificial sequence
<220> FEATURE:
<223> OTHER INFORMATION: Native Btk HD1 nucleotide sequence encoding Btk
      HD-1 insecticidal toxin protein (Cry1Ab), described in Example 2,
      and set forth in the upper line of Figure 3

<400> SEQUENCE: 4

atggataaca atccgaacat caatgaatgc attccttata attgtttaag taaccctgaa     60

gtagaagtat taggtggaga aagaatagaa actggttaca ccccaatcga tatttccttg    120

tcgctaacgc aatttctttt gagtgaattt gttcccggtg ctggatttgt gttaggacta    180

gttgatataa tatggggaat ttttggtccc tctcaatggg acgcatttct tgtacaaatt    240

gaacagttaa ttaaccaaag aatagaagaa ttcgctagga accaagccat ttctagatta    300

gaaggactaa gcaatcttta tcaaatttac gcagaatctt ttagagagtg ggaagcagat    360

cctactaatc cagcattaag agaagagatg cgtattcaat tcaatgacat gaacagtgcc    420

cttacaaccg ctattcctct tttgcagtt caaaattatc aagttcctct tttatcagta    480

tatgttcaag ctgcaaattt acatttatca gttttgagag atgtttcagt gtttggacaa    540

aggtggggat ttgatgccgc gactatcaat agtcgttata atgatttaac taggcttatt    600

ggcaactata cagatcatgc tgtacgctgg tacaatacgg gattagagcg tgtatgggga    660

ccggattcta gagattggat aagatataat caatttagaa gagaattaac actaactgta    720

ttagatatcg tttctctatt tccgaactat gatagtagaa cgtatccaat tcgaacagtt    780

tcccaattaa caagagaaat ttatacaaac ccagtattag aaaattttga tggtagtttt    840

cgaggctcgg ctcagggcat agaaggaagt attaggagtc cacatttgat ggatatactt    900

aatagtataa ccatctatac ggatgctcat agaggagaat attattggtc agggcatcaa    960

ataatggctt ctcctgtagg gttttcgggg ccagaattca cttttccgct atatggaact   1020

atgggaaatg cagctccaca acaacgtatt gttgctcaac taggtcaggg cgtgtataga   1080

acattatcgt ccaccttata tagaagacct tttaatatag ggataaataa tcaacaacta   1140

tctgttcttg acgggacaga atttgcttat ggaacctcct caaatttgcc atccgctgta   1200

tacagaaaaa gcggaacggt agattcgctg gatgaaatac cgccacagaa taacaacgtg   1260

ccacctaggc aaggatttag tcatcgatta agccatgttt caatgtttcg ttcaggcttt   1320

agtaatagta gtgtaagtat aataagagct cctatgttct cttggataca tcgtagtgct   1380

gaatttaata atataattcc ttcatcacaa attacacaaa tacctttaac aaaatctact   1440

aatcttggct ctggaacttc tgtcgttaaa ggaccaggat ttacaggagg agatattctt   1500

cgaagaactt cacctggcca gatttcaacc ttaagagtaa atattactgc accattatca   1560

caaagatatc gggtaagaat tcgctacgct tctaccacaa atttacaatt ccatacatca   1620

attgacggaa gacctattaa tcaggggaat ttttcagcaa ctatgagtag tgggagtaat   1680

ttacagtccg gaagctttag gactgtaggt tttactactc cgtttaactt ttcaaatgga   1740

tcaagtgtat ttacgttaag tgctcatgtc ttcaattcag gcaatgaagt ttatatagat   1800

cgaattgaat ttgttccggc agaagtaacc tttgaggcag aatat                  1845
```

-continued

<210> SEQ ID NO 5
<211> LENGTH: 1921
<212> TYPE: DNA
<213> ORGANISM: Artificial sequence
<220> FEATURE:
<223> OTHER INFORMATION: Synthetic hybrid of first 1360 bases synthetic HD-1 linked to modified HD-73 sequence, described in paragraph bridging pages 53-54, and as set forth in the lower line of Figure 4

<400> SEQUENCE: 5

```
atggacaaca acccaaacat caacgaatgc attccataca actgcttgag taacccagaa     60

gttgaagtac ttggtggaga acgcattgaa accggttaca ctcccatcga catctccttg    120

tccttgacac agtttctgct cagcgagttc gtgccaggtg ctgggttcgt tctcggacta    180

gttgacatca tctggggtat ctttggtcca tctcaatggg atgcattcct ggtgcaaatt    240

gagcagttga tcaaccagag gatcgaagag ttcgccagga accaggccat ctctaggttg    300

gaaggattga gcaatctcta ccaaatctat gcagagagct tcagagagtg ggaagccgat    360

cctactaacc cagctctccg cgaggaaatg cgtattcaat tcaacgacat gaacagcgcc    420

ttgaccacag ctatcccatt gttcgcagtc cagaactacc aagttcctct cttgtccgtg    480

tacgttcaag cagctaatct tcacctcagc gtgcttcgag acgttagcgt gtttgggcaa    540

aggtggggat tcgatgctgc aaccatcaat agccgttaca acgaccttac taggctgatt    600

ggaaactaca ccgaccacgc tgttcgttgg tacaacactg gcttggagcg tgtctggggt    660

cctgattcta gagattggat tagatacaac cagttcagga gagaattgac cctcacagtt    720

ttggacattg tgtctctctt cccgaactat gactccagaa cctaccctat ccgtacagtg    780

tcccaactta ccagagaaat ctatactaac ccagttcttg agaacttcga cggtagcttc    840

cgtggttctg cccaaggtat cgaaggctcc atcaggagcc cacacttgat ggacatcttg    900

aacagcataa ctatctacac cgatgctcac agaggagagt attactggtc tggacaccag    960

atcatggcct ctccagttgg attcagcggg cccgagttta cctttcctct ctatggaact   1020

atgggaaacg ccgctccaca acaacgtatc gttgctcaac taggtcaggg tgtctacaga   1080

accttgtctt ccaccttgta cagaagaccc ttcaatatcg gtatcaacaa ccagcaactt   1140

tccgttcttg acggaacaga gttcgcctat ggaacctctt ctaacttgcc atccgctgtt   1200

tacagaaaga gcggaaccgt tgattccttg gacgaaatcc caccacagaa caacaatgtg   1260

ccacccaggc aaggattctc ccacaggttg agccacgtgt ccatgttccg ttccggattc   1320

agcaacagtt ccgtgagcat catcagagct cctatgttct cttggataca ccgtagtgct   1380

gagttcaaca acatcatcgc atccgatagt attactcaaa tccctgcagt gaagggaaac   1440

tttctcttca acggttctgt catttcagga ccaggattca ctggtggaga cctcgttaga   1500

ctcaacagca gtggaaataa cattcagaat agagggtata ttgaagttcc aattcacttc   1560

ccatccacat ctaccagata tagagttcgt gtgaggtatg cttctgtgac ccctattcac   1620

ctcaacgtta attggggtaa ttcatccatc ttctccaata cagttccagc tacagctacc   1680

tccttggata atctccaatc cagcgatttc ggttactttg aaagtgccaa tgcttttaca   1740

tcttcactcg gtaacatcgt gggtgttaga aactttagtg ggactgcagg agtgattatc   1800

gacagattcg agttcattcc agttactgca acactcgagg ctgaatataa tctggaaaga   1860

gcgcagaagg cggtaatgcg ctgtttacgt ctacaaacca gcttggactc aagacaaatg   1920

g                                                                    1921
```

-continued

<210> SEQ ID NO 6
<211> LENGTH: 1921
<212> TYPE: DNA
<213> ORGANISM: Artificial sequence
<220> FEATURE:
<223> OTHER INFORMATION: Native Bt nucleotide sequence encoding N-terminal 450 HD-1 (Cry1Ab) amino acids and 451-615 of Bkt HD73 (Cry1Ac) described in Example 3 and as set forth in the upper line of Figure 4

<400> SEQUENCE: 6

```
atggataaca atccgaacat caatgaatgc attccttata attgtttaag taaccctgaa      60
gtagaagtat taggtggaga aagaatagaa actggttaca ccccaatcga tatttccttg     120
tcgctaacgc aatttctttt gagtgaattt gttcccggtg ctggatttgt gttaggacta     180
gttgatataa tatggggaat ttttggtccc tctcaatggg acgcatttct tgtacaaatt     240
gaacagttaa ttaaccaaag aatagaagaa ttcgctagga accaagccat ttctagatta     300
gaaggactaa gcaatcttta tcaaatttac gcagaatctt ttagagagtg ggaagcagat     360
cctactaatc cagcattaag agaagagatg cgtattcaat tcaatgacat gaacagtgcc     420
cttacaaccg ctattcctct tttgcagtt caaaattatc aagttcctct tttatcagta     480
tatgttcaag ctgcaaattt acatttatca gttttgagag atgtttcagt gtttggacaa     540
aggtggggat ttgatgccgc gactatcaat agtcgttata atgatttaac taggcttatt     600
ggcaactata cagatcatgc tgtacgctgg tacaatacgg gattagagcg tgtatgggga     660
ccggattcta gagattggat aagatataat caatttagaa gagaattaac actaactgta     720
ttagatatcg tttctctatt tccgaactat gatagtagaa cgtatccaat tcgaacagtt     780
tcccaattaa caagagaaat ttatacaaac ccagtattag aaaattttga tggtagtttt     840
cgaggctcgg ctcagggcat agaaggaagt attaggagtc cacatttgat ggatatactt     900
aatagtataa ccatctatac ggatgctcat agaggagaat attattggtc agggcatcaa     960
ataatggctt ctcctgtagg gttttcgggg ccagaattca cttttccgct atatggaact    1020
atgggaaatg cagctccaca acaacgtatt gttgctcaac taggtcaggg cgtgtataga    1080
acattatcgt ccaccttata tagaagacct tttaatatag ggataaataa tcaacaacta    1140
tctgttcttg acgggacaga atttgcttat ggaacctcct caaatttgcc atccgctgta    1200
tacagaaaaa gcggaacggt agattcgctg gatgaaatac cgccacagaa taacaacgtg    1260
ccacctaggc aaggatttag tcatcgatta agccatgttt caatgtttcg ttcaggcttt    1320
agtaatagta gtgtaagtat aataagagct cctatgttct cttggataca tcgtagtgct    1380
gaatttaata atataattgc atcggatagt attactcaaa tccctgcagt gaagggaaac    1440
tttctttta atggttctgt aatttcagga ccaggattta ctggtgggga cttagttaga    1500
ttaaatagta gtggaaataa cattcagaat agagggtata ttgaagttcc aattcacttc    1560
ccatcgacat ctaccagata tcgagttcgt gtacggtatg cttctgtaac cccgattcac    1620
ctcaacgtta attggggtaa ttcatccatt ttttccaata cagtaccagc tacagctacg    1680
tcattagata atctacaatc aagtgatttt ggttattttg aaagtgccaa tgcttttaca    1740
tcttcattag gtaatatagt aggtgttaga aattttagtg ggactgcagg agtgataata    1800
gacagatttg aatttattcc agttactgca acactcgagg ctgaatataa tctggaaaga    1860
gcgcagaagg cggtgaatgc gctgtttacg tctacaaacc aactagggct aaaaacaaat    1920
g                                                                    1921
```

-continued

```
<210> SEQ ID NO 7
<211> LENGTH: 1767
<212> TYPE: DNA
<213> ORGANISM: Artificial sequence
<220> FEATURE:
<223> OTHER INFORMATION: Truncated synthetic sequence encoding a hybrid
      Btk HD73 (Cry1Ac) from amino acid 29-615 and including codons
      encoding N-terminal MET-ALA as described in Example 3 and set
      forth in the lower line of Figure 8

<400> SEQUENCE: 7

atggccattg aaaccggtta cactcccatc gacatctcct tgtccttgac acagtttctg     60

ctcagcgagt tcgtgccagg tgctgggttc gttctcggac tagttgacat catctggggt    120

atctttggtc catctcaatg ggatgcattc ctggtgcaaa ttgagcagtt gatcaaccag    180

aggatcgaag agttcgccag gaaccaggcc atctctaggt tggaaggatt gagcaatctc    240

taccaaatct atgcagagag cttcagagag tgggaagccg atcctactaa cccagctctc    300

cgcgaggaaa tgcgtattca attcaacgac atgaacagcg ccttgaccac agctatccca    360

ttgttcgcag tccagaacta ccaagttcct ctcttgtccg tgtacgttca agcagctaat    420

cttcacctca gcgtgcttcg agacgttagc gtgtttgggc aaaggtgggg attcgatgct    480

gcaaccatca atagccgtta caacgacctt actaggctga ttggaaacta caccgaccac    540

gctgttcgtt ggtacaacac tggcttggag cgtgtctggg gtcctgattc tagagattgg    600

attagataca accagttcag gagagaattg accctcacag ttttggacat tgtgtctctc    660

ttcccgaact atgactccag aacctaccct atccgtacag tgtcccaact taccagagaa    720

atctatacta acccagttct tgagaacttc gacggtagct tccgtggttc tgcccaaggt    780

atcgaaggct ccatcaggag cccacacttg atggacatct tgaacagcat aactatctac    840

accgatgctc acagaggaga gtattactgg tctggacacc agatcatggc ctctccagtt    900

ggattcagcg ggcccgagtt tacctttcct ctctatggaa ctatgggaaa cgccgctcca    960

caacaacgta tcgttgctca actaggtcag ggtgtctaca gaaccttgtc ttccaccttg   1020

tacagaagac ccttcaatat cggtatcaac aaccagcaac tttccgttct tgacggaaca   1080

gagttcgcct atggaacctc ttctaacttg ccatccgctg tttacagaaa gagcggaacc   1140

gttgattcct tggacgaaat cccaccacag aacaacaatg tgccacccag gcaaggattc   1200

tcccacaggt tgagccacgt gtccatgttc cgttccggat tcagcaacag ttccgtgagc   1260

atcatcagag ctcctatgtt ctcttggata caccgtagtg ctgagttcaa caacatcatc   1320

gcatccgata gtattactca aatccctgca gtgaagggaa actttctctt caacggttct   1380

gtcatttcag gaccaggatt cactggtgga gacctcgtta gactcaacag cagtggaaat   1440

aacattcaga atagagggta tattgaagtt ccaattcact tcccatccac atctaccaga   1500

tatagagttc gtgtgaggta tgcttctgtg acccctattc acctcaacgt taattggggt   1560

aattcatcca tcttctccaa tacagttcca gctacagcta cctccttgga taatctccaa   1620

tccagcgatt tcggttactt tgaaagtgcc aatgctttta catcttcact cggtaacatc   1680

gtgggtgtta gaaactttag tgggactgca ggagtgatta tcgacagatt cgagttcatt   1740

ccagttactg caacactcga ggctgag                                       1767


<210> SEQ ID NO 8
<211> LENGTH: 1767
<212> TYPE: DNA
<213> ORGANISM: Artificial sequence
<220> FEATURE:
<223> OTHER INFORMATION: Native Bt sequence encoding hybrid Btk HD-73
```

-continued (Cry1Ac), described in Example 3 and set forth in the upper line of Figure 8

<400> SEQUENCE: 8

```
gaaagaatag aaactggtta caccccaatc gatatttcct tgtcgctaac gcaatttctt     60
ttgagtgaat ttgttcccgg tgctggattt gtgttaggac tagttgatat aatatgggga    120
atttttggtc cctctcaatg ggacgcattt cttgtacaaa ttgaacagtt aattaaccaa    180
agaatagaag aattcgctag gaaccaagcc atttctagat tagaaggact aagcaatctt    240
tatcaaattt acgcagaatc ttttagagag tgggaagcag atcctactaa tccagcatta    300
agagaagaga tgcgtattca attcaatgac atgaacagtg cccttacaac cgctattcct    360
ctttttgcag ttcaaaatta tcaagttcct cttttatcag tatatgttca agctgcaaat    420
ttacatttat cagttttgag agatgtttca gtgtttggac aaaggtgggg atttgatgcc    480
gcgactatca atagtcgtta taatgattta actaggctta ttggcaacta tacagatcat    540
gctgtacgct ggtacaatac gggattagag cgtgtatggg gaccggattc tagagattgg    600
ataagatata atcaatttag aagagaatta acactaactg tattagatat cgtttctcta    660
tttccgaact atgatagtag aacgtatcca attcgaacag tttcccaatt aacaagagaa    720
atttatacaa acccagtatt agaaaatttt gatggtagtt ttcgaggctc ggctcagggc    780
atagaaggaa gtattaggag tccacatttg atggatatac ttaatagtat aaccatctat    840
acggatgctc atagaggaga atattattgg tcagggcatc aaataatggc ttctcctgta    900
gggttttcgg ggccagaatt cacttttccg ctatatggaa ctatgggaaa tgcagctcca    960
caacaacgta ttgttgctca actaggtcag ggcgtgtata gaacattatc gtccacctta   1020
tatagaagac cttttaatat agggataaat aatcaacaac tatctgttct tgacgggaca   1080
gaatttgctt atggaacctc ctcaaatttg ccatccgctg tatacagaaa aagcggaacg   1140
gtagattcgc tggatgaaat accgccacag aataacaacg tgccacctag gcaaggattt   1200
agtcatcgat taagccatgt ttcaatgttt cgttcaggct ttagtaatag tagtgtaagt   1260
ataataagag ctcctatgtt ctcttggata catcgtagtg ctgaatttaa taatataatt   1320
gcatcggata gtattactca aatccctgca gtgaagggaa actttctttt taatggttct   1380
gtaatttcag gaccaggatt tactggtggg gacttagtta gattaaatag tagtggaaat   1440
aacattcaga atagagggta tattgaagtt ccaattcact tcccatcgac atctaccaga   1500
tatcgagttc gtgtacggta tgcttctgta accccgattc acctcaacgt taattggggt   1560
aattcatcca tttttccaa tacagtacca gctacagcta cgtcattaga taatctacaa   1620
tcaagtgatt ttggttattt tgaaagtgcc aatgctttta catcttcatt aggtaatata   1680
gtaggtgtta gaaattttag tgggactgca ggagtgataa tagacagatt tgaatttatt   1740
ccagttactg caacactcga ggctgaa                                       1767
```

<210> SEQ ID NO 9
<211> LENGTH: 3534
<212> TYPE: DNA
<213> ORGANISM: Artificial sequence
<220> FEATURE:
<223> OTHER INFORMATION: synthetic/wild-type full length sequence encoding HD-73(Cry1Ac), 1st 1845 nucleotides set forth lower line Fig 4, 1846-end is native sequence encoding C-terminus of HD73, described in Ex 3, set forth in the lower line of Figure 9

<400> SEQUENCE: 9

```
atggacaaca acccaaacat caacgaatgc attccataca actgcttgag taacccagaa     60
```

-continued

```
gttgaagtac ttggtggaga acgcattgaa accggttaca ctcccatcga catctccttg    120
tccttgacac agtttctgct cagcgagttc gtgccaggtg ctgggttcgt tctcggacta    180
gttgacatca tctggggtat ctttggtcca tctcaatggg atgcattcct ggtgcaaatt    240
gagcagttga tcaaccagag gatcgaagag ttcgccagga accaggccat ctctaggttg    300
gaaggattga gcaatctcta ccaaatctat gcagagagct tcagagagtg ggaagccgat    360
cctactaacc cagctctccg cgaggaaatg cgtattcaat tcaacgacat gaacagcgcc    420
ttgaccacag ctatcccatt gttcgcagtc cagaactacc aagttcctct cttgtccgtg    480
tacgttcaag cagctaatct tcacctcagc gtgcttcgag acgttagcgt gtttgggcaa    540
aggtggggat tcgatgctgc aaccatcaat agccgttaca acgaccttac taggctgatt    600
ggaaactaca ccgaccacgc tgttcgttgg tacaacactg gcttggagcg tgtctggggt    660
cctgattcta gagattggat tagatacaac cagttcagga gagaattgac cctcacagtt    720
ttggacattg tgtctctctt cccgaactat gactccagaa cctaccctat ccgtacagtg    780
tcccaactta ccagagaaat ctatactaac ccagttcttg agaacttcga cggtagcttc    840
cgtggttctg cccaaggtat cgaaggctcc atcaggagcc cacacttgat ggacatcttg    900
aacagcataa ctatctacac cgatgctcac agaggagagt attactggtc tggacaccag    960
atcatggcct ctccagttgg attcagcggg cccgagttta cctttcctct ctatggaact   1020
atgggaaacg ccgctccaca acaacgtatc gttgctcaac taggtcaggg tgtctacaga   1080
accttgtctt ccaccttgta cagaagaccc ttcaatatcg gtatcaacaa ccagcaactt   1140
tccgttcttg acggaacaga gttcgcctat ggaacctctt ctaacttgcc atccgctgtt   1200
tacagaaaga gcggaaccgt tgattccttg gacgaaatcc caccacagaa caacaatgtg   1260
ccacccaggc aaggattctc ccacaggttg agccacgtgt ccatgttccg ttccggattc   1320
agcaacagtt ccgtgagcat catcagagct cctatgttct cttggataca ccgtagtgct   1380
gagttcaaca acatcatcgc atccgatagt attactcaaa tccctgcagt gaagggaaac   1440
tttctcttca acggttctgt catttcagga ccaggattca ctggtggaga cctcgttaga   1500
ctcaacagca gtggaaataa cattcagaat agagggtata ttgaagttcc aattcacttc   1560
ccatccacat ctaccagata tagagttcgt gtgaggtatg cttctgtgac ccctattcac   1620
ctcaacgtta attggggtaa ttcatccatc ttctccaata cagttccagc tacagctacc   1680
tccttggata atctccaatc cagcgatttc ggttactttg aaagtgccaa tgcttttaca   1740
tcttcactcg gtaacatcgt gggtgttaga aactttagtg ggactgcagg agtgattatc   1800
gacagattcg agttcattcc agttactgca acactcgagg ctgaatataa tctggaaaga   1860
gcgcagaagg cggtgaatgc gctgtttacg tctacaaacc aactagggct aaaaacaaat   1920
gtaacggatt atcatattga tcaagtgtcc aatttagtta cgtatttatc ggatgaattt   1980
tgtctggatg aaaagcgaga attgtccgag aaagtcaaac atgcgaagcg actcagtgat   2040
gaacgcaatt tactccaaga ttcaaatttc aaagacatta ataggcaacc agaacgtggg   2100
tggggcggaa gtacagggat taccatccaa ggaggggatg acgtatttaa agaaaattac   2160
gtcacactat caggtacctt tgatgagtgc tatccaacat atttgtatca aaaaatcgat   2220
gaatcaaaat taaaagcctt tacccgttat caattaagag ggtatatcga agatagtcaa   2280
gacttagaaa tctatttaat tcgctacaat gcaaaacatg aaacagtaaa tgtgccaggt   2340
acgggttcct tatggccgct ttcagcccaa agtccaatcg gaaagtgtgg agagccgaat   2400
```

-continued

```
cgatgcgcgc cacaccttga atggaatcct gacttagatt gttcgtgtag ggatggagaa   2460

aagtgtgccc atcattcgca tcatttctcc ttagacattg atgtaggatg tacagactta   2520

aatgaggacc taggtgtatg ggtgatcttt aagattaaga cgcaagatgg gcacgcaaga   2580

ctagggaatc tagagtttct cgaagagaaa ccattagtag gagaagcgct agctcgtgtg   2640

aaaagagcgg agaaaaaatg gagagacaaa cgtgaaaaat tggaatggga aacaaatatc   2700

gtttataaag aggcaaaaga atctgtagat gctttatttg taaactctca atatgatcaa   2760

ttacaagcgg atacgaatat tgccatgatt catgcggcag ataaacgtgt tcatagcatt   2820

cgagaagctt atctgcctga gctgtctgtg attccgggtg tcaatgcggc tatttttgaa   2880

gaattagaag ggcgtatttt cactgcattc tccctatatg atgcgagaaa tgtcattaaa   2940

aatggtgatt ttaataatgg cttatcctgc tggaacgtga aagggcatgt agatgtagaa   3000

gaacaaaaca accaacgttc ggtccttgtt gttccggaat gggaagcaga agtgtcacaa   3060

gaagttcgtg tctgtccggg tcgtggctat atccttcgtg tcacagcgta caaggaggga   3120

tatggagaag gttgcgtaac cattcatgag atcgagaaca atacagacga actgaagttt   3180

agcaactgcg tagaagagga aatctatcca aataacacgg taacgtgtaa tgattatact   3240

gtaaatcaag aagaatacgg aggtgcgtac acttctcgta atcgaggata taacgaagct   3300

ccttccgtac cagctgatta tgcgtcagtc tatgaagaaa aatcgtatac agatggacga   3360

agagagaatc cttgtgaatt taacagaggg tatagggatt acacgccact accagttggt   3420

tatgtgacaa aagaattaga atacttccca gaaaccgata aggtatggat tgagattgga   3480

gaaacggaag gaacatttat cgtggacagc gtggaattac tccttatgga ggaa         3534
```

```
<210> SEQ ID NO 10
<211> LENGTH: 3534
<212> TYPE: DNA
<213> ORGANISM: Bacillus thuringiensis
<220> FEATURE:
<223> OTHER INFORMATION: wild type full length HD73 (Cry1Ac) gene,
      described in Example 3 and set forth in upper line of Figures 9-11

<400> SEQUENCE: 10

atggataaca atccgaacat caatgaatgc attccttata attgtttaag taaccctgaa     60

gtagaagtat taggtggaga aagaatagaa actggttaca ccccaatcga tatttccttg    120

tcgctaacgc aatttctttt gagtgaattt gttcccggtg ctggatttgt gttaggacta    180

gttgatataa tatggggaat ttttggtccc tctcaatggg acgcatttct tgtacaaatt    240

gaacagttaa ttaaccaaag aatagaagaa ttcgctagga accaagccat ttctagatta    300

gaaggactaa gcaatcttta tcaaatttac gcagaatctt ttagagagtg ggaagcagat    360

cctactaatc cagcattaag agaagagatg cgtattcaat tcaatgacat gaacagtgcc    420

cttacaaccg ctattcctct tttgcagtt caaaattatc aagttcctct tttatcagta    480

tatgttcaag ctgcaaattt acatttatca gttttgagag atgtttcagt gtttggacaa    540

aggtggggat ttgatgccgc gactatcaat agtcgttata atgatttaac taggcttatt    600

ggcaactata cagatcatgc tgtacgctgg tacaatacgg gattagagcg tgtatgggga    660

ccggattcta gagattggat aagatataat caatttagaa gagaattaac actaactgta    720

ttagatatcg tttctctatt tccgaactat gatagtagaa cgtatccaat tcgaacagtt    780

tcccaattaa caagagaaat ttatacaaac ccagtattag aaaattttga tggtagtttt    840

cgaggctcgg ctcagggcat agaaggaagt attaggagtc cacatttgat ggatatactt    900
```

-continued

```
aatagtataa ccatctatac ggatgctcat agaggagaat attattggtc agggcatcaa    960
ataatggctt ctcctgtagg gttttcgggg ccagaattca cttttccgct atatggaact   1020
atgggaaatg cagctccaca acaacgtatt gttgctcaac taggtcaggg cgtgtataga   1080
acattatcgt ccaccttata tagaagacct tttaatatag ggataaataa tcaacaacta   1140
tctgttcttg acgggacaga atttgcttat ggaacctcct caaatttgcc atccgctgta   1200
tacagaaaaa gcggaacggt agattcgctg gatgaaatac cgccacagaa taacaacgtg   1260
ccacctaggc aaggatttag tcatcgatta agccatgttt caatgtttcg ttcaggcttt   1320
agtaatagta gtgtaagtat aataagagct cctatgttct cttggataca tcgtagtgct   1380
gaatttaata atataattgc atcggatagt attactcaaa tccctgcagt gaagggaaac   1440
tttctttttta atggttctgt aatttcagga ccaggattta ctggtgggga cttagttaga   1500
ttaaatagta gtggaaataa cattcagaat agagggtata ttgaagttcc aattcacttc   1560
ccatcgacat ctaccagata tcgagttcgt gtacggtatg cttctgtaac ccccgattcac   1620
ctcaacgtta attggggtaa ttcatccatt ttttccaata cagtaccagc tacagctacg   1680
tcattagata atctacaatc aagtgatttt ggttattttg aaagtgccaa tgcttttaca   1740
tcttcattag gtaatatagt aggtgttaga aattttagtg ggactgcagg agtgataata   1800
gacagatttg aatttattcc agttactgca acactcgagg ctgaatataa tctggaaaga   1860
gcgcagaagg cggtgaatgc gctgtttacg tctacaaacc aactagggct aaaaacaaat   1920
gtaacggatt atcatattga tcaagtgtcc aatttagtta cgtatttatc ggatgaattt   1980
tgtctggatg aaaagcgaga attgtccgag aaagtcaaac atgcgaagcg actcagtgat   2040
gaacgcaatt tactccaaga ttcaaatttc aaagacatta ataggcaacc agaacgtggg   2100
tggggcggaa gtacagggat taccatccaa ggaggggatg acgtatttaa agaaaattac   2160
gtcacactat caggtacctt tgatgagtgc tatccaacat atttgtatca aaaaatcgat   2220
gaatcaaaat taaaagcctt tacccgttat caattaagag ggtatatcga agatagtcaa   2280
gacttagaaa tctatttaat tcgctacaat gcaaaacatg aaacagtaaa tgtgccaggt   2340
acgggttcct tatggccgct ttcagcccaa agtccaatcg gaaagtgtgg agagccgaat   2400
cgatgcgcgc cacaccttga atggaatcct gacttagatt gttcgtgtag ggatggagaa   2460
aagtgtgccc atcattcgca tcatttctcc ttagacattg atgtaggatg tacagactta   2520
aatgaggacc taggtgtatg ggtgatcttt aagattaaga cgcaagatgg gcacgcaaga   2580
ctagggaatc tagagtttct cgaagagaaa ccattagtag gagaagcgct agctcgtgtg   2640
aaaagagcgg agaaaaaatg gagagacaaa cgtgaaaaat tggaatggga aacaaatatc   2700
gtttataaag aggcaaaaga atctgtagat gctttatttg taaactctca atatgatcaa   2760
ttacaagcgg atacgaatat tgccatgatt catgcggcag ataaacgtgt tcatagcatt   2820
cgagaagctt atctgcctga gctgtctgtg attccgggtg tcaatgcggc tatttttgaa   2880
gaattagaag ggcgtatttt cactgcattc tccctatatg atgcgagaaa tgtcattaaa   2940
aatggtgatt ttaataatgg cttatcctgc tggaacgtga aagggcatgt agatgtagaa   3000
gaacaaaaca accaacgttc ggtccttgtt gttccggaat gggaagcaga agtgtcacaa   3060
gaagttcgtg tctgtccggg tcgtggctat atccttcgtg tcacagcgta caaggaggga   3120
tatggagaag gttgcgtaac cattcatgag atcgagaaca atacagacga actgaagttt   3180
agcaactgcg tagaagagga aatctatcca aataacacgg taacgtgtaa tgattatact   3240
gtaaatcaag aagaatacgg aggtgcgtac acttctcgta atcgaggata taacgaagct   3300
```

-continued

```
ccttccgtac cagctgatta tgcgtcagtc tatgaagaaa aatcgtatac agatggacga   3360

agagagaatc cttgtgaatt taacagaggg tatagggatt acacgccact accagttggt   3420

tatgtgacaa aagaattaga atacttccca gaaaccgata aggtatggat tgagattgga   3480

gaaacggaag gaacatttat cgtggacagc gtggaattac tccttatgga ggaa          3534
```

<210> SEQ ID NO 11
<211> LENGTH: 3534
<212> TYPE: DNA
<213> ORGANISM: Artificial sequence
<220> FEATURE:
<223> OTHER INFORMATION: Synthetic/modified sequence encoding HD73 (CryAc)described in Example 3 and set forth as lower line in Figure 10

<400> SEQUENCE: 11

```
atggacaaca acccaaacat caacgaatgc attccataca actgcttgag taacccagaa     60

gttgaagtac ttggtggaga acgcattgaa accggttaca ctcccatcga catctccttg    120

tccttgacac agtttctgct cagcgagttc gtgccaggtg ctgggttcgt tctcggacta    180

gttgacatca tctggggtat ctttggtcca tctcaatggg atgcattcct ggtgcaaatt    240

gagcagttga tcaaccagag gatcgaagag ttcgccagga accaggccat ctctaggttg    300

gaaggattga gcaatctcta ccaaatctat gcagagagct tcagagagtg ggaagccgat    360

cctactaacc cagctctccg cgaggaaatg cgtattcaat tcaacgacat gaacagcgcc    420

ttgaccacag ctatcccatt gttcgcagtc cagaactacc aagttcctct cttgtccgtg    480

tacgttcaag cagctaatct tcacctcagc gtgcttcgag acgttagcgt gtttgggcaa    540

aggtggggat tcgatgctgc aaccatcaat agccgttaca acgaccttac taggctgatt    600

ggaaactaca ccgaccacgc tgttcgttgg tacaacactg gcttggagcg tgtctggggt    660

cctgattcta gagattggat tagatacaac cagttcagga gagaattgac cctcacagtt    720

ttggacattg tgtctctctt cccgaactat gactccagaa cctaccctat ccgtacagtg    780

tcccaactta ccagagaaat ctatactaac ccagttcttg agaacttcga cggtagcttc    840

cgtggttctg cccaaggtat cgaaggctcc atcaggagcc cacacttgat ggacatcttg    900

aacagcataa ctatctacac cgatgctcac agaggagagt attactggtc tggacaccag    960

atcatggcct ctccagttgg attcagcggg cccgagttta cctttcctct ctatggaact   1020

atgggaaacg ccgctccaca acaacgtatc gttgctcaac taggtcaggg tgtctacaga   1080

accttgtctt ccaccttgta cagaagaccc ttcaatatcg gtatcaacaa ccagcaactt   1140

tccgttcttg acggaacaga gttcgcctat ggaacctctt ctaacttgcc atccgctgtt   1200

tacagaaaga gcggaaccgt tgattccttg gacgaaatcc caccacagaa caacaatgtg   1260

ccacccaggc aaggattctc ccacaggttg agccacgtgt ccatgttccg ttccggattc   1320

agcaacagtt ccgtgagcat catcagagct cctatgttct cttggataca ccgtagtgct   1380

gagttcaaca acatcatcgc atccgatagt attactcaaa tccctgcagt gaagggaaac   1440

tttctcttca acggttctgt catttcagga ccaggattca ctggtggaga cctcgttaga   1500

ctcaacagca gtggaaataa cattcagaat agagggtata ttgaagttcc aattcacttc   1560

ccatccacat ctaccagata tagagttcgt gtgaggtatg cttctgtgac ccctattcac   1620

ctcaacgtta attggggtaa ttcatccatc ttctccaata cagttccagc tacagctacc   1680

tccttggata atctccaatc cagcgatttc ggttactttg aaagtgccaa tgcttttaca   1740
```

-continued

```
tcttcactcg gtaacatcgt gggtgttaga aactttagtg ggactgcagg agtgattatc   1800

gacagattcg agttcattcc agttactgca acactcgagg ctgaatataa tctggaaaga   1860

gcgcagaagg cggtgaatgc gctgtttacg tctacaaacc agctcggcct caagaccaat   1920

gtgacggatt atcatattga tcaagtgtcc aacttggtga cctacctcag cgatgagttc   1980

tgtctggatg aaaagcgaga attgtccgag aaagtcaaac atgcgaagcg actcagtgat   2040

gaacgcaatt tactccaaga ttcaaatttc aaagacatta ataggcaacc agaacgtggg   2100

tggggcggaa gtacagggat taccatccag ggaggtgacg acgtgttcaa ggagaactac   2160

gtcacactat caggtacctt tgatgagtgc tatccaacat acctctacca gaagatcgac   2220

gagtccaagt tgaaagcctt tacccgttat caattaagag ggtatatcga agatagtcaa   2280

gacctcgaga tctacctcat ccgctacaat gcaaaacatg aaacagtaaa tgtgccaggt   2340

acgggttcct tatggccgct ttcagcccaa agtccaatcg gaaagtgtgg agagccgaat   2400

cgatgcgcgc cacaccttga atggaatcct gacttagatt gttcgtgtag ggatggagaa   2460

aagtgtgccc atcattcgca tcatttctcc ttagacattg atgtaggatg tacagactta   2520

aatgaggacc taggtgtatg ggtgatcttt aagattaaga cgcaagatgg gcacgcaaga   2580

ctagggaatc tagagtttct cgaagagaaa ccattagtag gagaagcgct agctcgtgtg   2640

aaaagagcgg agaaaaaatg gagagacaaa cgtgagaagt tggaatggga gaccaacatc   2700

gtctacaaag aggcaaaaga atctgtagat gctttatttg taaactctca atatgatcaa   2760

ttacaagcgg atacgaatat tgccatgatt catgcggcag ataaacgtgt tcatagcatt   2820

cgagaagctt atctgcctga gctgtctgtg attccgggtg tcaatgcggc tatttttgaa   2880

gaattagaag ggcgtatttt cactgcattc tccctctacg atgccagaaa cgtcatcaag   2940

aacggtgact tcaacaatgg cttatcctgc tggaacgtga aagggcatgt agatgtagaa   3000

gaacaaaaca accaacgttc ggtccttgtt gttccggaat gggaagcaga agtgtcacaa   3060

gaagttcgtg tctgtccggg tcgtggctat atccttcgtg tcacagcgta caaggaggga   3120

tatggagaag gttgcgtaac cattcatgag atcgagaaca atacagacga actgaagttt   3180

agcaactgcg tagaagagga aatctatcca aataacacgg taacgtgtaa tgattatact   3240

gtaaatcaag aagaatacgg aggtgcgtac acttctcgta atcgaggata taacgaagct   3300

ccttccgtac cagctgatta tgcgtcagtc tatgaagaaa aatcgtatac agatggacga   3360

agagagaatc cttgtgaatt taacagaggg tatagggatt acacgccact accagttggt   3420

tatgtgacaa aagaattaga atacttccca gaaaccgata aggtatggat tgagattgga   3480

gaaacggaag gaacatttat cgtggacagc gtggaattac tccttatgga ggaa         3534
```

```
<210> SEQ ID NO 12
<211> LENGTH: 3534
<212> TYPE: DNA
<213> ORGANISM: Artificial sequence
<220> FEATURE:
<223> OTHER INFORMATION: Fully synthetic sequence encoding insecticidal
      toxin encoding HD-73 (Cry1Ac) described in Example 3 and set forth
      in the lower line of Figure 11

<400> SEQUENCE: 12

atggacaaca acccaaacat caacgaatgc attccataca actgcttgag taacccagaa     60

gttgaagtac ttggtggaga acgcattgaa accggttaca ctcccatcga catctccttg    120

tccttgacac agtttctgct cagcgagttc gtgccaggtg ctgggttcgt tctcggacta    180

gttgacatca tctggggtat ctttggtcca tctcaatggg atgcattcct ggtgcaaatt    240
```

-continued

```
gagcagttga tcaaccagag gatcgaagag ttcgccagga accaggccat ctctaggttg    300
gaaggattga gcaatctcta ccaaatctat gcagagagct tcagagagtg ggaagccgat    360
cctactaacc cagctctccg cgaggaaatg cgtattcaat tcaacgacat gaacagcgcc    420
ttgaccacag ctatcccatt gttcgcagtc cagaactacc aagttcctct cttgtccgtg    480
tacgttcaag cagctaatct tcacctcagc gtgcttcgag acgttagcgt gtttgggcaa    540
aggtggggat tcgatgctgc aaccatcaat agccgttaca acgaccttac taggctgatt    600
ggaaactaca ccgaccacgc tgttcgttgg tacaacactg gcttggagcg tgtctggggt    660
cctgattcta gagattggat tagatacaac cagttcagga gagaattgac cctcacagtt    720
ttggacattg tgtctctctt cccgaactat gactccagaa cctaccctat ccgtacagtg    780
tcccaactta ccagagaaat ctatactaac ccagttcttg agaacttcga cggtagcttc    840
cgtggttctg cccaaggtat cgaaggctcc atcaggagcc cacacttgat ggacatcttg    900
aacagcataa ctatctacac cgatgctcac agaggagagt attactggtc tggacaccag    960
atcatggcct ctccagttgg attcagcggg cccgagttta cctttcctct ctatggaact   1020
atgggaaacg ccgctccaca acaacgtatc gttgctcaac taggtcaggg tgtctacaga   1080
accttgtctt ccaccttgta cagaagaccc ttcaatatcg gtatcaacaa ccagcaactt   1140
tccgttcttg acggaacaga gttcgcctat ggaacctctt ctaacttgcc atccgctgtt   1200
tacagaaaga gcggaaccgt tgattccttg gacgaaatcc caccacagaa caacaatgtg   1260
ccacccaggc aaggattctc ccacaggttg agccacgtgt ccatgttccg ttccggattc   1320
agcaacagtt ccgtgagcat catcagagct cctatgttct cttggataca ccgtagtgct   1380
gagttcaaca acatcatcgc atccgatagt attactcaaa tccctgcagt gaagggaaac   1440
tttctcttca acggttctgt catttcagga ccaggattca ctggtggaga cctcgttaga   1500
ctcaacagca gtggaaataa cattcagaat agagggtata ttgaagttcc aattcacttc   1560
ccatccacat ctaccagata tagagttcgt gtgaggtatg cttctgtgac ccctattcac   1620
ctcaacgtta attggggtaa ttcatccatc ttctccaata cagttccagc tacagctacc   1680
tccttggata atctccaatc cagcgatttc ggttactttg aaagtgccaa tgcttttaca   1740
tcttcactcg gtaacatcgt gggtgttaga aactttagtg ggactgcagg agtgattatc   1800
gacagattcg agttcattcc agttactgca acactcgagg ctgagtacaa ccttgagaga   1860
gcccagaagg ctgtgaacgc cctctttacc tccaccaatc agcttggctt gaaaactaac   1920
gttactgact atcacattga ccaagtgtcc aacttggtca cctaccttag cgatgagttc   1980
tgcctcgacg agaagcgtga actctccgag aaagttaaac acgccaagcg tctcagcgac   2040
gagaggaatc tcttgcaaga ctccaacttc aaagacatca acaggcagcc agaacgtggt   2100
tggggtggaa gcaccgggat caccatccaa ggaggcgacg atgtgttcaa ggagaactac   2160
gtcaccctct ccggaacttt cgacgagtgc taccctacct acttgtacca gaagatcgat   2220
gagtccaaac tcaaagcctt caccaggtat caacttagag gctacatcga agacagccaa   2280
gaccttgaaa tctactcgat caggtacaat gccaagcacg agaccgtgaa tgtcccaggt   2340
actggttccc tctggccact ttctgcccaa tctcccattg ggaagtgtgg agagcctaac   2400
agatgcgctc cacaccttga gtggaatcct gacttggact gctcctgcag ggatggcgag   2460
aagtgtgccc accattctca tcacttctcc ttggacatcg atgtgggatg tactgacctg   2520
aatgaggacc tcggagtctg ggtcatcttc aagatcaaga cccaagacgg acacgcaaga   2580
```

-continued

```
cttggcaacc ttgagtttct cgaagagaaa ccattggtcg gtgaagctct cgctcgtgtg   2640

aagagagcag agaagaagtg gagggacaaa cgtgagaaac tcgaatggga aactaacatc   2700

gtttacaagg aggccaaaga gtccgtggat gctttgttcg tgaactccca atatgatcag   2760

ttgcaagccg acaccaacat cgccatgatc cacgccgcag acaaacgtgt gcacagcatt   2820

cgtgaggctt acttgcctga gttgtccgtg atccctggtg tgaacgctgc catcttcgag   2880

gaacttgagg gacgtatctt taccgcattc tccttgtacg atgccagaaa cgtcatcaag   2940

aacggtgact tcaacaatgg cctcagctgc tggaatgtga aaggtcatgt ggacgtggag   3000

gaacagaaca atcagcgttc cgtcctggtt gtgcctgagt gggaagctga agtgtcccaa   3060

gaggttagag tctgtccagg tagaggctac attctccgtg tgaccgctta caaggaggga   3120

tacggtgagg gttgcgtgac catccacgag atcgagaaca acaccgacga gcttaagttc   3180

tccaactgcg tcgaggaaga aatctatccc aacaacaccg ttacttgcaa cgactacact   3240

gtgaatcagg aagagtacgg aggtgcctac actagccgta acagaggtta caacgaagct   3300

ccttccgttc ctgctgacta tgcctccgtg tacgaggaga aatcctacac agatggcaga   3360

cgtgagaacc cttgcgagtt caacagaggt tacagggact acacaccact tccagttggc   3420

tatgttacca aggagcttga gtactttcct gagaccgaca aagtgtggat cgagatcggt   3480

gaaaccgagg gaaccttcat cgtggacagc gtggagcttc tcttgatgga ggaa         3534
```

```
<210> SEQ ID NO 13
<211> LENGTH: 3531
<212> TYPE: DNA
<213> ORGANISM: Artificial sequence
<220> FEATURE:
<223> OTHER INFORMATION: Nucleotide sequence described as HD-73 (Cry1Ac)
      in Example 3 (page 59, lines 13-16), nucleotide 1-1830 as set
      forth in lower line of Figure 11

<400> SEQUENCE: 13
```

```
atggacaaca acccaaacat caacgaatgc attccataca actgcttgag taacccagaa     60

gttgaagtac ttggtggaga acgcattgaa accggttaca ctcccatcga catctccttg    120

tccttgacac agtttctgct cagcgagttc gtgccaggtg ctgggttcgt tctcggacta    180

gttgacatca tctggggtat ctttggtcca tctcaatggg atgcattcct ggtgcaaatt    240

gagcagttga tcaaccagag gatcgaagag ttcgccagga accaggccat ctctaggttg    300

gaaggattga gcaatctcta ccaaatctat gcagagagct tcagagagtg ggaagccgat    360

cctactaacc cagctctccg cgaggaaatg cgtattcaat tcaacgacat gaacagcgcc    420

ttgaccacag ctatcccatt gttcgcagtc cagaactacc aagttcctct cttgtccgtg    480

tacgttcaag cagctaatct tcacctcagc gtgcttcgag acgttagcgt gtttgggcaa    540

aggtggggat tcgatgctgc aaccatcaat agccgttaca acgaccttac taggctgatt    600

ggaaactaca ccgaccacgc tgttcgttgg tacaacactg gcttggagcg tgtctggggt    660

cctgattcta gagattggat tagatacaac cagttcagga gagaattgac cctcacagtt    720

ttggacattg tgtctctctt cccgaactat gactccagaa cctaccctat ccgtacagtg    780

tcccaactta ccagagaaat ctatactaac ccagttcttg agaacttcga cggtagcttc    840

cgtggttctg cccaaggtat cgaaggctcc atcaggagcc cacacttgat ggacatcttg    900

aacagcataa ctatctacac cgatgctcac agaggagagt attactggtc tggacaccag    960

atcatggcct ctccagttgg attcagcggg cccgagttta cctttcctct ctatggaact   1020

atgggaaacg ccgctccaca acaacgtatc gttgctcaac taggtcaggg tgtctacaga   1080
```

-continued

```
accttgtctt ccaccttgta cagaagaccc ttcaatatcg gtatcaacaa ccagcaactt   1140
tccgttcttg acggaacaga gttcgcctat ggaacctctt ctaacttgcc atccgctgtt   1200
tacagaaaga gcggaaccgt tgattccttg gacgaaatcc caccacagaa caacaatgtg   1260
ccacccaggc aaggattctc ccacaggttg agccacgtgt ccatgttccg ttccggattc   1320
agcaacagtt ccgtgagcat catcagagct cctatgttct catggattca tcgtagtgct   1380
gagttcaaca atatcattcc ttcctctcaa atcacccaaa tcccattgac caagtctact   1440
aaccttggat ctggaacttc tgtcgtgaaa ggaccaggct tcacaggagg tgatattctt   1500
agaagaactt ctcctggcca gattagcacc ctcagagtta acatcactgc accactttct   1560
caaagatatc gtgtcaggat tcgttacgca tctaccacta acttgcaatt ccacacctcc   1620
atcgacggaa ggcctatcaa tcagggtaac ttctccgcaa ccatgtcaag cggcagcaac   1680
ttgcaatccg gcagcttcag aaccgtcggt ttcactactc ctttcaactt ctctaacgga   1740
tcaagcgttt tcacccttag cgctcatgtg ttcaattctg gcaatgaagt gtacattgac   1800
cgtattgagt ttgtgcctgc cgaagttacc ctcgaggctg agtacaacct tgagagagcc   1860
cagaaggctg tgaacgccct ctttacctcc accaatcagc ttggcttgaa aactaacgtt   1920
actgactatc acattgacca agtgtccaac ttggtcacct accttagcga tgagttctgc   1980
ctcgacgaga agcgtgaact ctccgagaaa gttaaacacg ccaagcgtct cagcgacgag   2040
aggaatctct tgcaagactc caacttcaaa gacatcaaca ggcagccaga acgtggttgg   2100
ggtggaagca ccgggatcac catccaagga ggcgacgatg tgttcaagga gaactacgtc   2160
accctctccg gaactttcga cgagtgctac cctacctact tgtaccagaa gatcgatgag   2220
tccaaactca aagccttcac caggtatcaa cttagaggct acatcgaaga cagccaagac   2280
cttgaaatct actcgatcag gtacaatgcc aagcacgaga ccgtgaatgt cccaggtact   2340
ggttccctct ggccactttc tgcccaatct cccattggga agtgtggaga gcctaacaga   2400
tgcgctccac accttgagtg gaatcctgac ttggactgct cctgcaggga tggcgagaag   2460
tgtgcccacc attctcatca cttctccttg gacatcgatg tgggatgtac tgacctgaat   2520
gaggacctcg gagtctgggt catcttcaag atcaagaccc aagacggaca cgcaagactt   2580
ggcaaccttg agtttctcga agagaaacca ttggtcggtg aagctctcgc tcgtgtgaag   2640
agagcagaga agaagtggag ggacaaacgt gagaaactcg aatgggaaac taacatcgtt   2700
tacaaggagg ccaaagagtc cgtggatgct ttgttcgtga actcccaata tgatcagttg   2760
caagccgaca ccaacatcgc catgatccac gccgcagaca aacgtgtgca cagcattcgt   2820
gaggcttact tgcctgagtt gtccgtgatc cctggtgtga acgctgccat cttcgaggaa   2880
cttgagggac gtatctttac cgcattctcc ttgtacgatg ccagaaacgt catcaagaac   2940
ggtgacttca acaatggcct cagctgctgg aatgtgaaag gtcatgtgga cgtggaggaa   3000
cagaacaatc agcgttccgt cctggttgtg cctgagtggg aagctgaagt gtcccaagag   3060
gttagagtct gtccaggtag aggctacatt ctccgtgtga ccgcttacaa ggagggatac   3120
ggtgagggtt gcgtgaccat ccacgagatc gagaacaaca ccgacgagct taagttctcc   3180
aactgcgtcg aggaagaaat ctatcccaac aacaccgtta cttgcaacga ctacactgtg   3240
aatcaggaag agtacggagg tgcctacact agccgtaaca gaggttacaa cgaagctcct   3300
tccgttcctg ctgactatgc ctccgtgtac gaggagaaat cctacacaga tggcagacgt   3360
gagaaccctt gcgagttcaa cagaggttac agggactaca caccacttcc agttggctat   3420
```

-continued

```
gttaccaagg agcttgagta ctttcctgag accgacaaag tgtggatcga gatcggtgaa   3480

accgagggaa ccttcatcgt ggacagcgtg gagcttctct tgatggagga a            3531
```

<210> SEQ ID NO 14
<211> LENGTH: 1791
<212> TYPE: DNA
<213> ORGANISM: Artificial sequence
<220> FEATURE:
<223> OTHER INFORMATION: Synthetic nucleotide sequence encoding a Btt toxin (Cry3Aa), described in Example 5 and set forth in the lower line in Figure 12

<400> SEQUENCE: 14

```
atgactgcag acaacaacac cgaagccctc gacagttcta ccactaagga tgttatccag     60

aagggtatct ccgttgtggg agacctcttg ggcgtggttg gatttccctt cggtggagcc    120

ctcgtgagct tctatacaaa ctttctcaac accatttggc caagcgagga cccttggaaa    180

gcattcatgg agcaagttga agctcttatg gatcagaaga ttgcagatta tgccaagaac    240

aaggctttgg cagaactcca gggccttcag aacaatgtgg aggactacgt gagtgcattg    300

tccagctggc agaagaaccc tgttagctcc agaaatcctc acagccaagg taggatcaga    360

gagttgttct ctcaagccga atcccacttc agaaattcca tgcctagctt tgctatctcc    420

ggttacgagg ttcttttcct cactacctat gctcaagctg ccaacaccca cttgtttctc    480

cttaaggacg ctcaaatcta tggagaagag tggggatacg agaaagagga cattgctgag    540

ttctacaagc gtcaacttaa gctcacccaa gagtacactg accattgcgt gaaatggtat    600

aacgttggtc tcgataagct cagaggctct tcctacgagt cttgggtgaa cttcaacaga    660

tacaggagag agatgacctt gactgtgctc gatcttatcg cactctttcc cttgtacgat    720

gtgagactct acccaaagga agtgaaaact gagcttacca gagacgtgct cactgaccct    780

attgtcggag tcaacaacct taggggttat ggaactacct tcagcaatat cgaaaactac    840

attaggaaac cacatctctt cgactatctt cacagaattc aattccacac aaggtttcaa    900

ccaggatact atggtaacga ctccttcaac tattggtccg gtaactatgt ttccaccaga    960

ccaagcattg gatctaatga catcatcaca tctcccttct atggtaacaa gtccagtgaa   1020

cctgtgcaga accttgagtt caacggcgag aaagtctata gagccgtcgc aaacaccaat   1080

ctcgctgtgt ggccatccgc agtttactca ggcgtcacaa aggtggagtt tagtcagtat   1140

aacgatcaga ccgatgaggc cagcacccag acttacgact ccaaacgtaa cgttggcgca   1200

gtctcttggg attctatcga ccaattgcct ccagaaacca cagacgaacc attggagaag   1260

ggctacagcc accaacttaa ctatgtgatg tgcttcttga tgcaaggttc cagagggacc   1320

attccagtgt tgacctggac acacaagtcc gtggacttct tcaacatgat cgatagcaag   1380

aagatcactc aacttccctt ggtgaaagcc tacaagctgc aatctggtgc ttccgttgtc   1440

gcaggtccca gattcactgg aggtgacatc atccagtgca cagagaacgg cagcgcagct   1500

actatctacg tgacacctga tgtgtcttac tctcagaagt acagggcacg tattcattac   1560

gcatctacca gccagatcac cttcacactc agcttggatg gagcaccctt caaccagtat   1620

tactttgaca agaccatcaa caaaggtgac actctcacat acaatagctt caacttggca   1680

agtttcagca caccatttga actctcaggc aacaatcttc agatcggcgt caccggtctc   1740

agcgccggag acaaagtcta catcgacaag attgagttca tcccagtgaa c            1791
```

<210> SEQ ID NO 15
<211> LENGTH: 1791

-continued

<212> TYPE: DNA
<213> ORGANISM: Artificial sequence
<220> FEATURE:
<223> OTHER INFORMATION: Btt toxin (Cry3Aa), Example 5 and upper line in Figure 12

<400> SEQUENCE: 15
atgactgcag ataataatac ggaagcacta gatagctcta caacaaaaga tgtcattcaa 60
aaaggcattt ccgtagtagg tgatctccta ggcgtagtag gtttcccgtt tggtggagcg 120
cttgtttcgt tttatacaaa ctttttaaat actatttggc caagtgaaga cccgtggaag 180
gcttttatgg aacaagtaga agcattgatg gatcagaaaa tagctgatta tgcaaaaaat 240
aaagctcttg cagagttaca gggccttcaa aataatgtcg aagattatgt gagtgcattg 300
agttcatggc aaaaaaatcc tgtgagttca cgaaatccac atagccaggg gcggataaga 360
gagctgtttt ctcaagcaga aagtcatttt cgtaattcaa tgccttcgtt tgcaatttct 420
ggatacgagg ttctatttct aacaacatat gcacaagctg ccaacacaca tttattttta 480
ctaaaagacg ctcaaattta tggagaagaa tggggatacg aaaaagaaga tattgctgaa 540
ttttataaaa gacaactaaa acttacgcaa gaatatactg accattgtgt caaatggtat 600
aatgttggat tagataaatt aagaggttca tcttatgaat cttgggtaaa ctttaaccgt 660
tatcgcagag agatgacatt aacagtatta gatttaattg cactatttcc attgtatgat 720
gttcggctat acccaaaaga agttaaaacc gaattaacaa gagacgtttt aacagatcca 780
attgtcggag tcaacaacct taggggctat ggaacaacct tctctaatat agaaaattat 840
attcgaaaac cacatctatt tgactatctg catagaattc aatttcacac gcggttccaa 900
ccaggatatt atggaaatga ctctttcaat tattggtccg gtaattatgt ttcaactaga 960
ccaagcatag gatcaaatga tataatcaca tctccattct atggaaataa atccagtgaa 1020
cctgtacaaa atttagaatt taatggagaa aaagtctata gagccgtagc aaatacaaat 1080
cttgcggtct ggccgtccgc tgtatattca ggtgttacaa aagtggaatt tagccaatat 1140
aatgatcaaa cagatgaagc aagtacacaa acgtacgact caaaaagaaa tgttggcgcg 1200
gtcagctggg attctatcga tcaattgcct ccagaaacaa cagatgaacc tctagaaaag 1260
ggatatagcc atcaactcaa ttatgtaatg tgctttttaa tgcagggtag tagaggaaca 1320
atcccagtgt taacttggac acataaaagt gtagactttt ttaacatgat tgattcgaaa 1380
aaaattacac aacttccgtt agtaaaggca tataagttac aatctggtgc ttccgttgtc 1440
gcaggtccta ggtttacagg aggagatatc attcaatgca cagaaaatgg aagtgcggca 1500
actatttacg ttacaccgga tgtgtcgtac tctcaaaaat atcgagctag aattcattat 1560
gcttctacat ctcagataac atttacactc agtttagacg ggcaccatt taatcaatac 1620 tatttcgata aaacgataaa taaaggagac acattaacgt ataattcatt taatttagca 1680
agtttcagca caccattcga attatcaggg aataacttac aaataggcgt cacaggatta 1740
agtgctggag ataaagttta tatagacaaa attgaattta ttccagtgaa t 1791

<210> SEQ ID NO 16
<211> LENGTH: 1902
<212> TYPE: DNA
<213> ORGANISM: Artificial sequence
<220> FEATURE:
<223> OTHER INFORMATION: Synthetic nucleotide sequence encoding Bacillus thuringiensis kurstaki HD-1 insecticidal toxin P2 (Cry2Aa) described in Example 6 and set forth in the lower line in Figure 13

-continued

<400> SEQUENCE: 16

```
atggacaaca acgtcttgaa ctctggtaga acaaccatct gcgacgcata caacgtcgtg     60
gctcacgatc cattcagctt cgaacacaag agcctcgaca ctattcagaa ggagtggatg    120
gaatggaaac gtactgacca ctctctctac gtcgcacctg tggttggaac agtgtccagc    180
ttccttctca agaaggtcgg ctctctcatc ggaaaacgta tcttgtccga actctggggt    240
atcatctttc catctgggtc cactaatctc atgcaagaca tcttgaggga gaccgaacag    300
tttctcaacc agcgtctcaa cactgatacc ttggctagag tcaacgctga gttgatcggt    360
ctccaagcaa acattcgtga gttcaaccag caagtggaca acttcttgaa tccaactcag    420
aatcctgtgc ctctttccat cacttcttcc gtgaacacta tgcagcaact cttcctcaac    480
agattgcctc agtttcagat tcaaggctac cagttgctcc ttcttccact ctttgctcag    540
gctgccaaca tgcacttgtc cttcatacgt gacgtgatcc tcaacgctga cgaatgggga    600
atctctgcag ccactcttag gacatacaga gactacttga ggaactacac tcgtgattac    660
tccaactatt gcatcaacac ttatcagact gcctttcgtg gactcaatac taggcttcac    720
gacatgcttg agttcaggac ctacatgttc cttaacgtgt ttgagtacgt cagcatttgg    780
agtctcttca agtaccagag cttgatggtg tcctctggag ccaatctcta cgcctctggc    840
agtggaccac agcaaactca gagcttcaca gctcagaact ggccattctt gtatagcttg    900
ttccaagtca actccaacta cattctcagt ggtatctctg ggaccagact ctccataacc    960
tttcccaaca ttggtggact tccaggctcc actacaaccc atagccttaa ctctgccaga   1020
gtgaactaca gtggaggtgt cagctctgga ttgattggtg caactaactt gaaccacaac   1080
ttcaattgct ccaccgtctt gccacctctg agcacaccgt ttgtgaggtc ctggcttgac   1140
agcggtactg atcgcgaagg agttgctacc tctacaaact ggcaaaccga gtccttccaa   1200
accactctta gccttcggtg tggagctttc tctgcacgtg ggaattcaaa ctactttcca   1260
gactacttca ttaggaacat ctctggtgtt cctctcgtca tcaggaatga agacctcacc   1320
cgtccacttc attacaacca gattaggaac atcgagtctc catccggtac tccaggaggt   1380
gcaagagctt acctcgtgtc tgtccataac aggaagaaca acatctacgc tgccaacgag   1440
aatggcacca tgattcacct tgcaccagaa gattacactg gattcaccat ctctccaatc   1500
catgctaccc aagtgaacaa tcagacacgc accttcatct ccgaaaagtt cggaaatcaa   1560
ggtgactcct tgaggttcga gcaatccaac actaccgcta ggtacacttt gagaggcaat   1620
ggaaacagct acaaccttta cttgagagtt agctccattg gtaactccac catccgtgtt   1680
accatcaacg gacgtgttta cacagtctct aatgtgaaca ctacaacgaa caatgatggc   1740
gttaacgaca acggagccag attcagcgac atcaacattg gcaacatcgt ggcctctgac   1800
aacactaacg ttactttgga catcaatgtg accctcaatt ctggaactcc atttgatctc   1860
atgaacatca tgtttgtgcc aactaacctc cctccattgt ac                      1902
```

<210> SEQ ID NO 17
<211> LENGTH: 1899
<212> TYPE: DNA
<213> ORGANISM: Artificial sequence
<220> FEATURE:
<223> OTHER INFORMATION: P2 (Cry2Aa), Example 6 and set forth in upper line in Figure 13

<400> SEQUENCE: 17

```
atgaataatg tattgaatag tggaagaaca actatttgtg atgcgtataa tgtagtagcc     60
```

-continued

```
catgatccat ttagttttga acataaatca ttagatacca tccaaaaaga atggatggag    120

tggaaaagaa cagatcatag tttatatgta gctcctgtag tcggaactgt gtctagtttt    180

ttgctaaaga aagtggggag tcttattgga aaaaggatat tgagtgaatt atgggggata    240

atatttccta gtggtagtac aaatctaatg caagatattt taagggagac agaacaattc    300

ctaaatcaaa gacttaatac agataccctt gctcgtgtaa atgcagaatt gatagggctc    360

caagcgaata taagggagtt taatcaacaa gtagataatt ttttaaaccc tactcaaaac    420

cctgttcctt tatcaataac ttcttcggtt aatacaatgc agcaattatt tctaaataga    480

ttaccccagt tccagataca aggataccag ttgttattat tacctttatt tgcacaggca    540

gccaatatgc atctttcttt tattagagat gttattctta atgcagatga atggggtatt    600

tcagcagcaa cattacgtac gtatcgagat tacctgagaa attatacaag agattattct    660

aattattgta taaatacgta tcaaactgcg tttagagggt taaacacccg tttacacgat    720

atgttagaat ttagaacata tatgttttta aatgtatttg aatatgtatc catttggtca    780

ttgtttaaat atcagagtct tatggtatct tctggcgcta atttatatgc tagcggtagt    840

ggaccacagc agacacaatc atttacagca caaaactggc cattttttata ttctcttttc    900

caagttaatt cgaattatat attatctggt attagtggta ctaggctttc tattaccttc    960

cctaatattg gtggtttacc gggtagtact acaactcatt cattgaatag tgccagggtt   1020

aattatagcg gaggagtttc atctggtctc ataggggcga ctaatctcaa tcacaacttt   1080

aattgcagca cggtcctccc tcctttatca acaccatttg ttagaagttg gctggattca   1140

ggtacagatc gagagggcgt tgctacctct acgaattggc agacagaatc ctttcaaaca   1200

actttaagtt taaggtgtgg tgctttttca gcccgtggaa attcaaacta tttcccagat   1260

tattttatcc gtaatatttc tggggttcct ttagttatta gaaacgaaga tctaacaaga   1320

ccgttacact ataaccaaat aagaaatata gaaagtcctt cgggaacacc tggtggagca   1380

cgggcctatt tggtatctgt gcataacaga aaaaataata tctatgccgc taatgaaaat   1440

ggtactatga tccatttggc gccagaagat tatacaggat ttactatatc gccaatacat   1500

gccactcaag tgaataatca aactcgaaca tttatttctg aaaaatttgg aaatcaaggt   1560

gattccttaa gatttgaaca aagcaacacg acagctcgtt atacgcttag agggaatgga   1620

aatagttaca atctttattt aagagtatct tcaataggaa attcaactat tcgagttact   1680

ataaacggta gagtttatac tgtttcaaat gttaatacca ctacaaataa cgatggagtt   1740

aatgataatg gagctcgttt ttcagatatt aatatcggta atatagtagc aagtgataat   1800

actaatgtaa cgctagatat aaatgtgaca ttaaactccg gtactccatt tgatctcatg   1860

aatattatgt ttgtgccaac taatcttcca ccactttat                           1899
```

<210> SEQ ID NO 18
<211> LENGTH: 3567
<212> TYPE: DNA
<213> ORGANISM: Artificial sequence
<220> FEATURE:
<223> OTHER INFORMATION: Synthetic nucleotide sequence encoding Bt entomocidus insecticidal protein (Cry1Ca), described in Example 7 and set forth in the lower line of Figure 14

<400> SEQUENCE: 18

```
atggaggaga acaaccaaaa ccaatgcatt ccatacaact gcttgagtaa cccagaagag     60

gtattgcttg atggagaacg catttcaacc ggtaactctt ccatcgacat ctccttgtcc    120

ttggtccagt ttctggtcag caacttcgtg ccaggtggtg ggttccttgt cggactaatt    180
```

-continued

```
gacttcgtct ggggtatcgt tggtccatct caatgggatg cattcctggt gcaaattgag    240
cagttgatca acgagaggat cgctgagttc gccaggaacg ctgccatcgc taacttggaa    300
ggattgggca ataacttcaa catctatgtg gaggccttca aagagtggga agaggaccct    360
aacaacccag agacccgcac tagggtgatc gacagattca gaatcttgga cggcctcttg    420
gagagagata tcccatcctt cagaatctct ggcttcgaag ttcctctctt gtccgtgtac    480
gctcaagcag ctaatcttca cctcgctatc cttcgagaca gtgtcatctt tggggaaagg    540
tggggattga ccactatcaa cgtcaatgag aattacaaca gacttatcag gcacattgac    600
gagtacgccg accactgtgc taacacctac aaccgtggct tgaacaatct ccctaagtct    660
acttatcaag attggattac ctacaacagg ttgaggagag acttgaccct cacagttttg    720
gacattgcag ctttcttccc gaactatgac aacaggagat accctatcca accagtgggt    780
caacttacca gagaagtcta tactgaccca cttatcaact tcaaccctca gttgcaaagt    840
gtcgcccaac ttcccacatt caacgtcatg gagtccagcc gtatcaggaa cccacacttg    900
tttgacatct tgaacaacct tactatcttc accgattggt tcagcgttgg gcgtaacttc    960
tattggggtg gacacagggt catctcctct cttattggag gtgggaacat tacctctcct   1020
atctatggac gtgaggcaaa ccaggagcca ccacgtagtt tcaccttcaa cggtccagtc   1080
ttcagaacct tgtctaaccc taccttgaga ttgctccagc aaccttggcc agctccacct   1140
ttcaacctta gaggtgttga gggcgttgag ttctctactc ctaccaactc cttcacttac   1200
agaggtagag gaaccgttga ttccttgacc gaactcccac cagaggacaa tagcgtgcca   1260
cccagggaag gctactccca caggttgtgc cacgcaacct tcgtgcagcg ttccggaact   1320
ccattcctca ctacaggagt tgtgttctca tggactgatc gtagtgctac tctcactaat   1380
accattgatc ccgagaggat caatcaaatc ccattggtca agggtttccg tgtgtgggga   1440
ggaacttctg tcatcacagg accaggcttc acaggaggtg atattcttag aagaaacact   1500
tttggcgact ttgtgagcct ccaagttaac atcaactctc caattactca aagatatcgt   1560
ctcaggtttc gttacgcatc ttcccgtgac gctagagtca tcgtgctcac cggagcagct   1620
tctaccggtg tcggtggaca agtctccgtg aacatgccac tccagaagac tatggagatc   1680
ggcgagaact tgacatccag gaccttcaga tacaccgact tctctaaccc tttcagtttc   1740
cgtgccaacc ctgacatcat tggcattagc gaacaacctc tctttggagc tggtagcatc   1800
tcatctggcg aattgtacat tgacaagatt gagatcattc ttgccgacgc taccttcgag   1860
gctgagtctg accttgagag agcccagaag gctgtgaacg ccctctttac ctcctctaat   1920
cagattggct tgaaaactga cgttactgac tatcacattg accaagtgtc caacttggtc   1980
gactgcctta gcgatgagtt ctgcctcgac gagaagcgtg aactctccga gaaagttaaa   2040
cacgccaagc gtctcagcga cgagaggaat ctcttgcaag accccaactt cagaggcatc   2100
aacaggcagc cagaccgtgg ttggagagga agcaccgaca tcaccatcca aggaggcgac   2160
gatgtgttca aggagaacta cgtcaccctc ccaggaactg tggacgagtg ctaccctacc   2220
tacttgtacc agaagatcga tgagtccaaa ctcaaagcct acaccaggta tgaacttaga   2280
ggctacatcg aagacagcca agaccttgaa atctacctca tcaggtacaa tgccaagcac   2340
gagatcgtga atgtcccagg tactggttcc ctctggccac tttctgccca aatgcccatt   2400
gggaagtgtg gagagcctaa cagatgcgct ccacaccttg agtggaatcc tgacttggac   2460
tgctcctgca gggatggcga gaagtgtgcc caccattctc atcacttcac cttggacatc   2520
```

-continued

```
gatgtgggat gtactgacct gaatgaggac ctcggagtct gggtcatctt caagatcaag   2580

acccaagacg gacacgcaag acttggcaac cttgagtttc tcgaagagaa accattgctc   2640

ggtgaagctc tcgctcgtgt gaagagagca gagaagaagt ggagggacaa acgtgagaaa   2700

ctccaactcg agactaacat cgtttacaag gaggccaaag agtccgtgga tgctttgttc   2760

gtgaactccc aatatgatag gttgcaagtg gacaccaaca tcgccatgat ccacgctgca   2820

gacaaacgtg tgcacaggat tcgtgaggct tacttgcctg agttgtccgt gatccctggt   2880

gtgaacgctg ccatcttcga ggaacttgag ggacgtatct ttaccgcata ctccttgtac   2940

gatgccagaa acgtcatcaa gaacggtgac ttcaacaatg gcctcttgtg ctggaatgtg   3000

aaaggtcatg tggacgtgga ggaacagaac aatcaccgtt ccgtcctggt tatccctgag   3060

tgggaagctg aagtgtccca agaggttaga gtctgtccag gtagaggcta cattctccgt   3120

gtgaccgctt acaaggaggg atacggtgag ggttgcgtga ccatccacga gatcgaggac   3180

aacaccgacg agcttaagtt ctccaactgc gtcgaggaag aagtctatcc caacaacacc   3240

gttacttgca acaactacac tgggacccag gaagagtacg aaggtaccta cactagccgt   3300

aaccaaggtt acgacgaagc ttacggaaac aatccttccg ttcctgctga ctatgcctcc   3360

gtgtacgagg agaaatccta cacagatggc agacgtgaga acccttgcga gtccaacaga   3420

ggttacggtg actacacacc acttccagca ggctatgtta ccaaggacct tgagtacttt   3480

cctgagaccg acaaagtgtg gatcgagatc ggtgaaaccg agggaacctt catcgtggac   3540

agcgtggagc ttctcttgat ggaggaa                                      3567
```

<210> SEQ ID NO 19
<211> LENGTH: 3567
<212> TYPE: DNA
<213> ORGANISM: Artificial sequence
<220> FEATURE:
<223> OTHER INFORMATION: BTent (Cy1Ca), Example 7 and set forth in upper line in Figure 14

<400> SEQUENCE: 19

```
atggaggaaa ataatcaaaa tcaatgcata ccttacaatt gtttaagtaa tcctgaagaa     60

gtacttttgg atggagaacg gatatcaact ggtaattcat caattgatat ttctctgtca    120

cttgttcagt ttctggtatc taactttgta ccagggggag gatttttagt tggattaata    180

gattttgtat ggggaatagt tggcccttct caatgggatg catttctagt acaaattgaa    240

caattaatta atgaaagaat agctgaattt gctaggaatg ctgctattgc taatttagaa    300

ggattaggaa acaatttcaa tatatatgtg gaagcattta aagaatggga agaagatcct    360

aataatccag aaaccaggac cagagtaatt gatcgctttc gtatacttga tgggctactt    420

gaaagggaca ttccttcgtt tcgaatttct ggatttgaag taccccttt atccgtttat     480

gctcaagcgg ccaatctgca tctagctata ttaagagatt ctgtaatttt tggagaaaga    540

tggggattga caacgataaa tgtcaatgaa aactataata gactaattag gcatattgat    600

gaatatgctg atcactgtgc aaatacgtat aatcggggat taaataattt accgaaatct    660

acgtatcaag attggataac atataatcga ttacggagag acttaacatt gactgtatta    720

gatatcgccg ctttctttcc aaactatgac aataggagat atccaattca gccagttggt    780

caactaacaa gggaagttta tacggaccca ttaattaatt ttaatccaca gttacagtct    840

gtagctcaat tacctacttt taacgttatg gagagcagcc gaattagaaa tcctcattta    900

tttgatatat tgaataatct tacaatcttt acggattggt ttagtgttgg acgcaatttt    960
```

-continued

```
tattggggag gacatcgagt aatatctagc cttataggag gtggtaacat aacatctcct   1020
atatatggaa gagaggcgaa ccaggagcct ccaagatcct ttacttttaa tggaccggta   1080
tttaggactt tatcaaatcc tactttacga ttattacagc aaccttggcc agcgccacca   1140
tttaatttac gtggtgttga aggagtagaa ttttctacac ctacaaatag ctttacgtat   1200
cgaggaagag gtacggttga ttctttaact gaattaccgc ctgaggataa tagtgtgcca   1260
cctcgcgaag gatatagtca tcgtttatgt catgcaactt ttgttcaaag atctggaaca   1320
ccttttttaa caactggtgt agtattttct tggaccgatc gtagtgcaac tcttacaaat   1380
acaattgatc cagagagaat taatcaaata cctttagtga aaggatttag agtttggggg   1440
ggcacctctg tcattacagg accaggattt acaggagggg atatccttcg aagaaatacc   1500
tttggtgatt ttgtatctct acaagtcaat attaattcac caattaccca aagataccgt   1560
ttaagatttc gttacgcttc cagtagggat gcacgagtta tagtattaac aggagcggca   1620
tccacaggag tgggaggcca agttagtgta aatatgcctc ttcagaaaac tatggaaata   1680
ggggagaact taacatctag aacatttaga tataccgatt ttagtaatcc tttttcattt   1740
agagctaatc cagatataat tggataagt gaacaacctc tatttggtgc aggttctatt   1800
agtagcggtg aactttatat agataaaatt gaaattattc tagcagatgc aacatttgaa   1860
gcagaatctg atttagaaag agcacaaaag gcggtgaatg ccctgtttac ttcttccaat   1920
caaatcgggt taaaaaccga tgtgacggat tatcatattg atcaagtatc caatttagtg   1980
gattgtttat cagatgaatt ttgtctggat gaaaagcgag aattgtccga gaaagtcaaa   2040
catgcgaagc gactcagtga tgagcggaat ttacttcaag atccaaactt cagagggatc   2100
aatagacaac cagaccgtgg ctggagagga agtacagata ttaccatcca aggaggagat   2160
gacgtattca aagagaatta cgtcacacta ccgggtaccg ttgatgagtg ctatccaacg   2220
tatttatatc agaaaataga tgagtcgaaa ttaaaagctt atacccgtta tgaattaaga   2280
gggtatatcg aagatagtca agacttagaa atctatttga tccgttacaa tgcaaaacac   2340
gaaatagtaa atgtgccagg cacgggttcc ttatggccgc tttcagccca aatgccaatc   2400
ggaaagtgtg gagaaccgaa tcgatgcgcg ccacaccttg aatggaatcc tgatctagat   2460
tgttcctgca gagacgggga aaaatgtgca catcattccc atcatttcac cttggatatt   2520
gatgttggat gtacagactt aaatgaggac ttaggtgtat gggtgatatt caagattaag   2580
acgcaagatg gccatgcaag actagggaat ctagagtttc tcgaagagaa accattatta   2640
ggggaagcac tagctcgtgt gaaaagagcg gagaagaagt ggagagacaa acgagagaaa   2700
ctgcagttgg aaacaaatat tgtttataaa gaggcaaaag aatctgtaga tgctttattt   2760
gtaaactctc aatatgatag attacaagtg gatacgaaca tcgccatgat tcatgcggca   2820
gataaacgcg ttcatagaat ccgggaagcg tatctgccag agttgtctgt gattccaggt   2880
gtcaatgcgg ccattttcga agaattagag ggacgtattt ttacagcgta ttccttatat   2940
gatgcgagaa atgtcattaa aaatggcgat ttcaataatg gcttattatg ctggaacgtg   3000
aaaggtcatg tagatgtaga agagcaaaac aaccaccgtt cggtccttgt tatcccagaa   3060
tgggaggcag aagtgtcaca agaggttcgt gtctgtccag gtcgtggcta tatccttcgt   3120
gtcacagcat ataaagaggg atatggagag ggctgcgtaa cgatccatga gatcgaagac   3180
aatacagacg aactgaaatt cagcaactgt gtagaagagg aagtatatcc aaacaacaca   3240
gtaacgtgta ataattatac tgggactcaa gaagaatatg agggtacgta cacttctcgt   3300
aatcaaggat atgacgaagc ctatggtaat aacccttccg taccagctga ttacgcttca   3360
```

-continued

```
gtctatgaag aaaaatcgta tacagatgga cgaagagaga atccttgtga atctaacaga   3420

ggctatgggg attacacacc actaccggct ggttatgtaa caaaggattt agagtacttc   3480

ccagagaccg ataaggtatg gattgagatc ggagaaacag aaggaacatt catcgtggat   3540

agcgtggaat tactccttat ggaggaa                                       3567
```

<210> SEQ ID NO 20
<211> LENGTH: 762
<212> TYPE: DNA
<213> ORGANISM: Artificial sequence
<220> FEATURE:
<223> OTHER INFORMATION: Synthetic sequence encoding PLRV coat protein, disclosed in Example 9 and set forth in lower line of Figure 16

<400> SEQUENCE: 20

```
agatctagag gtaattgtta tgagtactgt cgtggttaag ggaaacgtga acggtggtgt     60

tcaacaacct agaaggagaa gaaggcaatc ccttcgtagg agagctaaca gagttcagcc    120

agtggttatg gtcactgctc ctgggcaacc aagaaggaga agaaggagaa gaggaggtaa    180

tcgcagatca agaagaactg gagttcccag aggaagaggt tcaagcgaga cattcgtgtt    240

tacaaaggac aacctcgtgg gcaactccca aggaagtttc accttcggac caagtgtttc    300

agactgtcca gcattcaagg atggaatact caaggcttac catgagtaca agatcacaag    360

tatcttgctt cagttcgtca gcgaggcctc ttccacctct ccaggctcca tcgcttatga    420

gttagatcca cattgcaaag tttcatccct ccagtcctac gtcaacaagt tccaaatcac    480

aaagggtggt gctaagacct atcaagctcg tatgatcaac ggagttgaat ggcacgattc    540

ttctgaggat cagtgcagaa tcctttggaa aggaaatgga aagtcttcag atccagctgg    600

atctttcaga gttaccatca gagttgctct tcaaaaccca aagtaataga attcggatca    660

gagcctggtc caagcccaca accaacaccc actccaactc cccaaaagca tgagcgattt    720

attgcttacg tcggcatacc tatgctgacc attcaagaat tc                       762
```

<210> SEQ ID NO 21
<211> LENGTH: 762
<212> TYPE: DNA
<213> ORGANISM: Artificial sequence
<220> FEATURE:
<223> OTHER INFORMATION: Wild type PLRV coat protein coding sequence (nt 20-643), described in Example 9 paragraph 2, and as set forth in upper line of Figure 16

<400> SEQUENCE: 21

```
agatctagag gtaattgtta tgagtactgt cgtggttaag ggaaacgtca acggtggtgt     60

acaacaacct agaaggagga gaaggcaatc ccttcgcagg agggctaaca gagtacagcc    120

agtggttatg gtcactgctc ctggcgaacc caggaggagg agacgcagaa gaggaggcaa    180

tcgcaggtca agaagaactg gagttcccag gggaaggggc tcaagcgaga cattcgtgtt    240

tacaaaggac aacctcgtgg gcaactccca aggaagtttc accttcggac caagtgtatc    300

agactgtcca gcattcaagg atggaatact caaggcctac catgagtaca agatcacaag    360

tatccttctt cagttcgtca gcgaggcctc ttccacctca ccaggatcca tcgcttatga    420

gttggaccca cattgcaaag tatcatccct ccagtcctac gtcaacaagt tccaaatcac    480

aaagggagga gctaagacct atcaagctag gatgatcaac ggagtagaat ggcacgattc    540

atctgaggat cagtgcagga tactttggaa aggaagtgga aaatcttcag acccagcagg    600

atctttcaga gtcaccatca gagtggctct tcaaaacccc aagtaataga ctccggatca    660
```

-continued gagcctggtc caagcccaca accaacaccc actccaactc cccaaaagca tgagcgattt 720
attgcttacg tcggcatacc tatgctgacc attcaagaat tc 762

<210> SEQ ID NO 22
<211> LENGTH: 18
<212> TYPE: DNA
<213> ORGANISM: Artificial sequence
<220> FEATURE:
<223> OTHER INFORMATION: BTK185 primer, Example 1, Table III

<400> SEQUENCE: 22
tccccagata atatcaac 18

<210> SEQ ID NO 23
<211> LENGTH: 48
<212> TYPE: DNA
<213> ORGANISM: Artificial Sequence
<220> FEATURE:
<223> OTHER INFORMATION: BTK240 primer, Example 1, Table III

<400> SEQUENCE: 23
ggcttgattc ctagcgaact cttcgattct ctggttgatg agctgttc 48

<210> SEQ ID NO 24
<211> LENGTH: 54
<212> TYPE: DNA
<213> ORGANISM: Artificial sequence
<220> FEATURE:
<223> OTHER INFORMATION: BTK462 primer, Example 1, Table III

<400> SEQUENCE: 24
caaaactgag aggtggaggt tggcagcttg aacgtacacg gagaggagag gaac 54

<210> SEQ ID NO 25
<211> LENGTH: 48
<212> TYPE: DNA
<213> ORGANISM: Artificial sequence
<220> FEATURE:
<223> OTHER INFORMATION: BTK669 primer, Example 1, Table III

<400> SEQUENCE: 25
agttagtgta agctctcttc tgaactggtt gtacctgatc caatctct 48

<210> SEQ ID NO 26
<211> LENGTH: 39
<212> TYPE: DNA
<213> ORGANISM: Artificial sequence
<220> FEATURE:
<223> OTHER INFORMATION: BTK930 primer, Example 1, Table III

<400> SEQUENCE: 26
agccatgatc tggtgaccgg accagtagta ttctcctct 39

<210> SEQ ID NO 27
<211> LENGTH: 32
<212> TYPE: DNA
<213> ORGANISM: Artificial sequence
<220> FEATURE:
<223> OTHER INFORMATION: BTK1110 primer, Example 1, Table III

<400> SEQUENCE: 27
agttgttggt tgttgatccc gatgttaaaa gg 32

<210> SEQ ID NO 28

-continued

```
<211> LENGTH: 37
<212> TYPE: DNA
<213> ORGANISM: Artificial sequence
<220> FEATURE:
<223> OTHER INFORMATION: BTK1380A primer, Example 1, Table III

<400> SEQUENCE: 28

gtgatgaagg gatgatgttg ttgaactcag cactacg                            37


<210> SEQ ID NO 29
<211> LENGTH: 100
<212> TYPE: DNA
<213> ORGANISM: Artificial sequence
<220> FEATURE:
<223> OTHER INFORMATION: BTK1380T primer, Example 1, Table III

<400> SEQUENCE: 29

cagaagttcc agagccaaga ttagtagact tggtgagtgg gatttgggtg atttgtgatg     60

aagggatgat gttgttgaac tcagcactac gatgtatcca                          100


<210> SEQ ID NO 30
<211> LENGTH: 27
<212> TYPE: DNA
<213> ORGANISM: Artificial sequence
<220> FEATURE:
<223> OTHER INFORMATION: BTK1600 primer, Example 1, Table III

<400> SEQUENCE: 30

tgatgtgtgg aactgaaggt ttgtggt                                        27


<210> SEQ ID NO 31
<211> LENGTH: 51
<212> TYPE: DNA
<213> ORGANISM: Artificial sequence
<220> FEATURE:
<223> OTHER INFORMATION: BTK1363 primer, Example 3, Table VI

<400> SEQUENCE: 31

aatactatcg gatgcgatga tgttgttgaa ctcagcacta cggtgtatcc a             51


<210> SEQ ID NO 32
<211> LENGTH: 33
<212> TYPE: DNA
<213> ORGANISM: Artificial sequence
<220> FEATURE:
<223> OTHER INFORMATION: 73K1437 primer, Example 3, Table VI

<400> SEQUENCE: 32

tcctgaaatg acagaaccgt tgaagagaaa gtt                                 33


<210> SEQ ID NO 33
<211> LENGTH: 48
<212> TYPE: DNA
<213> ORGANISM: Artificial sequence
<220> FEATURE:
<223> OTHER INFORMATION: 73K1471 primer, Example 3, Table VI

<400> SEQUENCE: 33

atttccactg ctgttgagtc taacgaggtc tccaccagtg aatcctgg                 48


<210> SEQ ID NO 34
<211> LENGTH: 61
<212> TYPE: DNA
<213> ORGANISM: Artificial sequence
<220> FEATURE:
<223> OTHER INFORMATION: 73K1561 primer, Example 3, Table VI
```

-continued

<400> SEQUENCE: 34
gtgaataggg gtcacagaag catacctcac acgaactcta tatctggtag atgttggatg 60
g 61

<210> SEQ ID NO 35
<211> LENGTH: 33
<212> TYPE: DNA
<213> ORGANISM: Artificial sequence
<220> FEATURE:
<223> OTHER INFORMATION: 73K1642 primer, Example 3, Table VI

<400> SEQUENCE: 35
tgtagctgga actgtattgg agaagatgga tga 33

<210> SEQ ID NO 36
<211> LENGTH: 48
<212> TYPE: DNA
<213> ORGANISM: Artificial sequence
<220> FEATURE:
<223> OTHER INFORMATION: 73K1675 primer, Example 3, Table VI

<400> SEQUENCE: 36
ttcaaagtaa ccgaaatcgc tggattggag attatccaag gaggtagc 48

<210> SEQ ID NO 37
<211> LENGTH: 39
<212> TYPE: DNA
<213> ORGANISM: Artificial sequence
<220> FEATURE:
<223> OTHER INFORMATION: 73K1741 primer, Example 3, Table VI

<400> SEQUENCE: 37
actaaagttt ctaacaccca cgatgttacc gagtgaaga 39

<210> SEQ ID NO 38
<211> LENGTH: 36
<212> TYPE: DNA
<213> ORGANISM: Artificial sequence
<220> FEATURE:
<223> OTHER INFORMATION: 73K1797 primer, Example 3, Table VI

<400> SEQUENCE: 38
aactggaatg aactcgaatc tgtcgataat cactcc 36

<210> SEQ ID NO 39
<211> LENGTH: 54
<212> TYPE: DNA
<213> ORGANISM: Artificial sequence
<220> FEATURE:
<223> OTHER INFORMATION: 73KTERM primer, Example 3, Table VI

<400> SEQUENCE: 39
ggacactaga tcttagtgat aatcggtcac atttgtcttg agtccaagct ggtt 54

<210> SEQ ID NO 40
<211> LENGTH: 10
<212> TYPE: PRT
<213> ORGANISM: Artificial sequence
<220> FEATURE:
<223> OTHER INFORMATION: RUBISCO SSU CTP cleavage site sequence,
described in Example 10

-continued

```
<400> SEQUENCE: 40

Gly Gly Arg Val Asn Cys Met Gln Ala Met
1               5                   10
```

The invention claimed is:

1. A method of making a structural gene that encodes an insecticidal protein, the method comprising:

(a) starting with a coding sequence, derived from *Bacillus thuringiensis* (B.t.), that encodes an insecticidal protein and that contains polyadenylation signal sequences listed in Table II;

(b) reducing the number of said polyadenylation signal sequences in the coding sequence by substituting sense codons for codons in the coding sequence; and (c) making a structural gene that comprises a coding sequence that includes the codons substituted according to step (b) and is characterized by the reduced number of Table II polyadenylation signal sequences, and that encodes the insecticidal protein.

2. The method of claim 1, wherein the coding sequence derived from B.t. contains ATTTA sequences, wherein the method further comprises reducing the number of said ATTTA sequences in the coding sequence by substituting sense codons for codons in the coding sequence, and wherein the structural gene of step (c) is characterized by the reduced number of ATTTA sequences.

3. The method of claim 2, wherein the structural gene of step (c) is devoid or substantially devoid of ATTTA sequences or devoid or substantially devoid of polyadenylation signal sequences listed in Table II.

4. A method of making a structural gene that encodes an insecticidal protein, the method comprising:

(a) starting with a portion of a coding sequence, wherein the coding sequence is derived from *Bacillus thuringiensis* (B.t.) and encodes an insecticidal protein and wherein portion contains ATTTA sequences and polyadenylation signal sequences listed in Table II;

(b) reducing the number of said ATTTA sequences and the number of said polyadenylation signal sequences in said portion of the coding sequence by substituting sense codons for codons in said portion, wherein said substituted sense codons maintain the original encoded amino acids; and (c) making a structural gene that comprises said portion with the substitute codons and the reduced number of ATTTA and polyadenylation signal sequences, wherein the structural gene comprises a nucleotide sequence that encodes an insecticidal protein.

5. The method of claim 4, wherein the structural gene of step (c) is devoid or substantially devoid of polyadenylation signal sequences listed in Table II, or is devoid or substantially devoid of ATTTA sequences.

6. The method of claim 4, wherein the structural gene of step (c) is devoid or substantially devoid of polyadenylation signal sequences listed in Table II, and is devoid or substantially devoid of ATTTA sequences.

7. A method of making a structural gene, the method comprising:

(a) starting with a coding sequence, derived from *Bacillus thuringiensis* (B.t.), that encodes an amino acid sequence and that contains ATTTA sequences and polyadenylation signal sequences listed in Table II;

(b) reducing the number of said ATTTA sequences and the number of said polyadenylation signal sequences in a portion of the coding sequence by substituting sense codons for codons in said portion, while maintaining the amino acid sequence; and (c) making a structural gene that comprises said portion with the codons substituted according to step (b) and characterized by the reduced number of ATTTA and polyadenylation signal sequences.

8. The method of claim 7, wherein the structural gene of step (c) is devoid or substantially devoid of polyadenylation signal sequences listed in Table II, or is devoid or substantially devoid of ATTTA sequences.

9. The method of claim 7, wherein the structural gene of step (c) is devoid or substantially devoid of polyadenylation signal sequences listed in Table II, and is devoid or substantially devoid of ATTTA sequences.

10. A method of making a structural gene that encodes an insecticidal protein, the method comprising:

(a) starting with an amino acid sequence of an insecticidal protein derived from *Bacillus thuringiensis* (B.t.), wherein wild-type B.t. gene sequence(s) encoding insecticidal polypeptide(s) from which the insecticidal protein is derived comprise polyadenylation signal sequences listed in Table II; and (b) making a structural gene that comprises a coding sequence that:

(i) encodes the amino acid sequence of the insecticidal protein; and (ii) contains fewer polyadenylation signal sequences listed in Table II, compared to the corresponding coding sequence(s) of the wild-type B.t. gene sequences(s).

11. The method of claim 10, wherein the wild-type B.t. gene sequence(s) further comprise ATTTA sequences, and wherein the structural gene made according to step (b) contains fewer ATTTA sequences compared to the wild-type B.t. gene sequences(s).

12. The method of claim 11, wherein the structural gene made according to step (b) is devoid or substantially devoid of said polyadenylation signal sequences or is devoid or substantially devoid of said ATTTA sequences.

13. The method of claim 11, wherein the structural gene made according to step (b) is devoid or substantially devoid of ATTTA sequences and is devoid or substantially devoid of said polyadenylation signal sequences.

14. A method of making a structural gene that encodes an insecticidal protein, the method comprising:

(a) starting with an amino acid sequence of an insecticidal protein derived from *Bacillus thuringiensis* (B.t.); and (b) making a structural gene that comprises a coding sequence that encodes the amino acid sequence and that is devoid or substantially devoid of polyadenylation signal sequences listed in Table II.

15. The method of claim 14, wherein step (b) comprises making a structural gene that also is devoid or substantially devoid of the ATTTA sequences.

16. The method of claim 14, wherein step (b) comprises making a structural gene that comprises a coding sequence that is devoid of the polyadenylation signal sequences.

17. The method of claim 15, wherein step (b) comprises making a structural gene that comprises a coding sequence that is devoid of the ATTTA sequences and devoid of the polyadenylation signal sequences.

18. A method of making a structural gene that encodes an insecticidal protein, the method comprising:

(a) starting with an amino acid sequence of a portion of an insecticidal protein derived from *Bacillus thuringiensis* (B.t.), wherein a wild-type B.t. coding sequence from which the portion was derived includes ATTTA sequences and polyadenylation signal sequences listed in Table II; and (b) making a structural gene that encodes an insecticidal protein and that comprises a sequence that encodes the amino acid sequence of the portion and that contains fewer ATTTA sequences and fewer of said polyadenylation signal sequences than the wildtype B.t. coding sequence from which said portion was derived.

19. The method of claim 18, wherein step (b) comprises making a structural gene that is devoid or substantially devoid of said ATTTA sequences and devoid or substantially devoid of said polyadenylation signal sequences.

20. The method according to any one of claims 1, 2-4, and 5-9, wherein the structural gene made according to the method is more highly expressed in a dicot plant cell than a structural gene that comprises the starting coding sequence(s) of step (a).

21. The method according to any one of claims 10-13, wherein the structural gene made according to the method is more highly expressed in a dicot plant cell than a structural gene that comprises the wild-type B.t. gene sequence(s) encoding polypeptide(s) from which the amino acid sequence of the insecticidal protein is derived.

22. The method according to any one of claims 2-4, 5-7, 11-12, 15, and 19, wherein the structural gene made according to the method contains no ATTTA sequences.

23. The method according to any one of claims 1, 2, 4, 5, 7, 10, 12, 15, and 19, wherein the structural gene made according to the method contains no polyadenylation signal sequences listed in Table II.

24. The method according to any one of claims 1, 2, 4, 7, 10-15, and 18, wherein the structural gene made according to the method contains a (G+C) content of about 50%.

25. The method according to claim 1, 4, or 7, wherein the starting coding sequence of step (a) has an (A+T) content of about 62%.

26. The method according to claim 10 or 11, wherein the wild-type gene sequence(s) from B.t. have an (A+T) content of about 62%.

27. The method according to any one of claims 1, 2, 4, and 5-7, wherein the starting coding sequence of step (a) is derived from a *Bacillus thuringiensis* (B.t.) crystal protein gene.

28. The method of any one of claims 1, 2, 4, 7, and 18, wherein the starting coding sequence of step (a) is derived from a *Bacillus thuringiensis* (B.t.) P2 protein or a *B.t. entomocidus* gene.

29. The method according to any one of claims 10 to 13, wherein the wild-type gene sequence(s) comprise *Bacillus thuringiensis* (B.t.) crystal protein gene sequences.

30. The method according to any one of claims 10 to 13, wherein the wild-type gene sequences(s) comprise *Bacillus thuringiensis* (B.t.) P2 gene sequences or *B.t. entomocidus* gene sequences.

31. The method according to any one of claims 1, 2-4, 5-6, 10-15, and 18, wherein the insecticidal protein is a *Bacillus thuringiensis* (B.t.) crystal protein.

32. The method according to any of claims 1, 2, 4, 7 and 18, wherein the starting coding sequence of step (a) is derived from *B.t. tenebrionus.*

33. The method according to any one of claims 1, 2, 4, 10-11, and 14-15, wherein the insecticidal protein is a B.t. P2 protein or a *B.t. entomocidus* protein.

34. The method according to any one of claims 1, 2, 4, and 7, wherein the coding sequence of step (a) comprises a sequence that encodes an insecticidal fragment of a B.t. insecticidal protein.

35. The method according to any one of claims 1, 2, 4, and 7, wherein the coding sequence(s) of step (a) encode(s) a full length B.t. insecticidal protein.

36. The method according to any one of claims 10-15 and 18, wherein the insecticidal protein derived from B.t. comprises an insecticidal fragment of a B.t. insecticidal protein.

37. The method according to any one of claims 10-15 and 18, wherein the insecticidal protein derived from B.t. comprises a full length B.t. insecticidal protein.

38. The method according to any one of claims 1, 2, 4, 10, 11, 14-15, and 18, wherein the insecticidal protein encoded by the structural gene comprises an amino acid sequence that is identical to the amino acid sequence of an insecticidal protein from B.t., or an insecticidal fragment thereof.

39. The method according to any one of claims 1, 2-4, 5-9, 10-15, and 18, comprising avoiding the introduction of sense codons that are rarely found in plant genomes into the resultant structural gene.

40. The method according to any one of claims 1, 2-4, 5-9, 10-15, and 18, comprising avoiding, in the resultant structural gene, the introduction of sense codons that contain a TA doublet.

41. The method according to any one of claims 1, 2-4, 5-9, 10-15, and 18, comprising avoiding, in the resultant structural gene, the introduction of sense codons that contain a CG doublet.

42. The method according to claim 1 or 2, further comprising reducing the number of regions in the coding sequence(s) with greater than five consecutive adenine and thymine (A+T) nucleotides by substituting sense codons for codons in the coding sequence(s).

43. The method according to claim 4 or 7, further comprising reducing the number of regions in said portion with greater than five consecutive adenine and thymine (A+T) nucleotides by substituting sense codons for codons in the portion.

44. The method according to any one of claims 10, 11, 14-15, and 18, wherein the structural gene comprises a coding sequence that does not contain more than five consecutive adenine and thymine (A+T) nucleotides.

45. The method according to claim 1 or 2, further comprising truncating the coding sequence to yield a truncated structural gene that encodes a truncated protein that retains insecticidal activity.

46. The method according to any one of claims 1, 2-4, 5-9, 10-15, and 18, further comprising attaching a plant promoter to the structural gene.

47. The method according to any one of claims 1, 2-4, 5-9, 10-15, and 18, further comprising including in the structural gene a sequence that encodes an amino-terminal chloroplast transit peptide.

48. The method according to any one of claims 1, 2-4, 5-9, 10-15, and 18, further comprising attaching to the structural gene a 3' non-translated nucleotide sequence that comprises a plant polyadenylation signal.

49. The method according to any one of claims 1, 2, 4, and 7, wherein the making step comprises performing site directed mutagenesis on a coding sequence from *Bacillus thuringiensis* to make the structural gene.

50. The method according to any one of claims 1, 2, 4, and 7, wherein the making comprises de novo synthesis of a fully synthetic structural gene.

51. A method of making a structural gene that encodes an insecticidal protein, the method comprising:

(a) starting with a sequence derived from *Bacillus thuringiensis* (B.t.), said sequence comprising: (i) a coding sequence for an insecticidal protein having an amino acid sequence, or (ii) an amino acid sequence of the insecticidal protein; and (b) making a structural gene that comprises a coding sequence that encodes the amino acid sequence and that is devoid or substantially devoid of ATTTA sequences, and devoid or substantially devoid of polyadenylation signal sequences listed in Table II.

52. A method of making a structural gene that encodes an insecticidal protein, the method comprising:

(a) designing a nucleotide sequence that encodes an insecticidal protein derived from *Bacillus thuringiensis* (B.t.) and that contains a reduced number of polyadenylation signal sequences listed in Table II, compared to a wild type B.t. coding sequence from which the insecticidal protein was derived, wherein the number of said polyadenylation signal sequences is reduced compared to the wild type B.t. coding sequence by substituting codons while maintaining the encoded amino acids; and (b) making a structural gene that comprises the nucleotide sequence, that encodes the insecticidal protein, and that is characterized by the reduced number of said polyadenylation signal sequences, compared to the wild type B.t. coding sequence.

53. The method of claim 52 wherein the insecticidal protein comprises a protein selected from the group consisting of: (a) B.t. insecticidal proteins; and (b) insecticidal fragments of (a).

54. The method of claim 52, wherein the wild-type B.t. coding sequence comprises ATTTA sequences, wherein the nucleotide sequence designed in step (a) contains a reduced number of the ATTTA sequences compared to the wild-type B.t coding sequence, wherein the number of the ATTTA sequences is reduced by substituting codons while maintaining the encoded amino acids, and wherein the structural gene made according to step (b) is characterized by the reduced number of ATTTA sequences compared to the wild-type B.t. coding sequence.

55. The method according to any one of claims 52-54, wherein the structural gene made according to the method is more highly expressed in a dicot plant cell than a structural gene that consists of the wild type B.t. coding sequence from which the insecticidal protein was derived.

56. A method of making a structural gene that encodes an insecticidal protein, the method comprising:

(a) designing a nucleotide sequence that encodes an insecticidal protein derived from *Bacillus thuringiensis* (B.t.) and that is devoid or substantially devoid of polyadenylation signal sequences listed in Table II; and (b) making a structural gene that comprises the nucleotide sequence and that encodes the insecticidal protein, wherein the structural gene is devoid or substantially devoid of said polyadenylation signal sequences.

57. The method of claim 56, wherein step (a) further comprises designing the nucleotide sequence to be devoid or substantially devoid of ATTTA sequences, and wherein the structural gene made according to step (b) is devoid or substantially devoid of the ATTTA sequences, and devoid or substantially devoid of the polyadenylation signal sequences.

58. A method of making a structural gene that encodes an insecticidal protein, the method comprising:

(a) starting with a coding sequence, derived from *Bacillus thuringiensis* (B.t.), that contains polyadenylation signal sequences listed in Table II, and that encodes an insecticidal protein having an amino acid sequence;

(b) making a structural gene that comprises a coding sequence that:

(i) encodes the amino acid sequence of the insecticidal protein; and (ii) contains fewer polyadenylation signal sequences listed in Table II, compared to the corresponding coding sequence derived from B.t.

59. A method of making a structural gene that encodes a protein, the method comprising:

(a) starting with a coding sequence that encodes a protein and that contains polyadenylation signal sequences listed in Table II;

(b) reducing the number of said polyadenylation signal sequences in the coding sequence by substituting sense codons for codons in the coding sequence; and (c) making a structural gene that comprises a coding sequence that includes the codons substituted according to step (b) and is characterized by the reduced number of Table II polyadenylation signal sequences, and that encodes the protein.

60. The method of claim 59, wherein the starting coding sequence of step (a) contains ATTTA sequences, and wherein step (b) further comprises reducing the number of said ATTTA sequences in the coding sequence by substituting sense codons for codons in the coding sequence.

61. A method of making a structural gene, the method comprising:

(a) starting with a coding sequence that encodes an amino acid sequence and that contains polyadenylation signal sequences listed in Table II;

(b) reducing the number of said polyadenylation signal sequences in a portion of the coding sequence by substituting sense codons for codons in said portion, while maintaining the amino acid sequence;

(c) making a structural gene that comprises said portion with the substitute codons and the reduced number of polyadenylation signal sequences; and (d) making a DNA construct that comprises the structural gene and at least one sequence selected from the group consisting of a plant promoter or a plant virus promoter.

62. The method of claim 61, wherein the starting coding sequence contains ATTTA sequences, and wherein step (b) further comprises reducing the number of said ATTTA sequences in said portion, while maintaining the amino acid sequence.

63. A method of making a structural gene that encodes a protein, the method comprising:

(a) starting with coding sequences, from one or more structural genes that encode a protein and that contain polyadenylation signal sequences listed in Table II;

(b) reducing the number of said polyadenylation signal sequences in the coding sequences by substituting sense codons for codons in the coding sequences; and (c) making a structural gene that comprises the coding sequences with the codons substituted according to step (b) and characterized by the reduced number of polyadenylation signal sequences, wherein the structural gene comprises a nucleotide sequence that encodes the protein.

64. The method of claim 63, wherein the starting coding sequences of step (a) contain ATTTA sequences, and wherein step (b) further comprises reducing the number of said ATTTA sequences in said coding sequences by substituting sense codons for codons in the coding sequence.

65. A method of making a structural gene that encodes a protein, the method comprising:

(a) starting with an amino acid sequence of a protein, wherein the amino acid sequence is derived from a coding sequence that contains polyadenylation signal sequences listed in Table II and ATTTA sequences;

(b) making a structural gene that comprises a coding sequence that encodes the amino acid sequence and that is devoid or substantially devoid of ATTTA sequences, and devoid or substantially devoid of polyadenylation signal sequences listed in Table II; and (c) making a DNA construct that comprises the structural gene and at least one sequence selected from the group consisting of a plant promoter or a plant virus promoter.

66. The method of claim 58, wherein the coding sequence derived from B.t. contains ATTTA sequences, and wherein step (b) comprises making a structural gene that contains fewer of the ATTTA sequences compared to the corresponding coding sequence derived from B.t.

67. A method of making a structural gene that encodes a protein, the method comprising: combining coding sequences to form a structural gene that encodes an insecticidal protein derived from *Bacillus thuringiensis* (B.t.), wherein said coding sequences and the structural gene are devoid or substantially devoid of polyadenylation signal sequences listed in Table II.

68. The method of claim 67, wherein said coding sequences and the structural gene are devoid or substantially devoid of ATTTA sequences.

69. The method according to any one of claims 51-54, and 56-68, further comprising attaching a plant promoter to the structural gene.

70. The method according to any one of claims 51-54, and 56-68, further comprising including in the structural gene a sequence that encodes an amino-terminal chloroplast transit peptide.

71. The method according to any one of claims 51-54, and 56-68, further comprising attaching to the structural gene a 3' non-translated nucleotide sequence that comprises a plant polyadenylation signal.

72. The method according to any one of claims 51, 58-64, and 66, wherein the structural gene made according to the method is more highly expressed in a dicot plant cell than a structural gene that comprises the starting coding sequence(s) of step (a).

73. The method according to any one of claims 51-54, and 56-68, wherein the structural gene made according to the method contains no ATTTA sequences.

74. The method according to any one of claims 51-54, and 56-68, wherein the structural gene made according to the method contains no polyadenylation signal sequences listed in Table II.

75. The method according to any one of claims 51, 58-64, and 66, wherein the starting coding sequence(s) of step (a) is (are) derived from *Bacillus thuringiensis*.

76. The method according to any one of claims 51-54 and 56-68, comprising avoiding the introduction of sense codons that are rarely found in plant genomes into the resultant structural gene.

77. The method according to any one of claims 51-54 and 56-68, comprising avoiding, in the resultant structural gene, the introduction of sense codons that contain a TA doublet.

78. The method according to any one of claims 51-54 and 56-68, comprising avoiding, in the resultant structural gene, the introduction of sense codons that contain a CG doublet.

79. The method according to any one of claims 51, 58-64, and 66, further comprising reducing the number of regions in the coding sequence(s) with greater than five consecutive adenine and thymine (A+T) nucleotides by substituting sense codons for codons in the coding sequence(s).

80. The method according to any one of claims 51-54, and 56-58, wherein the structural gene comprises a coding sequence that does not contain more than five consecutive adenine and thymine (A+T) nucleotides.

81. The method according to any one of claims 1, 2, 4, 7, 10, 11, 14-15, 51-54, and 56-68, further comprising including in the structural gene a sequence that encodes a secretory signal sequence.

82. The method of claim 54, wherein the structural gene is devoid or substantially devoid of the ATTTA sequences, or devoid or substantially devoid of the polyadenylation signal sequences.

83. A method of making a DNA construct for expression of an insecticidal protein derived from *Bacillus thuringiensis* (B.t.), the method comprising combining a 5' nontranslated sequence, a structural gene, and a 3' nontranslated region to form a construct for expression of the insecticidal protein, wherein the 5' nontranslated sequence contains a plant promoter or a plant virus promoter, wherein the structural gene comprises a sequence that encodes the insecticidal protein derived from B.t. and is devoid or substantially devoid of polyadenylation signal sequences listed in Table II, and wherein the 3' nontranslated sequence comprises a polyadenylation signal.

84. A method of making a structural gene that encodes an insecticidal protein, the method comprising:

(a) starting with a sequence derived from *Bacillus thuringiensis* (B.t.), said sequence comprising: (i) a coding sequence for an insecticidal protein having an amino acid sequence, or (ii) an amino acid sequence of the insecticidal protein; and (b) making a structural gene that comprises a coding sequence that encodes the amino acid sequence and that is devoid or substantially devoid of polyadenylation signal sequences listed in Table II.

85. A method of making a structural gene that encodes a protein, the method comprising:

(a) starting with an amino acid sequence of a protein, wherein the amino acid sequence is derived from a coding sequence that contains polyadenylation signal sequences listed in Table II;

(b) making a structural gene that comprises a coding sequence that encodes the amino acid sequence and that is devoid or substantially devoid of polyadenylation signal sequences listed in Table II; and (c) making a DNA construct that comprises the structural gene and at least one sequence selected from the group consisting of a plant promoter or a plant virus promoter.

86. The method according to any one of claims 1, 2-4, 5-9, 10-19, 51-54, 56-60, 63-64, 66-68, 82, and 84-85, further comprising making a DNA construct that comprises the structural gene and at least one sequence selected from the group consisting of a plant promoter or a plant virus promoter.

87. In a method that involves making a structural gene that encodes an insecticidal protein derived from *Bacillus thuringiensis* (B.t.) and that involves starting with a wild type B.t. coding sequence or with an amino acid sequence encoded thereby, the improvement which comprises reducing the number of polyadenylation signal sequences listed in Table II when making the structural gene, compared to the number of said polyadenylation signal sequences in the wild type B.t. coding sequence, by substituting codons relative to the wild-type B.t. coding sequence while maintaining the amino acid sequence.

88. In the method of claim 87, the further improvement which comprises reducing the number of ATTTA sequences when making the structural gene, compared to the number of said ATTTA sequences in the wild type B.t. coding sequence, by substituting codons relative to the wild type B.t. coding sequence while maintaining the amino acid sequence.

89. In the method of claim 87 or 88, the further improvement which comprises reducing the number of occurrences of greater than five consecutive adenine and thymine (A+T) nucleotides, compared to the wild type B.t. coding sequence, by substituting codons relative to the wild type B.t. coding sequence while maintaining the amino acid sequence.

90. In the method of claim 87, the further improvement wherein the structural gene made according to the method is devoid or substantially devoid of said polyadenylation signal sequences.

91. In the method of claim 88, the further improvement wherein the structural gene made according to the method is devoid or substantially devoid of ATTTA sequences.

92. In the method of claim 87, the improvement wherein the structural gene made according to the method contains none of said polyadenylation signal sequences.

93. In the method of claim 88, the improvement wherein the structural gene made according to the method contains no ATTTA sequences.

94. In the method of claim 87 or 88, the further improvement wherein the insecticidal protein is a B.t. crystal protein.

95. In the method of claim 87 or 88, the further improvement wherein the wild type B.t. coding sequence comprises a sequence that encodes an insecticidal fragment of a B.t. insecticidal protein.

96. In the method of claim 87 or 88, the further improvement which comprises avoiding, in the resultant structural gene, the introduction of codons that contain a TA doublet.

97. In the method of claim 87 or 88, the further improvement which comprises avoiding, in the resultant structural gene, the introduction of codons that contain a CG doublet.

98. In the method of claim 87 or 88, the further improvement which comprises attaching a plant promoter to the structural gene.

99. In the method of claim 87 or 88, the further improvement which comprises including in the structural gene a sequence that encodes an amino-terminal chloroplast transit peptide.

100. In the method of claim 87 or 88, the further improvement which comprises including in the structural gene a sequence that encodes a secretory signal sequence.

101. In the method of claim 87 or 88, the further improvement which comprises attaching to the structural gene a 3' non-translated nucleotide sequence that comprises a plant polyadenylation signal.

102. In the method according to any one of claims 87, 88, 90, and 91, the further improvement that comprises making a DNA construct that comprises the structural gene and at least one sequence selected from the group consisting of a plant promoter or a plant virus promoter.

103. A method of making a structural gene that encodes an insecticidal protein, the method comprising:

(a) starting with an insecticidal portion of a coding sequence, wherein the coding sequence is derived from Bacillus thuringiensis (B.t.) and encodes an insecticidal protein and wherein the insecticidal portion contains ATTTA sequences and polyadenylation signal sequences listed in Table II;

(b) reducing the number of said ATTTA sequences and the number of said polyadenylation signal sequences in said insecticidal portion of the coding sequence by substituting sense codons for codons in said portion; and (c) making a structural gene that comprises said insecticidal portion with the substitute codons and the reduced number of ATTTA and polyadenylation signal sequences, wherein the structural gene comprises a nucleotide sequence that encodes an insecticidal protein.

* * * * *

UNITED STATES PATENT AND TRADEMARK OFFICE

CERTIFICATE OF CORRECTION

PATENT NO. : 7,741,118 B1
APPLICATION NO. : 08/434105
DATED : June 22, 2010
INVENTOR(S) : David A. Fischhoff et al.

It is certified that error appears in the above-identified patent and that said Letters Patent is hereby corrected as shown below:

In the Claims:

At Column 108, line 46, add

--104. The method of claim 103, wherein the structural gene of step (c) is devoid or substantially devoid of polyadenylation signal sequences listed in Table II, or is devoid or substantially devoid of ATTTA sequences.

105. The method of claim 103, wherein the structural gene of step (c) is devoid or substantially devoid of polyadenylation signal sequences listed in Table II, and is devoid or substantially devoid of ATTTA sequences.

106. The method according to claim 103, wherein the structural gene made according to the method is more highly expressed in a dicot plant cell than a structural gene that comprises the starting coding sequence(s) of step (a).

107. The method according to claim 103, wherein the starting coding sequence of step (a) is derived from a *B.t.* crystal protein gene.

108. The method according to claim 103, further comprising reducing the number of regions in said portion with greater than five consecutive adenine and thymine (A+T) nucleotides by substituting sense codons for codons in the portion.

109. The method according to claim 103, further comprising attaching a plant promoter to the structural gene.

110. The method according to claim 103, further comprising including in the structural gene a sequence that encodes an amino-terminal chloroplast transit peptide.

111. The method according to claim 103, further comprising attaching to the structural gene a 3' non-translated nucleotide sequence that comprises a plant polyadenylation signal.

112. The method according to claim 103, further comprising including in the structural gene a sequence that encodes a secretory signal sequence.

113. The method according to claim 103, further comprising making a DNA construct that comprises the structural gene and at least one sequence selected from the group consisting of a plant promoter or a plant virus promoter. --.

Signed and Sealed this
Fifth Day of July, 2011

David J. Kappos
*Director of the United States Patent and Trademark Office*

UNITED STATES PATENT AND TRADEMARK OFFICE

CERTIFICATE OF CORRECTION

PATENT NO. : 7,741,118 B1
APPLICATION NO. : 08/434105
DATED : June 22, 2010
INVENTOR(S) : David A. Fischhoff et al.

It is certified that error appears in the above-identified patent and that said Letters Patent is hereby corrected as shown below:

Delete the title page and substitute therefore the attached title page showing the corrected number of claims in patent In the Claims:

At Column 108, line 46, add

--104. The method of claim 103, wherein the structural gene of step (c) is devoid or substantially devoid of polyadenylation signal sequences listed in Table II, or is devoid or substantially devoid of ATTTA sequences.

105. The method of claim 103, wherein the structural gene of step (c) is devoid or substantially devoid of polyadenylation signal sequences listed in Table II, and is devoid or substantially devoid of ATTTA sequences.

106. The method according to claim 103, wherein the structural gene made according to the method is more highly expressed in a dicot plant cell than a structural gene that comprises the starting coding sequence(s) of step (a).

107. The method according to claim 103, wherein the starting coding sequence of step (a) is derived from a *B.t.* crystal protein gene.

108. The method according to claim 103, further comprising reducing the number of regions in said portion with greater than five consecutive adenine and thymine (A+T) nucleotides by substituting sense codons for codons in the portion.

109. The method according to claim 103, further comprising attaching a plant promoter to the structural gene.

110. The method according to claim 103, further comprising including in the structural gene a sequence that encodes an amino-terminal chloroplast transit peptide.

This certificate supersedes the Certificate of Correction issued July 5, 2011.

Signed and Sealed this
Sixteenth Day of August, 2011

David J. Kappos
*Director of the United States Patent and Trademark Office*

111. The method according to claim 103, further comprising attaching to the structural gene a 3' non-translated nucleotide sequence that comprises a plant polyadenylation signal.

112. The method according to claim 103, further comprising including in the structural gene a sequence that encodes a secretory signal sequence.

113. The method according to claim 103, further comprising making a DNA construct that comprises the structural gene and at least one sequence selected from the group consisting of a plant promoter or a plant virus promoter. --.

(12) United States Patent
Fischhoff et al.

(10) Patent No.: US 7,741,118 B1
(45) Date of Patent: Jun. 22, 2010

(54) SYNTHETIC PLANT GENES AND METHOD FOR PREPARATION

(75) Inventors: David A. Fischhoff, Webster Groves, MO (US); Frederick J. Perlak, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 08/434,105

(22) Filed: May 3, 1995

Related U.S. Application Data

(60) Division of application No. 07/959,506, filed on Oct. 9, 1992, now Pat. No. 5,500,365, which is a continuation of application No. 07/476,661, filed on Feb. 12, 1990, now abandoned, which is a continuation-in-part of application No. 07/315,355, filed on Feb. 24, 1989, now abandoned.

(51) Int. Cl.
*C12N 15/09* (2006.01)

(52) U.S. Cl. .................................................... 435/440

(58) Field of Classification Search ...................... None
See application file for complete search history.

(56) References Cited

U.S. PATENT DOCUMENTS

| | | | | |
|---|---|---|---|---|
| 4,356,270 A | | 10/1982 | Itakura | |
| 4,448,885 A | | 5/1984 | Schnepf et al. | |
| 4,771,131 A | | 9/1988 | Herrnstadt et al. | |
| 4,859,596 A | | 8/1989 | Hollenberg et al. | |
| 4,888,282 A | * | 12/1989 | Beremand et al. | 435/193 |
| 4,943,674 A | | 7/1990 | Houck et al. | |
| 5,082,767 A | | 1/1992 | Hatfield et al. | |
| 5,250,515 A | | 10/1993 | Fuchs et al. | |
| 5,254,799 A | | 10/1993 | De Greve et al. | |
| 5,270,200 A | | 12/1993 | Sun et al. | |
| 5,380,831 A | | 1/1995 | Adang et al. | |
| 5,495,071 A | | 2/1996 | Fischhoff et al. | |
| 5,496,732 A | | 3/1996 | Smigocki et al. | |
| 5,500,365 A | | 3/1996 | Fischhoff et al. | |
| 5,567,600 A | | 10/1996 | Adang et al. | |
| 5,567,862 A | | 10/1996 | Adang et al. | |
| 5,625,136 A | | 4/1997 | Koziel et al. | |
| 5,689,052 A | | 11/1997 | Brown et al. | |
| 5,763,241 A | | 6/1998 | Fischhoff et al. | |
| 5,866,784 A | | 2/1999 | Van Mellaert et al. | |
| 5,880,275 A | | 3/1999 | Fischhoff et al. | |
| 6,075,185 A | | 6/2000 | Koziel et al. | |
| 6,180,774 B1 | | 1/2001 | Brown et al. | |
| 6,204,246 B1 | | 3/2001 | Bosch et al. | |
| 6,284,949 B1 | | 9/2001 | Fischhoff et al. | |
| 6,320,100 B1 | | 11/2001 | Koziel et al. | |
| 6,403,865 B1 | | 6/2002 | Koziel et al. | |
| 6,689,356 B1 | | 2/2004 | Zlotkin et al. | |
| 6,833,449 B1 | | 12/2004 | Barton et al. | |
| 2001/0003849 A1 | | 6/2001 | Barton et al. | |

FOREIGN PATENT DOCUMENTS

| | | |
|---|---|---|
| AU | B-36568/89 | 12/1989 |
| AU | B-46881/89 | 6/1990 |
| EP | 0063949 | 11/1982 |
| EP | 0108580 | 5/1984 |
| EP | 0142924 | 5/1985 |
| EP | 0159884 | 10/1985 |
| EP | 0192319 | 8/1986 |
| EP | 0193259 | 9/1986 |
| EP | 0221024 | 5/1987 |
| EP | 0267159 | 5/1988 |
| EP | 0269601 | 6/1988 |
| EP | 0275957 | 7/1988 |
| EP | 0305275 | 3/1989 |
| EP | 0318143 | 5/1989 |
| EP | 0332104 | 9/1989 |
| EP | 0340948 | 11/1989 |
| EP | 0348348 | 12/1989 |
| EP | 0359472 | 3/1990 |
| EP | 0385962 | 9/1990 |
| EP | 0431829 | 6/1991 |
| EP | 0228838 | 4/1992 |
| EP | 0140556 | 7/1992 |
| EP | 0126546 | 3/1994 |
| EP | 0408403 | 8/1994 |
| EP | 0612848 | 8/1994 |
| EP | 0223452 | 4/1996 |
| JP | 62319288 | 7/1989 |
| JP | 61283228 | 10/1998 |
| WO | WO-88/08880 | 11/1988 |
| WO | WO-90/10076 | 9/1990 |
| WO | WO-90/15139 | 12/1990 |
| WO | WO-91/10725 | 7/1991 |
| WO | WO-93/07278 | 4/1993 |

OTHER PUBLICATIONS

U.S. Appl. No. 07/285,924, filed Dec. 19, 1988.
U.S. Appl. No. 07/286,002, filed Dec. 19, 1988.
U.S. Appl. No. 07/286,087, filed Dec. 19, 1988.
U.S. Appl. No. 07/320,195, filed Mar. 7, 1989.
Adami et al., "Adenovirus mRNA Processing—In a Regulated Manner a Splice Site Choice Dominates Over Selection of a Poly A Site Located in an Intron," *RNA Processing Meeting*, pp. 26, May 11-15, 1988.
Adang et al., "Characterized Full-Length and Truncated Plasmid Clones of the Crystal Protein of *Bacillus Thuringiensis* subsp. *Kurstaki* HD-73 and their Toxicity to *Manduca Sexta*," *Genes*, 36:289-300 (1985).

(Continued)

*Primary Examiner*—Anne Marie Grunberg
(74) *Attorney, Agent, or Firm*—Marshall, Gerstein & Borun LLP

(57) ABSTRACT

A method for modifying structural gene sequences to enhance the expression of the protein product is disclosed. Also disclosed are novel structural genes which encode insecticidal proteins of B.t.k. HD-1, B.t.k. HD-73, *B.t. tenebrionis*, *B.t. entomocidus*, 2 protein of B.t.k. HD-1, and the coat protein of potato leaf roll virus.

113 Claims, 46 Drawing Sheets